United States Patent
Fischer et al.

(10) Patent No.: US 12,428,459 B2
(45) Date of Patent: Sep. 30, 2025

(54) PROTEIN TAG TO INDUCE LIGAND DEPENDENT DEGRADATION OF PROTEIN/PROTEIN-FUSIONS

(71) Applicant: DANA-FARBER CANCER INSTITUTE, INC., Boston, MA (US)

(72) Inventors: Eric S. Fischer, Chestnut Hill, MA (US); Shourya Sonkar Roy Burman, Brookline, MA (US); Tyler Faust, Brookline, MA (US); Hojong Yoon, Cambridge, MA (US); Radoslaw P. Nowak, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 574 days.

(21) Appl. No.: 17/642,874

(22) PCT Filed: Sep. 17, 2020

(86) PCT No.: PCT/US2020/051156
§ 371 (c)(1),
(2) Date: Mar. 14, 2022

(87) PCT Pub. No.: WO2021/055530
PCT Pub. Date: Mar. 25, 2021

(65) Prior Publication Data
US 2022/0402981 A1    Dec. 22, 2022

Related U.S. Application Data

(60) Provisional application No. 62/902,275, filed on Sep. 18, 2019.

(51) Int. Cl.
*C07K 14/47* (2006.01)
*C12N 15/62* (2006.01)

(52) U.S. Cl.
CPC .......... *C07K 14/4702* (2013.01); *C12N 15/62* (2013.01); *C07K 2319/85* (2013.01); *C07K 2319/95* (2013.01)

(58) Field of Classification Search
CPC .......... C07K 14/4702; C07K 2319/85; C07K 2319/95; C12N 15/62; A61K 31/381; A61K 31/404; A61K 38/00; A61K 2300/00
See application file for complete search history.

(56) References Cited

U.S. PATENT DOCUMENTS

2018/0000910 A1  1/2018 Chakraborty et al.
2018/0179509 A1  6/2018 Lin et al.

FOREIGN PATENT DOCUMENTS

WO   WO-2017181119 A2 * 10/2017  ............ A61K 35/15
WO   2019147783 A1    8/2019

OTHER PUBLICATIONS

Zhang, Meiling, David A. Case, and Jeffrey W. Peng. "Propagated perturbations from a peripheral mutation show interactions supporting WW domain thermostability." Structure 26.11 (2018):1474-1485. (Year: 2018).*
K Singh, Raushan, et al. "Protein engineering approaches in the post-genomic era." Current Protein and Peptide Science 19.1 (2018): 5-15. (Year: 2018).*
Bussiere et al (2019, Date posted: Aug. 16, 2019, Nature Chemical Biology, doi: 10.1038/s41589-019-0411-6, cited on IDS filed: Sep. 11, 2023) {herein Bussiere} (Year: 2019).*
Cheng et al. (2019, Date Publised: Jan. 2019, Biochim Biophys Acta Rev Cancer, doi: 10.1016/j.bbcan.2018.11.00, examiner cited) {herein Cheng} (Year: 2019).*
NCBI (Gene ID: 9584, updated Nov. 27, 2024){herein NCBI}. (Year: 2024).*
2019, Date posted: Aug. 16, 2019, Nature Chemical Biology, doi: 10.1038/s41589-019-0411-6, cited on IDS filed: Sep. 11, 2023) {herein Bussiere} (Year: 2019).*
Bussiere et al., "The structural basis of Indisulam-mediated recruitment of RBM39 to the DCAF15-DDB1-DDA1 E3 ligase complex," bioRxiv, Jan. 2019, pp. 1-10.
Bussier et al., "Structural basis of indisulam-mediated RBM39 recruitment to DCAF15 E3 ligase complex," Nature Chemical Biology, vol. 16, No. 1, pp. 15-23 (Dec. 9, 2019), 16 pages.
Faust et al., "Structural complementarity facilitates E7820-mediated degradation of RBM39 by DCAF15," Nature Chemical Biology, vol. 16, No. 1, pp. 7-14 (Nov. 4, 2019), 13 pages.
Han et al., "Anticancer sulfonamides target splicing by inducing RBM39 degradation via recruitment to DCAF15," Science, vol. 356, No. 6336, p. eaal3755 (Mar. 16, 2017), 15 pages.
Mai et al., "Functional interaction between nonreceptor tyrosine kinase c-Abl and SR-Rich protein RBM39," Biochemical and Biophysical Research Communications, vol. 473, No. 1, pp. 355-360 (Mar. 24, 2016), 6 pages.
Jehara et al., "Selective degradation of splicing factor CAPERa by anticancer sulfonamides," Nature Chemical Biology, vol. 13, No. 6, pp. 675-680 (Apr. 24, 2017), 10 pages.

* cited by examiner

*Primary Examiner* — Manjunath N Rao
*Assistant Examiner* — Erica Nicole Jones-Foster
(74) *Attorney, Agent, or Firm* — ArentFox Schiff LLP; Daniel W. Clarke

(57) ABSTRACT

Described herein are compositions and methods for modulating protein abundance in a target-specific manner via degron tags.

27 Claims, 59 Drawing Sheets
Specification includes a Sequence Listing.

Tasisulam (3)

Indisulam (2)

E7820 (1)

| | | |
|---|---|---|
| RBM39_RRM2 | 250 | MRLYVGSLHFNITEDMLRGIFEPFGRIESIQLMVDSETGRSKGYGFITFSDSECAKKALE |
| RBM23_RRM2 | 263 | MRLYVGSLHFNITEDMLRGIFEPFCKIDNIVLMKDSDTGRSKGYGFITFSDSECARRALE |

| | | |
|---|---|---|
| RBM39_RRM2 | 310 | QLNGFELAGRPMKVGHVTE (SEQ ID NO: 18) |
| RBM23_RRM2 | 323 | QLNGFELAGRPMRVGHVTE (SEQ ID NO: 19) |

DCAF15-E7820-RBM39$_{RRM2}$

CRBN-lenalidomide-CK1α

Conservation high — low

| Compound | EC$_{50}$ [µM] |
|---|---|
| E7820 | 0.74 |
| Indisulam | 3.24 |
| Tasisulam | >10 |

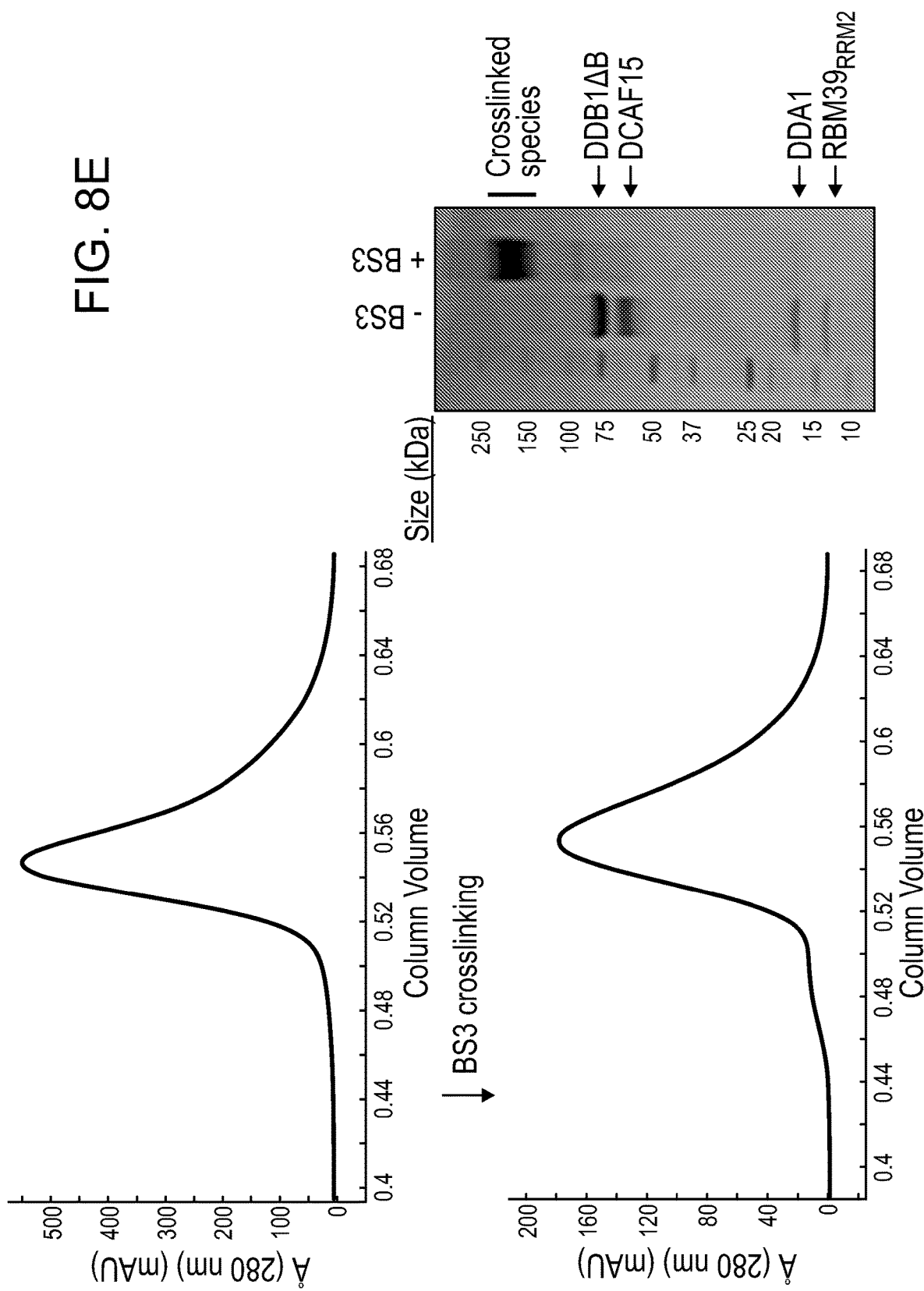

RBM39 interacting residues

E7820 interacting residues

Iodide-E7820 (5)

DCAF15-NTD          DCAF15-CTD

| Compound | $K_2$ [μM] |
|---|---|
| E7820 (1) | 1.56 |
| Iodide-E7820 (5) | 2.17 |

Diazirine-E7820 (6)

| Compound | IC$_{50}$ [µM] |
|---|---|
| E7820 (1) | 6.97 |
| Indisulam (2) | >50 |
| Desmethyl-E7820 (7) | >50 |

| RBM39 residue | Resistance mutation |
|---|---|
| M265 | L |
| G268 | V, W, R, E |
| E271 | Q, G |
| P272 | S |

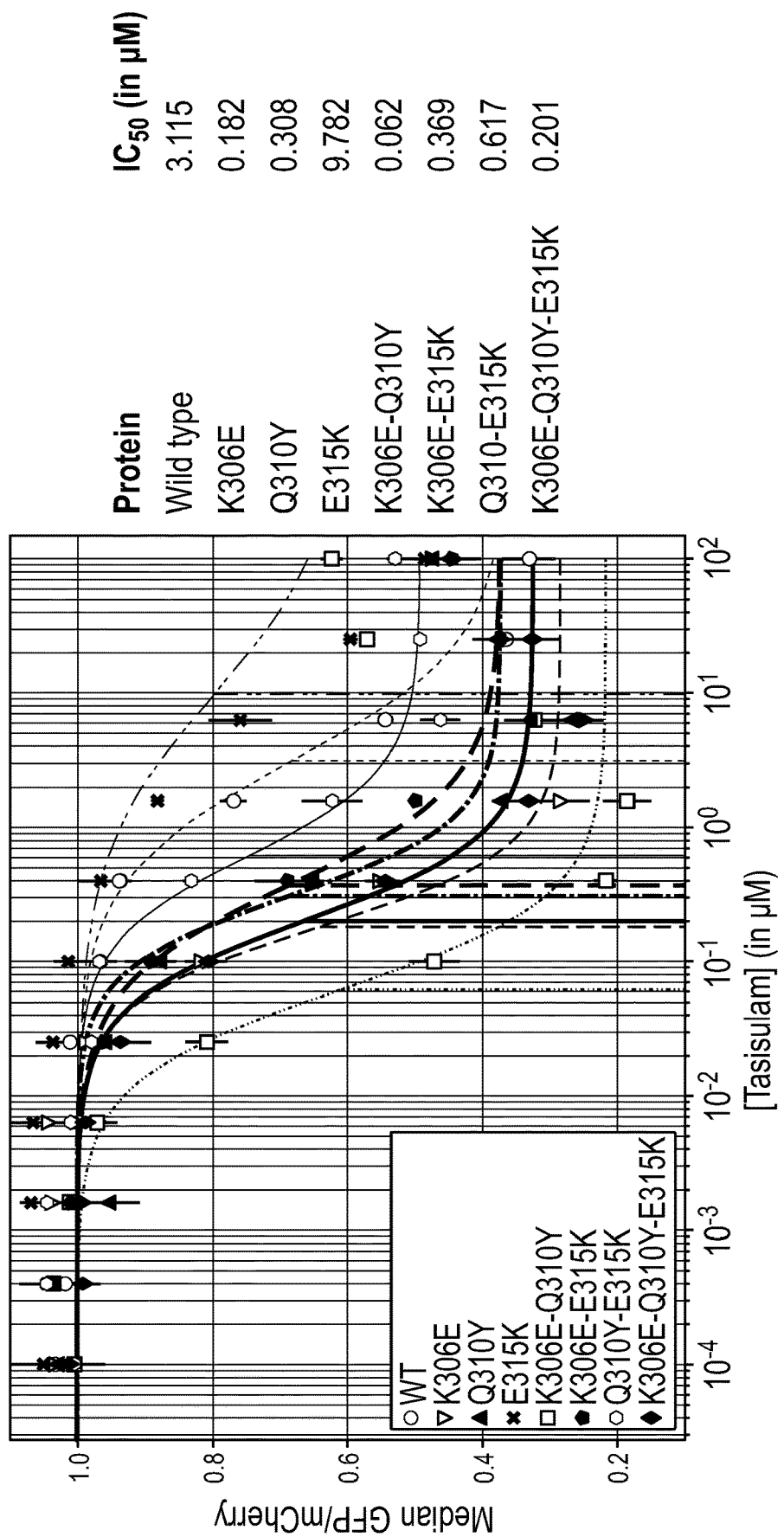

SEQUENCE LISTING

```
<160> NUMBER OF SEQ ID NOS: 21

<210> SEQ ID NO 1
<211> LENGTH: 530
<212> TYPE: PRT
<213> ORGANISM: Homo sapiens

<400> SEQUENCE: 1

Met Ala Asp Asp Ile Asp Ile Glu Ala Met Leu Glu Ala Pro Tyr Lys
1               5                   10                  15

Lys Asp Glu Asn Lys Leu Ser Ser Ala Asn Gly His Glu Glu Arg Ser
            20                  25                  30

Lys Lys Arg Lys Lys Ser Lys Ser Arg Ser Arg Ser His Glu Arg Lys
        35                  40                  45

Arg Ser Lys Ser Lys Glu Arg Lys Arg Ser Arg Asp Arg Glu Arg Lys
    50                  55                  60

Lys Ser Lys Ser Arg Glu Arg Lys Arg Ser Arg Ser Lys Glu Arg Arg
65                  70                  75                  80

Arg Ser Arg Ser Arg Ser Arg Asp Arg Arg Phe Arg Gly Arg Tyr Arg
```

```
                    85                  90                  95
Ser Pro Tyr Ser Gly Pro Lys Phe Asn Ser Ala Ile Arg Gly Lys Ile
                100                 105                 110
Gly Leu Pro His Ser Ile Lys Leu Ser Arg Arg Ser Arg Ser Lys
            115                 120                 125
Ser Pro Phe Arg Lys Asp Lys Ser Pro Val Arg Glu Pro Ile Asp Asn
130                 135                 140
Leu Thr Pro Glu Glu Arg Asp Ala Arg Thr Val Phe Cys Met Gln Leu
145                 150                 155                 160
Ala Ala Arg Ile Arg Pro Arg Asp Leu Glu Glu Phe Phe Ser Thr Val
                165                 170                 175
Gly Lys Val Arg Asp Val Arg Met Ile Ser Asp Arg Asn Ser Arg Arg
                180                 185                 190
Ser Lys Gly Ile Ala Tyr Val Glu Phe Val Asp Val Ser Ser Val Pro
                195                 200                 205
Leu Ala Ile Gly Leu Thr Gly Gln Arg Val Leu Gly Val Pro Ile Ile
            210                 215                 220
Val Gln Ala Ser Gln Ala Glu Lys Asn Arg Ala Ala Met Ala Asn
225                 230                 235                 240
Asn Leu Gln Lys Gly Ser Ala Gly Pro Met Arg Leu Tyr Val Gly Ser
                245                 250                 255
Leu His Phe Asn Ile Thr Glu Asp Met Leu Arg Gly Ile Phe Glu Pro
            260                 265                 270
Phe Gly Arg Ile Glu Ser Ile Gln Leu Met Met Asp Ser Glu Thr Gly
        275                 280                 285
Arg Ser Lys Gly Tyr Gly Phe Ile Thr Phe Ser Asp Ser Glu Cys Ala
        290                 295                 300
Lys Lys Ala Leu Glu Gln Leu Asn Gly Phe Glu Leu Ala Gly Arg Pro
305                 310                 315                 320
Met Lys Val Gly His Val Thr Glu Arg Thr Asp Ala Ser Ser Ala Ser
                325                 330                 335
Ser Phe Leu Asp Ser Asp Glu Leu Glu Arg Thr Gly Ile Asp Leu Gly
            340                 345                 350
Thr Thr Gly Arg Leu Gln Leu Met Ala Arg Leu Ala Glu Gly Thr Gly
            355                 360                 365
Leu Gln Ile Pro Pro Ala Ala Gln Gln Ala Leu Gln Met Ser Gly Ser
        370                 375                 380
Leu Ala Phe Gly Ala Val Ala Glu Phe Ser Phe Val Ile Asp Leu Gln
385                 390                 395                 400
Thr Arg Leu Ser Gln Gln Thr Glu Ala Ser Ala Leu Ala Ala Ala
                405                 410                 415
Ser Val Gln Pro Leu Ala Thr Gln Cys Phe Gln Leu Ser Asn Met Phe
            420                 425                 430
Asn Pro Gln Thr Glu Glu Val Gly Trp Asp Thr Glu Ile Lys Asp
            435                 440                 445
Asp Val Ile Glu Glu Cys Asn Lys His Gly Gly Val Ile His Ile Tyr
        450                 455                 460
Val Asp Lys Asn Ser Ala Gln Gly Asn Val Tyr Val Lys Cys Pro Ser
465                 470                 475                 480
Ile Ala Ala Ala Ile Ala Ala Val Asn Ala Leu His Gly Arg Trp Phe
                485                 490                 495
Ala Gly Lys Met Ile Thr Ala Ala Tyr Val Pro Leu Pro Thr Tyr His
            500                 505                 510
```

Asn Leu Phe Pro Asp Ser Met Thr Ala Thr Gln Leu Leu Val Pro Ser
        515                 520                 525

Arg Arg
    530

<210> SEQ ID NO 2
<211> LENGTH: 5060
<212> TYPE: DNA
<213> ORGANISM: Homo sapiens

<400> SEQUENCE: 2

| | | | | | |
|---|---|---|---|---|---|
| atgtgtgctg | gtgaatgtga | gtacagggaa | gcagcggccg | ccatttcagg | gagcttgtcg | 60 |
| acgctgtcgc | agggtggat | cctgagctgc | cgaagccgcc | gtcctgctct | cccgcgtggg | 120 |
| cttctctaat | tccattgttt | tttttagatt | ctctcgggcc | tagccgtcct | tggaacccga | 180 |
| tattcgggct | gggcggttcc | gcggcctggg | cctaggggct | taacagtagc | aacagaagcg | 240 |
| gcggcggcgg | cagcagcagc | agcagcagca | gcaatctctt | cccgaacacg | agcaccacag | 300 |
| gcgcccgaag | gccggaacag | gcgtttagag | aaaatggcag | acgatattga | tattgaagca | 360 |
| atgcttgagg | ctccttacaa | gaaggatgag | aacaagttga | gcagtgccaa | cggccatgaa | 420 |
| gaacgtagca | aaagaggaa | aaaagcaag | agcagaagtc | gtagtcatga | acgaaagaga | 480 |
| agcaaaagta | aggaacggaa | gcgaagtaga | gacagagaaa | ggaaaaagag | caaaagccgt | 540 |
| gaaagaaagc | gaagtagaag | caaagagagg | cgacggagcc | gctcaagaag | tcgagatcga | 600 |
| agatttagag | gccgctacag | aagtccttac | tccggaccaa | aatttaacag | tgccatccga | 660 |
| ggaaagattg | ggttgcctca | tagcatcaaa | ttaagcagac | gacgttcccg | aagcaaaagt | 720 |
| ccattcagaa | aagacaagag | ccctgtgaga | gaacctattg | ataattaac | tcctgaggaa | 780 |
| agagatgcaa | ggacagtctt | ctgtatgcag | ctggcggcaa | gaattcgacc | aagggatttg | 840 |
| gaagagttttt | tctctacagt | aggaaaggtt | cgagatgtga | ggatgatttc | tgacagaaat | 900 |
| tcaagacgtt | ccaaaggaat | tgcttatgtg | gagttcgtcg | atgttagctc | agtgcctcta | 960 |
| gcaataggat | taactggcca | acgagtttta | ggcgtgccaa | tcatagtaca | ggcatcacag | 1020 |
| gcagaaaaaa | acagagctgc | agcaatggca | aacaatttac | aaaagggaag | tgctggacct | 1080 |
| atgaggcttt | atgtgggctc | attcacttc | aacataactg | aagatatgct | tcgtgggatc | 1140 |
| tttgagcctt | ttggaagaat | tgaaagtatc | cagctgatga | tggacagtga | aactggtcga | 1200 |
| tccaagggat | atggatttat | tacatttttct | gactcagaat | gtgccaaaaa | ggctttggaa | 1260 |
| caacttaatg | gatttgaact | agcaggaaga | ccaatgaaag | ttggtcatgt | tactgaacgt | 1320 |
| actgatgctt | cgagtgctag | ttcatttttg | gacagtgatg | aactggaaag | gactggaatt | 1380 |
| gatttgggaa | caactggtcg | tcttcagtta | atggcaagac | ttgcagaggg | tacaggtttg | 1440 |
| cagattccgc | cagcagcaca | gcaagctcta | cagatgagtg | gctctttggc | atttggtgct | 1500 |
| gtggcagaat | tctctttttgt | tatagatttg | caaacaagac | tttcccagca | gactgaagct | 1560 |
| tcagctttag | ctgcagctgc | ctctgttcag | ccacttgcaa | cacaatgttt | ccaactctct | 1620 |
| aacatgtttta | accctcaaac | agaagaagaa | gttggatggg | ataccgagat | taaggatgat | 1680 |
| gtgattgaag | aatgtaataa | acatggagga | gttattcata | tttatgttga | caaaaattca | 1740 |
| gctcagggca | atgtgtatgt | gaagtgccca | tcaattgctg | cagctattgc | tgctgtcaat | 1800 |
| gcattgcatg | gcaggtggtt | tgctggtaaa | atgataacag | cagcatatgt | acctcttcca | 1860 |
| acttaccaca | acctgtttcc | tgattctatg | acagcaacac | agctactggt | tccaagtaga | 1920 |

-continued

```
cgatgaagga agatatagtc ccttatgtat atagcttttt ttctttcttg agaattcatc    1980
ttgagttatc ttttatttag ataaaaataa agaggcaagg atctactgtc atttgtatgc    2040
aatttcctgt taccttgaaa aaataaaaat gttaacagga atgcagtgtg ctcattctcc    2100
ctaaatagta aatcccactg tatacaaaac tgttctcttg ttctgccttt taaaatgttc    2160
atgtagaaaa ttaatgaact ataggaatag ctctaggaga acaaatgtgc tttctgtaaa    2220
aaggcagacc agggatgtaa tgttttaat  gtttcagaag cctaactttt tacacagtgg    2280
ttacatttca catttcacta atgttgatat ttggctgatg gttgagcagt ttctgaaata    2340
cacatttagt gtatggaaat acaagacagc taaagggctg tttggttagc atctcatctt    2400
gcattctgat caattggcaa gaaagggaga tttcaaaatt atatttcttg atggtatctt    2460
ttcaattaat gtatctgtaa aagtttcttt gtaaatacta tgtgttctgg tgtgtcttaa    2520
aattccaaac aaaatgatcc ctgcatttcc tgaagatgtt taaacgtgag agtctggtag    2580
gcaaagcagt ctgagaaaga aataggaaat gcagaaatag gttttgtctg gttgcatata    2640
atctttgctc tttttaagct ctgtgagctc tgaaatatat ttttgggtta cttcagtgtg    2700
tttgacaaga cagcttgata tttctatcaa acaaatgact ttcatattgc aacaatcttt    2760
gtaagaacca ctcaaataaa agtctcttaa aaaggccaca ggagatcttc attttttcaaa   2820
tgttttaaag ttacagaaat ttgagaacag aattagcttc ttttagtctc aattcagtac    2880
ttgcctcttg ggaaaatgtt ccgagtctgc ggaaacttgc cctcacgttg tcccccatga    2940
attcctttat tctattagag tctagccctg tgtattttag aagaatgtat caaaactgag    3000
gggtttacca aaaagaaaag gaaacagcct ggccttaaaa cctgggcatt cttggtctcc    3060
tgcattgtct gggcatattt atgaagaaat tttcaccatt tacaatacat acttaacaaa    3120
atggcttaac ttcaaactgg tttccaaaat tgatttatat attaatatat taaataaggt    3180
gcatatatta ctgtattaag gggttttgag ctttcatact agttgggaag caagctgtca    3240
ccatttatac tcaattctct tcaactgttt atctcttggt aaatcttttg agtaggaaat    3300
gctgctccta gcttatcttc aaatactgag ttccttacct catttgttca acttttttt    3360
ttgttagcat tgaagcacaa gttttacagg cttattcaga atttcatatc agtcgttttg    3420
tttgacattt atcccaataa ttgttctagt gatttaattt gtatggaaac tcccaaggtt    3480
caatttcttt ttcttttga gatggagtct tgctctttgg cccaggctgg agtgcagtga    3540
tgtgatctca gctccatctc ccaggttcaa gcaattctcc cacctcagtc tcctgaagag    3600
ctgggacagg tgcgcaccac cgtgcccagc taattttttgt attttttagca gagacggtgt    3660
tagcccggct ggtctcacac tgacctcaag tgatctgtcc gccttggcct cccaaagtgc    3720
cgggattaca ggcatgagcc accgcgccca gcctcattga aaatttacttt ttcaatacca    3780
gactgcagag ttctttgggg cagagacact ctgtcagtgt gctcttttttc caaagtatct    3840
cctgctatca gttttttcccc ttgaaccaag tcttcctaac aaatttgttg tgtcattgct    3900
ttctagggaa ctggaccagc aaatgtggcc tttagtggtt aatctcatct gtgccaaaat    3960
ttagttgcta ccagagtgaa atttggtgtg taaataatgt tcagaggaaa tgtggttgga    4020
gtgtagtaac ttgaatagtg tcgtgcatag aaaacagctc attctgagtg aaactgttta    4080
tgtccaatca gttcctgagt cagcatccca ctggttcgaa aatctgtaac taatctggta    4140
atgtccttaa tttcctcctg cctgtcagtg ttccaaagtg ttcatctagt tttcttttat    4200
ctttataata attactacca tctttgaaag ttctgtttaa gaaatgctta atgggcaatg    4260
cgggttagta actccagggt ctgcgtggcc tgggcaggtg agatggacaa ctgcctcatt    4320
```

```
acagaagctt tttatcatca aactagtaag ttttgtggag ggcaagctat atagattgtt    4380
gatgagtggt tagaaaatca tctggaattt agccagttga gaagctacag aagtttctat    4440
ttttttttac agtggatgaa ctgttttgct ttttctgata aagccactag gtatatctaa    4500
ataacaacct cgggctggac gtggtgcctt atgcctgtat atgtgaacac tgggaggcgg    4560
aggcgggtgg atcatgaggt caagagtttg agaccagcct ggccaacaca gtgaaacccc    4620
gtctctacta agaatacaaa ttttttttgt tttgagacag agtctcgctc tgtcgcccag    4680
gctggagtgc aatggctcga tctcagctca ctgcaacctc caccttctgg gttcaagcga    4740
ttctcctgcc tcagcctccc gagtagctgg gaatacaggc gcgtgtcaac acacccggct    4800 taagttttg tatttttagt agagacgggg tgtcaccgtg ttacccaaga tggtctccat    4860
ctcctgacct tgtgatccac cagcctttgc ctcccaaagt gctgggatta caggcataag    4920
ccaccgcgcc cagcctaaca atacaaaatt tagctaggca tggtggcacg tgcctgttat    4980
cacagctact cgggaggctg aggcaggaga aacgcttgaa cacaggaggc agaagttgcg    5040
gtaagccgag atcgtgccac                                                5060
```

<210> SEQ ID NO 3
<211> LENGTH: 524
<212> TYPE: PRT
<213> ORGANISM: Homo sapiens

<400> SEQUENCE: 3

```
Met Ala Asp Asp Ile Asp Ile Glu Ala Met Leu Glu Ala Pro Tyr Lys
1               5                   10                  15

Lys Asp Glu Asn Lys Leu Ser Ser Ala Asn Gly His Glu Glu Arg Ser
            20                  25                  30

Lys Lys Arg Lys Lys Ser Lys Ser Arg Ser Arg Ser His Glu Arg Lys
        35                  40                  45

Arg Ser Lys Ser Lys Glu Arg Lys Arg Ser Arg Asp Arg Glu Arg Lys
    50                  55                  60

Lys Ser Lys Ser Arg Glu Arg Lys Arg Ser Arg Ser Lys Glu Arg Arg
65                  70                  75                  80

Arg Ser Arg Ser Arg Ser Arg Asp Arg Arg Phe Arg Gly Arg Tyr Arg
                85                  90                  95

Ser Pro Tyr Ser Gly Pro Lys Phe Asn Ser Ala Ile Arg Gly Lys Ile
            100                 105                 110

Gly Leu Pro His Ser Ile Lys Leu Ser Arg Arg Arg Ser Arg Ser Lys
        115                 120                 125

Ser Pro Phe Arg Lys Asp Lys Ser Pro Val Arg Glu Pro Ile Asp Asn
    130                 135                 140

Leu Thr Pro Glu Glu Arg Asp Ala Arg Thr Val Phe Cys Met Gln Leu
145                 150                 155                 160

Ala Ala Arg Ile Arg Pro Arg Asp Leu Glu Glu Phe Phe Ser Thr Val
                165                 170                 175

Gly Lys Val Arg Asp Val Arg Met Ile Ser Asp Arg Asn Ser Arg Arg
            180                 185                 190

Ser Lys Gly Ile Ala Tyr Val Glu Phe Val Asp Val Ser Ser Val Pro
        195                 200                 205

Leu Ala Ile Gly Leu Thr Gly Gln Arg Val Leu Gly Val Pro Ile Ile
    210                 215                 220

Val Gln Ala Ser Gln Ala Glu Lys Asn Arg Ala Ala Ala Met Ala Asn
225                 230                 235                 240
```

```
Asn Leu Gln Lys Gly Ser Ala Gly Pro Met Arg Leu Tyr Val Gly Ser
                245                 250                 255

Leu His Phe Asn Ile Thr Glu Asp Met Leu Arg Gly Ile Phe Glu Pro
                260                 265                 270

Phe Gly Arg Ile Glu Ser Ile Gln Leu Met Met Asp Ser Glu Thr Gly
                275                 280                 285

Arg Ser Lys Gly Tyr Gly Phe Ile Thr Phe Ser Asp Ser Glu Cys Ala
                290                 295                 300

Lys Lys Ala Leu Glu Gln Leu Asn Gly Phe Glu Leu Ala Gly Arg Pro
305                 310                 315                 320

Met Lys Val Gly His Val Thr Glu Arg Thr Asp Ala Ser Ala Ser
                325                 330                 335

Ser Phe Leu Asp Ser Asp Glu Leu Glu Arg Thr Gly Ile Asp Leu Gly
                340                 345                 350

Thr Thr Gly Arg Leu Gln Leu Met Ala Arg Leu Ala Glu Gly Thr Gly
                355                 360                 365

Leu Gln Ile Pro Pro Ala Ala Gln Ala Leu Gln Met Ser Gly Ser
                370                 375                 380

Leu Ala Phe Gly Ala Val Ala Asp Leu Gln Thr Arg Leu Ser Gln Gln
385                 390                 395                 400

Thr Glu Ala Ser Ala Leu Ala Ala Ala Ser Val Gln Pro Leu Ala
                405                 410                 415

Thr Gln Cys Phe Gln Leu Ser Asn Met Phe Asn Pro Gln Thr Glu Glu
                420                 425                 430

Glu Val Gly Trp Asp Thr Glu Ile Lys Asp Asp Val Ile Glu Glu Cys
                435                 440                 445

Asn Lys His Gly Gly Val Ile His Ile Tyr Val Asp Lys Asn Ser Ala
                450                 455                 460

Gln Gly Asn Val Tyr Val Lys Cys Pro Ser Ile Ala Ala Ile Ala
465                 470                 475                 480

Ala Val Asn Ala Leu His Gly Arg Trp Phe Ala Gly Lys Met Ile Thr
                485                 490                 495

Ala Ala Tyr Val Pro Leu Pro Thr Tyr His Asn Leu Phe Pro Asp Ser
                500                 505                 510

Met Thr Ala Thr Gln Leu Leu Val Pro Ser Arg Arg
                515                 520

<210> SEQ ID NO 4
<211> LENGTH: 5042
<212> TYPE: DNA
<213> ORGANISM: Homo sapiens

<400> SEQUENCE: 4
atgtgtgctg gtgaatgtga gtacagggaa gcagcggccg ccatttcagg gagcttgtcg      60
acgctgtcgc aggggtggat cctgagctgc cgaagccgcc gtcctgctct cccgcgtggg     120
cttctctaat tccattgttt tttttagatt ctctcgggcc tagccgtcct ggaacccga     180 tattcgggct gggcggttcc gcggcctggg cctaggggct taacagtagc aacagaagcg     240
gcggcggcgg cagcagcagc agcagcagca gcaatctctt cccgaacacg agcaccacag     300
gcgcccgaag gccggaacag gcgtttagag aaaatggcag acgatattga tattgaagca     360
atgcttgagg ctccttacaa gaaggatgag aacaagttga gcagtgccaa cggccatgaa     420
gaacgtagca aaaagaggaa aaaaagcaag agcagaagtc gtagtcatga cgaaagaga     480
```

```
agcaaaagta aggaacggaa gcgaagtaga gacagagaaa ggaaaaagag caaaagccgt    540
gaaagaaagc gaagtagaag caaagagagg cgacggagcc gctcaagaag tcgagatcga    600
agatttagag gccgctacag aagtccttac tccggaccaa aatttaacag tgccatccga    660
ggaaagattg ggttgcctca tagcatcaaa ttaagcagac gacgttcccg aagcaaaagt    720
ccattcagaa aagacaagag ccctgtgaga gaacctattg ataatttaac tcctgaggaa    780
agagatgcaa ggacagtctt ctgtatgcag ctggcggcaa gaattcgacc aagggatttg    840
gaagagtttt tctctacagt aggaaaggtt cgagatgtga ggatgatttc tgacagaaat    900
tcaagacgtt ccaaaggaat tgcttatgtg gagttcgtcg atgttagctc agtgcctcta    960
gcaataggat taactggcca acgagtttta ggcgtgccaa tcatagtaca ggcatcacag   1020
gcagaaaaaa acagagctgc agcaatggca acaatttac aaaagggaag tgctggacct   1080
atgaggcttt atgtgggctc attacacttc aacataactg aagatatgct tcgtgggatc   1140
tttgagcctt ttggaagaat tgaaagtatc cagctgatga tggacagtga aactggtcga   1200
tccaagggat atggatttat tacatttttct gactcagaat gtgccaaaaa ggctttggaa   1260
caacttaatg gatttgaact agcaggaaga ccaatgaaag ttggtcatgt tactgaacgt   1320
actgatgctt cgagtgctag ttcattttttg gacagtgatg aactggaaag gactggaatt   1380
gatttgggaa caactggtcg tcttcagtta atggcaagac ttgcagaggg tacaggtttg   1440
cagattccgc cagcagcaca gcaagctcta cagatgagtg gctctttggc atttggtgct   1500
gtggcagatt tgcaaacaag actttcccag cagactgaag cttcagcttt agctgcagct   1560
gcctctgttc agccacttgc aacacaatgt ttccaactct ctaacatgtt taaccctcaa   1620
acagaagaag aagttggatg ggataccgag attaaggatg atgtgattga agaatgtaat   1680
aaacatggag gagttattca tatttatgtt gacaaaaatt cagctcaggg caatgtgtat   1740
gtgaagtgcc catcaattgc tgcagctatt gctgctgtca atgcattgca tggcaggtgg   1800
tttgctggta aaatgataac agcagcatat gtacctcttc caacttacca caacctgttt   1860
cctgattcta tgacagcaac acagctactg gttccaagta gacgatgaag gaagatatag   1920
tcccttatgt atatagcttt ttttcttttct tgagaattca tcttgagtta tcttttattt   1980
agataaaaat aaagaggcaa ggatctactg tcatttgtat gcaatttcct gttaccttga   2040
aaaaataaaa atgttaacag gaatgcagtg tgctcattct ccctaaatag taaatcccac   2100
tgtatacaaa actgttctct tgttctgcct tttaaaatgt tcatgtagaa aattaatgaa   2160
ctataggaat agctctagga gaacaaatgt gctttctgta aaaaggcaga ccagggatgt   2220
aatgttttta atgtttcaga agcctaactt tttacacagt ggttacattt cacatttcac   2280
taatgttgat atttggctga tggttgagca gtttctgaaa tacacattta gtgtatggaa   2340
atacaagaca gctaaagggc tgtttggtta gcatctcatc ttgcattctg atcaattggc   2400
aagaaaggga gatttcaaaa ttatatttct tgatggtatc ttttcaatta atgtatctgt   2460
aaaagtttct ttgtaaatac tatgtgttct ggtgtgtctt aaaattccaa acaaaatgat   2520
ccctgcattt cctgaagatg tttaaacgtg agagtctggt aggcaaagca gtctgagaaa   2580
gaaataggaa atgcagaaat aggttttgtc tggttcata taatctttgc tcttttttaag   2640 ctctgtgagc tctgaaatat attttttgggt tacttcagtg tgtttgacaa gacagcttga   2700
tatttctatc aaacaaatga ctttcatatt gcaacaatct ttgtaagaac cactcaaata   2760
aaagtctctt aaaaaggcca caggagatct tcatttttca aatgttttaa agttacagaa   2820
atttgagaac agaattagct tcttttagtc tcaattcagt acttgcctct tgggaaaatg   2880
```

```
ttccgagtct gcggaaactt gccctcacgt tgtcccccat gaattccttt attctattag   2940
agtctagccc tgtgtatttt agaagaatgt atcaaaactg aggggtttac caaaaagaaa   3000
aggaaacagc ctggccttaa aacctgggca ttcttggtct cctgcattgt ctgggcatat   3060
ttatgaagaa atttcacca tttacaatac atacttaaca aaatggctta acttcaaact   3120
ggtttccaaa attgatttat atattaatat attaaataag gtgcatatat tactgtatta   3180
aggggttttg agctttcata ctagttggga agcaagctgt caccatttat actcaattct   3240
cttcaactgt ttatctcttg gtaaatcttt tgagtaggaa atgctgctcc tagcttatct   3300
tcaaatactg agttccttac ctcatttgtt caacttttt ttttgttagc attgaagcac   3360
aagtttaca ggcttattca gaatttcata tcagtcgttt tgtttgacat ttatcccaat   3420
aattgttcta gtgatttaat ttgtatggaa actcccaagg ttcaatttct ttttctttt   3480
gagatggagt cttgctcttt ggcccaggct ggagtgcagt gatgtgatct cagctccatc   3540
tcccaggttc aagcaattct cccacctcag tctcctgaag agctgggaca ggtgcgcacc   3600
accgtgccca gctaatttt tgtatttag cagagacggt gttagcccgg ctggtctcac   3660
actgacctca gtgatctgt ccgccttggc ctcccaaagt gccgggatta caggcatgag   3720
ccaccgcgcc cagcctcatt gaaaattac tttcaatac cagactgcag agttctttgg   3780
ggcagagaca ctctgtcagt gtgctctttt tccaaagtat ctcctgctat cagttttttcc   3840
ccttgaacca agtcttccta acaaatttgt tgtgtcattg ctttctaggg aactggacca   3900
gcaaatgtgg cctttagtgg ttaatctcat ctgtgccaaa atttagttgc taccagagtg   3960
aaatttggtg tgtaaataat gttcagagga atgtggttg gagtgtagta acttgaatag    4020
tgtcgtgcat agaaaacagc tcattctgag tgaaactgtt tatgtccaat cagttcctga   4080
gtcagcatcc cactggttcg aaaatctgta actaatctgg taatgtcctt aatttcctcc   4140
tgcctgtcag tgttccaaag tgttcatcta gttttctttt atctttataa taattactac   4200
catctttgaa agttctgttt aagaaatgct taatgggcaa tgcgggttag taactccagg   4260
gtctgcgtgg cctgggcagg tgagatggac aactgcctca ttacagaagc ttttttatcat   4320
caaactagta agttttgtgg agggcaagct atatagattg ttgatgagtg gttagaaaat   4380
catctggaat ttagccagtt gagaagctac agaagtttct atttttttt acagtggatg   4440
aactgtttttg cttttctga taaagccact aggtatatct aaataacaac ctcgggctgg   4500
acgtggtgcc ttatgcctgt atatgtgaac actgggaggc ggaggcgggt ggatcatgag   4560
gtcaagagtt tgagaccagc ctggccaaca cagtgaaacc ccgtctctac taagaataca   4620
aatttttttt gttttgagac agagtctcgc tctgtcgccc aggctggagt gcaatggctc   4680
gatctcagct cactgcaacc tccaccttct gggttcaagc gattctcctg cctcagcctc   4740
ccgagtagct gggaatacag gcgcgtgtca acacacccgg cttaagtttt tgtattttta   4800
gtagagacgg ggtgtcaccg tgttacccaa gatggtctcc atctcctgac cttgtgatcc   4860
accagccttt gcctcccaaa gtgctgggat tacaggcata agccaccgcg cccagcctaa   4920
caatacaaaa tttagctagg catggtggca cgtgcctgtt atcacagcta ctcgggaggc   4980
tgaggcagga gaaacgcttg aacacaggag gcagaagttg cggtaagccg agatcgtgcc   5040
ac                                                                  5042
```

<210> SEQ ID NO 5
<211> LENGTH: 508
<212> TYPE: PRT

<213> ORGANISM: Homo sapiens

<400> SEQUENCE: 5

```
Met Ala Asp Asp Ile Asp Ile Glu Ala Met Leu Glu Ala Pro Tyr Lys
1               5                   10                  15
Lys Asp Glu Asn Lys Leu Ser Ser Ala Asn Gly His Glu Glu Arg Ser
            20                  25                  30
Lys Lys Arg Lys Lys Ser Lys Ser Arg Ser Arg Ser His Glu Arg Lys
        35                  40                  45
Arg Ser Lys Ser Lys Glu Arg Lys Arg Ser Asp Arg Glu Arg Lys
    50                  55                  60
Lys Ser Lys Ser Arg Glu Arg Lys Arg Ser Ser Lys Glu Arg Arg
65                  70                  75                  80
Arg Ser Arg Ser Arg Ser Arg Asp Arg Arg Phe Arg Gly Arg Tyr Arg
                85                  90                  95
Ser Pro Tyr Arg Arg Arg Ser Arg Ser Lys Ser Pro Phe Arg Lys Asp
            100                 105                 110
Lys Ser Pro Val Arg Glu Pro Ile Asp Asn Leu Thr Pro Glu Glu Arg
        115                 120                 125
Asp Ala Arg Thr Val Phe Cys Met Gln Leu Ala Ala Arg Ile Arg Pro
130                 135                 140
Arg Asp Leu Glu Glu Phe Phe Ser Thr Val Gly Lys Val Arg Asp Val
145                 150                 155                 160
Arg Met Ile Ser Asp Arg Asn Ser Arg Arg Ser Lys Gly Ile Ala Tyr
                165                 170                 175
Val Glu Phe Val Asp Val Ser Ser Val Pro Leu Ala Ile Gly Leu Thr
            180                 185                 190
Gly Gln Arg Val Leu Gly Val Pro Ile Ile Val Gln Ala Ser Gln Ala
        195                 200                 205
Glu Lys Asn Arg Ala Ala Ala Met Ala Asn Asn Leu Gln Lys Gly Ser
210                 215                 220
Ala Gly Pro Met Arg Leu Tyr Val Gly Ser Leu His Phe Asn Ile Thr
225                 230                 235                 240
Glu Asp Met Leu Arg Gly Ile Phe Glu Pro Phe Gly Arg Ile Glu Ser
                245                 250                 255
Ile Gln Leu Met Met Asp Ser Glu Thr Gly Arg Ser Lys Gly Tyr Gly
            260                 265                 270
Phe Ile Thr Phe Ser Asp Ser Glu Cys Ala Lys Lys Ala Leu Glu Gln
        275                 280                 285
Leu Asn Gly Phe Glu Leu Ala Gly Arg Pro Met Lys Val Gly His Val
290                 295                 300
Thr Glu Arg Thr Asp Ala Ser Ser Ala Ser Ser Phe Leu Asp Ser Asp
305                 310                 315                 320
Glu Leu Glu Arg Thr Gly Ile Asp Leu Gly Thr Thr Gly Arg Leu Gln
                325                 330                 335
Leu Met Ala Arg Leu Ala Glu Gly Thr Gly Leu Gln Ile Pro Pro Ala
            340                 345                 350
Ala Gln Gln Ala Leu Gln Met Ser Gly Ser Leu Ala Phe Gly Ala Val
        355                 360                 365
Ala Glu Phe Ser Phe Val Ile Asp Leu Gln Thr Arg Leu Ser Gln Gln
370                 375                 380
Thr Glu Ala Ser Ala Leu Ala Ala Ala Ser Val Gln Pro Leu Ala
385                 390                 395                 400
```

```
Thr Gln Cys Phe Gln Leu Ser Asn Met Phe Asn Pro Gln Thr Glu Glu
                405                 410                 415

Glu Val Gly Trp Asp Thr Glu Ile Lys Asp Asp Val Ile Glu Glu Cys
            420                 425                 430

Asn Lys His Gly Gly Val Ile His Ile Tyr Val Asp Lys Asn Ser Ala
        435                 440                 445

Gln Gly Asn Val Tyr Val Lys Cys Pro Ser Ile Ala Ala Ile Ala
    450                 455                 460

Ala Val Asn Ala Leu His Gly Arg Trp Phe Ala Gly Lys Met Ile Thr
465                 470                 475                 480

Ala Ala Tyr Val Pro Leu Pro Thr Tyr His Asn Leu Phe Pro Asp Ser
                485                 490                 495

Met Thr Ala Thr Gln Leu Leu Val Pro Ser Arg Arg
                500                 505

<210> SEQ ID NO 6
<211> LENGTH: 4994
<212> TYPE: DNA
<213> ORGANISM: Homo sapiens

<400> SEQUENCE: 6
atgtgtgctg gtgaatgtga gtacagggaa gcagcggccg ccatttcagg gagcttgtcg      60
acgctgtcgc aggggtggat cctgagctgc gaagccgcc gtcctgctct cccgcgtggg     120
cttctctaat tccattgttt tttttagatt ctctcgggcc tagccgtcct tggaacccga     180
tattcgggct gggcggttcc gcggcctggg cctaggggct taacagtagc aacagaagcg     240
gcggcggcgg cagcagcagc agcagcagca gcaatctctt cccgaacacg agcaccacag     300
gcgcccgaag gccggaacag gcgtttagag aaaatggcag acgatattga tattgaagca     360
atgcttgagg ctccttacaa gaaggatgag aacaagttga gcagtgccaa cggccatgaa     420
gaacgtagca aaagaggaa aaaagcaag agcagaagtc gtagtcatga acgaaagaga     480
agcaaaagta aggaacggaa gcgaagtaga gacagagaaa ggaaaaagag caaaagccgt     540
gaaagaaagc gaagtagaag caaagagagg cgacggagcc gctcaagaag tcgagatcga     600
agatttagag gccgctacag aagtccttac agacgacgtt cccgaagcaa aagtccattc     660
agaaaagaca gagccctgt gagagaacct attgataatt taactcctga ggaaagagat     720
gcaaggacag tcttctgtat gcagctggcg gcaagaattc gaccaaggga tttggaagag     780
tttttctcta cagtaggaaa ggttcgagat gtgaggatga tttctgacag aaattcaaga     840
cgttccaaag gaattgctta tgtggagttc gtcgatgtta gctcagtgcc ctagcaata     900 ggattaactg gccaacgagt tttaggcgtg ccaatcatag tacaggcatc acaggcagaa     960
aaaaacagag ctgcagcaat ggcaaacaat ttacaaaagg gaagtgctgg acctatgagg    1020
ctttatgtgg gctcattaca cttcaacata actgaagata tgcttcgtgg gatctttgag    1080
ccttttggaa gaattgaaag tatccagctg atgatggaca gtgaaactgg tcgatccaag    1140
ggatatggat ttattacatt ttctgactca gaatgtgcca aaaggctttt ggaacaactt    1200
aatggatttg aactagcagg aagaccaatg aaagttggtc atgttactga acgtactgat    1260
gcttcgagtg ctagttcatt tttggacagt gatgaactgg aaaggactgg aattgatttg    1320
ggaacaactg gtcgtcttca gttaatggca agacttgcag agggtacagg tttgcagatt    1380
ccgccagcag cacagcaagc tctacagatg agtggctctt tggcatttgg tgctgtggca    1440
gaattctctt ttgttatga tttgcaaaca agactttccc agcagactga agcttcagct    1500
```

```
ttagctgcag ctgcctctgt tcagccactt gcaacacaat gtttccaact ctctaacatg    1560
tttaaccctc aaacagaaga agaagttgga tgggataccg agattaagga tgatgtgatt    1620
gaagaatgta ataaacatgg aggagttatt catatttatg ttgacaaaaa ttcagctcag    1680
ggcaatgtgt atgtgaagtg cccatcaatt gctgcagcta ttgctgctgt caatgcattg    1740
catggcaggt ggtttgctgg taaaatgata acagcagcat atgtacctct tccaacttac    1800
cacaacctgt ttcctgattc tatgacagca acacagctac tggttccaag tagacgatga    1860
aggaagatat agtcccttat gtatatagct ttttttcttt cttgagaatt catcttgagt    1920
tatcttttat ttagataaaa ataaagaggc aaggatctac tgtcatttgt atgcaatttc    1980
ctgttacctt gaaaaaataa aaatgttaac aggaatgcag tgtgctcatt ctccctaaat    2040
agtaaatccc actgtataca aaactgttct cttgttctgc cttttaaaat gttcatgtag    2100
aaaattaatg aactatagga atagctctag gagaacaaat gtgctttctg taaaaaggca    2160
gaccagggat gtaatgtttt taatgtttca gaagcctaac ttttttacaca gtggttacat    2220 ttcacatttc actaatgttg atatttggct gatggttgag cagtttctga aatacacatt    2280
tagtgtatgg aaatacaaga cagctaaagg gctgtttggt tagcatctca tcttgcattc    2340
tgatcaattg gcaagaaagg gagatttcaa aattatattt cttgatggta tcttttcaat    2400
taatgtatct gtaaaagttt ctttgtaaat actatgtgtt ctggtgtgtc ttaaaattcc    2460
aaacaaaatg atccctgcat ttcctgaaga tgtttaaacg tgagagtctg gtaggcaaag    2520
cagtctgaga aagaaatagg aaatgcagaa ataggttttg tctggttgca tataatcttt    2580
gctcttttta agctctgtga gctctgaaat atattttggg gttacttcag tgtgtttgac    2640
aagacagctt gatatttcta tcaaacaaat gactttcata ttgcaacaat ctttgtaaga    2700
accactcaaa taaagtctc ttaaaaaggc cacaggagat cttcattttt caaatgtttt    2760
aaagttacag aaatttgaga acagaattag cttcttttag tctcaattca gtacttgcct    2820
cttgggaaaa tgttccgagt ctgcggaaac ttgccctcac gttgtccccc atgaattcct    2880
ttattctatt agagtctagc cctgtgtatt ttagaagaat gtatcaaaac tgaggggttt    2940
accaaaaaga aaaggaaaca gcctggcctt aaaacctggg cattcttggt ctcctgcatt    3000
gtctgggcat atttatgaag aaattttcac catttacaat acatacttaa caaaatggct    3060
taacttcaaa ctggttttcca aaattgattt atatattaat atattaaata aggtgcatat    3120
attactgtat taaggggttt tgagctttca tactagttgg gaagcaagct gtcaccattt    3180
atactcaatt ctcttcaact gtttatctct tggtaaatct tttgagtagg aaatgctgct    3240
cctagcttat cttcaaatac tgagttcctt acctcatttg ttcaacttt tttttgtta    3300 gcattgaagc acaagtttta caggcttatt cagaatttca tatcagtcgt tttgtttgac    3360
atttatccca ataattgttc tagtgattta atttgtatgg aaactcccaa ggttcaattt    3420
cttttctttt ttgagatgga gtcttgctct ttggcccagg ctggagtgca gtgatgtgat    3480
ctcagctcca tctcccaggt tcaagcaatt ctcccacctc agtctcctga agagctggga    3540
caggtgcgca ccaccgtgcc cagctaattt ttgtattttt agcagagacg tgttagccc     3600 ggctggtctc acactgacct caagtgatct gtccgcttg gcctcccaaa gtgccgggat    3660
tacaggcatg agccaccgcg cccagcctca ttgaaaattt acttttcaat accagactgc    3720
agagttcttt ggggcagaga cactctgtca gtgtgctctt tttccaaagt atctcctgct    3780
atcagttttt cccccttgaac caagtcttcc taacaaattt gttgtgtcat tgctttctag    3840
ggaactggac cagcaaatgt ggcctttagt ggttaatctc atctgtgcca aaatttagtt    3900
```

```
gctaccagag tgaaatttgg tgtgtaaata atgttcagag gaaatgtggt tggagtgtag    3960
taacttgaat agtgtcgtgc atagaaaaca gctcattctg agtgaaactg tttatgtcca    4020
atcagttcct gagtcagcat cccactggtt cgaaaatctg taactaatct ggtaatgtcc    4080
ttaatttcct cctgcctgtc agtgttccaa agtgttcatc tagttttctt ttatcttttat   4140 aataattact accatctttg aaagttctgt ttaagaaatg cttaatgggc aatgcgggtt    4200
agtaactcca gggtctgcgt ggcctgggca ggtgagatgg acaactgcct cattacagaa    4260 gcttttatc atcaaactag taagttttgt ggagggcaag ctatatagat tgttgatgag     4320
tggttagaaa atcatctgga atttagccag ttgagaagct acagaagttt ctatttttt     4380 ttacagtgga tgaactgttt tgcttttct gataaagcca ctaggtatat ctaaataaca     4440
acctcgggct ggacgtggtg ccttatgcct gtatatgtga acactgggag gcggaggcgg    4500
gtggatcatg aggtcaagag tttgagacca gcctggccaa cacagtgaaa ccccgtctct    4560
actaagaata caaatttttt ttgttttgag acagagtctc gctctgtcgc ccaggctgga    4620
gtgcaatggc tcgatctcag ctcactgcaa cctccacctt ctgggttcaa gcgattctcc    4680
tgcctcagcc tcccgagtag ctgggaatac aggcgcgtgt caacacaccc ggcttaagtt    4740
tttgtatttt tagtagagac ggggtgtcac cgtgttaccc aagatggtct ccatctcctg    4800
accttgtgat ccaccagcct ttgcctccca aagtgctggg attacaggca taagccaccg    4860
cgcccagcct aacaatacaa aatttagcta ggcatggtgg cacgtgcctg ttatcacagc    4920
tactcgggag gctgaggcag gagaaacgct tgaacacagg aggcagaagt tgcggtaagc    4980
cgagatcgtg ccac                                                     4994

<210> SEQ ID NO 7
<211> LENGTH: 449
<212> TYPE: PRT
<213> ORGANISM: Homo sapiens

<400> SEQUENCE: 7

Met Glu Ser Cys Ser Val Thr Gln Ala Gly Ala Gln Trp Arg Val Leu
1               5                   10                  15

Gly Ser Leu Gln Pro Pro Pro Gly Phe Lys Gln Phe Leu Cys His
            20                  25                  30

Ser Leu Pro Ser Ser Trp Asp Tyr Arg Ser Asp Arg Met Ala Ser Asp
        35                  40                  45

Asp Phe Asp Ile Val Ile Glu Ala Met Leu Glu Ala Pro Tyr Lys Lys
    50                  55                  60

Glu Glu Asp Glu Gln Gln Arg Lys Glu Val Lys Lys Asp Tyr Pro Ser
65                  70                  75                  80

Asn Thr Thr Ser Ser Thr Ser Asn Ser Gly Asn Glu Thr Ser Gly Ser
                85                  90                  95

Ser Thr Ile Gly Glu Thr Ser Asn Arg Ser Arg Asp Arg Asp Arg Tyr
            100                 105                 110

Arg Arg Arg Asn Ser Arg Ser Arg Ser Pro Gly Arg Gln Cys Arg His
        115                 120                 125

Arg Ser Arg Ser Trp Asp Arg Arg His Gly Ser Glu Ser Arg Ser Arg
    130                 135                 140

Asp His Arg Arg Glu Asp Arg Val His Tyr Arg Ser Pro Pro Leu Ala
145                 150                 155                 160

Thr Gly Glu Pro Val Asp Asn Leu Ser Pro Glu Glu Arg Asp Ala Arg
                165                 170                 175
```

```
Thr Val Phe Cys Met Gln Leu Ala Ala Arg Ile Arg Pro Arg Asp Leu
            180                 185                 190
Glu Asp Phe Phe Ser Ala Val Gly Lys Val Arg Asp Val Arg Ile Ile
            195                 200                 205
Ser Asp Arg Asn Ser Arg Arg Ser Lys Gly Ile Ala Tyr Val Glu Phe
210                 215                 220
Cys Glu Ile Gln Ser Val Pro Leu Ala Ile Gly Leu Thr Gly Gln Arg
225                 230                 235                 240
Leu Leu Gly Val Pro Ile Ile Val Gln Ala Ser Gln Ala Glu Lys Asn
                245                 250                 255
Arg Leu Ala Ala Met Ala Asn Asn Leu Gln Lys Gly Asn Gly Gly Pro
            260                 265                 270
Met Arg Leu Tyr Val Gly Ser Leu His Phe Asn Ile Thr Glu Asp Met
        275                 280                 285
Leu Arg Gly Ile Phe Glu Pro Phe Gly Lys Ile Asp Asn Ile Val Leu
    290                 295                 300
Met Lys Asp Ser Asp Thr Gly Arg Ser Lys Gly Tyr Gly Phe Ile Thr
305                 310                 315                 320
Phe Ser Asp Ser Glu Cys Ala Arg Arg Ala Leu Glu Gln Leu Asn Gly
                325                 330                 335
Phe Glu Leu Ala Gly Arg Pro Met Arg Val Gly His Val Thr Glu Arg
            340                 345                 350
Leu Asp Gly Gly Thr Asp Ile Thr Phe Pro Asp Gly Asp Gln Glu Leu
        355                 360                 365
Asp Leu Gly Ser Ala Gly Gly Arg Phe Gln Leu Met Ala Lys Leu Ala
    370                 375                 380
Glu Gly Ala Gly Ile Gln Leu Pro Ser Thr Ala Ala Ala Ala Ala
385                 390                 395                 400
Ala Ala Ala Gln Ala Ala Ala Leu Gln Leu Asn Gly Ala Val Pro Leu
                405                 410                 415
Gly Ala Leu Asn Pro Ala Ala Leu Thr Ala Leu Ser Pro Ala Leu Asn
            420                 425                 430
Leu Ala Ser Gln Cys Phe Gln Leu Ser Ser Leu Phe Thr Pro Gln Thr
        435                 440                 445
Met

<210> SEQ ID NO 8
<211> LENGTH: 10178
<212> TYPE: DNA
<213> ORGANISM: Homo sapiens

<400> SEQUENCE: 8
agagctgccg ccattttgcg ggaagaggag gctctgtacc tgcagtgctg cttttcttgc      60
ctagactcta ggaactatcc gagctccact ccccacaaca tactcaaagg aacggagaga     120
accgggaccc ccctgcgggg acccggaact ggatggaaga aacatactc tatgtggatg      180 agattgagtg gaccttgacc cataagttgg acatgaaga gagcgtttga aaactaccaa     240
cctgggccgg gtgcagtggc tcacgcctgt aatcccagca ctttgggtgg ccgaggcggg     300
cggatcacga ggtcaggaga tcgcgaccat cctggctaac acggcgaaac cccgtctcta     360
ctaaaaatac aaaaaaaaa caaaaagaa gaaaaagaa aaaactacca gcctgaaaat        420
gcatagtgtt tgctacctta ttgcttttag cacatctaga aagacactaa acccagtgag     480
attatctgac aggatggcat ctgatgactt tgacatagtg attgaggcca tgctggaagc     540
```

-continued

| | |
|---|---|
| tccctataaa aaagaagagt cgtagtcgag atcgggatcg gtatagacgg agaaatagtc | 600 |
| ggagccgaag tccaggtcgg cagtgtcgtc accgtagccg tagctgggat cgtcgacatg | 660 |
| gtagtgagtc gcgaagtcgg gaccatcgtc gtgaggatcg tgtgcattac aggagtcctc | 720 |
| cacttgccac tggttatagg tatggacaca gtaagagtcc tcatttcaga gagaagagcc | 780 |
| cagtcaggga gccagttgat aatctgagtc ctgaggagcg tgatgcccgc acagttttct | 840 |
| gtatgcagtt agctgcccga attcggcctc gagatctgga ggacttttc tctgctgtag | 900 |
| gcaaggttcg cgatgtacgt atcatctcag atcggaactc acgtcgttct aagggcattg | 960 |
| cctacgtgga attctgtgaa atccagtctg tgccactggc cattgggctg actgggcagc | 1020 |
| ggttgctggg agtgcctatc attgtacagg cttcacaggc agagaaaaac cgactggcag | 1080 |
| ccatggccaa caacctgcaa aagggcaatg gtggaccaat gcgcctctat gtgggttccc | 1140 |
| tgcacttcaa tatcactgaa gacatgctcc ggggcatctt tgagccctt ggtaaaattg | 1200 |
| ataatattgt cctgatgaag gactcagata caggccgctc taaaggttat ggtttcatca | 1260 |
| cgttctctga ttctgagtgt gcccggcggg ccctggaaca gttgaatggg tttgagcttg | 1320 |
| ctggtcgacc tatgagggtt ggccatgtga ctgagcgact ggatggtggc acagacatca | 1380 |
| cttttcctga tggggaccag gagctggatc tgggatcagc aggtggacgt tttcagctca | 1440 |
| tggcaaaact ggcagaaggc gctggaatcc aactgccaag cactgctgct gctgctgctg | 1500 |
| ccgccgccgc ccaggctgct gccttgcaac tgaatggagc agttcccttg ggggccctga | 1560 |
| atccagcagc tctgactgct ctgagtccag ccctgaacct tgcctcccag tgtttccagc | 1620 |
| tctccagcct ctttaccccc cagaccatgt aaatcagtgg cacagtatac tgcctccttg | 1680 |
| tgcctctgga tcctgccact tcacatctac tcttccatgg ccccatttct ccattttgtg | 1740 |
| gaccaagcca tcctgagggc atggacattg tctctgagga aattggggcc acccttaaga | 1800 |
| taccaagaaa agctcctgcc catggtccca ctggaaatgg actctgctga gcaaagccac | 1860 |
| cagttgaaga gaacagaatc cacacctgca ttgaatacct gtttctccat gtgtatcgtc | 1920 |
| tctgagatta ccttcttgcc ctttccaaca ccttagtgat tcctcaattt ctcccccatt | 1980 |
| gggaaggcca tagggcatac tgaaggaact gacctctctc cttttcctgt acctttaacc | 2040 |
| tttagtctgt caaggaaaac ccttaggacc tctgaatcaa gaggactgag tttgtgggtg | 2100 |
| aaccttgaag gtgctctttc tgctacaagg gccctgggag atagcatgga cgtgcattga | 2160 |
| gaagccagcc tcagacctta gcttgaagca gcttgaggcc agacctactg tagcctcagc | 2220 |
| atcttgctag gaggcatgga agtgatctat cctgccagga ggcctcagag tgatctgtcc | 2280 |
| tgccaggagg tgtgagagtg atctgtcctg tgaggcattt aggggctttc aggaatttag | 2340 |
| taaaaggtgg agtatgcctt tccagtatct tccatcttcc tttgtatact tgtccttcct | 2400 |
| cccatttcct ccctttggcc cgaggtagga ggatggaggg aggctgctac tctaccactt | 2460 |
| cctgtgtgcc tctactgtgg cctcaaccct ggcaattata gctactccca tcccttacct | 2520 |
| gggcatgtgt gagcccttct cactggattt atacccttg tgtctgtgta cataaatata | 2580 |
| tatacatata tatatacata aaactttgt acaaaaggca agcctcctcc ttgtggcagc | 2640 |
| tgttgcccat ttgtgtgtgg tctttgttgt gtgtctgaca acttctcatt agcccaactt | 2700 |
| atgatgtttc tagggatata aaacattagt aacatcattg tgtttattta tttaaccacc | 2760 |
| tttagaaaga aaaatgaaaa ctcacacctg ggtggggtc ccattctgta tctgcattac | 2820 |
| actgttgatc tatggttgtc ttctccatct atcttcatcc taactatctc catcccagct | 2880 |

```
acccactgga cagaattacc caaacagcca agttgcagca ccaggacaga cttagactta   2940
acaggctcct tctctgtgcc taatgacaga tctttccagc agatggcact atgacagtac   3000
tgcattctac acttgttttt ttctagtggg gcggggcggg gagggggggg ggttgtgatc   3060
ttgaagagtt aagtaccaga gctaagctga gctttcttaa ctctattggc ctttgtacct   3120
gcctttgacc ctctttgtag tagcgatccc aatccaatat ccaaggggt tgggtcttg    3180
tataacagca gggttctcct gacctgatgt ctactgttgt tcctctgtca gtcccctcaa   3240
ctcctgcttt ccatgtggct ctgcctggga taacacaggc ctgggaccag tgaattgtag   3300
ggaactgagt attccagaaa tacctctgtg aaagggaagg tgcacctacc actgccttaa   3360
taataagggg gtgggagaga ggctgtctca cccagcttag ggaccaaatg agaaggcctg   3420
aattcagggg cagggctctg tggggctcct tttttgatct ctatggcaac aaaatgctaa   3480
gactttctta tgctaaaaat atggataatt gctgttaggt tttaatttgt cagctctcag   3540
acttctaagc cagtgatgtt agcctctggg gttgctttta acacaaaatc atttaaatac   3600
ttgaagcctg cttgagtcat aaaaggccag tgggactcta gctcctaagt ctgtttgctg   3660
cttctgtaac aatagcacag actaatttgt aaagaaaaga ggtgtaggct gggtgcactg   3720
gctcacgcct gtaatcccag cactttggga ggccgaggtg ggtggatcac gaggtcagtt   3780
caagaccagc ctggccaaca tggtgaaact ctgtctctac tagaaataca aaaagtagct   3840
gggcatggtg gtgggtgcct gtaatcccag ctactcagga ggctgagaca ggagaatcgc   3900
ttgagcctgg gaggcggagg ttgcagtgag ccgaggatgc accactgcac tccagcctgg   3960
gcaacagagc gagcctccat ctcaaaaaaa cagaaaagtg tatttctcac agttctggag   4020
gctgggaatt tcaagagcat ggtgcctgca tcaggtgggg gtcatcccat gtcagaaggg   4080
cacaaggtag aaatgagtac atgagacaaa gggaccatgg gccaaacttg ctttataaca   4140
gccctctctc atgataacct gctgtgtgat agtgacatta atccactcat gagggctctg   4200
tccttgtgac tcagtcacct cgtattaagc cccatcttca acactgttgc attgggagtc   4260
aaatttccaa tgtgaacttt tgggggacac attcaaacca cagcatttct gattcttcca   4320
ggcctagatc tcacatgatg ttgctgttct cctggttacc accccatcc cttcccccat   4380
cttatcctag tttgctttct ggaccggggg aaaagggaag gaggatgcac tattttagg    4440
tagaagctgc tggctatgac ccagcacccc tacagttatt gatttggctt ctaatgtatc   4500
ttgagaagtg cagtgggtac cgttttgtt agtcatcctg aggccatgaa ctgggtcttc    4560
tcatggctgg cttggctcct tcagactatt ataaatatcc acaggccttg cctccctgcc   4620
ttcctctgct tggtttcctt atgtttccat ccctagctac cttggccttc ctacactcgg   4680
atccttccac ctcagttctt tcttgttctt agttcctcac atagcctctt gctgggagag   4740
agacaatgtt ggaagtaagg acgtatctaa gacaatttcc agtcttactc catataaggt   4800
gatggtatct agtgagtgac agttgctgtc cgtgtgtgac tcagtgcctt cttgttactc   4860
atccctccat acgaggtggt tagagtggag agaagcgggc tgtgaacaga ctctgggccc   4920
agcttaaggt aaaagaaact tccctcaaca tctacctgca catggtggct ggtggcgtag   4980
gggtgacatt gtgatctaga tccttttgcca gcatagttag aatttcccta ccagtcttca   5040
gttctagaaa agattctcac ctgattttg acttccagtc tatgcttctg tattcactaa    5100
ggtggcagca tttcctccct gttctttaaa ctgctgtgct cttgacacag gaattctgcc   5160
tgcttcctca gactcccaac aaccccccaga taggagttac cagtagaagc agaggcttga  5220
cctgtgaact tttagtcctg gagcatatca tgaagggaat tgagtaaaaa cctgaaggat   5280
```

| | | | | |
|---|---|---|---|---|
| ggaattatat | cacagtccct | cttttccgtg | taatggaaag | gctttagtga aaatcaggca | 5340 |
| gcaacacttg | gacagtgaaa | agagactctg | aaaggtgagg | tgacaggagg tggcataatg | 5400 |
| gtcattgtta | acatttatgc | aaggttggtt | gtaggttagg | tgttctaatc gtgtattaag | 5460 |
| tcacaaaatc | ctcacaacaa | tcctctcaag | tagtttatta | tctttacttt gtaaacaagg | 5520 |
| aaacatatcc | aaataagtta | ataattttc | cccataagca | caaagttagc aagttaggga | 5580 |
| ttccaatcca | agtactctcg | cttcagatcc | cttgatctta | accttacctg cctctcagca | 5640 |
| ccaccatgga | agacaaggcc | ttggagtcag | tgaggaagtg | tcacttttcc tatccctgta | 5700 |
| cccatagctc | tccgtagact | cagaattttt | ccactgccat | gtctttgctt atcttgagtg | 5760 |
| acagtgtttg | tgggtgaacc | ttgaaggtgc | tctttctgct | acaagggccc tgggagatag | 5820 |
| catgggcatg | tgcattgaga | agccagcctc | agaccttatc | ttgaagcagc ttgaggccag | 5880 |
| acctactgta | ggctcagcat | cttgctagga | ggcatgggag | tgatctaacc tgccagctat | 5940 |
| ctctcttcct | ttcctccttc | tgctgatcaa | agtcctgtcc | tttaagaccc tgaagctttc | 6000 |
| ctaggtggag | ttgatctctc | ttttcagtat | tctttgtcct | cttgtgggtc atcttactct | 6060 |
| acttttattt | agtaaataaa | ataattgcaa | taaaaattat | tttattgaaa actccattac | 6120 |
| ttgatggtta | cagcctgatg | aggccagact | tggatgtctt | tctcatgatt gctttgcctt | 6180 |
| gcacatatta | aatgtctgta | gaattgaatg | aatgctgttc | attaaagtgt taaagtcagc | 6240 |
| accaggcttt | ccaaaggctg | cccttctag | gctgcttttc | ccagcagcct catccattcc | 6300 |
| ttcctcactc | caccaggaga | gaagatgcag | ctttactctt | tctgatgtta ccatggtagc | 6360 |
| ctgtgatact | ttctttctaa | agtgctgctt | gccatccacc | agagactgat gtttccatgg | 6420 |
| caaccaggtg | aaggcaatag | tcacgagctg | gatgcaggaa | aggaattccg gtctgagaag | 6480 |
| ctgcatatct | gaatcttcta | gcttcagaca | tcctttcccc | tctctcataa cttttgcgct | 6540 |
| ttatatccag | gactggtttg | ctctctggtg | tgcccttggt | tgagagagct ctgtgaaagt | 6600 |
| gaggtgaagc | agaccaacca | acttagatca | cgtgggaagg | tgggtgcaag gaaagagctg | 6660 |
| agcaaagatc | acttcaaaaa | gttggatgaa | gtctattagt | tgttcagatg atctgctctc | 6720 |
| aagagcccct | aaggagttgg | ctggagtttc | tggagagcca | ttaagcagtt attttgaga | 6780 |
| gcaatgggta | gatggatgag | gtgcctgaag | actggaaagc | agccagtcag tgccggattg | 6840 |
| tagaaaggag | aaacaatgac | cttggaaatc | ggagacccgt | caaacttgcc aatgttccag | 6900 |
| aaaggatggg | agtttcagtc | agcttcagg | catcaggaag | cctacttgct tagaattagt | 6960 |
| ggtgctaaga | attcgcctcc | tcaactcctg | agcataagca | agctagggga cctccaccct | 7020 |
| gtagccgagt | gtcacactct | ggaaccacac | agcatggttc | agatccctct tccctcacaa | 7080 |
| actagctgaa | taagcttggg | taggttactt | cacttctctc | acacttcatc tgtaaaaagg | 7140 |
| aaatgataac | acctatctca | tagggatgtt | gtgagaattc | attgagaaag gtttggaact | 7200 |
| tggctcatta | ctgtcctcag | tatttcact | cctctggatg | cctactcact tgattttcta | 7260 |
| gctgacttca | ttctccccaa | ctttagagct | caaggtttat | ggggaaaagc aagggcagtg | 7320 |
| caatggtgaa | aataaatctt | cattttaaa | taaataaatt | gttcctgcac tgaagcccca | 7380 |
| agcttacaag | gtcttgggtc | acacacaacc | tgccagttt | tcaggaaaac agatcccact | 7440 |
| agcccaatct | ctttatgctt | gaggctctgt | ccacatagtt | agatttaac cagatggttt | 7500 |
| cgaaaaatca | aaatgagccc | ccctcacagg | taccttcaag | gtacctaaca ccattagctt | 7560 |
| tgtctggcag | gggaaaaata | ccagggcact | cagttttgtt | ttgttttgag acagggtctg | 7620 |

```
gctctgttgc ccatgctgga gtacagtggt gccatcacag ctcactgcag tctcaacctc    7680
ctgagctcaa atgatcctct tgattagctg aactacagg  tatgtgccac tatgcccagc    7740
taagttttgt attttttgta gagatggggt cttgctatgt tgcccaggtg gtcttgaact    7800
cctgggctta agtgatcctc cctccttagc ctcccaaagt gctaggatta taggtgtgag    7860
ccaccacaac tgcctgagag caccctctgt taccacccctt tccttagcgt ctcagcctcc    7920
cccaagcacc tgtctttgtt ggtctccaga gcctagccct acactggcat tttccttttct    7980
gaataagtat ttttttatt  tatttatttt tattttttct ttgagatgga gtttcgcttt    8040
tgttgcccag gctggagtgc aatggtgcga tctcggctca ccgcaacctc tgcttcctgg    8100
gttcaagtga ttctcctgcc tcagcctcct gagtagctgg gattacaggc gtgcgccacc    8160
actcccagct aattttgtat ttttagtgga cagggtttt  ctccatgttg gtcaggctgg    8220
tctcgaactc ctgacctcag gtgatccacc cgccttggcc tcccaaagtg ctgggattac    8280
agtcctgagc cactgcactg ggccttattt atttatttt  aattaattaa ttaattttt    8340
ttgagatgga gtcttgcttt gtcgcccagg ctggagtgca gtggcgcaat ctcggtcac    8400
tgcaagctct gcctcccagg ttcatgccat tctcctgcct cagcctccca gtagctggg    8460
actacaggca cctgccacta tgcccggcta attttttgta ttttttagta gagatggggt    8520
ttcactgttt tagccaggat ggtttcgatc tcctgaccta gtgatccgct cgcctcggcc    8580
tcccagagtg ctgggattac aggcgtgagc cactgcgccc ggctgggcct tatttatgta    8640
tttttctgag acagagtctc atgctatcac ccaggctgga gtgcagtggc atgatctctg    8700
ctcactgcga tctctgctca cttcaacctc tgcttcccgg gttcaagtga ttctcccacc    8760
tcagcctccc gagtagctgg aattacaggc acccaccacc atgcctggct aattttttgta    8820
attttttta  gtagaaatag ggtttcacca tgttggccag gctggtctct cttgaccct    8880
caagtgatcc acccacctcg gcctcccaaa gtgctgggat tacaggcgtg agccaattgc    8940
ccgacctgag taagtatttt aaatcagcac aggtcctctg cttaaagtca agttgtaatt    9000
tgaacacaaa aatggaaaat catgcagtaa ataccatcg  tggagcttca attgccaatc    9060
tgtcccccaa ccttccatca gatgacaaaa cccaaaaaag tgttacccgt gagtcctatg    9120
gaaggcacgt tggactttgt agaccataac ttaaattttt atctccaaat ggtgctgtgc    9180
tttgagagtt tagcaagctg ctttgatgcc taaataaagg gccaggacat aggttgcaaa    9240
aggcattact acttccaccg cttctctgta taatgcttga gaattacaa  agatctttgc    9300
tcttttattt agtcctcatg acttcgctat aaggtaggta ttcttcattt tagagttggg    9360
atagcatagc tgagttcagc aaaccagaca ggttaagagt gacttcatcc acagaccccc    9420
atccaggaaa catcctgagc actaattgaa aagcattcaa gggcttactg aatttgcatt    9480
cacatctgga gttttcaagg ccactaagct gtggaaactt gacatcaata ttcaaataga    9540
tgaaaaggga ccttaagcat atccatcagg gagtcaccga gatgataaag gcctgagaag    9600
cagtatgctc ttgtccggca tttgtgtcct ttgacgactg caccatccac ccaaattttg    9660
ctgccttctt tataggaagg gccttttcct catgtggtgg gctgcccact gtttcttctc    9720
tgtgcatttg ctcatgtagt ttgaccacaa ggaatgcttt tccttcttttc tctcaactat    9780
ctatagccta catatccttt aaggcccagt ttctaaaata tgtcttccaa atttactgtt    9840
tcttccattc agaattcctg gagcacatga ggtagccccc agttagatag aatgtggtat    9900
tgtttgctgc tattttgcct gttttgtgct gtatcacctc atccatctcc ccagcttaat    9960
tgcaagctat ttgacgggca gaaattgtgt cttatttgta tttgtttttcc ccattgggcc   10020
```

```
cggcacactg attggcatat tgcagatgtt tagtacttga gagaaacaaa atgtcttcta    10080
gcatttgtgg atgaaagatt aaaatgtcca ggaaaattta cttagattga tgtggattga    10140
aactatatta gattaataaa aagatgtgtg tgtgtgaa                             10178
```

<210> SEQ ID NO 9
<211> LENGTH: 405
<212> TYPE: PRT
<213> ORGANISM: Homo sapiens

<400> SEQUENCE: 9

```
Met Ala Ser Asp Asp Phe Asp Ile Val Ile Glu Ala Met Leu Glu Ala
1               5                   10                  15

Pro Tyr Lys Lys Glu Glu Asp Glu Gln Gln Arg Lys Glu Val Lys Lys
            20                  25                  30

Asp Tyr Pro Ser Asn Thr Thr Ser Thr Ser Asn Ser Gly Asn Glu
        35                  40                  45

Thr Ser Gly Ser Ser Thr Ile Gly Glu Thr Ser Asn Arg Ser Arg Asp
    50                  55                  60

Arg Asp Arg Tyr Arg Arg Asn Ser Arg Ser Arg Ser Pro Gly Arg
65                  70                  75                  80

Gln Cys Arg His Arg Ser Arg Ser Trp Asp Arg Arg His Gly Ser Glu
                85                  90                  95

Ser Arg Ser Arg Asp His Arg Arg Glu Asp Arg Val His Tyr Arg Ser
            100                 105                 110

Pro Pro Leu Ala Thr Gly Glu Pro Val Asp Asn Leu Ser Pro Glu Glu
        115                 120                 125

Arg Asp Ala Arg Thr Val Phe Cys Met Gln Leu Ala Ala Arg Ile Arg
    130                 135                 140

Pro Arg Asp Leu Glu Asp Phe Phe Ser Ala Val Gly Lys Val Arg Asp
145                 150                 155                 160

Val Arg Ile Ile Ser Asp Arg Asn Ser Arg Arg Ser Lys Gly Ile Ala
                165                 170                 175

Tyr Val Glu Phe Cys Glu Ile Gln Ser Val Pro Leu Ala Ile Gly Leu
            180                 185                 190

Thr Gly Gln Arg Leu Leu Gly Val Pro Ile Ile Val Gln Ala Ser Gln
        195                 200                 205

Ala Glu Lys Asn Arg Leu Ala Ala Met Ala Asn Asn Leu Gln Lys Gly
    210                 215                 220

Asn Gly Gly Pro Met Arg Leu Tyr Val Gly Ser Leu His Phe Asn Ile
225                 230                 235                 240

Thr Glu Asp Met Leu Arg Gly Ile Phe Glu Pro Phe Gly Lys Ile Asp
                245                 250                 255

Asn Ile Val Leu Met Lys Asp Ser Asp Thr Gly Arg Ser Lys Gly Tyr
            260                 265                 270

Gly Phe Ile Thr Phe Ser Asp Ser Glu Cys Ala Arg Arg Ala Leu Glu
        275                 280                 285

Gln Leu Asn Gly Phe Glu Leu Ala Gly Arg Pro Met Arg Val Gly His
    290                 295                 300

Val Thr Glu Arg Leu Asp Gly Gly Thr Asp Ile Thr Phe Pro Asp Gly
305                 310                 315                 320

Asp Gln Glu Leu Asp Leu Gly Ser Ala Gly Gly Arg Phe Gln Leu Met
                325                 330                 335

Ala Lys Leu Ala Glu Gly Ala Gly Ile Gln Leu Pro Ser Thr Ala Ala
```

|     |     |     | 340 |     |     |     | 345 |     |     |     | 350 |     |     |
| --- | --- | --- | --- | --- | --- | --- | --- | --- | --- | --- | --- | --- | --- |
| Ala | Ala | Ala | Ala | Ala | Ala | Gln | Ala | Ala | Leu | Gln | Leu | Asn | Gly |
|     |     |     | 355 |     |     |     | 360 |     |     |     | 365 |     |     |
| Ala | Val | Pro | Leu | Gly | Ala | Leu | Asn | Pro | Ala | Ala | Leu | Thr | Ala | Leu | Ser |
|     |     |     | 370 |     |     |     | 375 |     |     |     | 380 |     |     |     |     |
| Pro | Ala | Leu | Asn | Leu | Ala | Ser | Gln | Cys | Phe | Gln | Leu | Ser | Ser | Leu | Phe |
| 385 |     |     |     |     | 390 |     |     |     |     | 395 |     |     |     |     | 400 |
| Thr | Pro | Gln | Thr | Met |
|     |     |     |     | 405 |

<210> SEQ ID NO 10
<211> LENGTH: 9905
<212> TYPE: DNA
<213> ORGANISM: Homo sapiens

<400> SEQUENCE: 10

```
agagctgccg ccattttgcg ggaagaggag gctctgtacc tgcagtgctg cttttcttgc      60
ctagactcta ggaactatcc gagctccact ccccacaaca tactcaaagg aacgagagaa     120
accgggaccc cctgcgggg acccggaact gatctgacag gatggcatct gatgactttg     180
acatagtgat tgaggccatg ctggaagctc cctataaaa agaagaggat gagcaacaaa     240
ggaaagaagt taaaaaggat tatcctagca ataccaccag cagcaccagc aacagtggca     300
atgagaccag tggaagcagc accatcgggg agacaagcaa tcgtagtcga gatcgggatc     360
ggtatagacg gagaaatagt cggagccgaa gtccaggtcg gcagtgtcgt caccgtagcc     420
gtagctggga tcgtcgacat ggtagtgagt cgcgaagtcg gaccatcgt cgtgaggatc     480
gtgtgcatta caggagtcct ccacttgcca ctggggagcc agttgataat ctgagtcctg     540
aggagcgtga tgcccgcaca gttttctgta tgcagttagc tgcccgaatt cggcctcgag     600
atctggagga cttttctct gctgtaggca aggttcgcga tgtacgtatc atctcagatc     660
ggaactcacg tcgttctaag ggcattgcct acgtggaatt ctgtgaaatc cagtctgtgc     720
cactggccat tgggctgact gggcagcggt tgctgggagt gcctatcatt gtacaggctt     780
cacaggcaga gaaaaaccga ctggcagcca tggccaacaa cctgcaaaag gcaatggtg     840
gaccaatgcg cctctatgtg ggttccctgc acttcaatat cactgaagac atgctccggg     900
gcatctttga gcccttggt aaaattgata atattgtcct gatgaaggac tcagatacag     960
gccgctctaa aggttatggt ttcatcacgt tctctgattc tgagtgtgcc cggcgggccc    1020
tggaacagtt gaatgggttt gagcttgctg gtcgacctat gagggttggc catgtgactg    1080
agcgactgga tggtggcaca gacatcactt ttcctgatgg ggaccaggag ctggatctgg    1140
gatcagcagg tggacgtttt cagctcatgg caaaactggc agaaggcgct ggaatccaac    1200
tgccaagcac tgctgctgct gctgctgccg ccgccgccca ggctgctgcc ttgcaactga    1260
atggagcagt tcccttgggg gccctgaatc cagcagctct gactgctctg agtccagccc    1320
tgaaccttgc ctcccagtgt ttccagctct ccagcctctt taccccccag accatgtaaa    1380
tcagtggcac agtatactgc ctccttgtgc ctctggatcc tgccacttca catctactct    1440
tccatggccc catttctcca ttttgtggac caagccatcc tgagggcatg acattgtct    1500
ctgaggaaat tggggccacc cttaagatac caagaaaagc tcctgcccat ggtcccactg    1560
gaaatggact ctgctgagca aagccaccag ttgaagagaa cagaatccac acctgcattg    1620
aatacctgtt tctccatgtg tatcgtctct gagattacct tcttgccctt tccaacacct    1680
tagtgattcc tcaatttctc ccccattggg aaggccatag ggcatactga aggaactgac    1740
```

```
ctctctccctt ttcctgtacc tttaacctttt agtctgtcaa ggaaaaccct taggacctct    1800
gaatcaagag gactgagttt gtgggtgaac cttgaaggtg ctctttctgc tacaagggcc    1860
ctgggagata gcatggacgt gcattgagaa gccagcctca gaccttagct tgaagcagct    1920
tgaggccaga cctactgtag cctcagcatc ttgctaggag gcatggaagt gatctatcct    1980
gccaggaggc ctcagagtga tctgtcctgc caggaggtgt gagagtgatc tgtcctgtga    2040
ggcatttagg ggctttcagg aatttagtaa aaggtggagt atgcctttcc agtatcttcc    2100
atcttccttt gtatacttgt ccttcctccc atttcctccc tttgcccga ggtaggagga    2160 tggagggagg ctgctactct accacttcct gtgtgcctct actgtggcct caaccctggc    2220
aattatagct actcccatcc cttacctggg catgtgtgag cccttctcac tggattttat    2280
acccttgtgt ctgtgtacat aaatatatat acatatatat atacataaaa actttgtaca    2340
aaaggcaagc ctcctccttg tggcagctgt tgcccatttg tgtgtggtct ttgttgtgtg    2400
tctgacaact tctcattagc ccaacttatg atgtttctag ggatataaaa cattagtaac    2460
atcattgtgt ttatttattt aaccacctttt agaaagaaaa atgaaaactc acacctgggt    2520
ggggttccca ttctgtatct gcattacact gttgatctat ggttgtcttc tccatctatc    2580
ttcatcctaa ctatctccat cccagctacc cactggacag aattacccaa acagccaagt    2640
tgcagcacca ggacagactt agacttaaca ggctccttct ctgtgcctaa tgacagatct    2700
ttccagcaga tggcactatg acagtactgc attctacact tgttttttc tagtggggcg    2760 gggcggggag gggggggggt tgtgatcttg aagagttaag taccagagct aagctgagct    2820
ttcttaactc tattggcctt tgtacctgcc tttgaccctc tttgtagtag cgatcccaat    2880
ccaatatcca aagggttttg ggtcttgtat aacagcaggg ttctcctgac ctgatgtcta    2940
ctgttgttcc tctgtcagtc ccctcaactc ctgctttcca tgtggctctg cctgggataa    3000
cacaggcctg ggaccagtga attgtaggga actgagtatt ccagaaatac ctctgtgaaa    3060
gggaaggtgc acctaccact gccttaataa taagggggtg ggagagaggc tgtctcaccc    3120
agcttaggga ccaaatgaga aggcctgaat tcagggggcag ggctctgtgg ggctccttt    3180 ttgatctcta tggcaacaaa atgctaagac tttcttatgc taaaaatatg gataattgct    3240
gttaggtttt aatttgtcag ctctcagact tctaagccag tgatgttagc ctctggggtt    3300
gcttttaaca caaaatcatt taaatacttg aagcctgctt gagtcataaa aggccagtgg    3360
gactctagct cctaagtctg tttgctgctt ctgtaacaat agcacagact aatttgtaaa    3420
gaaaagaggt gtaggctggg tgcactggct cacgcctgta atcccagcac tttgggaggc    3480
cgaggtgggt ggatcacgag gtcagttcaa gaccagcctg gccaacatgg tgaaactctg    3540
tctctactag aaatacaaaa agtagctggg catggtggtg ggtgcctgta atcccagcta    3600
ctcaggaggc tgagacagga gaatcgcttg agcctgggag gcggaggttg cagtgagccg    3660
aggatgcacc actgcactcc agcctgggca acagagcgag cctccatctc aaaaaaacag    3720
aaaagtgtat ttctcacagt tctggaggct gggaatttca agagcatggt gcctgcatca    3780
ggtgggggtc atcccatgtc agaagggcac aaggtagaaa tgagtacatg agacaaaggg    3840
accatgggcc aaacttgctt tataacagcc ctctctcatg ataacctgct gtgtgatagt    3900
gacattaatc cactcatgag ggctctgtcc ttgtgactca gtcacctcgt attaagcccc    3960
atcttcaaca ctgttgcatt gggagtcaaa tttccaatgt gaactttgg gggacacatt    4020 caaaccacag catttctgat tcttccaggc ctagatctca catgatgttg ctgttctcct    4080
```

-continued

```
ggttaccacc cccatcccTT ccccCATCTT ATCCTAGTTT GCTTTCTGGA CCGGGGAAA      4140
agggaaggag gatgcactat ttttaggtag aagctgctgg ctatgaccca gcaccctac      4200
agttattgat ttggcttcta atgtatcttg agaagtgcag tgggtaccgt ttttgttagt    4260
catcctgagg ccatgaactg ggtcttctca tggctggctt ggctccttca gactattata    4320
aatatccaca ggccttgcct ccctgccttc ctctgcttgg tttccttatg tttccatccc    4380
tagctacctt ggccttccta cactcggatc cttccacctc agttcttt ct tgttcttagt    4440
tcctcacata gcctcttgct gggagagaga caatgttgga agtaaggacg tatctaagac    4500
aatttccagt cttactccat ataaggtgat ggtatctagt gagtgacagt tgctgtccgt    4560
gtgtgactca gtgccttctt gttactcatc cctccatacg aggtggttag agtggagaga    4620
agcgggctgt gaacagactc tgggcccagc ttaaggtaaa agaaacttcc ctcaacatct    4680
acctgcacat ggtggctggt ggcgtagggg tgacattgtg atctagatcc tttgccagca    4740
tagttagaat ttccctacca gtcttcagtt ctagaaaaga ttctcacctg atttttgact    4800
tccagtctat gcttctgtat tcactaaggt ggcagcattt cctccctgtt ctttaaactg    4860
ctgtgctctt gacacaggaa ttctgcctgc ttcctcagac tcccaacaac ccccagatag    4920
gagttaccag tagaagcaga ggcttgacct gtgaacttt agtcctggag catatcatga    4980
agggaattga gtaaaaacct gaaggatgga attatatcac agtccctctt ttccgtgtaa    5040
tggaaaggct ttagtgaaaa tcaggcagca acacttggac agtgaaaaga gactctgaaa    5100
ggtgaggtga caggaggtgg cataatggtc attgttaaca tttatgcaag gttggttgta    5160
ggttaggtgt tctaatcgtg tattaagtca caaaatcctc acaacaatcc tctcaagtag    5220
tttattatct ttactttgta aacaaggaaa catatccaaa taagttaaat aattttcccc    5280
ataagcacaa agttagcaag ttagggattc caatccaagt actctcgctt cagatccctt    5340
gatcttaacc ttacctgcct ctcagcacca ccatggaaga caaggccttg gagtcagtga    5400
ggaagtgtca ctttttcctat ccctgtaccc atagctctcc gtagactcag aatttttcca    5460
ctgccatgtc tttgcttatc ttgagtgaca gtgtttgtgg gtgaaccttg aaggtgctct    5520
ttctgctaca agggccctgg gagatagcat gggcatgtgc attgagaagc cagcctcaga    5580
ccttatcttg aagcagcttg aggccagacc tactgtaggc tcagcatctt gctaggaggc    5640
atgggagtga tctaacctgc cagctatctc tcttcctttc ctccttctgc tgatcaaagt    5700
cctgtccttt aagaccctga agctttccta ggtggagttg atctctcttt tcagtattct    5760
ttgtcctctt gtgggtcatc ttactctact tttatttagt aaataaaata attgcaataa    5820
aaattatttt attgaaaact ccattacttg atggttacag cctgatgagg ccagacttgg    5880
atgtctttct catgattgct ttgccttgca catattaaat gtctgtagaa ttgaatgaat    5940
gctgttcatt aaagtgttaa agtcagcacc aggctttcca aaggctgccc cttctaggct    6000
gcttttccca gcagcctcat ccattccttc ctcactccac caggagagaa gatgcagctt    6060
tactctttct gatgttacca tggtagcctg tgatactttc tttctaaagt gctgcttgcc    6120
atccaccaga gactgatgtt tccatggcaa ccaggtgaag gcaatagtca cgagctggat    6180
gcaggaaagg aattccggtc tgagaagctg catatctgaa tcttctagct tcagacatcc    6240
tttcccctct ctcataactt tgcgctttta tatccaggac tggtttgctc tctggtgtgc    6300
ccttggttga gagagctctg tgaaagtgag gtgaagcaga ccaaccaact tagatcacgt    6360
gggaaggtgg gtgcaaggaa agagctgagc aaagatcact tcaaaaagtt ggatgaagtc    6420
tattagttgt tcagatgatc tgctctcaag agcccttaag gagttggctg gagtttctgg    6480
```

```
agagccatta agcagttatt tttgagagca atgggtagat ggatgaggtg cctgaagact   6540
ggaaagcagc cagtcagtgc cggattgtag aaaggagaaa caatgacctt ggaaatcgga   6600
gacccgtcaa acttgccaat gttccagaaa ggatgggagt ttcagtcagc tttcaggcat   6660
caggaagcct acttgcttag aattagtggt gctaagaatt cgcctcctca actcctgagc   6720
ataagcaagc taggggacct ccaccctgta gccgagtgtc acactctgga accacacagc   6780
atggttcaga tccctcttcc ctcacaaact agctgaataa gcttgggtag gttacttcac   6840
ttctctcaca cttcatctgt aaaaaggaaa tgataacacc tatctcatag ggatgttgtg   6900
agaattcatt gagaaaggtt tggaacttgg ctcattactg tcctcagtat tttcactcct   6960
ctggatgcct actcacttga ttttctagct gacttcattc tccccaactt tagagctcaa   7020
ggtttatggg gaaaagcaag ggcagtgcaa tggtgaaaat aaatcttcat ttttaaataa   7080
ataaattgtt cctgcactga agccccaagc ttacaaggtc ttgggtcaca cacaacctgc   7140
ctagttttca ggaaaacaga tcccactagc ccaatctctt tatgcttgag gctctgtcca   7200
catagttaga ttttaaccag atggtttcga aaatcaaaa tgagcccccc tcacaggtac   7260
cttcaaggta cctaacacca ttagctttgt ctggcagggg aaaaatacca gggcactcag   7320
ttttgttttg ttttgagaca gggtctggct ctgttgccca tgctggagta cagtggtgcc   7380
atcacagctc actgcagtct caacctcctg agctcaaatg atcctcttga ttagctggaa   7440
ctacaggtat gtgccactat gcccagctaa gttttgtatt ttttgtagag atggggtctt   7500
gctatgttgc ccaggtggtc ttgaactcct gggcttaagt gatcctccct ccttagcctc   7560
ccaaagtgct aggattatag gtgtgagcca ccacaactgc ctgagagcac cctctgttac   7620
caccctttcc ttagcgtctc agcctccccc aagcacctgt ctttgttggt ctccagagcc   7680
tagccctaca ctggcatttt cctttctgaa taagtatttt ttttatttat ttatttttat   7740
ttttctttg agatggagtt tcgcttttgt tgcccaggct ggagtgcaat ggtgcgatct   7800
cggctcaccg caacctctgc ttcctgggtt caagtgattc tcctgcctca gcctcctgag   7860
tagctgggat tacaggcgtg cgccaccact cccagctaat tttgtatttt tagtggagac   7920
agggtttctc catgttggtc aggctggtct cgaactcctg acctcaggtg atccaccc gc   7980
cttggcctcc caaagtgctg ggattacagt cctgagccac tgcactgggc cttatttatt   8040
tatttttaat taattaatta atttttttg agatggagtc ttgcttttgtc gcccaggctg   8100
gagtgcagtg gcgcaatctc gggtcactgc aagctctgcc tcccaggttc atgccattct   8160
cctgcctcag cctcccaagt agctgggact acaggcacct gccactatgc ccggctaatt   8220
ttttgtattt tttagtagag atggggtttc actgttttag ccaggatggt ttcgatctcc   8280
tgacctagtg atccgctcgc ctcggcctcc cagagtgctg ggattacagg cgtgagccac   8340
tgcgcccggc tgggccttat ttatgtattt ttctgagaca gagtctcatg ctatcaccca   8400
ggctggagtg cagtggcatg atctctgctc actgcgatct ctgctcactt caacctctgc   8460
ttcccgggtt caagtgattc tcccacctca gcctcccgag tagctggaat tacaggcacc   8520
caccaccatg cctggctaat ttttgtaatt ttttttagta gaaatagggt ttaccatgt    8580
tggccaggct ggtctctctc ttgacctcaa gtgatccacc cacctcggcc tcccaaagtg   8640
ctgggattac aggcgtgagc caattgcccg acctgagtaa gtattttaaa tcagcacagg   8700
tcctctgctt aaagtcaagt tgtaatttga acacaaaaat ggaaaatcat gcagtaaaat   8760
accatcgtgg agcttcaatt gccaatctgt cccccaacct tccatcagat gacaaaaccc   8820
```

```
aaaaaagtgt tacccgtgag tcctatggaa ggcacgttgg actttgtaga ccataactta    8880 aattttatc tccaaatggt gctgtgcttt gagagtttag caagctgctt tgatgcctaa     8940
ataaagggcc aggacatagg ttgcaaaagg cattactact tccaccgctt ctctgtataa    9000
tgcttgagaa attacaaaga tctttgctct tttatttagt cctcatgact tcgctataag    9060
gtaggtattc ttcattttag agttgggata gcatagctga gttcagcaaa ccagacaggt    9120
taagagtgac ttcatccaca gaccccatc caggaaacat cctgagcact aattgaaaag     9180
cattcaaggg cttactgaat ttgcattcac atctggagtt ttcaaggcca ctaagctgtg    9240
gaaacttgac atcaatattc aaatagatga aagggaccct taagcatatc catcaggag     9300 tcaccgagat gataaaggcc tgagaagcag tatgctcttg tccggcattt gtgtcctttg    9360
acgactgcac catccaccca aattttgctg ccttctttat aggaagggcc ttttcctcat    9420
gtggtgggct gcccactgtt tcttctctgt gcatttgctc atgtagtttg accacaagga    9480
atgcttttcc ttctttctct caactatcta tagcctacat atcctttaag gcccagtttc    9540
taaaatatgt cttccaaatt tactgtttct tccattcaga attcctggag cacatgaggt    9600
agcccccagt tagatagaat gtggtattgt ttgctgctat tttgcctgtt ttgtgctgta    9660
tcacctcatc catctcccca gcttaattgc aagctatttg acgggcagaa attgtgtctt    9720
atttgtattt gttttcccca ttgggcccgg cacactgatt ggcatattgc agatgtttag    9780
tacttgagag aaacaaaatg tcttctagca tttgtggatg aaagattaaa atgtccagga    9840
aaatttactt agattgatgt ggattgaaac tatattagat taataaaaag atgtgtgtgt    9900
gtgaa                                                                9905
```

<210> SEQ ID NO 11
<211> LENGTH: 83
<212> TYPE: PRT
<213> ORGANISM: Artificial Sequence
<220> FEATURE:
<223> OTHER INFORMATION: Synthetic polypeptide

<400> SEQUENCE: 11

```
Met Arg Leu Tyr Val Gly Ser Leu His Phe Asn Ile Thr Glu Asp Met
1               5                   10                  15

Leu Arg Gly Ile Phe Glu Pro Phe Gly Arg Ile Glu Ser Ile Gln Leu
            20                  25                  30

Met Met Asp Ser Glu Thr Gly Arg Ser Lys Gly Tyr Gly Phe Ile Thr
        35                  40                  45

Phe Ser Asp Ser Glu Cys Ala Lys Glu Ala Leu Glu Gln Leu Asn Gly
    50                  55                  60

Phe Glu Leu Ala Gly Arg Pro Met Lys Val Gly His Val Thr Glu Arg
65                  70                  75                  80

Thr Asp Ala
```

<210> SEQ ID NO 12
<211> LENGTH: 83
<212> TYPE: PRT
<213> ORGANISM: Artificial Sequence
<220> FEATURE:
<223> OTHER INFORMATION: Synthetic polypeptide

<400> SEQUENCE: 12

```
Met Arg Leu Tyr Val Gly Ser Leu His Phe Asn Ile Thr Glu Asp Met
1               5                   10                  15

Leu Arg Gly Ile Phe Glu Pro Phe Gly Arg Ile Glu Ser Ile Gln Leu
```

```
                    20                  25                  30
Met Met Asp Ser Glu Thr Gly Arg Ser Lys Gly Tyr Gly Phe Ile Thr
            35                  40                  45

Phe Ser Asp Ser Glu Cys Ala Lys Lys Ala Leu Glu Tyr Leu Asn Gly
        50                  55                  60

Phe Glu Leu Ala Gly Arg Pro Met Lys Val Gly His Val Thr Glu Arg
65                  70                  75                  80

Thr Asp Ala

<210> SEQ ID NO 13
<211> LENGTH: 83
<212> TYPE: PRT
<213> ORGANISM: Artificial Sequence
<220> FEATURE:
<223> OTHER INFORMATION: Synthetic polypeptide

<400> SEQUENCE: 13

Met Arg Leu Tyr Val Gly Ser Leu His Phe Asn Ile Thr Glu Asp Met
1               5                   10                  15

Leu Arg Gly Ile Phe Glu Pro Phe Gly Arg Ile Glu Ser Ile Gln Leu
            20                  25                  30

Met Met Asp Ser Glu Thr Gly Arg Ser Lys Gly Tyr Gly Phe Ile Thr
        35                  40                  45

Phe Ser Asp Ser Glu Cys Ala Lys Lys Ala Leu Glu Gln Leu Asn Gly
    50                  55                  60

Phe Lys Leu Ala Gly Arg Pro Met Lys Val Gly His Val Thr Glu Arg
65                  70                  75                  80

Thr Asp Ala

<210> SEQ ID NO 14
<211> LENGTH: 83
<212> TYPE: PRT
<213> ORGANISM: Artificial Sequence
<220> FEATURE:
<223> OTHER INFORMATION: Synthetic polypeptide

<400> SEQUENCE: 14

Met Arg Leu Tyr Val Gly Ser Leu His Phe Asn Ile Thr Glu Asp Met
1               5                   10                  15

Leu Arg Gly Ile Phe Glu Pro Phe Gly Arg Ile Glu Ser Ile Gln Leu
            20                  25                  30

Met Met Asp Ser Glu Thr Gly Arg Ser Lys Gly Tyr Gly Phe Ile Thr
        35                  40                  45

Phe Ser Asp Ser Glu Cys Ala Lys Glu Ala Leu Glu Tyr Leu Asn Gly
    50                  55                  60

Phe Glu Leu Ala Gly Arg Pro Met Lys Val Gly His Val Thr Glu Arg
65                  70                  75                  80

Thr Asp Ala

<210> SEQ ID NO 15
<211> LENGTH: 83
<212> TYPE: PRT
<213> ORGANISM: Artificial Sequence
<220> FEATURE:
<223> OTHER INFORMATION: Synthetic polypeptide

<400> SEQUENCE: 15

Met Arg Leu Tyr Val Gly Ser Leu His Phe Asn Ile Thr Glu Asp Met
1               5                   10                  15
```

Leu Arg Gly Ile Phe Glu Pro Phe Gly Arg Ile Glu Ser Ile Gln Leu
              20                  25                  30

Met Met Asp Ser Glu Thr Gly Arg Ser Lys Gly Tyr Gly Phe Ile Thr
                35                  40                  45

Phe Ser Asp Ser Glu Cys Ala Lys Glu Ala Leu Glu Gln Leu Asn Gly
        50                  55                  60

Phe Lys Leu Ala Gly Arg Pro Met Lys Val Gly His Val Thr Glu Arg
65                  70                  75                  80

Thr Asp Ala

<210> SEQ ID NO 16
<211> LENGTH: 83
<212> TYPE: PRT
<213> ORGANISM: Artificial Sequence
<220> FEATURE:
<223> OTHER INFORMATION: Synthetic polypeptide

<400> SEQUENCE: 16

Met Arg Leu Tyr Val Gly Ser Leu His Phe Asn Ile Thr Glu Asp Met
1               5                   10                  15

Leu Arg Gly Ile Phe Glu Pro Phe Gly Arg Ile Glu Ser Ile Gln Leu
              20                  25                  30

Met Met Asp Ser Glu Thr Gly Arg Ser Lys Gly Tyr Gly Phe Ile Thr
                35                  40                  45

Phe Ser Asp Ser Glu Cys Ala Lys Lys Ala Leu Glu Tyr Leu Asn Gly
        50                  55                  60

Phe Lys Leu Ala Gly Arg Pro Met Lys Val Gly His Val Thr Glu Arg
65                  70                  75                  80

Thr Asp Ala

<210> SEQ ID NO 17
<211> LENGTH: 83
<212> TYPE: PRT
<213> ORGANISM: Artificial Sequence
<220> FEATURE:
<223> OTHER INFORMATION: Synthetic polypeptide

<400> SEQUENCE: 17

Met Arg Leu Tyr Val Gly Ser Leu His Phe Asn Ile Thr Glu Asp Met
1               5                   10                  15

Leu Arg Gly Ile Phe Glu Pro Phe Gly Arg Ile Glu Ser Ile Gln Leu
              20                  25                  30

Met Met Asp Ser Glu Thr Gly Arg Ser Lys Gly Tyr Gly Phe Ile Thr
                35                  40                  45

Phe Ser Asp Ser Glu Cys Ala Lys Glu Ala Leu Glu Tyr Leu Asn Gly
        50                  55                  60

Phe Lys Leu Ala Gly Arg Pro Met Lys Val Gly His Val Thr Glu Arg
65                  70                  75                  80

Thr Asp Ala

<210> SEQ ID NO 18
<211> LENGTH: 79
<212> TYPE: PRT
<213> ORGANISM: Artificial Sequence
<220> FEATURE:
<223> OTHER INFORMATION: Synthetic polypeptide

<400> SEQUENCE: 18

```
Met Arg Leu Tyr Val Gly Ser Leu His Phe Asn Ile Thr Glu Asp Met
1               5                   10                  15

Leu Arg Gly Ile Phe Glu Pro Phe Gly Arg Ile Glu Ser Ile Gln Leu
                20                  25                  30

Met Met Asp Ser Glu Thr Gly Arg Ser Lys Gly Tyr Gly Phe Ile Thr
            35                  40                  45

Phe Ser Asp Ser Glu Cys Ala Lys Lys Ala Leu Glu Gln Leu Asn Gly
        50                  55                  60

Phe Glu Leu Ala Gly Arg Pro Met Lys Val Gly His Val Thr Glu
65                  70                  75

<210> SEQ ID NO 19
<211> LENGTH: 79
<212> TYPE: PRT
<213> ORGANISM: Artificial Sequence
<220> FEATURE:
<223> OTHER INFORMATION: Synthetic polypeptide

<400> SEQUENCE: 19

Met Arg Leu Tyr Val Gly Ser Leu His Phe Asn Ile Thr Glu Asp Met
1               5                   10                  15

Leu Arg Gly Ile Phe Glu Pro Phe Gly Lys Ile Asp Asn Ile Val Leu
                20                  25                  30

Met Lys Asp Ser Asp Thr Gly Arg Ser Lys Gly Tyr Gly Phe Ile Thr
            35                  40                  45

Phe Ser Asp Ser Glu Cys Ala Arg Arg Ala Leu Glu Gln Leu Asn Gly
        50                  55                  60

Phe Glu Leu Ala Gly Arg Pro Met Arg Val Gly His Val Thr Glu
65                  70                  75

<210> SEQ ID NO 20
<211> LENGTH: 26
<212> TYPE: PRT
<213> ORGANISM: Homo sapiens

<400> SEQUENCE: 20

His Gly Phe Met Leu His Thr Lys Tyr Gln Val Val Tyr Pro Phe Pro
1               5                   10                  15

Thr Phe Gln Pro Ala Phe Gln Leu Lys Lys
                20                  25

<210> SEQ ID NO 21
<211> LENGTH: 9
<212> TYPE: PRT
<213> ORGANISM: Homo sapiens

<400> SEQUENCE: 21

Trp Leu Val Pro Glu Ser Ser Gly Arg
1               5
```

PROTEIN TAG TO INDUCE LIGAND DEPENDENT DEGRADATION OF PROTEIN/PROTEIN-FUSIONS

RELATED APPLICATIONS

RELATED APPLICATIONS

This application is a National Stage application, filed under 35 U.S.C. § 371, of International Application No. PCT/US2020/051156, filed Sep. 17, 2020, which claims the benefit of priority under 35 U.S.C. § 119 (e) to U.S. Provisional Application No. 62/902,275, filed on Sep. 18, 2019, each of which is incorporated herein by reference in its entirety.

GOVERNMENT LICENSE RIGHTS

This invention was made with government support under grant number R01 CA218278 awarded by the National Institutes of Health. The government has certain rights in the invention.

SEQUENCE LISTING

The instant application contains a Sequence Listing which has been submitted electronically in ASCHII format and is hereby incorporated by reference in its entirety. Said ASCII copy, created on Sep. 17, 2020, is named 52095-6380001WO_ST25.txt and is 74 KB bytes in size.

BACKGROUND OF THE INVENTION

Pharmacologic intervention for many newly discovered disease targets—such as transcription factors, multi-protein complexes or scaffold proteins—is challenging because they lack an enzymatic function to facilitate the design of classical low molecular weight inhibitors. An alternative approach, small molecule-induced protein degradation, circumvents the need for an enzymatic function in the target protein (Salami et al., Science 355:1163-1167 (2017). The therapeutic potential of targeted protein degradation has been demonstrated by the success of thalidomide-related anti-cancer drugs (often referred to as immunomodulatory drugs, or IMiDs). IMiDs bind CRBN, the substrate receptor of the CUL4-RBX1-DDB1-CRBN ($CRL4^{CRBN}$) E3 ubiquitin ligase (Chamberlain et al., Nat. Struct. Mol. Biol., 21:803-809 (2014); Fischer et al., Curr. Opin. Struct. Biol., 37:115-122 (2016); Fischer et al., Nature 512:49-53 (2014); Ito et al., Science 327:1345-1350 (2010)), and generate a novel binding surface to recruit and ubiquitinate neo-substrates (Lu et al., Science 343:305-309 (2014); Kronke et al., Science 343:301-305 (2014); Gandhi et al., Br. J. Haematol., 164:811-821 (2014); Donovan et al., Elife 7:38430 (2018); Sievers et al., Science 362:aat0572 (2018)) Such molecular glues present an opportunity to target virtually any protein for degradation, even in the absence of a defined binding pocket. However, IMiDs have nanomolar affinity for CRBN, and the almost invariable conservation of the drug binding pocket and neo-substrate interaction surface suggests that IMiDs hijack an evolutionarily conserved mechanism, akin to what was found for the plant hormones auxin and jasmonate (Sheard et al., Nature 468:400-405 (2010); Tan et al., Nature 446:640-645 (2007)). Whether molecular glue degraders critically depend on such high affinity interactions, and if these interactions can be achieved for ligases that have not evolved for ligand binding, is of critical importance for the further development of this new therapeutic modality.

Recently, the aryl-sulfonamides E7820, indisulam and tasisulam were shown to induce targeted degradation of the splicing factor RNA Binding Motif Protein 39 (RBM39) through recruitment of the E3 ubiquitin ligase CUL4-RBX1-DDB1-DCAF15 ($CRL4^{DCAF15}$) (Uehara et al., Nat. Chem. Biol., 13:675-680 (2017); Han et al., Science 356:aal3755 (2017)), which suggested a molecular glue mechanism. Indisulam was initially discovered in a phenotypic screen and found to be cytotoxic to specific cancer cell lines and in pre-clinical models (Ozawa et al., Eur. J. Cancer 37:2275-2282 (2001)), while tasisulam and E7820 are derivatives around the sulfonamide core. E7820, indisulam and tasisulam were investigated in multiple phase I and II clinical trials involving advanced-stage solid tumors with a modest number of clinical responses, potentially due to an insufficient understanding of the mechanism of action and lack of informed patient stratification (Han et al., Science 356: aal3755 (2017); Wang et al., Cancer Cell 35:369-384 (2019)). However, novel genetic dependencies in acute myeloid leukemia (AML) suggest a potential for clinical development (Wang et al., Cancer Cell 35:369-384 (2019)), and a recent phase II study encourages development with appropriate biomarkers (Assi et al., Cancer 124:2758-2765 (2018)). Moreover, the aryl-sulfonamides appear to promote binding of deoxyribonucleic acid (DNA) damage binding protein 1 (DDB1) and Cullin-4 (CUL4) associated factor 15 (DCAF15) to the RNA recognition motif (RRM) of RBM39, which suggests that derivatives of the aryl-sulfonamides may be used to target other RRM-containing proteins. However, a detailed picture of the mechanism by which sulfonamides engage $CRL4^{DCAF15}$ to promote turnover of the neo-substrate RBM39 is critically required to further leverage this new class of drugs for the targeting of RBM39, more generally of RRM containing proteins, and for the broad application of molecular glue degraders.

SUMMARY OF THE INVENTION

A first aspect of the present invention is directed to a polypeptide (referred to herein as a degron tag) which is a ribonucleic acid (RNA) recognition motif (RRM), or a variant thereof, present within an RRM-containing protein, e.g., an RNA binding motif (RBM) protein such as RBM23 or RBM39, wherein in the presence of an aryl sulfonamide, the RRM or variant thereof is selectively bound and targeted for degradation by E3 ubiquitin ligase Cullin Really Interesting New Gene (RING) ligase 4 $(CRL4)^{DCAF15}$.

In some embodiments, the RRM is naturally occurring. In other embodiments, the RRM is non-naturally occurring. For example, in some cases, the variant of RRM differs from wild-type RRM at least in terms of at least 1 amino acid substitution. In some aspects, the degron tag, i.e., the variant of RRM, when in the presence of an aryl sulfonamide, is selectively bound and targeted for degradation by E3 ubiquitin ligase $CRL4^{DCAF15}$ to a greater extent than the wild-type RRM or RRM-containing protein, e.g., RBM23 or RBM39. For example, in some embodiments, the degron tag, i.e., the variant of RRM, when in the presence of an aryl sulfonamide, leads to degradation of an RRM or RRM-containing protein, e.g., RBM23 or RBM39, mediated by $CRL4^{DCAF15}$ that is 2-100 fold greater than degradation of the wild-type RRM or RRM-containing protein mediated by $CRL4^{DCAF15}$.

In some cases, the RRM comprises RRM2. For example, the RRM comprises RBM39$_{RRM2}$ or RBM23$_{RRM2}$.

Another aspect of the invention is directed to a fusion protein including a POI and the degron tag. The nucleic acid sequence encoding the degron tag is integrated genomically in-frame in a 5' or 3' orientation with a nucleic acid sequence of a POI, wherein insertion of the nucleic acid encoding the degron tag into the genomic sequence results in a POI-degron tag hybrid protein upon expression. In some embodiments, the degron tag may be located N-terminal to the POI or C-terminal to the POI. In other cases, the degron tag is located within the POI.

Other aspects of the invention are directed to nucleic acid molecules encoding the fusion proteins (as a continuous reading frame), vectors containing the nucleic acid molecules, and cells transformed with the vectors. In some embodiments, the nucleic acid molecule encodes a chimeric antigen receptor (CAR), which includes an extracellular ligand binding domain, a transmembrane domain, and a cytoplasmic domain including at least one intracellular signaling domain, and a degron tag. In some embodiments, the cell is an immune effector cell such as a T-cell transformed with a nucleic acid molecule encoding a CAR-degron tag fusion protein.

A further aspect of the invention is directed to a method of degrading an endogenous or exogenous protein of interest, comprising contacting a cell in vitro or in vivo with an effective amount of an aryl-sulfonamide compound, wherein said protein of interest is endogenous or exogenous to the cell. Thus, the invention further provides a method of degrading an endogenous protein of interest, comprising: contacting a cell in vitro or in vivo with an effective amount of an aryl-sulfonamide compound, wherein the cell expresses the nucleic acid encoding the degron tag in frame with an endogenous nucleic acid encoding an endogenous protein of interest.

The invention further provides a method of degrading an exogenous protein of interest, comprising: contacting a cell in vitro or in vivo with an effective amount of an aryl-sulfonamide compound, wherein the cell expresses a nucleic acid encoding an exogenous protein of interest.

In some embodiments, the method is conducted in vivo with a subject who has previously been treated via gene therapy wherein the therapeutic gene includes the nucleic acid encoding the degon tag in the same reading frame.

In some embodiments, the method is conducted in vivo with a subject who has previously been treated with allogeneic or autologous immune effector cells transformed with a nucleic acid encoding a fusion protein including a chimeric antigen receptor and the degron tag. Any of the inventive methods may entail contacting the cell or administering to the subject an aryl-sulfonamide which is E7820, indisulam, or tasisulam.

The present invention provides a simpler and more widely applicable method for chemical regulation of protein expression at the post-translational level. Advantages over prior methods may include: a) minimal modification of the target protein; b) relatively universal applicability to target proteins and cell types; and c) dose-dependent control by small molecule drugs with proven safety and bioavailability in mammals, and which in many embodiments are FDA-approved or which are in clinical trials.

Presented herein is the cryo-EM structure of the DDB1-DCAF15-DDA1 core ligase complex bound to RBM39 and E7820 at 4.4 Å resolution, together with crystal structures of engineered subcomplexes. DCAF15 adopts a novel fold stabilized by DDA1, and that extensive protein-protein contacts between the ligase and substrate mitigate low affinity interactions between aryl-sulfonamides and DCAF15. The data demonstrated that aryl-sulfonamides neo-functionalize a shallow, non-conserved pocket on DCAF15 to selectively bind and degrade RBM39 and the closely related splicing factor RBM23 without the requirement for a high affinity ligand, which has broad implications for the de novo discovery of molecular glue degraders. Without intending to be bound by any theory of operation, it is believed that aryl-sulfonamides bind DCAF15 forming a complex (DCAF15-aryl-sulfonamide) which has binding specificity for the degron tag sequences. Consequently, degron tag-protein of interest fusion proteins ("degron-POI fusion proteins") become substrates for DCAF15-dependent ubiquitination and degradation. Therefore, the degron tags of the present invention may be useful for targeted degradation of POIs especially in clinical settings.

BRIEF DESCRIPTION OF THE DRAWINGS

FIG. 1A is a graph of time-resolved fluorescence energy transfer (TR-FRET) for the titration of BodipyFL-RBM39$_{RRM2}$ to DDB1ΔB-DCAF15$_{biotin}$ in the presence of E7820 (1, $K_D^{app}$=2.0 μM), indisulam (2, $K_D^{app}$=2.1 μM), or tasisulam (3, $K_D^{app}$=3.5 μM) at 50 μM. FIG. 1B is a graph of TR-FRET for the titration of BodipyFL-E7820 (4) probe to DDB1ΔB-DCAF15$_{biotin}$ or RBM39$_{RRM2\text{-}biotin}$. Compound binding was only observed for DDB1ΔB-DCAF15$_{biotin}$ ($K_D^{app}$=3.8 μM). FIG. 1C is a graph showing the competitive titration of BodipyFL-E7820 (4) with aryl sulfonamides in TR-FRET assay. DDB1ΔB-DCAF15$_{biotin}$ is at 200 nM, BodipyFL-E7820 (4) is at 5 μM, and aryl-sulfonamides are at 0.002-100 μM. TR-FRET data in FIG. 1A-FIG. 1C are plotted as means±s.d. from three independent replicates (n=3). FIG. 1D is a 4.4 Å cryo-EM map of the DDB1ΔB-DCAF15-DDA1-E7820-RBM39$_{RRM2}$ complex segmented to indicate DDA1, DCAF15, RBM39$_{RRM2}$, DDB1-BPC, DDB1-BPA, and DDB1-CTD. FIG. 1E is a Cryo-EM map shown with the fitted and refined model. (Right), close-up of the region of the RBM39-DCAF15 interface, with the resistance mutation site G268V and the putative E7820 density outlined in dotted lines. FIG. 1F is a graph depicting domain representation of the proteins present in the complex. Regions omitted from the constructs are indicated by hatched lines FIG. 2A is a cartoon representation of the DDB1ΔB-DCAF15-DDA1-E7820-RBM39$_{RRM2}$ complex. DDA1, DCAF15-NTD, DCAF15-CTD, RBM39$_{RRM2}$, DDB1-BPC, DDB1-BPA, and DDB1-CTD. E7820 is shown as spheres. (Right) A different view of the complex, shown in transparent surface representation. FIG. 2B is a cartoon representation of DCAF15 indicating secondary structure elements, DCAF15-NTD and DCAF15-CTD. DCAF15 alpha helices and beta strands are numbered from the N- to C-terminus, which are shown as circles for both the NTD and CTD of DCAF15. FIG. 2C is a cartoon view of DCAF15, highlighting the five stacked β-sheets. Helices from the NTD and CTD are also shown.

FIG. 3A is a cartoon representation of the DDB1ΔB-DCAF15$_{split}$-

E7820-RBM39 complex with DDA1 highlighted as a surface representation. DDA1 binds at the top of DDB1-BPA, winds down the back side of the propeller, and ends in a helix buried in DCAF15. FIG. 3B is a cartoon representation of DDB1, DCAF15, and DDA1 according to the conservation scores as calculated in ConSurf (Landau et al., Nucleic Acids Res., 33:299-302 (2005)). The top 3 bins of conservation in ConSurf (high conservation) and the bottom 6 bins (average and variable conservation, shown as "low") are depicted. FIG. 3C is a graph of TR-FRET for the titration of BodipyFL-RBM39$_{RRM2}$ to DDB1ΔB-DCAF15$_{biotin}$ ($K_D^{app}$=1.9 μM) or DDB1ΔB-DCAF15$_{biotin}$-DDA1 ($K_D^{app}$=0.62 μM) in the presence of E7820 (50 μM), demonstrating enhanced recruitment of RBM39$_{RRM2}$ to the DDA1-containing complex. FIG. 3D is a graph of TR-FRET for the titration of E7820 to DDB1ΔB-DCAF15$_{biotin}$ ($EC_{50}$=0.74 μM) or DDB1ΔB-DCAF15$_{biotin}$-DDA1 and BodipyFL-RBM39$_{RRM2}$ ($EC_{50}$=0.33 μM). FIG. 3E is a graph of TR-FRET for the titration of BodipyFL-E7820 to DDB1ΔB-DCAF15$_{biotin}$ ($K_D^{app}$=3.8 μM) or DDB1ΔB-DCAF15$_{biotin}$-DDA1 ($K_D^{app}$=3.8 μM). TR-FRET data in FIG. 3C-FIG. 3E are plotted as means±s.d. from three independent replicates (n=3).

FIG. 4A is a sketch of E7820 and its interactions with DCAF15 and RBM39. Water-mediated hydrogen bonds are highlighted. FIG. 4B shows the chemical structures of E7820 (1), indisulam (2), and tasisulam (3). FIG. 4C is a cartoon representation showing that E7820 interacts predominantly through the sulfonamide moiety and the indole moiety with residues in the DCAF15-NTD. Additional hydrophobic interactions with the DCAF15-CTD, and sulfur-π interaction as well as water-mediated hydrogen bonds with RBM39 stabilize E7820 in a shallow pocket. FIG. 4D is a surface representation of DCAF15 and E7820, indisulam and tasisulam.

FIG. 5A is a surface representation of DCAF15 and RBM39$_{RRM2}$ indicating the extensive interacting interface on DCAF15 and RBM39. E7820 is shown as well. FIG. 5B is a cartoon representation of the side chain interactions between DCAF15, RBM39 and E7820. RBM39 buries a large hydrophobic surface on the DCAF15 α7 helix, in addition to four salt-bridges with DCAF15 on the opposing side of the binding interface. FIG. 5C is a scatter plot depicting identification of the novel E7820 substrate, RBM23, in Kelly cells. Kelly cells were treated with E7820 (10 μM) for 5 hours, and protein abundance was analyzed using TMT quantification mass spectrometry (two-sided moderated t-test as implemented in limma, n=3 for DMSO, n=1 for E7820). FIG. 5D is a graph showing the alignment of the second RRM domain from RBM39 and RBM23. Residues in black are completely conserved, gray shading represents similar substitutions, and white indicates no conservation. Circles above the alignment indicate the positions of resistance mutations in RBM39 for indisulam-dependent toxicity. FIG. 5E is a graph showing the TR-FRET for the titration of E7820 to DDB1ΔB-DCAF15 in the presence of BodipyFL-RBM39$_{RRM2-WT}$ ($EC_{50}$=0.74 μM), BodipyFL-RBM23$_{RRM2-WT}$ ($EC_{50}$=1.0 μM). TR-FRET data is plotted as means±s.d. from three independent replicates (n=3).

FIG. 6A is a model of the CRL4$^{DCAF15}$ ligase bound to E7820 and RBM39$_{RRM2}$. The N- and C-termini of RBM39$_{RRM2}$ (circles) are positioned near RBX1 in the ligase, while RBM39$_{RRM2}$ itself is bound on a non-proximal side face of DCAF15. The DCAF15$_{split}$ crystal structure was superimposed onto the DDB1-DDB2-CUL4A-RBX1 crystal structure (pdb: 4a0k). FIG. 6B is a surface representation showing the evolutionary conservation of DCAF15 (top) and CRBN (bottom). The substrate receptors are represented as a surface, according to the conservation scores as calculated in ConSurf with the top 3 bins of conservation and the bottom 6 bins to highlight the most conserved surfaces (Landau et al., Nucleic Acids Res., 33:299-302 (2005)). DCAF15 is shown bound to E7820 and the α1 helix (residues 262-274) of RBM39$_{RRM2}$, while CRBN is shown bound to lenalidomide and the β-hairpin loop (residues 29-49) of CK1α. Lenalidomide and CK1α both bind in a highly conserved pocket of CRBN.

FIG. 7A is a schematic representation of TR-FRET-based DCAF15-RBM39 dimerization assay. FIG. 7B is a graph of TR-FRET for the titration of BodipyFL-RBM39$_{RRM2}$ (0.02-20 μM) to DDB1ΔB-DCAF15$_{biotin}$ at 200 nM in the absence (DMSO) or presence of aryl-sulfonamides at 50 μM. Data is plotted as means±s.d. from three independent replicates (n=3). FIG. 7C is a graph showing the assessment of E7820 binding to DDB1ΔB-DCAF15$_{biotin}$ using isothermal calorimetry. FIG. 7D is a schematic representation of TR-FRET-based DCAF15 binding assay. Compound 4 is titrated to the DDB1ΔB-DCAF15$_{biotin}$, and the probe is displaced by competitor compounds. FIG. 7E is the chemical structure of BodipyFL-E7820 (4). FIG. 7F is a graph of TR-FRET for the titration of E7820 ($EC_{50}$=0.74 μM), indisulam ($EC_{50}$=3.2 μM) or tasisulam ($EC_{50}$>10 μM) to DDB1ΔB-DCAF15$_{biotin}$ and BodipyFL-RBM39$_{RRM2}$. Data is plotted as means±s.d. from three independent replicates (n=3). FIG. 7G is an immunoblot showing cellular degradation of endogenous RBM39. HEK293T cells were treated with increasing concentrations of E7820 for 6 h, and protein levels were assessed by western blot with fluorescent secondary antibodies. Shown is the uncropped blot with molecular size markers. The positions of RBM39 and GAPDH are indicated, and the asterisk marks a non-specific band. Quantitation of RBM39 and GAPDH bands was performed with the LI-COR imaging system, and % RBM39 is calculated as [RBM39 intensity/GAPDH intensity].

FIG. 8A-FIG. 8H are a series of plots, images, and micrographs showing the Cryo-EM of the 10 Å DDB1-DCAF15-RBM39$_{RRM2}$ complex bound to E7820 and the 4.4 Å DDB1ΔB-DCAF15-DDA1-RBM39$_{RRM2}$ complex bound to E7820. FIG. 8A is a plot of the monodisperse peak of the complex by gel filtration. The bar indicates the fraction used for the Coomassie-stained SDS-PAGE gel, shown to the right of the trace. Gel filtration of the complex was repeated at least three times with similar results. FIG. 8B is a series of images for the reference-free 2D class averages. The class average highlighted with a green box has signal for the three β-propellers of DDB1 and DCAF15, however only β-propellers A and C of DDB1 (outlined with a white hatched line) are aligned well, due to the inherent flexibility of DDB1 β-propeller B and DCAF15. FIG. 8C is a representative cryo-EM micrograph at −2.3 μm defocus. Scale bar indicates 20 nm. Data collection was performed one time on this sample. FIG. 8D is an imaging showing the reconstruction of the complex, highlighting the density for DDB1 β-propeller A, DDB1 β-propeller C, and DCAF15 at an average resolution of 10 Å. FIG. 8E is a plot of the DDB1ΔB-DCAF15-DDA1-RBM39$_{RRM2}$ complex bound to E7820 complex which displays a monodisperse gel filtration peak after BS3 cross-linking. The higher molecular weight cross-linked complex (~180 kDa) is indicated on the SDS-PAGE gel to the right. Cross-linking and gel filtration of this complex was performed at least three times with similar results. FIG. 8F is a representative micrograph of the DDA1-containing complex imaged with a Volta phase plate (VPP) at −1.1 μm defocus. Scale bar represents 20 nm. Data collection was performed on this complex from two independent grids over the course of four imaging sessions. FIG. 8G is a series of images for reference-free 2D class averages. FIG. 8H is a data processing scheme for the crosslinked DDB1ΔB-DCAF15-DDA1-E7820-RBM39$_{RRM2}$ complex. Initial 2D and 3D classification resulted in 923,678 particles for Ctf Refinement and Bayesian polishing. Three subsequent rounds of 3D classification and refinement improved map resolution to a final average resolution of 4.4 Å. Percentages refer to the particles in each class. Density maps indicate the classes that were used for the next round of processing and indicated density maps include 3D refinements.

FIG. 9A is a local resolution map of the final reconstruction calculated using Relion 3.0, colored according to the scale on the right. FIG. 9B is a graph showing Fourier shell correlation (FSC) plots for unmasked and masked maps, as well as phase randomized masked maps. Average resolution is indicated at FSC=0.143. FIG. 9C is an Euler angle distribution of the 4.4 Å reconstruction in two views. FIG. 9D are a series of representations showing the regions of the cryo-EM model for DDA1, DCAF15, and DDB1 shown fit into the density from the sharpened map, demonstrating side chain density for multiple residues. Each density in mesh is shown at a threshold of 0.021 (from Chimera). FIG. 9E is the crystal structure of DDB1ΔB-DCAF15$_{split}$-DDA1-RBM39$_{RRM2}$ bound to E7820 was docked and real space-refined into the unsharpened cryo-EM map of DDB1ΔB-DCAF15-DDA1-RBM39$_{RRM2}$ bound to E7820 using phenix dock in map and phenix real space refine. Shown is the crystal structure (in cartoon) fit into the unsharpened cryo-EM density. The majority of the cryo-EM density is accounted for by the crystal structure, both indicating that the cryo-EM map is also missing the flexible region between the DCAF15 NTD and CTD and that DCAF15$_{split}$ recapitulates the fold of full-length DCAF15. The cryo-EM density is shown at a threshold of 0.0145 (from Chimera). FIG. 9F is a cartoon representation showing the density for E7820 in the sharpened 4.4 Å cryo-EM reconstruction. Shown is the same docked model as in e, and the compound was placed by superimposing the E7820 bound crystal structure demonstrating density for E7820 sandwiched between the DCAF15 NTD, DCAF15 CTD, and RBM39$_{RRM2}$. The sharpened cryo-EM density (B-factor of −129 from relion post processing) is shown at a threshold of 0.0247 (from Chimera).

FIG. 10A is a series of immunoblots showing viruses expressing Strep II-tagged wild type and mutant DCAF15 were co-infected with viruses expressing DDB1ΔB and RBM39$_{RRM2}$ in Hi5 insect cells for 40 hours. STPEP purifications from Hi5 lysate were used to assess the interaction of DCAF15 mutants with DDB1ΔB and RBM39$_{RRM2}$. Unless indicated, infections and pull downs contained E7820. Mutants in the helix-loop-helix (HLH) domain are indicated with cyan text while mutants displaying an RBM39$_{RRM2}$ binding defect, without altering DCAF15 expression levels, are indicated in red. DCAF15 mutant pull downs were performed one time. FIG. 10B is a graph showing limited proteolytic cleavage of the DDB1ΔB-X.t. DCAF15 complex with chymotrypsin followed by gel filtration demonstrates that two DCAF15 fragments, approximately 30 and 35 kDa in size, are associated with DDB1ΔB. Limited proteolysis on this complex was performed at least two times with similar results. FIG. 10C is a plot of disorder prediction in DCAF15 using PrDOS with a 5% false positive rate. The plot indicates an internal region of DCAF15, residues 272-382, that is predicted to be disordered. The table inset to the right indicates that 50% of the internal region is composed of serine, alanine, and proline residues. FIG. 10D is a representative gel filtration trace of the DDB1ΔB-DCAF15$_{split}$-DDA1-RBM39$_{RRM2}$ complex bound to E7820, demonstrating a monodispersed peak. The bar indicates the fraction displayed on the gel to the right of the trace for both b and d. Gel filtration was performed at least three times with this complex with similar results. FIG. 10E is a graph of TR-FRET for the titration of E7820 (0.002-33 μM) to full length DDB1ΔB-DCAF15 at 200 nM or DDB1ΔB-DCAF15$_{split}$ at 200 nM in the presence of BodipyFL-RBM39$_{RRM2}$ at 200 nM. DCAF15-RBM39 dimerization is measured and the data shows equivalent binding for full length DCAF15 and DCAF15$_{split}$. Data is plotted as means±s.d. from three independent replicates (n=3).

FIG. 11A is graphic showing the superposition of the CSA (pdb: 4a11) and DDB2 (pdb: 3ei4) helix-loop-helix (HLH) motif with DCAF15. The DDB1 BPA, BPC, and CTD are shown as a surface representation. FIG. 11B is a cartoon representation of the DCAF15 HLH burying several hydrophobic residues, between DDB1 BPA and BPC. Also shown are three salt bridges (black dotted lines) between DCAF15 E41, R55, and R52 and DDB1 R722, E117, and D137, respectively. FIG. 11C is a graphic showing the overall conservation of DCAF15, shown in surface representation and colored according to the scale on the bottom right. DCAF15 conservation was analyzed by ConSurf (Landau et al., Nucleic Acids Res., 33:299-302 (2005)). DCAF15 sequences were first obtained with phmmer (Potter et al., Nucleic Acids Res., 46:200-204 (2018)) using the full-length human DCAF15 sequence. An alignment of the sequences from phmmer was then used in hmmsearch to obtain more divergent DCAF15 orthologues. Finally, the 356 sequences from hmmsearch were aligned with Clustal Omega (Larkin et al., Bioinformatics 23:2947-2948 (2007)), and the multiple sequence alignment (MSA) was used in ConSurf. Shown in shaded cartoon representation are DDB1-BPA, DDB1-BPC, and DDA1. The black box outlines the E7820 interacting residues shown in FIG. 11D and the dotted box outlines the RBM39 interacting residues shown in FIG. 11E. FIG. 11D is a cartoon representation showing the conservation of the DCAF15 residues that interact with E7820. FIG. 11E is a cartoon representation of the conservation of DCAF15 residues that interact with RBM39$_{RRM2}$.

FIG. 12A is a graphic which shown in mesh is the 2Fo-Fc electron density map for E7820, contoured at 1.0 sigma. FIG. 12L is a graph of TR-FRET for the titration of E7820 (0.002-33 μM) to full length DDB1ΔB-DCAF15 at 200 nM in the presence of BodipyFL-RBM39$_{RRM2-WT}$ (EC$_{50}$=0.74 μM) or BodipyFL-RBM39$_{RRM2-G268V}$ at 200 nM. Data is plotted as means±s.d. from three independent replicates (n=3). FIG. 12N is a cartoon representation showing the network of residues involved in backbone hydrogen bonds between RBM39 and DCAF15 (NTD residues and CTD residues are shown).

FIG. 17A-FIG. 17C are a series of graphs depicting compound-dependent degradation of the designed degron tags fused to enhanced green fluorescence protein (eGFP) with mCherry expression under the same promoter as an internal control. FIG. 17A is a graph of dose-dependent degradation of the designed degron tags with E7820 upon 20-hour treatment. FIG. 17B is a graph of dose-dependent degradation of the designed degron tags with Indisulam upon 20-hour treatment. FIG. 17C is a graph of dose-dependent degradation of the designed degron tags with Tasisulam upon 20-hour treatment.

DETAILED DESCRIPTION OF THE INVENTION

Figure 1A:
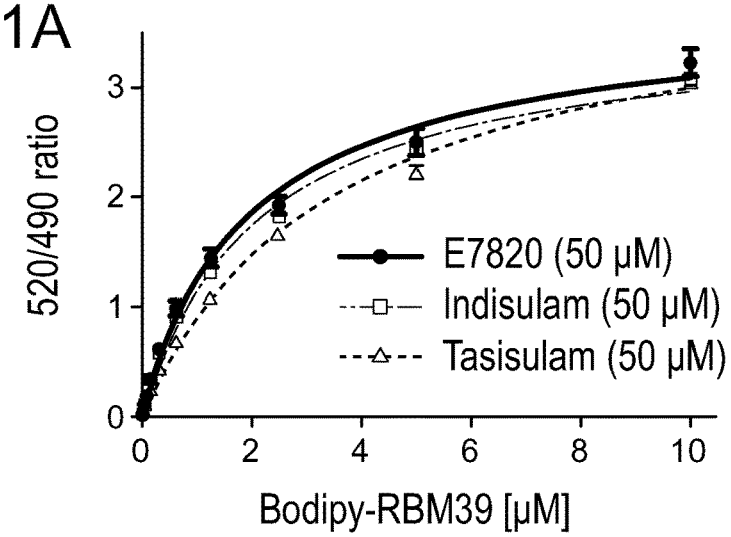
FIG. 1A-FIG. 1F are a series of graphs and cryogenic electron microscopy (Cryo-EM) maps showing the Cryo-EM structure of the DDB1ΔB-DCAF15-DDA1 complex bound to E7820 and RBM39$_{RRM2}$.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless stated otherwise, a "nucleotide sequence encoding an amino acid sequence" includes all nucleotide sequences that are degenerate versions of each other and that encode the same amino acid sequence.

The terms "peptide", "polypeptide", and "protein" are used herein consistent with their art-recognized meanings.

As used herein, the terms "peptide fragments", "protein domains", "peptide domains" and "domains" refer to amino acid sequences that are less than the full protein sequence of any protein mentioned herein. The terms "protein domains", "peptide domains" and "domains" are also more specifically used herein to refer to functional domains known in the art, e.g. zinc-finger domains, extracellular domains, intracellular domains, signaling domains, intracellular signaling domains, cytoplasmic domains and transmembrane domains.

A "vector" is a composition of matter which contains a nucleic acid and which can be used to deliver the nucleic acid to the interior of a cell. Numerous vectors are known in the art including linear polynucleotides, polynucleotides associated with ionic or amphiphilic compounds, plasmids and viruses. Thus, the term "vector" includes an autonomously replicating plasmid or a virus. The term should also be construed to include non-plasmid and non-viral compounds which facilitate transfer of nucleic acid into cells, such as, for example, polylysine compounds and liposomes. Representative examples of viral vectors include adenoviral vectors, adeno-associated virus vectors, lentivirus vectors and retroviral vectors.

Ranges: throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range including both integers and non-integers. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 etc. This applies regardless of the breadth of the range.

Degron Tags

Degron tags of the present invention are a polypeptide (degron tag) which is a ribonucleic acid (RNA) recognition motif (RRM), e.g., RRM2 of RBM39, or a variant thereof present in an RRM-containing protein, e.g., an RBM protein such as RBM23 or RBM39, wherein in the presence of an aryl sulfonamide, the RRM or variant thereof is selectively bound and targeted for degradation by E3 ubiquitin ligase $CRL4^{DCAF15}$.

In some embodiments, the RRM is naturally occurring.

In other cases, the RRM is non-naturally occurring. For example, in some cases, the variant of RRM differs from wild-type RRM, e.g., $RBM39_{RRM2}$ or $RBM23_{RRM2}$, at least in terms of at least 1 amino acid substitution. In some aspects, the degron tag, i.e., the variant of RRM, when in the presence of an aryl sulfonamide, is selectively bound and targeted for degradation by E3 ubiquitin ligase $CRL4^{DCAF15}$ to a greater extent than the wild-type RRM or RRM-containing protein, e.g., RBM23 or RBM39. For example, in some embodiments, the degron tag, i.e., the variant of RRM, when in the presence of an aryl sulfonamide, leads to degradation of an RRM or RRM-containing protein, e.g., RBM23 or RBM39, mediated by $CRL4^{DCAF15}$ that is 2-100 fold greater than degradation of the wild-type RRM or RRM-containing protein mediated by $CRL4^{DCAF15}$.

In some embodiments, the RRM is RRM2.

Thus, in some embodiments, the degron tag differs from $RBM39_{RRM2}$ or $RBM23_{RRM2}$ at least in terms of at least 1 amino acid substitution.

An exemplary human RBM39 (isoform 1) amino acid sequence is set forth below with RRM2 highlighted in bold (SEQ ID NO: 1; GenBank Accession No: NP 909122, Version NP 909122.1, incorporated herein by reference):

```
  1  maddidieam leapykkden klssanghee rskkrkksks rsrsherkrs kskerkrsrd
 61  rerkksksre rkrsrskerr rsrsrsrdrr frgryrspys gpkfnsairg kiglphsikl
121  srrrsrsksp frkdkspvre pidnltpeer dartvfcmql aarirprdle effstvgkvr
181  dvrmisdrns rrskgiayve fvdvssvpla igltgqrvlg vpiivqasqa eknraaaman
241  nlqkgsagpm rlyvgslhfn itedmlrgif epfgriesiq lmmdsetgrs kgygfitfsd
301  secakkaleq lngfelagrp mkvghvtert dassassfld sdelertgid lgttgrlqlm
361  arlaegtglq ippaaqqalq msgslafgav aefsfvidlq trlsqqteas alaaaasvqp
421  latqcfqlsn mfnpqteeev gwdteikddv ieecnkhggv ihiyvdknsa qgnvyvkcps
481  iaaaiaavna lhgrwfagkm itaayvplpt yhnlfpdsmt atqllvpsrr
```

An exemplary human RBM39 (isoform 1) nucleic acid sequence is set forth below (SEQ ID NO: 2; GenBank Accession No: NM 184234, Version NM 184234.3, incorporated herein by reference):

```
  1  atgtgtgctg gtgaatgtga gtacagggaa gcagcggccg ccatttcagg gagcttgtcg
 61  acgctgtcgc aggggtggat cctgagctgc cgaagccgcc gtcctgctct cccgcgtggg
121  cttctctaat tccattgttt tttttagatt ctctcgggcc tagccgtcct tggaacccga
181  tattcgggct gggcggttcc gcggcctggg cctaggggct taacagtagc aacagaagcg
241  gcggcggcgg cagcagcagc agcagcagca gcaatctctt cccgaacacg agcaccacag
301  gcgcccgaag gccggaacag gcgtttagag aaaatggcag acgatattga tattgaagca
361  atgcttgagg ctccttacaa gaaggatgag aacaagttga gcagtgccaa cggccatgaa
421  gaacgtagca aaaagaggaa aaaaagcaag agcagaagtc gtagtcatga acgaaagaga
481  agcaaaagta aggaacgaa gcgaagtaga gacagagaaa ggaaaaagag caaaagccgt
541  gaaagaaagc gaagtagaag caaagagagg cgacggagcc gctcaagaag tcgagatcga
```

-continued

```
 601 agatttagag gccgctacag aagtccttac tccggaccaa aatttaacag tgccatccga
 661 ggaaagattg ggttgcctca tagcatcaaa ttaagcagac gacgttcccg aagcaaaagt
 721 ccattcagaa aagacaagag ccctgtgaga gaacctattg ataatttaac tcctgaggaa
 781 agagatgcaa ggacagtctt ctgtatgcag ctggcggcaa gaattcgacc aagggatttg
 841 gaagagtttt tctctacagt aggaaaggtt cgagatgtga ggatgatttc tgacagaaat
 901 tcaagacgtt ccaaaggaat tgcttatgtg gagttcgtcg atgttagctc agtgcctcta
 961 gcaataggat taactggcca acgagtttta ggcgtgccaa tcatagtaca ggcatcacag
1021 gcagaaaaaa acagagctgc agcaatggca aacaatttac aaaagggaag tgctggacct
1081 atgaggcttt atgtgggctc attacacttc aacataactg aagatatgct tcgtgggatc
1141 tttgagcctt ttggaagaat tgaaagtatc cagctgatga tggacagtga aactggtcga
1201 tccaagggat atggatttat tacattttct gactcagaat gtgccaaaaa ggctttggaa
1261 caacttaatg gatttgaact agcaggaaga ccaatgaaag ttggtcatgt tactgaacgt
1321 actgatgctt cgagtgctag ttcatttttg acagtgatg aactggaaag gactggaatt
1381 gatttgggaa caactggtcg tcttcagtta atggcaagac ttgcagaggg tacaggtttg
1441 cagattccgc cagcagcaca gcaagctcta cagatgagtg gctctttggc atttggtgct
1501 gtggcagaat tctcttttgt tatagatttg caaacaagac tttcccagca gactgaagct
1561 tcagctttag ctgcagctgc ctctgttcag ccacttgcaa cacaatgttt ccaactctct
1621 aacatgttta accctcaaac agaagaagaa gttggatggg ataccgagat taaggatgat
1681 gtgattgaag aatgtaataa acatggagga gttattcata tttatgttga caaaaattca
1741 gctcagggca atgtgtatgt gaagtgccca tcaattgctg cagctattgc tgctgtcaat
1801 gcattgcatg caggtggtt tgctggtaaa atgataacag cagcatatgt acctcttcca
1861 acttaccaca acctgttttcc tgattctatg acagcaacac agctactggt tccaagtaga
1921 cgatgaagga agatatagtc cctatgtat atagctttt ttctttcttg agaattcatc
1981 ttgagttatc ttttatttag ataaaaataa agaggcaagg atctactgtc atttgtatgc
2041 aatttcctgt taccttgaaa aaataaaaat gttaacagga atgcagtgtg ctcattctcc
2101 ctaaatagta aatcccactg tatacaaaac tgttctcttg ttctgccttt taaaatgttc
2161 atgtagaaaa ttaatgaact ataggaatag ctctaggaga acaaatgtgc tttctgtaaa
2221 aaggcagacc agggatgtaa tgttttaat gtttcagaag cctaactttt tacacagtgg
2281 ttacatttca catttcacta atgttgatat ttggctgatg gttgagcagt ttctgaaata
2341 cacatttagt gtatggaaat acaagacagc taaagggctg tttggttagc atctcatctt
2401 gcattctgat caattggcaa gaaagggaga tttcaaaatt atatttcttg atggtatctt
2461 ttcaattaat gtatctgtaa aagtttcttt gtaaatacta tgtgttctgg tgtgtcttaa
2521 aattccaaac aaaatgatcc ctgcatttcc tgaagatgtt taaacgtgag agtctggtag
2581 gcaaagcagt ctgagaaaga aataggaaat gcagaaatag gttttgtctg ttgcatata
2641 atctttgctc tttttaagct ctgtgagctc tgaaatatat ttttgggtta cttcagtgtg
2701 tttgacaaga cagcttgata tttctatcaa acaaatgact ttcatattgc aacaatcttt
2761 gtaagaacca ctcaaataaa agtctcttaa aaaggccaca ggagatcttc attttttcaaa
2821 tgttttaaag ttacagaaat ttgagaacag aattagcttc ttttagtctc aattcagtac
2881 ttgcctcttg ggaaaatgtt ccgagtctgc ggaaacttgc cctcacgttg tcccccatga
2941 attcctttat tctattagag tctagccctg tgtatttag aagaatgtat caaaactgag
3001 gggtttacca aaaagaaaag gaaacagcct ggccttaaaa cctgggcatt cttggtctcc
```

-continued

```
3061  tgcattgtct gggcatattt atgaagaaat tttcaccatt tacaatacat acttaacaaa
3121  atggcttaac ttcaaactgg tttccaaaat tgatttatat attaatatat taaataaggt
3181  gcatatatta ctgtattaag gggttttgag ctttcatact agttgggaag caagctgtca
3241  ccatttatac tcaattctct tcaactgttt atctcttggt aaatcttttg agtaggaaat
3301  gctgctccta gcttatcttc aaatactgag ttccttacct catttgttca acttttttt
3361  ttgttagcat tgaagcacaa gttttacagg cttattcaga atttcatatc agtcgttttg
3421  tttgacattt atcccaataa ttgttctagt gatttaattt gtatggaaac tcccaaggtt
3481  caatttcttt ttcttttga gatggagtct tgctctttgg cccaggctgg agtgcagtga
3541  tgtgatctca gctccatctc ccaggttcaa gcaattctcc cacctcagtc tcctgaagag
3601  ctgggacagg tgcgcaccac cgtgcccagc taattttgt attttagca gagacggtgt
3661  tagcccggct ggtctcacac tgacctcaag tgatctgtcc gccttggcct cccaaagtgc
3721  cgggattaca ggcatgagcc accgcgccca gcctcattga aaatttactt ttcaatacca
3781  gactgcagag ttctttgggg cagagacact ctgtcagtgt gctctttttc caaagtatct
3841  cctgctatca gttttcccc ttgaaccaag tcttcctaac aaatttgttg tgtcattgct
3901  ttctagggaa ctggaccagc aaatgtggcc tttagtggtt aatctcatct gtgccaaaat
3961  ttagttgcta ccagagtgaa atttggtgtg taaataatgt tcagaggaaa tgtggttgga
4021  gtgtagtaac ttgaatagtg tcgtgcatag aaaacagctc attctgagtg aaactgttta
4081  tgtccaatca gttcctgagt cagcatccca ctggttcgaa aatctgtaac taatctggta
4141  atgtccttaa tttcctcctg cctgtcagtg ttccaaagtg ttcatctagt tttcttttat
4201  ctttataata attactacca tcttgaaag ttctgtttaa gaaatgctta atgggcaatg
4261  cgggttagta actccagggt ctgcgtggcc tgggcaggtg agatggacaa ctgcctcatt
4321  acagaagctt tttatcatca aactagtaag ttttgtggag ggcaagctat atagattgtt
4381  gatgagtggt tagaaaatca tctggaattt agccagttga gaagctacag aagtttctat
4441  ttttttttac agtggatgaa ctgttttgct ttttctgata aagccactag gtatatctaa
4501  ataacaacct cgggctggac gtggtgcctt atgcctgtat atgtgaacac tgggaggcgg
4561  aggcgggtgg atcatgaggt caagagtttg agaccagcct ggccaacaca gtgaaacccc
4621  gtctctacta agaatacaaa tttttttgt tttgagacag agtctcgctc tgtcgcccag
4681  gctggagtgc aatggctcga tctcagctca ctgcaacctc caccttctgg gttcaagcga
4741  ttctcctgcc tcagcctccc gagtagctgg gatacaggc gcgtgtcaac acacccggct
4801  taagtttttg tatttttagt agagacgggg tgtcaccgtg ttacccaaga tggtctccat
4861  ctcctgacct tgtgatccac cagcctttgc ctcccaaagt gctgggatta caggcataag
4921  ccaccgcgcc cagcctaaca atacaaaatt tagctaggca tggtggcacg tgcctgttat
4981  cacagctact cgggaggctg aggcaggaga aacgcttgaa cacaggaggc agaagttgcg
5041  gtaagccgag atcgtgccac
```

An exemplary human RBM39 (isoform 2) amino acid sequence is set forth below with RRM2 highlighted in bold (SEQ ID NO: 3; GenBank Accession No: NP 004893, Version NP 004893.1, incorporated herein by reference):

```
  1  maddidieam leapykkden klssanghee rskkrkksks rsrsherkrs kskerkrsrd
 61  rerkksksre rkrsrskerr rsrsrsrdrr frgryrspys gpkfnsairg kiglphsikl
121  srrrsrsksp frkdkspvre pidnltpeer dartvfcmql aarirprdle effstvgkvr
```

```
181  dvrmisdrns rrskgiayve fvdvssvpla igltgqrvlg vpiivqasqa eknraaaman 241  nlqkgsagpm rlyvgslhfn itedmlrgif epfgriesiq lmmdsetgrs kgygfitfsd 301  secakkaleq lngfelagrp mkvghvtert dassassfld sdelertgid lgttgrlqlm 361  arlaegtglq ippaaqqalq msgslafgav adlqtrlsqq teasalaaaa svqplatqcf 421  qlsnmfnpqt eeevgwdtei kddvieecnk hggvihiyvd knsaqgnvyv kcpsiaaaia 481  avnalhgrwf agkmitaayv plptyhnlfp dsmtatqllv psrr
```

An exemplary human RBM39 (isoform 2) nucleic acid sequence is set forth below (SEQ ID NO: 4; GenBank Accession No: NM 004902, Version NM 004902.4, incorporated herein by reference):

```
   1  atgtgtgctg gtgaatgtga gtacagggaa gcagcggccg ccatttcagg gagcttgtcg
  61  acgctgtcgc aggggtggat cctgagctgc cgaagccgcc gtcctgctct cccgcgtggg
 121  cttctctaat tccattgttt tttttagatt ctctcgggcc tagccgtcct tggaacccga
 181  tattcgggct gggcggttcc gcggcctggg cctaggggct taacagtagc aacagaagcg
 241  gcggcggcgg cagcagcagc agcagcagca gcaatctctt cccgaacacg agcaccacag
 301  gcgcccgaag gccggaacag gcgtttagaa aaaatggcag acgatattga tattgaagca
 361  atgcttgagg ctccttacaa gaaggatgag aacaagttga gcagtgccaa cggccatgaa
 421  gaacgtagca aaaagaggaa aaaaagcaag agcagaagtc gtagtcatga acgaaagaga
 481  agcaaaagta aggaacggaa gcgaagtaga gacagagaaa ggaaaaagag caaaagccgt
 541  gaaagaaagc gaagtagaag caaagagagg cgacggagcc gctcaagaag tcgagatcga
 601  agatttagag gccgctacag aagtccttac tccggaccaa aatttaacag tgccatccga
 661  ggaaagattg ggttgcctca tagcatcaaa ttaagcagac gacgttcccg aagcaaaagt
 721  ccattcagaa aagacaagag ccctgtgaga gaacctattg ataatttaac tcctgaggaa
 781  agagatgcaa ggacagtctt ctgtatgcag ctggcggcaa gaattcgacc aagggatttg
 841  gaagagtttt tctctacagt aggaaaggtt cgagatgtga ggatgatttc tgacagaaat
 901  tcaagacgtt ccaaaggaat tgcttatgtg gagttcgtcg atgttagctc agtgcctcta
 961  gcaataggat taactggcca acgagtttta ggcgtgccaa tcatagtaca ggcatcacag
1021  gcagaaaaaa acagagctgc agcaatggca aacaatttac aaaagggaag tgctggacct
1081  atgaggcttt atgtgggctc attacacttc aacataactg aagatatgct tcgtgggatc
1141  tttgagcctt ttggaagaat tgaaagtatc cagctgatga tggacagtga aactggtcga
1201  tccaagggat atggatttat tacattttct gactcagaat gtgccaaaaa ggctttggaa
1261  caacttaatg gatttgaact agcaggaaga ccaatgaaag ttggtcatgt tactgaacgt
1321  actgatgctt cgagtgctag ttcatttttg gacagtgatg aactggaaag gactggaatt
1381  gatttgggaa caactggtcg tcttcagtta atggcaagac ttgcagaggg tacaggtttg
1441  cagattccgc cagcagcaca gcaagctcta cagatgagtg gctctttggc atttggtgct
1501  gtggcagatt tgcaaacaag actttcccag cagactgaag cttcagcttt agctgcagct
1561  gcctctgttc agccacttgc aacacaatgt ttccaactct ctaacatgtt taaccctcaa
1621  acagaagaag aagttggatg ggatccgaga attaaggatg atgtgattga agaatgtaat
1681  aaacatggag gagttattca tatttatgtt gacaaaaatt cagctcaggg caatgtgtat
1741  gtgaagtgcc catcaattgc tgcagctatt gctgctgtca atgcattgca tggcaggtgg
1801  tttgctggta aaatgataac agcagcatat gtacctcttc caacttacca caacctgttt
```

-continued

```
1861  cctgattcta tgacagcaac acagctactg gttccaagta gacgatgaag gaagatatag
1921  tcccttatgt atatagcttt ttttctttct tgagaattca tcttgagtta tcttttattt
1981  agataaaaat aaagaggcaa ggatctactg tcatttgtat gcaatttcct gttaccttga
2041  aaaaataaaa atgttaacag gaatgcagtg tgctcattct ccctaaatag taaatcccac
2101  tgtatacaaa actgttctct tgttctgcct tttaaaatgt tcatgtagaa aattaatgaa
2161  ctataggaat agctctagga gaacaaatgt gctttctgta aaaaggcaga ccagggatgt
2221  aatgttttta atgtttcaga agcctaactt tttacacagt ggttacattt cacatttcac
2281  taatgttgat atttggctga tggttgagca gtttctgaaa tacacattta gtgtatggaa
2341  atacaagaca gctaaagggc tgtttggtta gcatctcatc ttgcattctg atcaattggc
2401  aagaaaggga gatttcaaaa ttatatttct tgatggtatc ttttcaatta atgtatctgt
2461  aaaagtttct ttgtaaatac tatgtgttct ggtgtgtctt aaaattccaa acaaaatgat
2521  ccctgcattt cctgaagatg tttaaacgtg agagtctggt aggcaaagca gtctgagaaa
2581  gaaataggaa atgcagaaat aggttttgtc tggttgcata taatctttgc tctttttaag
2641  ctctgtgagc tctgaaatat attttgggt tacttcagtg tgtttgacaa gacagcttga
2701  tatttctatc aaacaaatga ctttcatatt gcaacaatct ttgtaagaac cactcaaata
2761  aaagtctctt aaaaaggcca caggagatct tcattttca aatgttttaa agttacagaa
2821  atttgagaac agaattagct tcttttagtc tcaattcagt acttgcctct tgggaaaatg
2881  ttccgagtct gcggaaactt gccctcacgt tgtccccat gaattccttt attctattag
2941  agtctagccc tgtgtatttt agaagaatgt atcaaaactg aggggtttac caaaaagaaa
3001  aggaaacagc ctggccttaa aacctgggca ttcttggtct cctgcattgt ctgggcatat
3061  ttatgaagaa attttcacca tttacaatac atacttaaca aaatggctta acttcaaact
3121  ggtttccaaa attgatttat atattaatat attaaataag gtgcatatat tactgtatta
3181  aggggttttg agctttcata ctagttggga agcaagctgt caccatttat actcaattct
3241  cttcaactgt ttatctcttg gtaaatcttt tgagtaggaa atgctgctcc tagcttatct
3301  tcaaatactg agttccttac ctcatttgtt caactttttt ttttgttagc attgaagcac
3361  aagttttaca ggcttattca gaatttcata tcagtcgttt tgtttgacat ttatcccaat
3421  aattgttcta gtgatttaat ttgtatggaa actcccaagg ttcaatttct ttttcttttt
3481  gagatggagt cttgctcttt ggcccaggct ggagtgcagt gatgtgatct cagctccatc
3541  tcccaggttc aagcaattct cccacctcag tctcctgaag agctgggaca ggtgcgcacc
3601  accgtgccca gctaattttt gtattttag cagagacggt gttagcccgg ctggtctcac
3661  actgacctca gtgatctgt ccgccttggc ctcccaaagt gccgggatta caggcatgag
3721  ccaccgcgcc cagcctcatt gaaaatttac ttttcaatac cagactgcag agttctttgg
3781  ggcagagaca ctctgtcagt gtgctctttt tccaaagtat ctcctgctat cagttttcc
3841  ccttgaacca agtcttccta acaaatttgt tgtgtcattg ctttctaggg aactggacca
3901  gcaaatgtgg cctttagtgg ttaatctcat ctgtgccaaa atttagttgc taccagagtg
3961  aaatttggtg tgtaaataat gttcagagga aatgtggttg gagtgtagta acttgaatag
4021  tgtcgtgcat agaaaacagc tcattcgtag tgaaactgtt tatgtccaat cagttcctga
4081  gtcagcatcc cactggttcg aaaatctgta actaatctgg taatgtcctt aatttcctcc
4141  tgcctgtcag tgttccaaag tgttcatcta gtttctttt atctttataa taattactac
4201  catctttgaa agttctgttt aagaaatgct taatgggcaa tgcgggttag taactccagg
```

-continued

```
4261  gtctgcgtgg cctgggcagg tgagatggac aactgcctca ttacagaagc ttttatcat 4321  caaactagta agttttgtgg agggcaagct atatagattg ttgatgagtg gttagaaaat 4381  catctggaat ttagccagtt gagaagctac agaagtttct atttttttt acagtggatg 4441  aactgttttg cttttctga taaagccact aggtatatct aaataacaac ctcgggctgg 4501  acgtggtgcc ttatgcctgt atatgtgaac actgggaggc ggaggcgggt ggatcatgag 4561  gtcaagagtt tgagaccagc ctggccaaca cagtgaaacc ccgtctctac taagaataca 4621  aatttttttt gttttgagac agagtctcgc tctgtcgccc aggctggagt gcaatggctc 4681  gatctcagct cactgcaacc tccaccttct gggttcaagc gattctcctg cctcagcctc 4741  ccgagtagct gggaatacag gcgcgtgtca acacacccgg cttaagtttt tgtattttta 4801  gtagacggg gtgtcaccg tgttacccaa gatggtctcc atctcctgac cttgtgatcc 4861  accagccttt gcctcccaaa gtgctgggat tacaggcata agccaccgcg cccagcctaa 4921  caatacaaaa tttagctagg catggtggca cgtgcctgtt atcacagcta ctcgggaggc 4981  tgaggcagga gaaacgcttg aacacaggag gcagaagttg cggtaagccg agatcgtgcc 5041  ac
```

An exemplary human RBM39 (isoform 3) amino acid sequence is set forth below with RRM2 highlighted in bold (SEQ ID NO: 5; GenBank Accession No: AAI31544, Version AAI31544.1, incorporated herein by reference):

```
  1  maddidieam leapykkden klssanghee rskkrkksks rsrsherkrs kskerkrsrd 61  rerkksksre rkrsrskerr rsrsrsrdrr frgryrspyr rrsrskspfr kdkspvrepi 121  dnltpeerda rtvfcmqlaa rirprdleef fstvgkvrdv rmisdrnsrr skgiayvefv 181  dvssvplaig ltgqrvlgvp iivqasqaek nraaamannl qkgsagpmrl yvgslhfnit 241  edmlrgifep fgriesiqlm mdsetgrskg ygfitfsdse cakkaleqln gfelagrpmk 301  vghvtertda ssassfldsd elertgidlg ttgrlqlmar laegtglqip paaqqalqms 361  gslafgavae fsfvidlqtr lsqqteasal aaaasvqpla tqcfqlsnmf npqteeevgw 421  dteikddvie ecnkhggvih iyvdknsaqg nvyvkcpsia aaiaavnalh grwfagkmit 481  aayvplptyh nlfpdsmtat qllvpsrr
```

An exemplary human RBM39 (isoform 3) nucleic acid sequence is set forth below (SEQ ID NO: 6; GenBank Accession No: NM 001242599, Version NM 001242599.2, incorporated herein by reference):

```
  1  atgtgtgctg gtgaatgtga gtacagggaa gcagcggccg ccatttcagg gagcttgtcg 61  acgctgtcgc aggggtggat cctgagctgc cgaagccgcc gtcctgctct cccgcgtggg 121  cttctctaat tccattgttt tttttagatt ctctcgggcc tagccgtcct tggaacccga 181  tattcgggct gggcggttcc gcggcctggg cctaggggct taacagtagc aacagaagcg 241  gcggcggcgg cagcagcagc agcagcagca gcaatctctt cccgaacacg agcaccacag 301  gcgcccgaag gccggaacag gcgtttagag aaaatggcag acgatattga tattgaagca 361  atgcttgagg ctccttacaa gaaggatgag aacaagttga gcagtgccaa cggccatgaa 421  gaacgtagca aaagaggaa aaaagcaag agcagaagtc gtagtcatga acgaaagaga 481  agcaaaagta aggaacgaaa gcgaagtaga acagagaaa ggaaaaagag caaaagccgt 541  gaaagaaagc gaagtagaag caaagagagg cgacggagcc gctcaagaag tcgagatcga
```

```
 601  agatttagag gccgctacag aagtccttac agacgacgtt cccgaagcaa aagtccattc 661  agaaaagaca agagccctgt gagagaacct attgataatt taactcctga ggaaagagat 721  gcaaggacag tcttctgtat gcagctggcg gcaagaattc gaccaaggga tttggaagag 781  tttttctcta cagtaggaaa ggttcgagat gtgaggatga tttctgacag aaattcaaga 841  cgttccaaag gaattgctta tgtggagttc gtcgatgtta gctcagtgcc tctagcaata 901  ggattaactg ccaacgagt tttaggcgtg ccaatcatag tacaggcatc acaggcagaa 961  aaaaacagag ctgcagcaat ggcaaacaat ttacaaaagg gaagtgctgg acctatgagg 1021  ctttatgtgg gctcattaca cttcaacata actgaagata tgcttcgtgg gatctttgag 1081  cctttttggaa gaattgaaag tatccagctg atgatggaca gtgaaactgg tcgatccaag 1141  ggatatggat ttattacatt ttctgactca gaatgtgcca aaaaggcttt ggaacaactt 1201  aatggatttg aactagcagg aagaccaatg aaagttggtc atgttactga acgtactgat 1261  gcttcgagtg ctagttcatt tttggacagt gatgaactgg aaaggactgg aattgatttg 1321  ggaacaactg gtcgtcttca gttaatggca agacttgcag agggtacagg tttgcagatt 1381  ccgccagcag cacagcaagc tctacagatg agtggctctt tggcatttgg tgctgtggca 1441  gaattctctt ttgttataga tttgcaaaca agactttccc agcagactga agcttcagct 1501  ttagctgcag ctgcctctgt tcagccactt gcaacacaat gtttccaact ctctaacatg 1561  tttaaccctc aaacagaaga agaagttgga tgggataccg agattaagga tgatgtgatt 1621  gaagaatgta ataaacatgg aggagttatt catatttatg ttgacaaaaa ttcagctcag 1681  ggcaatgtgt atgtgaagtg cccatcaatt gctgcagcta ttgctgctgt caatgcattg 1741  catggcaggt ggtttgctgg taaaatgata acagcagcat atgtacctct tccaacttac 1801  cacaacctgt ttcctgattc tatgacagca acacagctac tggttccaag tagacgatga 1861  aggaagatat agtccctat gtatatagct ttttttcttt cttgagaatt catcttgagt 1921  tatcttttat ttagataaaa ataagaggc aaggatctac tgtcatttgt atgcaatttc 1981  ctgttacctt gaaaaaataa aaatgttaac aggaatgcag tgtgctcatt ctccctaaat 2041  agtaaatccc actgtataca aaactgttct cttgttctgc cttttaaaat gttcatgtag 2101  aaaattaatg aactatagga atagctctag gagaacaaat gtgctttctg taaaaaggca 2161  gaccagggat gtaatgtttt taatgtttca gaagcctaac ttttacaca gtggttacat 2221  ttcacatttc actaatgttg atatttggct gatggttgag cagtttctga aatacacatt 2281  tagtgtatgg aaatacaaga cagctaaagg gctgtttggt tagcatctca tcttgcattc 2341  tgatcaattg gcaagaaagg gagatttcaa aattatattt cttgatggta tcttttcaat 2401  taatgtatct gtaaaagttt cctttgtaaat actatgtgtt ctggtgtgtc ttaaaattcc 2461  aaacaaaatg atccctgcat ttcctgaaga tgtttaaacg tgagagtctg gtaggcaaag 2521  cagtctgaga aagaaatagg aaatgcagaa ataggtttg tctggttgca tataatcttt 2581  gctctttta agctctgtga gctctgaaat atattttgg gttacttcag tgtgtttgac 2641  aagacagctt gatatttcta tcaaacaaat gactttcata ttgcaacaat ctttgtaaga 2701  accactcaaa taaagtctc ttaaaaaggc cacaggagat cttcattttt caaatgtttt 2761  aaagttacag aaatttgaga acagaattag cttcttttag tctcaattca gtacttgcct 2821  cttgggaaaa tgttccgagt ctgcggaaac ttgccctcac gttgtccccc atgaattcct 2881  ttattctatt agagtctagc cctgtgtatt ttagaagaat gtatcaaaac tgaggggttt 2941  accaaaaaga aaaggaaaca gcctggcctt aaaacctggg cattcttggt ctcctgcatt
```

```
3001  gtctgggcat atttatgaag aaattttcac catttacaat acatacttaa caaaatggct
3061  taacttcaaa ctggtttcca aaattgattt atatattaat atattaaata aggtgcatat
3121  attactgtat taaggggttt tgagctttca tactagttgg gaagcaagct gtcaccattt
3181  atactcaatt ctcttcaact gtttatctct tggtaaatct tttgagtagg aaatgctgct
3241  cctagcttat cttcaaatac tgagttcctt acctcatttg ttcaactttt tttttttgtta
3301  gcattgaagc acaagtttta caggcttatt cagaatttca tatcagtcgt tttgtttgac
3361  atttatccca ataattgttc tagtgattta atttgtatgg aaactcccaa ggttcaattt
3421  ctttttcttt ttgagatgga gtcttgctct ttggcccagg ctggagtgca gtgatgtgat
3481  ctcagctcca tctcccaggt tcaagcaatt ctcccacctc agtctcctga gagctggga
3541  caggtgcgca ccaccgtgcc cagctaattt ttgtatttt agcagagacg gtgttagccc
3601  ggctggtctc acactgacct caagtgatct gtccgccttg gcctcccaaa gtgccgggat
3661  tacaggcatg agccaccgcg cccagcctca ttgaaaattt acttttcaat accagactgc
3721  agagttcttt ggggcagaga cactctgtca gtgtgctctt tttccaaagt atctcctgct
3781  atcagttttt cccttgaac caagtcttcc taacaaattt gttgtgtcat tgctttctag
3841  ggaactggac cagcaaatgt ggcctttagt ggttaatctc atctgtgcca aaatttagtt
3901  gctaccagag tgaaatttgg tgtgtaaata atgttcagag gaaatgtggt tggagtgtag
3961  taacttgaat agtgtcgtgc atagaaaaca gctcattctg agtgaaactg tttatgtcca
4021  atcagttcct gagtcagcat cccactggtt cgaaaatctg taactaatct ggtaatgtcc
4081  ttaatttcct cctgcctgtc agtgttccaa agtgttcatc tagttttctt ttatctttat
4141  aataattact accatctttg aaagttctgt ttaagaaatg cttaatgggc aatgcgggtt
4201  agtaactcca gggtctgcgt ggcctgggca ggtgagatgg acaactgcct cattacagaa
4261  gctttttatc atcaaactag taagttttgt ggagggcaag ctatatagat tgttgatgag
4321  tggttagaaa atcatctgga atttagccag ttgagaagct acagaagttt ctatttttt
4381  ttacagtgga tgaactgttt tgcttttct gataaagcca ctaggtatat ctaaataaca
4441  acctcgggct ggacgtggtg ccttatgcct gtatatgtga acactgggag gcggaggcgg
4501  gtggatcatg aggtcaagag tttgagacca gcctggccaa cacagtgaaa ccccgtctct
4561  actaagaata caaatttttt ttgttttgag acagagtctc gctctgtcgc ccaggctgga
4621  gtgcaatggc tcgatctcag ctcactgcaa cctccacctt ctgggttcaa gcgattctcc
4681  tgcctcagcc tcccgagtag ctgggaatac aggcgcgtgt caacacaccc ggcttaagtt
4741  tttgtatttt tagtagagac ggggtgtcac cgtgttaccc aagatggtct ccatctcctg
4801  accttgtgat ccaccagcct ttgcctccca aagtgctggg attacaggca taagccaccg
4861  cgcccagcct aacaatacaa aatttagcta ggcatggtgg cacgtgcctg ttatcacagc
4921  tactcgggag gctgaggcag gagaaacgct tgaacacagg aggcagaagt tgcggtaagc
4981  cgagatcgtg ccac
```

An exemplary human RBM23 (isoform 5) amino acid sequence is set forth below with RRM2 highlighted in bold (SEQ ID NO: 7; GenBank Accession No: EAW66226, Version EAW66226.1, incorporated herein by reference):

```
  1    mescsvtqag aqwrvlgslq ppppgfkqfl chslpsswdy rsdrmasddf divieamlea
 61    pykkeedeqq rkevkkdyps nttsstsnsg netsgsstig etsnrsrdrd ryrrrnsrsr
121    spgrqcrhrs rswdrrhgse srsrdhrred rvhyrsppla tgepvdnlsp eerdartvfc
181    mqlaarirpr dledffsavg kvrdvriisd rnsrrskgia yvefceiqsv plaigltgqr
```

```
241    llgvpiivqa sqaeknrlaa mannlqkgng gpmrlyvgsl hfnitedmlr gifepfgkid 301    nivlmkdsdt grskgygfit fsdsecarra leqlngfela grpmrvghvt erldggtdit 361    fpdgdqeldl gsaggrfqlm aklaegagiq lpstaaaaaa aaaqaaalql ngavplgaln 421    paaltalspa lnlasqcfql sslftpqtm
```

An exemplary human RBM23 (isoform 5) nucleic acid sequence is set forth below (SEQ ID NO: 8; GenBank Accession No: NM 001352762, Version NM 001352762.2, incorporated herein by reference):

```
   1   agagctgccg ccattttgcg ggaagaggag gctctgtacc tgcagtgctg cttttcttgc
  61   ctagactcta ggaactatcc gagctccact ccccacaaca tactcaaagg aacggagaga
 121   accgggaccc ccctgcgggg acccggaact ggatggaaga aaacatactc tatgtggatg
 181   agattgagtg gaccttgacc cataagttgg gacatgaaga gagcgtttga aaactaccaa
 241   cctgggccgg gtgcagtggc tcacgcctgt aatcccagca ctttgggtgg ccgaggcggg
 301   cggatcacga ggtcaggaga tcgcgaccat cctggctaac acggcgaaac cccgtctcta
 361   ctaaaaatac aaaaaaaaaa caaaaaagaa gaaaaaagaa aaaactacca gcctgaaaat
 421   gcatagtgtt tgctacctta ttgcttttag cacatctaga aagacactaa acccagtgag
 481   attatctgac aggatggcat ctgatgactt tgacatagtg attgaggcca tgctggaagc
 541   tccctataaa aaagaagagt cgtagtcgag atcgggatcg gtatagacgg agaaatagtc
 601   ggagccgaag tccaggtcgg cagtgtcgtc accgtagccg tagctgggat cgtcgacatg
 661   gtagtgagtc gcgaagtcgg gaccatcgtc gtgaggatcg tgtgcattac aggagtcctc
 721   cacttgccac tggttatagg tatggacaca gtaagagtcc tcatttcaga gagaagagcc
 781   cagtcaggga gccagttgat aatctgagtc ctgaggagcg tgatgcccgc acagttttct
 841   gtatgcagtt agctgcccga attcggcctc gagatctgga ggactttttc tctgctgtag
 901   gcaaggttcg cgatgtacgt atcatctcag atcggaactc acgtcgttct aagggcattg
 961   cctacgtgga attctgtgaa atccagtctg tgccactggc cattgggctg actgggcagc
1021   ggttgctggg agtgcctatc attgtacagg cttcacaggc agagaaaaac cgactggcag
1081   ccatggccaa caacctgcaa aagggcaatg gtggaccaat gcgcctctat gtgggttccc
1141   tgcacttcaa tatcactgaa gacatgctcc ggggcatctt tgagcccttt ggtaaaattg
1201   ataatattgt cctgatgaag gactcagata caggccgctc taaggttat ggtttcatca
1261   cgttctctga ttctgagtgt gcccggcggg ccctggaaca gttgaatggg tttgagcttg
1321   ctggtcgacc tatgagggtt ggccatgtga ctgagcgact ggatggtggc acagacatca
1381   cttttcctga tggggaccag gagctggatc tgggatcagc aggtggacgt tttcagctca
1441   tggcaaaact ggcagaaggc gctgaatcaa actgccaag cactgctgct gctgctgctg
1501   ccgccgccgc ccaggctgct gccttgcaac tgaatggagc agttcccttg ggggccctga
1561   atccagcagc tctgactgct ctgagtccag ccctgaacct tgcctcccag tgtttccagc
1621   tctccagcct ctttaccccc cagaccatgt aaatcagtgg cacagtatac tgcctccttg
1681   tgcctctgga tcctgccact tcacatctac tcttccatgg ccccatttct ccatttgtgt
1741   gaccaagcca tcctgagggc atggacattg tctctgagga aattggggcc acccttaaga
1801   taccaagaaa agctcctgcc catggtccca ctggaaatgg actctgctga gcaaagccac
1861   cagttgaaga gaacagaatc cacacctgca ttgaatacct gttctccat gtgtatcgtc
1921   tctgagatta ccttcttgcc ctttccaaca ccttagtgat tcctcaattt ctccccccatt
```

-continued

```
1981  gggaaggcca tagggcatac tgaaggaact gacctctctc cttttcctgt acctttaacc 2041  tttagtctgt caaggaaaac ccttaggacc tctgaatcaa gaggactgag tttgtgggtg 2101  aaccttgaag gtgctctttc tgctacaagg gccctgggag atagcatgga cgtgcattga 2161  gaagccagcc tcagacctta gcttgaagca gcttgaggcc agacctactg tagcctcagc 2221  atcttgctag gaggcatgga agtgatctat cctgccagga ggcctcagag tgatctgtcc 2281  tgccaggagg tgtgagagtg atctgtcctg tgaggcattt aggggctttc aggaatttag 2341  taaaaggtgg agtatgcctt tccagtatct tccatcttcc tttgtatact tgtccttcct 2401  cccatttcct cccctttggcc cgaggtagga ggatggaggg aggctgctac tctaccactt 2461  cctgtgtgcc tctactgtgg cctcaacccct ggcaattata gctactccca tcccttacct 2521  gggcatgtgt gagcccttct cactggattt tatacccctg tgtctgtgta cataaatata 2581  tatacatata tatatacata aaaactttgt acaaaaggca agcctcctcc ttgtggcagc 2641  tgttgcccat ttgtgtgtgg tctttgttgt gtgtctgaca acttctcatt agcccaactt 2701  atgatgtttc tagggatata aaacattagt aacatcattg tgtttattta tttaaccacc 2761  tttagaaaga aaatgaaaa ctcacacctg gtgggggttc ccattctgta tctgcattac 2821  actgttgatc tatggttgtc ttctccatct atcttcatcc taactatctc catcccagct 2881  acccactgga cagaattacc caaacagcca agttgcagca ccaggacaga cttagactta 2941  acaggctcct tctctgtgcc taatgacaga tcttttccagc agatggcact atgacagtac 3001  tgcattctac acttgttttt ttctagtggg gcggggcggg gagggggggg ggttgtgatc 3061  ttgaagagtt aagtaccaga gctaagctga gctttcttaa ctctattggc ctttgtacct 3121  gcctttgacc ctctttgtag tagcgatccc aatccaatat ccaaaggggt ttgggtcttg 3181  tataacagca gggttctcct gacctgatgt ctactgttgt tcctctgtca gtcccctcaa 3241  ctcctgcttt ccatgtggct ctgcctggga taacacaggc ctgggaccag tgaattgtag 3301  ggaactgagt attccagaaa tacctctgtg aaagggaagg tgcacctacc actgccttaa 3361  taataagggg gtgggagaga ggctgtctca cccagcttag ggaccaaatg agaaggcctg 3421  aattcagggg cagggctctg tggggctcct ttttgatct ctatggcaac aaaatgctaa 3481  gactttctta tgctaaaaat atggataatt gctgttaggt tttaatttgt cagctctcag 3541  acttctaagc cagtgatgtt agcctctggg gttgctttta acacaaaatc atttaaatac 3601  ttgaagcctg cttgagtcat aaaaggccag tgggactcta gctcctaagt ctgtttgctg 3661  cttctgtaac aatagcacag actaatttgt aaagaaaaga ggtgtaggct gggtgcactg 3721  gctcacgcct gtaatcccag cactttggga ggccgaggtg ggtggatcac gaggtcagtt 3781  caagaccagc ctggccaaca tggtgaaact ctgtctctac tagaaataca aaaagtagct 3841  gggcatggtg gtgggtgcct gtaatcccag ctactcagga ggctgagaca ggagaatcgc 3901  ttgagcctgg gaggcggagg ttgcagtgag ccgaggatgc accactgcac tccagcctgg 3961  gcaacagagc gagcctccat ctcaaaaaaa cagaaaagtg tatttctcac agttctggag 4021  gctgggaatt tcaagagcat ggtgcctgca tcaggtgggg gtcatcccat gtcagaaggg 4081  cacaaggtag aaatgagtac atgagacaaa gggaccatgg gccaaacttg ctttataaca 4141  gccctctctc atgataacct gctgtgtgat agtgacatta atccactcat gagggctctg 4201  tccttgtgac tcagtcacct cgtattaagc cccatcttca acactgttgc attgggagtc 4261  aaatttccaa tgtgaacttt tgggggacac attcaaacca cagcatttct gattcttcca 4321  ggcctagatc tcacatgatg ttgctgttct cctggttacc acccccatcc cttcccccat 4381  cttatcctag tttgctttct ggaccggggg aaaagggaag gaggatgcac tattttagg
```

-continued

```
4441   tagaagctgc tggctatgac ccagcacccc tacagttatt gatttggctt ctaatgtatc
4501   ttgagaagtg cagtgggtac cgttttttgtt agtcatcctg aggccatgaa ctgggtcttc
4561   tcatggctgg cttggctcct tcagactatt ataaatatcc acaggccttg cctccctgcc
4621   ttcctctgct tggtttcctt atgtttccat ccctagctac cttgccttc ctacactcgg
4681   atccttccac ctcagttctt tcttgttctt agttcctcac atagcctctt gctgggagag
4741   agacaatgtt ggaagtaagg acgtatctaa gacaatttcc agtcttactc catataaggt
4801   gatggtatct agtgagtgac agttgctgtc cgtgtgtgac tcagtgcctt cttgttactc
4861   atccctccat acgaggtggt tagagtggag agaagcgggc tgtgaacaga ctctgggccc
4921   agcttaaggt aaaagaaact tccctcaaca tctacctgca catggtggct ggtggcgtag
4981   gggtgacatt gtgatctaga tcctttgcca gcatagttag aatttcccta ccagtcttca
5041   gttctagaaa agattctcac ctgattttttg acttccagtc tatgcttctg tattcactaa
5101   ggtggcagca tttcctccct gttctttaaa ctgctgtgct cttgacacag gaattctgcc
5161   tgcttcctca gactcccaac aaccccccaga taggagttac cagtagaagc agaggcttga
5221   cctgtgaact tttagtcctg agcatatca tgaagggaat tgagtaaaaa cctgaaggat
5281   ggaattatat cacagtccct cttttccgtg taatggaaag gctttagtga aaatcaggca
5341   gcaacacttg gacagtgaaa agagactctg aaaggtgagg tgacaggagg tggcataatg
5401   gtcattgtta acatttatgc aaggttggtt gtaggttagg tgttctaatc gtgtattaag
5461   tcacaaaatc ctcacaacaa tcctctcaag tagtttatta tctttacttt gtaaacaagg
5521   aaacatatcc aaataagtta ataattttc cccataagca caaagttagc aagttaggga
5581   ttccaatcca agtactctcg cttcagatcc cttgatctta accttacctg cctctcagca
5641   ccaccatgga agacaaggcc ttggagtcag tgaggaagtg tcacttttcc tatccctgta
5701   cccatagctc tccgtagact cagaattttt ccactgccat gtctttgctt atcttgagtg
5761   acagtgtttg tgggtgaacc ttgaaggtgc tctttctgct acaagggccc tgggagatag
5821   catgggcatg tgcattgaga agccagcctc agaccttatc ttgaagcagc ttgaggccag
5881   acctactgta ggctcagcat cttgctagga ggcatgggag tgatctaacc tgccagctat
5941   ctctcttcct ttcctccttc tgctgatcaa agtcctgtcc tttaagaccc tgaagctttc
6001   ctaggtggag ttgatctctc ttttcagtat tctttgtcct cttgtgggtc atcttactct
6061   acttttattt agtaaataaa ataattgcaa taaaaattat tttattgaaa actccattac
6121   ttgatggtta cagcctgatg aggccagact tggatgtctt tctcatgatt gctttgcctt
6181   gcacatatta aatgtctgta gaattgaatg aatgctgttc attaaagtgt taaagtcagc
6241   accaggcttt ccaaaggctg ccccttctag gctgcttttc ccagcagcct catccattcc
6301   ttcctcactc caccaggaga gaagatgcag ctttactctt tctgatgtta ccatggtagc
6361   ctgtgatact ttctttctaa agtgctgctt gccatccacc agagactgat gtttccatgg
6421   caaccaggtg aaggcaatag tcacgagctg gatgcaggaa aggaattccg gtctgagaag
6481   ctgcatatct gaatcttcta gcttcagaca tcctttcccc tctctcataa cttttgcgct
6541   ttatatccag gactggtttg ctctctggtg tgcccttggt tgagagagct ctgtgaaagt
6601   gaggtgaagc agaccaacca acttagatca cgtgggaagg tgggtgcaag gaaagagctg
6661   agcaaagatc acttcaaaaa gttggatgaa gtctattagt tgttcagatg atctgctctc
6721   aagagccctt aaggagttgg ctggagtttc tggagagcca ttaagcagtt attttttgaga
6781   gcaatgggta gatggatgag gtgcctgaag actggaaagc agccagtcag tgccggattg
```

-continued

```
6841  tagaaaggag aaacaatgac cttggaaatc ggagaccgt  caaacttgcc aatgttccag
6901  aaaggatggg agtttcagtc agctttcagg catcaggaag cctacttgct tagaattagt
6961  ggtgctaaga attcgcctcc tcaactcctg agcataagca agctagggga cctccaccct
7021  gtagccgagt gtcacactct ggaaccacac agcatggttc agatccctct tccctcacaa
7081  actagctgaa taagcttggg taggttactt cacttctctc acacttcatc tgtaaaaagg
7141  aaatgataac acctatctca tagggatgtt gtgagaattc attgagaaag gtttggaact
7201  tggctcatta ctgtcctcag tatttttcact cctctggatg cctactcact tgattttcta
7261  gctgacttca ttctccccaa ctttagagct caaggtttat ggggaaaagc aagggcagtg
7321  caatggtgaa ataaatctt  cattttttaaa taaataaatt gttcctgcac tgaagcccca
7381  agcttacaag gtcttgggtc acacacaacc tgcctagttt tcaggaaaac agatcccact
7441  agcccaatct ctttatgctt gaggctctgt ccacatagtt agattttaac cagatggttt
7501  cgaaaaatca aaatgagccc ccctcacagg taccttcaag gtacctaaca ccattagctt
7561  tgtctggcag gggaaaaata ccagggcact cagttttgtt ttgttttgag acagggtctg
7621  gctctgttgc ccatgctgga gtacagtggt gccatcacag ctcactgcag tctcaacctc
7681  ctgagctcaa atgatcctct tgattagctg gaactacagg tatgtgccac tatgcccagc
7741  taagttttgt attttttgta gagatggggt cttgctatgt tgcccaggtg gtcttgaact
7801  cctgggctta agtgatcctc cctccttagc ctcccaaagt gctaggatta taggtgtgag
7861  ccaccacaac tgcctgagag caccctctgt taccacccttc tccttagcgt ctcagcctcc
7921  cccaagcacc tgtctttgtt ggtctccaga gcctagccct acactggcat tttcctttct
7981  gaataagtat ttttttttatt tatttatttt tattttttct ttgagatgga gtttcgcttt
8041  tgttgcccag gctggagtgc aatggtgcga tctcggctca ccgcaacctc tgcttcctgg
8101  gttcaagtga ttctcctgcc tcagcctcct gagtagctgg gattacaggc gtgcgccacc
8161  actcccagct aatttttgtat ttttagtgga dacagggttt ctccatgttg tcaggctgg
8221  tctcgaactc ctgacctcag gtgatccacc cgccttggcc tcccaaagtg ctgggattac
8281  agtcctgagc cactgcactg ggccttattt atttattttt aattaattaa ttaattttt
8341  ttgagatgga gtcttgcttt gtcgcccagg ctggagtgca gtggcgcaat ctcgggtcac
8401  tgcaagctct gcctcccagg ttcatgccat tctcctgcct cagcctccca agtagctggg
8461  actacaggca cctgccacta tgcccggcta atttttttgta ttttttagta gagatggggt
8521  ttcactgttt tagccaggat ggtttcgatc tcctgaccta gtgatccgct cgcctcggcc
8581  tcccagagtg ctgggattac aggcgtgagc cactgcgccc ggctgggcct tatttatgta
8641  tttttctgag acagagtctc atgctatcac ccaggctgga gtgcagtggc atgatctctg
8701  ctcactgcga tctctgctca cttcaacctc tgcttccgg gttcaagtga ttctcccacc
8761  tcagcctccc gagtagctgg aattacaggc acccaccacc atgcctggct aatttttgta
8821  atttttttta gtagaaatag ggtttcacca tgttggccag gctggtctct ctcttgacct
8881  caagtgatcc acccacctcg gcctcccaaa gtgctgggat tacaggcgtg agccaattgc
8941  ccgacctgag taagtatttt aaatcagcac aggtcctctg cttaaagtca agttgtaatt
9001  tgaacacaaa atgaaaat catgcagtaa ataccatcg tggagcttca attgccaatc
9061  tgtcccccaa ccttccatca gatgacaaaa cccaaaaaag tgttaccgt gagtcctatg
9121  gaaggcacgt tggactttgt agaccataac ttaattttt atctccaaat ggtgctgtgc
9181  tttgagagtt tagcaagctg ctttgatgcc taaataaagg gccaggacat aggttgcaaa
9241  aggcattact acttccaccg cttctctgta taatgcttga gaaattacaa agatctttgc
```

-continued

```
 9301  tcttttattt agtcctcatg acttcgctat aaggtaggta ttcttcattt tagagttggg
 9361  atagcatagc tgagttcagc aaaccagaca ggttaagagt gacttcatcc acagaccccc
 9421  atccaggaaa catcctgagc actaattgaa aagcattcaa gggcttactg aatttgcatt
 9481  cacatctgga gttttcaagg ccactaagct gtggaaactt gacatcaata ttcaaataga
 9541  tgaaaaggga ccttaagcat atccatcagg gagtcaccga gatgataaag gcctgagaag
 9601  cagtatgctc ttgtccggca tttgtgtcct ttgacgactg caccatccac ccaaattttg
 9661  ctgccttctt tataggaagg gcctttcct catgtggtgg gctgcccact gtttcttctc
 9721  tgtgcatttg ctcatgtagt ttgaccacaa ggaatgcttt tccttctttc tctcaactat
 9781  ctatagccta catatccttt aaggcccagt ttctaaaata tgtcttccaa atttactgtt
 9841  tcttccattc agaattcctg gagcacatga ggtagccccc agttagatag aatgtggtat
 9901  tgtttgctgc tattttgcct gttttgtgct gtatcacctc atccatctcc ccagcttaat
 9961  tgcaagctat ttgacgggca gaaattgtgt cttatttgta tttgttttcc ccattgggcc
10021  cggcacactg attggcatat tgcagatgtt tagtacttga gagaaacaaa atgtcttcta
10081  gcatttgtgg atgaaagatt aaaatgtcca ggaaaattta ettagattga tgtggattga
10141  aactatatta gattaataaa aagatgtgtg tgtgtgaa
```

An exemplary human RBM23 (isoform 3) amino acid sequence is set forth below with RRM2 highlighted in bold (SEQ ID NO: 9; GenBank Accession No: EAW66224, Version EAW66224.1, incorporated herein by reference):

```
  1  masddfdivi eamleapykk eedeqqrkev kkdypsntts stsnsgnets gsstigetsn
 61  rsrdrdryrr rnsrsrspgr qcrhrsrswd rrhgsesrsr dhrredrvhy rspplatgep
121  vdnlspeerd artvfcmqla arirprdled ffsavgkvrd vriisdrnsr rskgiayvef
181  ceiqsvplai gltgqrllgv piivqasqae knrlaamann lqkgnggpmr lyvgslhfni
241  tedmlrgife pfgkidnivl mkdsdtgrsk gygfitfsds ecarraleql ngfelagrpm
301  rvghvterld ggtditfpdg dqeldlgsag grfqlmakla egagiqlpst aaaaaaaaaq
361  aaalqlngav plgalnpaal talspalnla sqcfqlsslf tpqtm
```

An exemplary human RBM23 (isoform 3) nucleic acid sequence is set forth below (SEQ ID NO: 10; GenBank Accession No: NM 001077352, Version NM 001077352.2, incorporated herein by reference):

```
  1  agagctgccg ccattttgcg ggaagaggag gctctgtacc tgcagtgctg cttttcttgc
 61  ctagactcta ggaactatcc gagctccact ccccacaaca tactcaaagg aacggagaga
121  accgggaccc ccctgcgggg acccggaact gatctgacag gatggcatct gatgactttg
181  acatagtgat tgaggccatg ctggaagctc cctataaaaa agaagaggat gagcaacaaa
241  ggaaagaagt taaaaaggat tatcctagca ataccaccag cagcaccagc aacagtggca
301  atgagaccag tggaagcagc accatcgggg agacaagcaa tcgtagtcga gatcgggatc
361  ggtatagacg gagaaatagt cggagccgaa gtccaggtcg gcagtgtcgt caccgtagcc
421  gtagctggga tcgtcgacat ggtagtgagt cgcgaagtcg ggaccatcgt cgtgaggatc
481  gtgtgcatta caggagtcct ccacttgcca ctggggagcc agttgataat ctgagtcctg
541  aggagcgtga tgcccgcaca gttttctgta tgcagttagc tgcccgaatt cggcctcgag
```

-continued

```
 601 atctggagga cttttttctct gctgtaggca aggttcgcga tgtacgtatc atctcagatc
 661 ggaactcacg tcgttctaag ggcattgcct acgtggaatt ctgtgaaatc cagtctgtgc
 721 cactggccat tgggctgact gggcagcggt tgctgggagt gcctatcatt gtacaggctt
 781 cacaggcaga gaaaaaccga ctggcagcca tggccaacaa cctgcaaaag gcaatggtg
 841 gaccaatgcg cctctatgtg ggttccctgc acttcaatat cactgaagac atgctccggg
 901 gcatctttga gccctttggt aaaattgata atattgtcct gatgaaggac tcagatacag
 961 gccgctctaa aggttatggt ttcatcacgt tctctgattc tgagtgtgcc cggcgggccc
1021 tggaacagtt gaatgggttt gagcttgctg gtcgacctat gagggttggc catgtgactg
1081 agcgactgga tggtggcaca gacatcactt ttcctgatgg ggaccaggag ctggatctgg
1141 gatcagcagg tggacgtttt cagctcatgg caaaactggc agaaggcgct ggaatccaac
1201 tgccaagcac tgctgctgct gctgctgccg ccgccgccca ggctgctgcc ttgcaactga
1261 atggagcagt tcccttgggg gccctgaatc cagcagctct gactgctctg agtccagccc
1321 tgaaccttgc ctcccagtgt ttccagctct ccagcctctt taccccccag accatgtaaa
1381 tcagtggcac agtatactgc ctccttgtgc ctctggatcc tgccacttca catctactct
1441 tccatggccc catttctcca ttttgtggac caagccatcc tgagggcatg acattgtct
1501 ctgaggaaat tggggccacc cttaagatac caagaaaagc tcctgcccat ggtcccactg
1561 gaaatggact ctgctgagca aagccaccag ttgaagagaa cagaatccac acctgcattg
1621 aatacctgtt tctccatgtg tatcgtctct gagattacct tcttgccctt ccaacacct
1681 tagtgattcc tcaatttctc ccccattggg aaggccatag gcatactga aggaactgac
1741 ctctctcctt ttcctgtacc tttaacctt agtctgtcaa ggaaaaccct taggacctct
1801 gaatcaagag gactgagttt gtgggtgaac cttgaaggtg ctctttctgc tacaagggcc
1861 ctgggagata gcatggacgt gcattgagaa gccagcctca gaccttagct tgaagcagct
1921 tgaggccaga cctactgtag cctcagcatc ttgctaggag gcatggaagt gatctatcct
1981 gccaggaggc ctcagagtga tctgtcctgc caggaggtgt gagagtgatc tgtcctgtga
2041 ggcatttagg ggctttcagg aatttagtaa aaggtggagt atgcctttcc agtatcttcc
2101 atcttccttt gtatacttgt ccttcctccc atttcctccc tttggcccga ggtaggagga
2161 tggagggagg ctgctactct accacttcct gtgtgcctct actgtggcct caaccctggc
2221 aattatagct actcccatcc cttacctggg catgtgtgag cccttctcac tggattttat
2281 acccttgtgt ctgtgtacat aaatatatat acatatatat atacataaaa actttgtaca
2341 aaaggcaagc ctcctccttg tggcagctgt tgcccatttg tgtgtggtct ttgttgtgtg
2401 tctgacaact tctcattagc ccaacttatg atgtttctag ggatataaaa cattagtaac
2461 atcattgtgt ttatttattt aaccacctttt agaagaaaa atgaaaactc acacctgggt
2521 ggggttccca ttctgtatct gcattacact gttgatctat ggttgtcttc tccatctatc
2581 ttcatcctaa ctatctccat cccagctacc cactggacag aattacccaa acagccaagt
2641 tgcagcacca ggacagactt agacttaaca ggctccttct ctgtgcctaa tgcagatct
2701 ttccagcaga tggcactatg acagtactgc attctacact tgttttttc tagtggggcg
2761 gggcgggag ggggggggt tgtgatcttg aagagttaag taccagagct aagctgagct
2821 ttcttaactc tattggcctt tgtacctgcc tttgaccctc tttgtagtag cgatcccaat
2881 ccaatatcca aaggggtttg ggtcttgtat aacagcaggg ttctcctgac ctgatgtcta
2941 ctgttgttcc tctgtcagtc ccctcaactc ctgctttcca tgtggctctg cctgggataa
3001 cacaggcctg ggaccagtga attgtaggga actgagtatt ccagaaatac ctctgtgaaa
```

-continued

```
3061  gggaaggtgc acctaccact gccttaataa taaggggggtg ggagagaggc tgtctcaccc
3121  agcttaggga ccaaatgaga aggcctgaat tcaggggcag ggctctgtgg ggctcctttt
3181  ttgatctcta tggcaacaaa atgctaagac tttcttatgc taaaaatatg gataattgct
3241  gttaggtttt aatttgtcag ctctcagact tctaagccag tgatgttagc ctctggggtt
3301  gcttttaaca caaaatcatt taaatacttg aagcctgctt gagtcataaa aggccagtgg
3361  gactctagct cctaagtctg tttgctgctt ctgtaacaat agcacagact aatttgtaaa
3421  gaaaagaggt gtaggctggg tgcactggct cacgcctgta atcccagcac tttgggaggc
3481  cgaggtgggt ggatcacgag gtcagttcaa gaccagcctg gccaacatgg tgaaactctg
3541  tctctactag aaatacaaaa agtagctggg catggtggtg ggtgcctgta atcccagcta
3601  ctcaggaggc tgagacagga gaatcgcttg agcctgggag gcggaggttg cagtgagccg
3661  aggatgcacc actgcactcc agcctgggca acagagcgag cctccatctc aaaaaaacag
3721  aaaagtgtat ttctcacagt tctggaggct gggaatttca agagcatggt gcctgcatca
3781  ggtggggtc atcccatgtc agaagggcac aaggtagaaa tgagtacatg agacaaaggg
3841  accatgggcc aaacttgctt tataacagcc ctctctcatg ataacctgct gtgtgatagt
3901  gacattaatc cactcatgag ggctctgtcc ttgtgactca gtcacctcgt attaagcccc
3961  atcttcaaca ctgttgcatt gggagtcaaa tttccaatgt gaacttttgg gggacacatt
4021  caaaccacag catttctgat tcttccaggc ctagatctca catgatgttg ctgttctcct
4081  ggttaccacc cccatcccct tccccatctt atcctagttt gctttctgga ccgggggaaa
4141  agggaaggag gatgcactat ttttaggtag aagctgctgg ctatgaccca gcacccctac
4201  agttattgat ttggcttcta atgtatcttg agaagtgcag tgggtaccgt ttttgttagt
4261  catcctgagg ccatgaactg ggtcttctca tggctggctt ggctccttca gactattata
4321  aatatccaca ggccttgcct ccctgccttc ctctgcttgg tttccttatg tttccatccc
4381  tagctacctt ggccttccta cactcggatc cttccacctc agttctttct tgttcttagt
4441  tcctcacata gcctcttgct gggagagaga caatgttgga agtaaggacg tatctaagac
4501  aatttccagt cttactccat ataaggtgat ggtatctagt gagtgacagt tgctgtccgt
4561  gtgtgactca gtgccttctt gttactcatc cctccatacg aggtggttag agtggagaga
4621  agcgggctgt gaacagactc tgggcccagc ttaaggtaaa agaaacttcc ctcaacatct
4681  acctgcacat ggtggctggt ggcgtagggg tgacattgtg atctagatcc tttgccagca
4741  tagttagaat ttccctacca gtcttcagtt ctagaaaaga ttctcacctg attttttgact
4801  tccagtctat gcttctgtat tcactaaggt ggcagcattt cctccctgtt ctttaaactg
4861  ctgtgctctt gacacaggaa ttctgcctgc ttcctcagac tcccaacaac ccccagatag
4921  gagttaccag tagaagcaga ggcttgacct gtgaactttt agtcctggag catatcatga
4981  agggaattga gtaaaaacct gaaggatgga attatatcac agtccctctt ttccgtgtaa
5041  tggaaaggct ttagtgaaaa tcaggcagca acacttggac agtgaaaaga gactctgaaa
5101  ggtgaggtga caggaggtgg cataatggtc attgttaaca tttatgcaag gttggttgta
5161  ggttaggtgt tctaatcgtg tattaagtca caaaatcctc acaacaatcc tctcaagtag
5221  tttattatct ttactttgta aacaaggaaa catatccaaa taagttaaat aattttcccc
5281  ataagcacaa agttagcaag ttagggattc caatccaagt actctcgctt cagatcccct
5341  gatcttaacc ttacctgcct ctcagcacca ccatggaaga caaggccttg gagtcagtga
5401  ggaagtgtca cttttcctat ccctgtaccc atagctctcc gtagactcag aattttttcca
```

-continued

```
5461  ctgccatgtc tttgcttatc ttgagtgaca gtgtttgtgg gtgaaccttg aaggtgctct
5521  ttctgctaca agggccctgg gagatagcat gggcatgtgc attgagaagc cagcctcaga
5581  ccttatcttg aagcagcttg aggccagacc tactgtaggc tcagcatctt gctaggaggc
5641  atgggagtga tctaacctgc cagctatctc tcttcctttc ctccttctgc tgatcaaagt
5701  cctgtccttt aagaccctga agctttccta ggtggagttg atctctcttt tcagtattct
5761  ttgtcctctt gtgggtcatc ttactctact tttatttagt aaataaaata attgcaataa
5821  aaattatttt attgaaaact ccattacttg atggttacag cctgatgagg ccagacttgg
5881  atgtctttct catgattgct ttgccttgca catattaaat gtctgtagaa ttgaatgaat
5941  gctgttcatt aaagtgttaa agtcagcacc aggctttcca aaggctgccc cttctaggct
6001  gcttttccca gcagcctcat ccattccttc ctcactccac caggagagaa gatgcagctt
6061  tactctttct gatgttacca tggtagcctg tgatactttc tttctaaagt gctgcttgcc
6121  atccaccaga gactgatgtt ccatggcaa ccaggtgaag gcaatagtca cgagctggat
6181  gcaggaaagg aattccggtc tgagaagctg catatctgaa tcttctagct tcagacatcc
6241  tttcccctct ctcataactt tgcgctttta tatccaggac tggtttgctc tctggtgtgc
6301  ccttggttga gagagctctg tgaaagtgag gtgaagcaga ccaaccaact tagatcacgt
6361  gggaaggtgg gtgcaaggaa agagctgagc aaagatcact tcaaaaagtt ggatgaagtc
6421  tattagttgt tcagatgatc tgctctcaag agcccttaag gagttggctg gagtttctgg
6481  agagccatta agcagttatt tttgagagca atgggtagat ggatgaggtg cctgaagact
6541  ggaaagcagc cagtcagtgc cggattgtag aaaggagaaa caatgacctt ggaaatcgga
6601  gacccgtcaa acttgccaat gttccagaaa ggatgggagt tcagtcagc tttcaggcat
6661  caggaagcct acttgcttag aattagtggt gctaagaatt cgcctcctca actcctgagc
6721  ataagcaagc taggggacct ccaccctgta gccgagtgtc acactctgga accacacagc
6781  atggttcaga tccctcttcc ctcacaaact agctgaataa gcttgggtag gttacttcac
6841  ttctctcaca cttcatctgt aaaaaggaaa tgataacacc tatctcatag ggatgttgtg
6901  agaattcatt gagaaaggtt tggaacttgg ctcattactg tcctcagtat tttcactcct
6961  ctggatgcct actcacttga ttttctagct gacttcattc tccccaactt tagagctcaa
7021  ggtttatggg gaaaagcaag ggcagtgcaa tggtgaaaat aaatcttcat ttttaaataa
7081  ataaattgtt cctgcactga agccccaagc ttacaaggtc ttgggtcaca cacaacctgc
7141  ctagttttca ggaaaacaga tcccactagc ccaatctctt tatgcttgag gctctgtcca
7201  catagttaga ttttaaccag atggtttcga aaaatcaaaa tgagccccc tcacaggtac
7261  cttcaaggta cctaacacca ttagctttgt ctggcagggg aaaaatacca gggcactcag
7321  ttttgttttg ttttgagaca gggtctggct ctgttgccca tgctggagta cagtggtgcc
7381  atcacagctc actgcagtct caacctcctg agctcaaatg atcctcttga ttagctggaa
7441  ctacaggtat gtgccactat gcccagctaa gttttgtatt ttttgtagag atggggtctt
7501  gctatgttgc ccaggtggtc ttgaactcct gggcttaagt gatcctccct ccttagcctc
7561  ccaaagtgct aggattatag gtgtgagcca ccacaactgc ctgagagcac cctctgttac
7621  caccctttcc ttagcgtctc agcctccccc aagcacctgt ctttgttggt ctccagagcc
7681  tagccctaca ctggcatttt cctttctgaa taagtatttt ttttatttat ttatttttat
7741  tttttctttg agatggagtt tcgcttttgt tgcccaggct ggagtgcaat ggtgcgatct
7801  cggctcaccg caacctctgc ttcctgggtt caagtgattc tcctgcctca gcctcctgag
7861  tagctgggat tacaggcgtg cgccaccact cccagctaat tttgtatttt tagtggagac
```

-continued

```
7921  agggtttctc catgttggtc aggctggtct cgaactcctg acctcaggtg atccacccgc
7981  cttggcctcc caaagtgctg ggattacagt cctgagccac tgcactgggc cttatttatt
8041  tatttttaat taattaatta attttttttg agatggagtc ttgctttgtc gcccaggctg
8101  gagtgcagtg gcgcaatctc gggtcactgc aagctctgcc tcccaggttc atgccattct
8161  cctgcctcag cctcccaagt agctgggact acaggcacct gccactatgc ccggctaatt
8221  ttttgtattt tttagtagag atggggtttc actgttttag ccaggatggt ttcgatctcc
8281  tgacctagtg atccgctcgc ctcggcctcc cagagtgctg ggattacagg cgtgagccac
8341  tgcgcccggc tgggccttat ttatgtattt ttctgagaca gagtctcatg ctatcaccca
8401  ggctggagtg cagtggcatg atctctgctc actgcgatct ctgctcactt caacctctgc
8461  ttcccgggtt caagtgattc tcccacctca gcctcccgag tagctggaat tacaggcacc
8521  caccaccatg cctggctaat ttttgtaatt tttttttagta gaaatagggt ttcaccatgt
8581  tggccaggct ggtctctctc ttgacctcaa gtgatccacc cacctcggcc tcccaaagtg
8641  ctgggattac aggcgtgagc caattgcccg acctgagtaa gtattttaaa tcagcacagg
8701  tcctctgctt aaagtcaagt tgtaatttga acacaaaaat ggaaaatcat gcagtaaaat
8761  accatcgtgg agcttcaatt gccaatctgt cccccaacct tccatcagat gacaaaaccc
8821  aaaaaagtgt tacccgtgag tcctatggaa ggcacgttgg actttgtaga ccataactta
8881  aattttttatc tccaaatggt gctgtgcttt gagagtttag caagctgctt tgatgcctaa
8941  ataaagggcc aggacatagg ttgcaaaagg cattactact tccaccgctt ctctgtataa
9001  tgcttgagaa attacaaaga tctttgctct tttatttagt cctcatgact tcgctataag
9061  gtaggtattc ttcattttag agttgggata gcatagctga gttcagcaaa ccagacaggt
9121  taagagtgac ttcatccaca gaccccatc caggaaacat cctgagcact aattgaaaag
9181  cattcaaggg cttactgaat ttgcattcac atctggagtt ttcaaggcca ctaagctgtg
9241  gaaacttgac atcaatattc aaatagatga aaagggacct taagcatatc catcagggag
9301  tcaccgagat gataaaggcc tgagaagcag tatgctcttg tccggcattt gtgtcctttg
9361  acgactgcac catccaccca aattttgctg ccttctttat aggaagggcc ttttcctcat
9421  gtggtgggct gcccactgtt tcttctctgt gcatttgctc atgtagtttg accacaagga
9481  atgcttttcc ttctttctct caactatcta tagcctacat atcctttaag gcccagtttc
9541  taaaatatgt cttccaaatt tactgtttct tccattcaga attcctggag cacatgaggt
9601  agcccccagt tagatagaat gtggtattgt ttgctgctat tttgcctgtt ttgtgctgta
9661  tcacctcatc catctcccca gcttaattgc aagctatttg acgggcagaa attgtgtctt
9721  atttgtattt gttttcccca ttgggcccgg cacactgatt ggcatattgc agatgtttag
9781  tacttgagag aaacaaaatg tcttctagca tttgtggatg aaagattaaa atgtccagga
9841  aaatttactt agattgatgt ggattgaaac tatattagat taataaaaag atgtgtgtgt
9901  gtgaa
```

In some embodiments, the degron tag differs from the wild-type RRM or RRM-containing protein in terms of at least 1 amino acid substitution at H258, R275, S285, E286, T287, K306, Q310, or E315, or a combination of two or more thereof, when numbered in accordance with SEQ ID NO:1.

In some embodiments, the degron tag compromises a substitution of K306, when numbered in accordance with SEQ ID NO:1.

In certain embodiments, the degron tag compromises a K306E substitution, when numbered in accordance with SEQ ID NO:1.

In certain embodiments, the degron tag compromises a K306L substitution, when numbered in accordance with SEQ ID NO:1.

In certain embodiments, the degron tag compromises a K306T substitution, when numbered in accordance with SEQ ID NO:1.

In certain embodiments, the degron tag compromises a K306A substitution, when numbered in accordance with SEQ ID NO:1.

In some embodiments, the degron tag compromises a substitution of Q310, when numbered in accordance with SEQ ID NO:1.

In certain embodiments, the degron tag compromises a Q310Y substitution, when numbered in accordance with SEQ ID NO:1.

In some embodiments, the degron tag compromises a substitution of E315, when numbered in accordance with SEQ ID NO:1.

In certain embodiments, the degron tag compromises an E315K substitution, when numbered in accordance with SEQ ID NO:1.

In other embodiments, the degron tag comprises a combination of two or more substitutions at K306, Q310 and E315, when numbered in accordance with SEQ ID NO:1.

In some embodiments, the degron tags comprises substitutions at K306 and Q310, when numbered in accordance with SEQ ID NO:1.

In certain embodiments, the degron tag comprises K306E and Q310Y substitutions, when numbered in accordance with SEQ ID NO:1.

In some embodiments, the degron tags comprises substitutions at K306 and E315, when numbered in accordance with SEQ ID NO:1.

In certain embodiments, the degron tag comprises K306E and E315K substitutions, when numbered in accordance with SEQ ID NO:1.

In some embodiments, the degron tags comprises substitutions at Q310 and E315, when numbered in accordance with SEQ ID NO:1.

In certain embodiments, the degron tag comprises Q310Y and E315K substitutions, when numbered in accordance with SEQ ID NO:1.

In some embodiments, the degron tags comprises substitutions at K306, Q310 and E315, when numbered in accordance with SEQ ID NO:1.

In certain embodiments, the degron tag comprises K306E, K306L, K306T, K306A, Q310Y and E315K substitutions, when numbered in accordance with SEQ ID NO:1.

Representative examples of degron tags of the present invention include:

```
                                            (SEQ ID NO: 11)
MRLYVGSLHFNITEDMLRGIFEPFGRIESIQLMMDSETGRSKGYGFITF
SDSECAKEALEQLNGFELAGRPMKVGHVTERTDA, (SEQ ID NO: 12)
MRLYVGSLHFNITEDMLRGIFEPFGRIESIQLMMDSETGRSKGYGFITF
SDSECAKKALEYLNGFELAGRPMKVGHVTERTDA, (SEQ ID NO: 13)
MRLYVGSLHFNITEDMLRGIFEPFGRIESIQLMMDSETGRSKGYGFITF
SDSECAKKALEQLNGFKLAGRPMKVGHVTERTDA, (SEQ ID NO: 14)
MRLYVGSLHFNITEDMLRGIFEPFGRIESIQLMMDSETGRSKGYGFITF
SDSECAKEALEYLNGFELAGRPMKVGHVTERTDA, (SEQ ID NO: 15)
MRLYVGSLHFNITEDMLRGIFEPFGRIESIQLMMDSETGRSKGYGFITF
SDSECAKEALEQLNGFKLAGRPMKVGHVTERTDA, (SEQ ID NO: 16)
MRLYVGSLHFNITEDMLRGIFEPFGRIESIQLMMDSETGRSKGYGFITF
SDSECAKKALEYLNGFKLAGRPMKVGHVTERTDA, (SEQ ID NO: 17)
MRLYVGSLHFNITEDMLRGIFEPFGRIESIQLMMDSETGRSKGYGFITF
SDSECAKEALEYLNGFKLAGRPMKVGHVTERTDA, (SEQ ID NO: 18)
MRLYVGSLHFNITEDMLRGIFEPFGRIESIQLMMDSETGRSKGYGFITF
SDSECAKKALEQLNGFELAGRPMKVGHVTE,
and
                                            (SEQ ID NO: 19)
MRLYVGSLHFNITEDMLRGIFEPFGKIDNIVLMKDSDTGRSKGYGFITF
SDSECARRALEQLNGFELAGRPMRVGHVTE.
```

Fusion Proteins containing Degron Tags

Genetically modified cells carry an inherent and potentially life-long hazard of cancerous transformations. Stem cells administered to regenerate tissues damaged by disease or treatment, correct congenital malformations, or rejuvenate aging tissues may have unknown risks (Mavroudi et al., J. Cancer Res. Ther. 2:22-33 (2014)). Likewise there could be unintended consequences from administering autologous cells modified ex vivo to act as in-patient factories to produce biological molecules, such as insulin, to alleviate the need for repeated injections (Sanlioglu et al., Expert Rev. Mol. Med. 14:e18 (2012)).

Safety switches (e.g., suicide genes) are of particular value in therapies dependent upon long-lived and/or proliferating cells. Moreover, suicide genes should be considered an adjunct to any clinical gene therapy in order to exploit their dual safety and monitoring functions. Many factors govern which suicide gene system is optimal. Among these are the anticipated urgency to rid a patient of the cells, whether it is better to be able to leave non-proliferating genetically modified cells intact or to kill all transduced cells, the overall potency of a particular system, the importance of bystander-cell killing, and immunogenicity.

The ability to degrade a particular endogenous protein of interest by creating POI-degron tag fusions and administering an aryl-sulfonamide can be used to treat disorders wherein expression of a protein above certain threshold levels within the cell leads to a diseased state. Other applications of this technology include 1) targeted degradation of proteins where pathology is a function of gain of function mutation(s), 2) targeted degradation of proteins where pathology is a function of amplification or increased expression, 3) targeted degradation of proteins that are manifestations of monogenetic disease, 4) targeted degradation of proteins where genetic predisposition manifests over longer periods and often after alternative biological compensatory mechanisms are no longer adequate, for example, but not limited to, hypercholesterolemia and proteinopathies. In addition, POI-degron tag fusions can be used to evaluate the function of an endogenous protein or validate an endogenous protein as a target for therapy of a disease state.

Accordingly, the degron tags of the present invention can be utilized to produce a stably expressed endogenous protein-degron tag fusion protein or exogenous protein-degron tag fusion protein. Endogenous proteins originate within an organism, tissue or cell and is expressed by that same organism, tissue or cell, whereas exogenous proteins originate outside of an organism, tissue or cell and are introduced into the organism, tissue or cell. The nucleic acid sequence encoding the degron tag is integrated genomically in-frame in a 5' or 3' orientation with a nucleic acid sequence of an endogenous protein associated with a disease, wherein insertion of the nucleic acid encoding the degron tag into the genomic sequence results in an endogenous protein-degron tag hybrid protein upon expression.

In some embodiments, the degron tag is located N-terminal to the protein of interest.

In some embodiments, the degron tag is located C-terminal to the protein of interest.

Chimeric Antigen Receptor (CAR)-Degron Tag Fusions

Genetically modified T cells expressing chimeric antigen receptors (CAR-T therapy) have shown to have therapeutic efficacy in a number of cancers, including lymphoma (Till et al., Blood 119:3940-3950 (2012)), chronic lymphocytic leukemia (Porter et al., NEJM 365:725-733 (2011)), acute lymphoblastic leukemia (Grupp et al., NEJM 368:1509-1518 (2013)) and neuroblastoma (Louis et al., Blood 118: 6050-6056 (2011)). Two autologous CAR-T cell therapies (Kymriah™ and Yescarta™) have been approved by the FDA. Kymriah™ (tisagenlecleucel) is approved for the treatment of patients up to 25 years of age with B-cell precursor acute lymphoblastic leukemia (ALL) that is refractory or in relapse (R/R) and for the treatment of adults with R/R diffuse large B-cell lymphoma (DLBCL), the most common form of non-Hodgkin's lymphoma, as well as high grade B-cell lymphoma and DLBCL arising from follicular lymphoma. Yescarta™ (axicabtagene ciloleucel) is approved for the treatment of adults with R/R large B cell lymphoma including DLBCL not otherwise specified, primary mediastinal large B-cell lymphoma, high grade B-cell lymphoma, and DLBCL arising from follicular lymphoma. In common, both are CD19-specific CAR-T cell therapies lysing CD19-positive targets (normal and malignant B lineage cells).

CAR-T therapy is not, however, without significant side effects. Although most adverse events with CAR-T are tolerable and acceptable, the administration of CAR-T cells has, in a number of cases, resulted in severe systemic inflammatory reactions, including cytokine release syndrome and tumor lysis syndrome (Xu et al. *Leukemia Lymphoma* 54:255-60 (2013)).

Cytokine release syndrome (CRS) is an inflammatory response clinically manifesting with fever, nausea, headache, tachycardia, hypotension, hypoxia, as well as cardiac and/or neurologic manifestations. Severe cytokine release syndrome is described as a cytokine storm, and can be fatal. CRS is believed to be a result of the sustained activation of a variety of cell types such as monocytes and macrophages, T cells and B cells, and is generally characterized by an increase in levels of TNFα and IFNγ within 1 to 2 hours of stimulus exposure, followed by increases in interleukin (IL)-6 and IL-10 and, in some cases, IL-2 and IL-8 (Doessegger et al., Nat. Clin. Transl. Immuno. 4:e39 (2015)).

Tumor lysis syndrome (TLS) is a metabolic syndrome that is caused by the sudden killing of tumor cells with chemotherapy, and subsequent release of cellular contents with the release of large amounts of potassium, phosphate, and nucleic acids into the systemic circulation. Catabolism of the nucleic acids to uric acid lease to hyperuricemia; the marked increase in uric acid excretion can result in the precipitation of uric acid in the renal tubules and renal vasoconstriction, impaired autoregulation, decreased renal flow, oxidation, and inflammation, resulting in acute kidney injury. Hyperphosphatemia with calcium phosphate deposition in the renal tubules can also cause acute kidney injury. High concentrations of both uric acid and phosphate potentiate the risk of acute kidney injury because uric acid precipitates more readily in the presence of calcium phosphate and vice versa that results in hyperkalemia, hyperphosphatemia, hypocalcemia, uremia, and acute renal failure. It usually occurs in patients with bulky, rapidly proliferating, treatment-responsive tumors (Wintrobe et al., "Complications of hematopoietic neoplasms" Wintrobe's Clinical Hematology, 11$^{th}$ ed., Lippincott Williams & Wilkins, Vol. II, 1919-44 (2003)).

The dramatic clinical activity of CAR-T cell therapy necessitates the need to implement safety strategies to rapidly reverse or abort the T cell responses in patients undergoing CRS or associated adverse events.

Accordingly, the present invention includes fusion proteins that are CARs containing at least one degron tag. The CARs of the present invention are further characterized in that they include an extracellular ligand binding domain capable of binding to an antigen, a transmembrane domain, and an intracellular domain in this order from the N-terminal side, wherein the intracellular domain includes at least one signaling domain. The degron tag(s) can be located at the N-terminus or between the extracellular binding domain and the transmembrane domain, provided that there is no disruption to antigen binding or insertion into the membrane. Similarly, degron tag(s) can be located at the C-terminus, between the transmembrane domain and the intracellular domain or between signaling domains when more than one is present, provided that there is no disruption to intracellular signaling or insertion into the membrane. The degron tag is preferably located at the C-terminus.

In one embodiment, the fusion protein is the CAR used in tisagenlecleucel (Kymriah™) immunotherapy plus a degron tag. Tisagenlecleucel is genetically modified, antigen-specific, autologous T cells that target CD19. The extracellular domain of the CAR is a murine anti-CD19 single chain antibody fragment (scFv) from murine monoclonal FMC63 hybridoma. The intracellular domain of the CAR is a T cell signaling domain derived from human CD3ζ and a co-stimulatory domain derived from human 4-1BB (CD137). The transmembrane domain and a spacer, located between the scFv domain and the transmembrane domain, are derived from human CD8α. The degron tag may be any of the degron tags disclosed herein under the section entitled "Degron Tags".

In one embodiment, the fusion protein is the CAR used in axicabtagene ciloleucel (Yescarta™) immunotherapy plus a degron tag. Axicabtagene ciloleucel is genetically modified, antigen-specific, autologous T cells that target CD19. The extracellular domain of the CAR is a murine anti-CD19 single chain antibody fragment (scFv). The intracellular domain of the CAR is two signaling domains, one derived from human CD3 and one derived from human CD28. The degron tag may be any of the degron tags disclosed herein under the section entitled "Degron Tags".

The present invention provides a nucleic acid encoding a CAR as described herein. The nucleic acid encoding the CAR can be easily prepared from an amino acid sequence of the specified CAR by a conventional method. A base sequence encoding an amino acid sequence can be readily obtained from, for example, the aforementioned amino acid sequences or publicly available reference sequences, for example, NCBI RefSeq IDs or accession numbers of GenBank, for an amino acid sequence of each domain, and the nucleic acid of the present invention can be prepared using a standard molecular biological and/or chemical procedure. RefSeq IDs for commonly used CAR domains are known in the art, for example, U.S. Pat. No. 9,175,308 discloses a number of specific amino acid sequences particularly used as CAR transmembrane and intracellular signaling domains. As one example, based on the base sequence, a nucleic acid can be synthesized, and the nucleic acid of the present invention can be prepared by combining DNA fragments which are obtained from a cDNA library using a polymerase chain reaction (PCR).

Immune effector cells expressing the CAR of the present invention can be engineered by introducing the nucleic acid encoding a CAR described above into a cell. In one embodiment, the step is carried out ex vivo. For example, a cell can be transformed ex vivo with a vector carrying the nucleic acid of the present invention to produce a cell expressing the CAR of the present invention.

Representative examples of immune effector cells include cytotoxic lymphocytes, T-cells, cytotoxic T-cells, T helper cells, Th17 T-cells, natural killer (NK) cells, natural killer T (NKT) cells, mast cells, dendritic cells, killer dendritic cells, or B cells derived from a mammal, for example, a human cell, or a cell derived from a non-human mammal such as a monkey, a mouse, a rat, a pig, a horse, or a dog. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell (a dendritic cell, a B cell, a hematopoietic stem cell, a macrophage, a monocyte, a NK cell or a hematopoietic cell (a neutrophil, a basophil)), an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present invention, use of a T-cell, a precursor cell of a T-cell (a hematopoietic stem cell, a lymphocyte precursor cell etc.) or a cell population containing them is preferable. Representative examples of T-cells include CD8-positive T-cells, CD4-positive T-cells, regulatory T-cells, cytotoxic T-cells, and tumor infiltrating lymphocytes. The cell population containing a T-cell and a precursor cell of a T-cell includes a PBMC. The aforementioned cells may be collected from a living body, obtained by expansion culture of a cell collected from a living body, or established as a cell strain. When transplantation of the produced CAR-expressing cell or a cell differentiated from the produced CAR-expressing cell into a living body is desired, it is preferable to introduce the nucleic acid into a cell collected from the living body itself or a conspecific living body thereof. Thus, the immune effector cells may be autologous or allogeneic.

The cell expressing the CAR can be used as a therapeutic agent for a disease. The therapeutic agent can be the cell expressing the CAR as an active ingredient, and may further include a suitable excipient. The disease against which the cell expressing the CAR is administered is not limited as long as the disease shows sensitivity to the cell. Representative examples of diseases treatable with cells expressing CARs of the present invention include a cancer (blood cancer (leukemia), solid tumor, etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis. The cell expressing the CAR of the present invention that binds to an antigen possessed by a cell that is desired to be decreased or eliminated for treatment of the aforementioned diseases, that is, a tumor antigen, a viral antigen, a bacterial antigen or the like is administered for treatment of these diseases. The cell of the present invention can also be utilized for prevention of an infectious disease after bone marrow transplantation or exposure to radiation, donor lymphocyte transfusion for the purpose of remission of recurrent leukemia, and the like. The therapeutic agent including the cell expressing the CAR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

In one embodiment, the antigen binding moiety portion of the CAR of the invention is designed to treat a particular cancer. For example, a CAR designed to target CD19 can be used to treat cancers and disorders including pre-B ALL (pediatric indication), adult ALL, mantle cell lymphoma, diffuse large B-cell lymphoma, and salvage post allogenic bone marrow transplantation.

When "an immunologically effective amount", "an anti-tumor effective amount", "a tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). In some embodiments, the CAR expressing cells described herein may be administered at a dosage of $10^4$ to $10^9$ cells/kg body weight, preferably $10^5$ to $10^6$ cells/kg body weight, including all integer and non-integer values within those ranges. T-cell compositions may also be administered multiple times at these dosages. The cells can be administered by using infusion techniques that are commonly known in immunotherapy (see, e.g., Rosenberg et al., New Eng. J. of Med. 319:1676 (1988)). The optimal dosage and treatment regime for a particular patient can readily be determined by one skilled in the art of medicine by monitoring the patient for signs of disease and adjusting the treatment accordingly.

The administration of the CAR expressing cells may be carried out in any convenient manner, including by aerosol inhalation, injection, ingestion, transfusion, implantation or transplantation. The CAR expressing cells described herein may be administered to a patient subcutaneously, intradermally, intratumorally, intranodally, intramedullary, intramuscularly, by intravenous (i. v.) injection, or intraperitoneally. In one embodiment, the CAR expressing cells of the present invention are administered to a patient by intradermal or subcutaneous injection. In another embodiment, the CAR expressing cells of the present invention are preferably administered by i.v. injection. The CAR expressing cells may be injected directly into a tumor, lymph node, or site of infection.

Further features of CAR proteins, nucleic acids encoding CAR proteins, immune effector cells expressing CARs and methods of using CAR expressing cells for the treatment of diseases are disclosed in US Patent Application Publication 2018/0169109.

Endogenous POIs-Degron Tag Fusions

In certain embodiments, a nucleic acid encoding a degron tag can be genomically inserted in-frame with a gene encoding a protein that is involved in a disorder. Representative examples of particular genes involved in disorders that may be targeted for degron tag insertion include alpha-1 antitrypsin (A1AT), apolipoprotein B (apoB), angiopoietin-like protein 3 (ANGPTL3), proprotein convertase subtilisin/kexin type 9 (PCSK9), apolipoprotein C3 (APOC3), catenin (CTNNB1), low density lipoprotein receptor (LDLR), C-reactive protein (CRP), apolipoprotein a (Apo(a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule 1 (ICAM-1), glucagon receptor (GCGR), glucocorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystrophia myotonic protein kinase (DMPK), cellular nucleic acid-binding protein (CNBP or ZNF9), clusterin (CLU), eukaryotic translation initiation factor 4E (eIF-4e), MDM2, MDM4, heat shock protein 27 (HSP 27), signal transduction and activator of transcription 3 protein (STAT3), vascular endothelial growth factor (VEGF), kinesin spindle protein (KIF11), hepatitis B genome, the androgen receptor (AR), Atonal homolog 1 (ATOH1), vascular endothelial growth factor receptor 1 (FLT1), retinoschism 1 (RS1), retinal pigment epithelium-specific 65 kDa protein (RPE65), Rab escort protein 1 (CHM), and the sodium channel, voltage gated, type X, alpha subunit (PN3 or SCN10A). Additional proteins of interest that may be targeted by degron tag insertion include proteins associated with gain of function mutations, for example, cancer causing proteins.

In particular embodiments, the protein of interest is apoB-100, ANGPTL3, PCSK9, APOC3, CRP, ApoA, Factor XI, Factor VII, antithrombin III, phosphatidylinositol glycan class A (PIG-A), the C5 component of complement, Alpha-1-antitrypsin (A1AT), TMPRSS6, ALAS-1, DGAT-2, KLB1, CCN2, ICAM, glucagon receptor, glucocorticoid receptor, PTP-1B, FGFR4, VCAM-1, VLA-4, GCCR, TTR, SMN1, GHR, DMPK, or sodium channel isoform Nav1.8.

In one embodiment, the degron tag is genomically integrated in-frame, either 5' or 3', into the gene encoding for an endogenous protein associated with a proteopathy. In one embodiment the degron tag is genomically integrated in-frame, either 5' or 3', into the gene encoding for an endogenous protein associated with a disorder such as Alzheimer's disease (Amyloid peptide (Aβ); Tau protein), Cerebral β-amyloid angiopathy (Amyloid β peptide (ADA Retinal ganglion cell degeneration in glaucoma (Amyloid β peptide (ADA Prion diseases (Prion protein), Parkinson's disease and other synucleinopathies (α-Synuclein), Tauopathies (Microtubule-associated protein tau (Tau protein)), Frontotemporal lobar degeneration (FTLD) (Ubi+, Tau−) (TDP-43), FTLD-FUS (Fused in sarcoma (FUS) protein), Amyotrophic lateral sclerosis (ALS) (Superoxide dismutase, TDP-43, FUS), Huntington's disease and other triplet repeat disorders (Proteins with tandem glutamine expansions), Familial British dementia (ABri), Familial Danish dementia (Adan), Hereditary cerebral hemorrhage with amyloidosis (Icelandic) (HCHWA-I) (Cystatin C), CADASIL (Notch3), Alexander disease (Glial fibrillary acidic protein (GFAP)), Seipinopathies (Seipin), Familial amyloidotic neuropathy, Senile systemic amyloidosis (Transthyretin), Serpinopathies (Serpins), AL (light chain) amyloidosis (primary systemic amyloidosis) (Monoclonal immunoglobulin light chains), AH (heavy chain) amyloidosis (Immunoglobulin heavy chains), AA (secondary) amyloidosis (Amyloid A protein), Type II diabetes (Islet amyloid polypeptide (IAPP; amylin)), Aortic medial amyloidosis (Medin (lactadherin)), ApoAI amyloidosis (Apolipoprotein AI), ApoAII amyloidosis (Apolipoprotein AII), ApoAIV amyloidosis (Apolipoprotein AIV), Familial amyloidosis of the Finnish type (FAF) (Gelsolin), Lysozyme amyloidosis (Lysozyme), Fibrinogen amyloidosis (Fibrinogen), Dialysis amyloidosis (Beta-2 microglobulin), Inclusion body myositis/myopathy (Amyloid β peptide (ADA Cataracts (Crystallins), Retinitis pigmentosa with rhodopsin mutations (rhodopsin), Medullary thyroid carcinoma (Calcitonin), Cardiac atrial amyloidosis (Atrial natriuretic factor), Pituitary prolactinoma (Prolactin), Hereditary lattice corneal dystrophy (Keratoepithelin), Cutaneous lichen amyloidosis (Keratins), Mallory bodies (Keratin intermediate filament proteins), Corneal lactoferrin amyloidosis (Lactoferrin), Pulmonary alveolar proteinosis (Surfactant protein C (SP-C)), Odontogenic (Pindborg) tumor amyloid (Odontogenic ameloblast-associated protein), Seminal vesicle amyloid (Semenogelin I), Cystic Fibrosis (cystic fibrosis transmembrane conductance regulator (CFTR) protein), Sickle cell disease (Hemoglobin), and Critical illness myopathy (CIM) (Hyperproteolytic state of myosin ubiquitination).

In-frame insertion of the nucleic acid sequence encoding the degron tag can be performed or achieved by any known and effective genomic editing processes. In one aspect, the present invention utilizes the clustered regularly interspaced short palindromic repeats (CRISPR)-Cas9 system to produce knock-in endogenous protein-degron tag fusion proteins that are produced from the endogenous locus and are readily degraded in a reversible and dose-responsive fashion dependent on administration of an aryl-sulfonamide. In certain embodiments, the CRISPR-Cas9 system is employed in order to insert an expression cassette for degron tag present in a homologous recombination (HR) "donor" sequence with the degron tag nucleic acid sequence serving as a "donor" sequence inserted into the genomic locus of a protein of interest during homologous recombination following CRISPR-Cas endonucleation. The HR targeting vector contains homology arms at the 5' and 3' end of the expression cassette homologous to the genomic DNA surrounding the targeting gene of interest locus. By fusing the nucleic acid sequence encoding the degron tag in frame with the target gene of interest, the resulting fusion protein contains a degron tag that is targeted by a DCAF15-aryl-sulfonamide complex.

A donor sequence can contain a non-homologous sequence flanked by two regions of homology to allow for efficient HR at the location of interest. Additionally, donor sequences can be a vector molecule containing sequences that are not homologous to the region of interest in cellular chromatin. A donor molecule can contain several, discontinuous regions of homology to cellular chromatin. For example, for targeted insertion of sequences not normally present in a region of interest, for example, the degron tags of the present invention, the sequences can be present in a donor nucleic acid molecule and flanked by regions of homology to the sequence in the region of interest. Alternatively, a donor molecule may be integrated into a cleaved target locus via non-homologous end joining (NHEJ) mechanisms. See, e.g., US Patent Application Publications 2011/0207221 and 2013/0326645.

The donor degron tag encoding sequence for insertion can be DNA or RNA, single-stranded and/or double-stranded and can be introduced into a cell in linear or circular form. See, e.g., US Patent Application Publications 2010/0047805, 2011/0281361, and 2011/0207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. (See, e.g., Chang et al. Proc. Natl. Acad. Sci. 84:4959-4963 (1987) and Nehls et al. Science, 272:886-889 (1996)). Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

The donor polynucleotide encoding a degron tag can be introduced into a cell as part of a vector molecule having additional sequences such as, for example, CRISPR-Cas sequences, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The present invention takes advantage of well-characterized insertion strategies, for example the clustered regularly interspaced short palindromic repeats (CRISPR)-Cas9 system. In general, the "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus. (See, e.g., Ruan, J. et al. Sci. Rep. 5:14253 (2015); and Park, A. et al., PLoS ONE 9(4):e95101 (2014)).

In some embodiments, the methods include modifying expression of a polynucleotide in a eukaryotic cell by introducing a nucleic acid encoding a degron tag.

In some embodiments, the polypeptides of the CRISPR-Cas system and donor sequence are administered or introduced to the cell. The nucleic acids typically are administered in the form of an expression vector, such as a viral expression vector. In some embodiments, the expression vector is a retroviral expression vector, an adenoviral expression vector, a DNA plasmid expression vector, or an adeno-associated virus (AAV) expression vector. In some embodiments, one or more polynucleotides encoding CRISPR-Cas system and donor sequence are delivered to the cell. In some embodiments, the delivery is by delivery of more than one vector.

Methods of delivering nucleic acid sequences to cells as described herein are described, for example, in U.S. Pat. Nos. 8,586,526; 6,453,242; 6,503,717; 6,534,261; 6,599,692; 6,607,882; 6,689,558; 6,824,978; 6,933,113; 6,979,539; 7,013,219; and 7,163,824.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355, and lipofection reagents are sold commercially (e.g., Transfectam™ and Lipofectin™). Cationic and neutral lipids that are suitable for efficient receptor-recognition lipofection of polynucleotides include those described in WO 1991/17424 and WO 1991/16024. Delivery can be to cells (e.g. in vitro or ex vivo administration) or target tissues (e.g. in vivo administration).

The various polynucleotides as described herein may also be delivered using vectors containing sequences encoding one or more of compositions described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824.

At least six viral vector approaches are currently available for gene transfer in clinical trials, which utilize approaches that involve complementation of defective vectors by genes inserted into helper cell lines to generate the transducing agent. pLASN and MFG-S are examples of retroviral vectors that have been used in clinical trials. (Dunbar et al., Blood 85:3048-305 (1995); Kohn et al., Nat. Med. 1:1017-1023 (1995); Malech et al., PNAS 94(22):12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol. Immunother. 44(1):10-20 (1997); and Dranoff et al., Hum. Gene Ther. 1:111-112 (1997)).

Vectors can be delivered in vivo by administration to an individual subject, typically by systemic administration (e.g., intravenous, intraperitoneal, intramuscular, intrathecal, intratracheal, subdermal, or intracranial infusion) or topical application. Alternatively, vectors can be delivered to cells ex vivo, such as cells explanted from an individual patient (e.g., lymphocytes, bone marrow aspirates or tissue biopsy) or universal donor hematopoietic stem cells, followed by reimplantation of the cells into a patient, usually after selection for cells which have incorporated the vector.

In some embodiments, non-CRISPR-CAS viral and non-viral based gene transfer methods can be used to insert nucleic acids encoding a degron tag in frame in the genomic locus of a protein of interest in mammalian cells or target tissues. Such methods can be used to administer nucleic acids encoding components of a zing finger protein (ZFP), zing finger nuclease (ZFN), transcription activator-like effector protein (TALE), and/or transcription activator-like effector nuclease (TALEN) system to cells in culture, or in a host organism including a donor sequence encoding a degron tag for in-frame insertion into the genomic locus of a protein of interest.

Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-173 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); and Yu et al., Gene Therapy 1:13-26 (1994).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); and U.S.

Pat. Nos. 4,186,183, 4,217,344, 4,235,871, 4,261,975, 4,485,054, 4,501,728, 4,774,085, 4,837,028, and 4,946, 787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al., Nature Biotechnology 27(7):643 (2009)).

Further methods for creating fusion proteins including an endogenous protein and an exogenous protein fragment or domain (e.g., a degron tag) and methods of using them for the treatment of diseases are disclosed in US Patent Application Publication 2018/0179522.

Pharmaceutical Compositions

The aryl-sulfonamide compounds of the present invention are known in the art, examples of which include E7820, indisulam, or tasisulam. E7820, indisulam, or tasisulam are clinical stage compounds. An aryl-sulfonamide compound has the general formula of $R_1SO_2NR_2R_3$ wherein $R_1$ is an optionally substituted aryl group and $R_2$ and $R_3$ are each independently H or an organic functional group.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$—aryl where $R^c$ is an alkylene chain such as methylene or ethylene.

The aryl-sulfonamide compounds of the present invention may be formulated into several different types of pharmaceutical compositions that contain a therapeutically effective amount of the compound, and a pharmaceutically acceptable carrier. Generally, the aryl-sulfonamide compounds may be formulated into a given type of composition in accordance with conventional pharmaceutical practice such as conventional mixing, dissolving, granulating, dragee-making, levigating, emulsifying, encapsulating, entrapping and compression processes (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Accordingly, aryl-sulfonamide compounds may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Aryl-sulfonamide compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone crospovidone), crosslinked sodium carboxymetyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, aryl-sulfonamide compounds may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

To the extent that aryl-sulfonamide compounds are water-soluble, they may be formulated as solutions for parenteral and oral delivery forms. Parenteral administration may also be advantageous in that the compound may be administered relatively quickly such as in the case of a single-dose treatment and/or an acute condition.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, aryl-sulfonamide compounds may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include excipients such as wetting agents, suspending agents, coloring, sweetening, flavoring, and perfuming agents.

Other routes of administration that may be suitable for the aryl-sulfonamide compounds include buccal, inhalation, topical, transdermal, transmucosal, ophthalmic, rectal and vaginal. As is known in the art, parenteral administration includes intravenous, subcutaneous, intramuscular, intramedullary, and direct intraventricular.

The compositions may be formulated for buccal or sublingual administration, examples of which include tablets, lozenges and gels.

The compositions may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Aryl-sulfonamide compounds may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Maibach H. I. and Smith H. E. (eds.), Percutaneous Penetration Enhancers, CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfate, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allantoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic Formulations Include Eye Drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" or "effective amount" refers to an amount of an aryl-sulfonamide compound or a pharmaceutically acceptable salt or a stereoisomer thereof; or a composition including the aryl-sulfonamide compound or a pharmaceutically acceptable salt or a stereoisomer thereof, effective in producing the desired therapeutic response. The term "therapeutically effective amount" includes the amount of the compound or a pharmaceutically acceptable salt or a stereoisomer thereof, when administered, may induce DCAF15-mediated degradation of an endogenous or exogenous protein of interest.

With respect to the therapeutic amount of the aryl-sulfonamide compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed and the particular pharmaceutically acceptable carrier utilized.

The total daily dosage of the aryl-sulfonamide compounds and usage thereof may be decided in accordance with standard medical practice, e.g., by the attending physician using sound medical judgment. The specific therapeutically effective dose for any particular subject will depend upon a variety of factors including the disease or disorder being treated and the severity thereof (e.g., its present status); the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, Goodman and Gilman's, The Pharmacological Basis of Therapeutics, 10th ed., A. Gilman, J. Hardman and L. Limbird, eds., McGraw-Hill Press, 155-173, 2001).

Aryl-sulfonamide compounds may be effective over a wide dosage range. In some embodiments, the total daily dosage (e.g., for adult humans) may range from about 0.001 to about 1600 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, from about 5 to about 40 mg per day, and in yet other embodiments from about 10 to about 30 mg per day. In certain embodiments, the total daily dosage may range from about 350 to about 800 mg. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.0001 mg to about 1000 mg/kg of body weight per day. In some embodiments, the compound may be administered at a dose in range from about 0.01 mg to about 200 mg/kg of body weight per day. In some embodiments, a dose of from 0.1 to 100, e.g., from 1 to 30 mg/kg per day in one or more dosages per day may be effective. In certain embodiments, the compound may be administered at a dose in the range of about 25 to about 50 mg/kg of body weight per day. By way of example, a suitable dose for oral administration may be in the range of 1-30 mg/kg of body weight per day, and a suitable dose for intravenous administration may be in the range of 1-10 mg/kg of body weight per day.

The methods of the present invention may entail administration of aryl-sulfonamide compounds or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days).

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the compound of the present invention or a pharmaceutical composition. The kits or pharmaceutical systems of the invention may also include printed instructions for using the bispecific compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: RBM39 Recruitment to CRL4$^{DCAF15}$ Depends on Sulfonamides

Figure 1B:
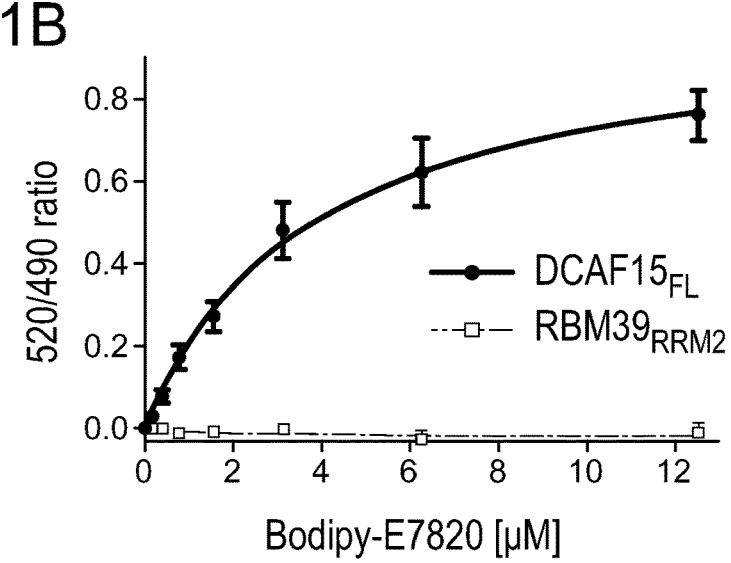
Figure 7A:
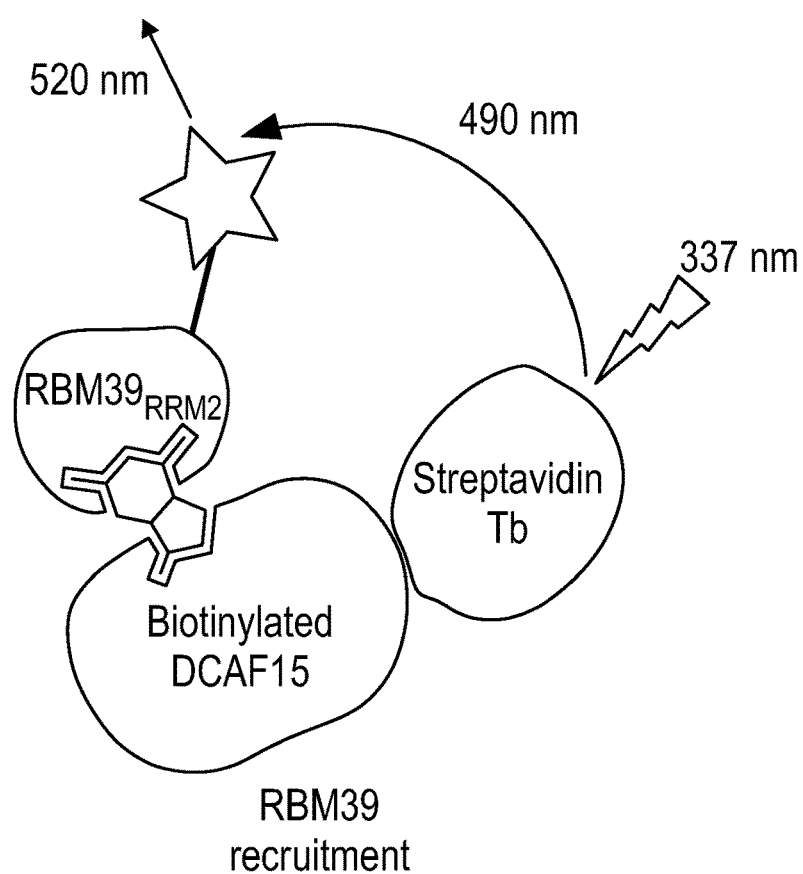
FIG. 7A-FIG. 7G are a series of cartoon representations, graphs, and structures depicting the biochemical characterization of DCAF15 binding to aryl-sulfonamides and RBM39$_{RRM2}$.
Figure 7B:
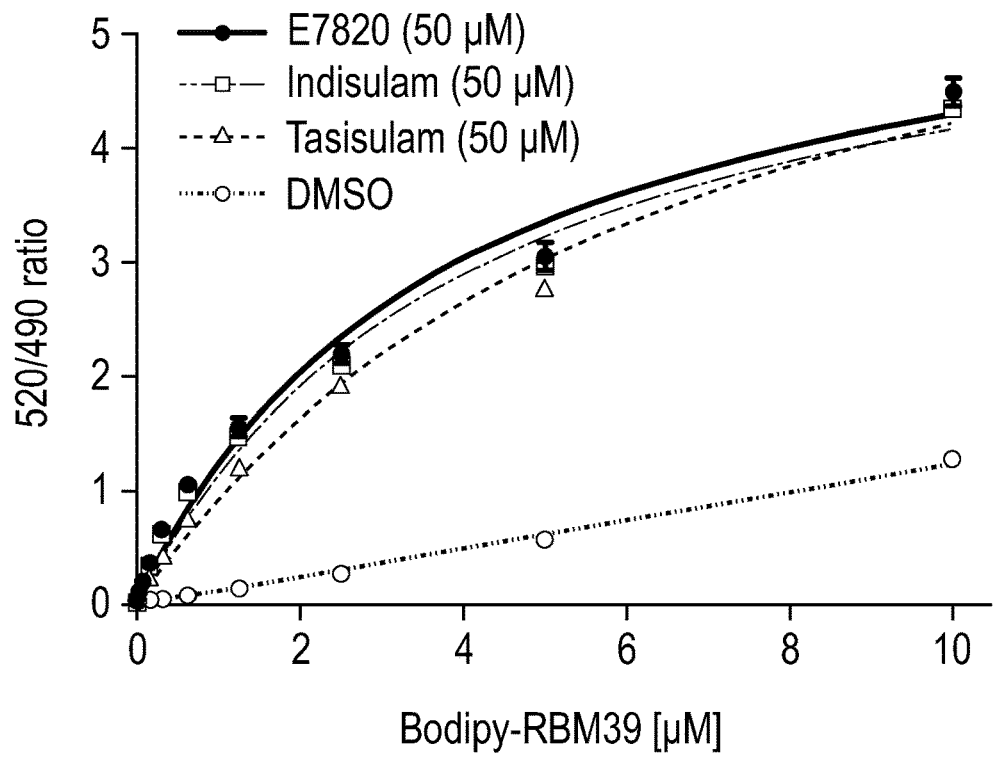
Figure 7C:
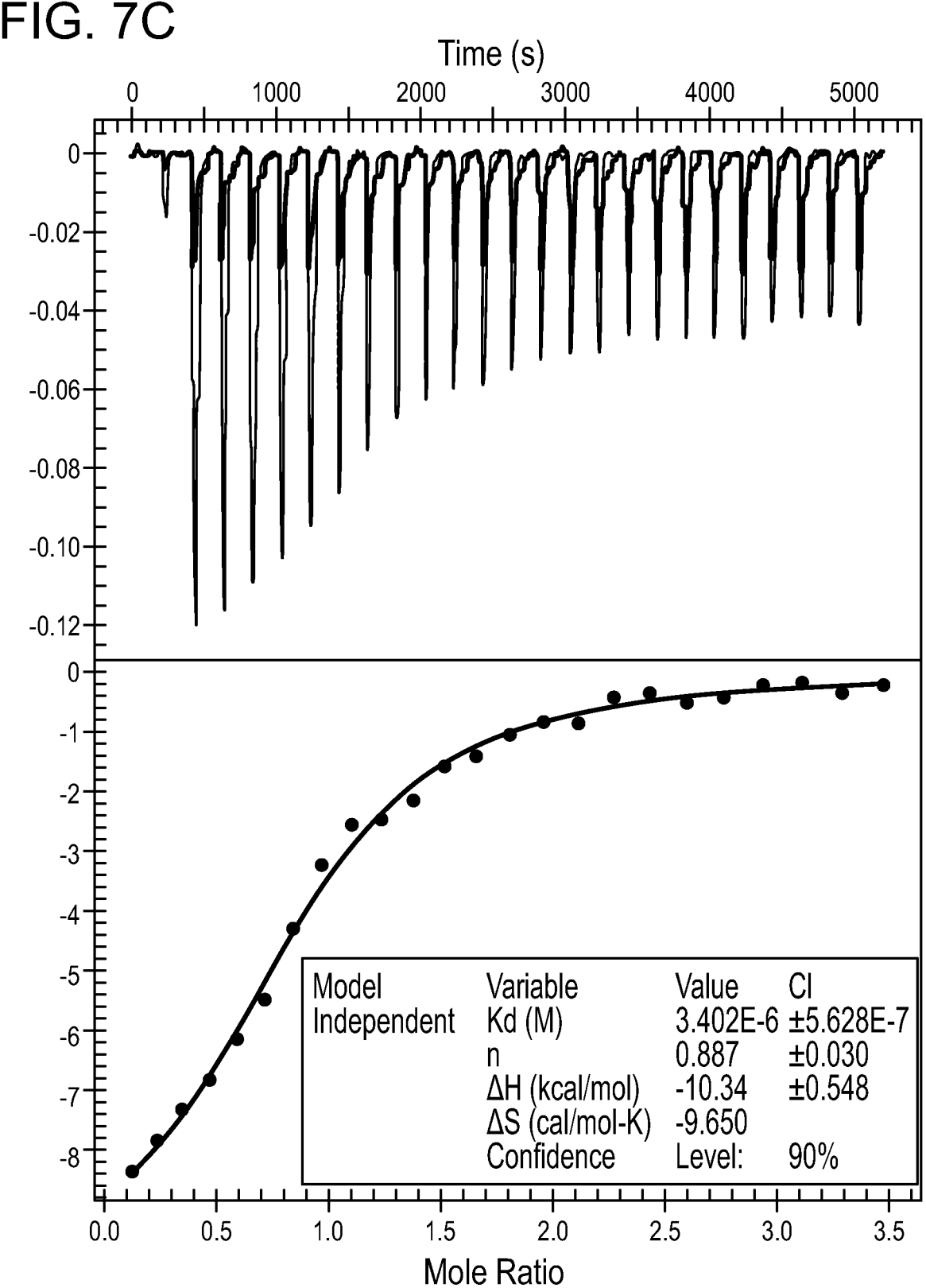
Figure 7D:
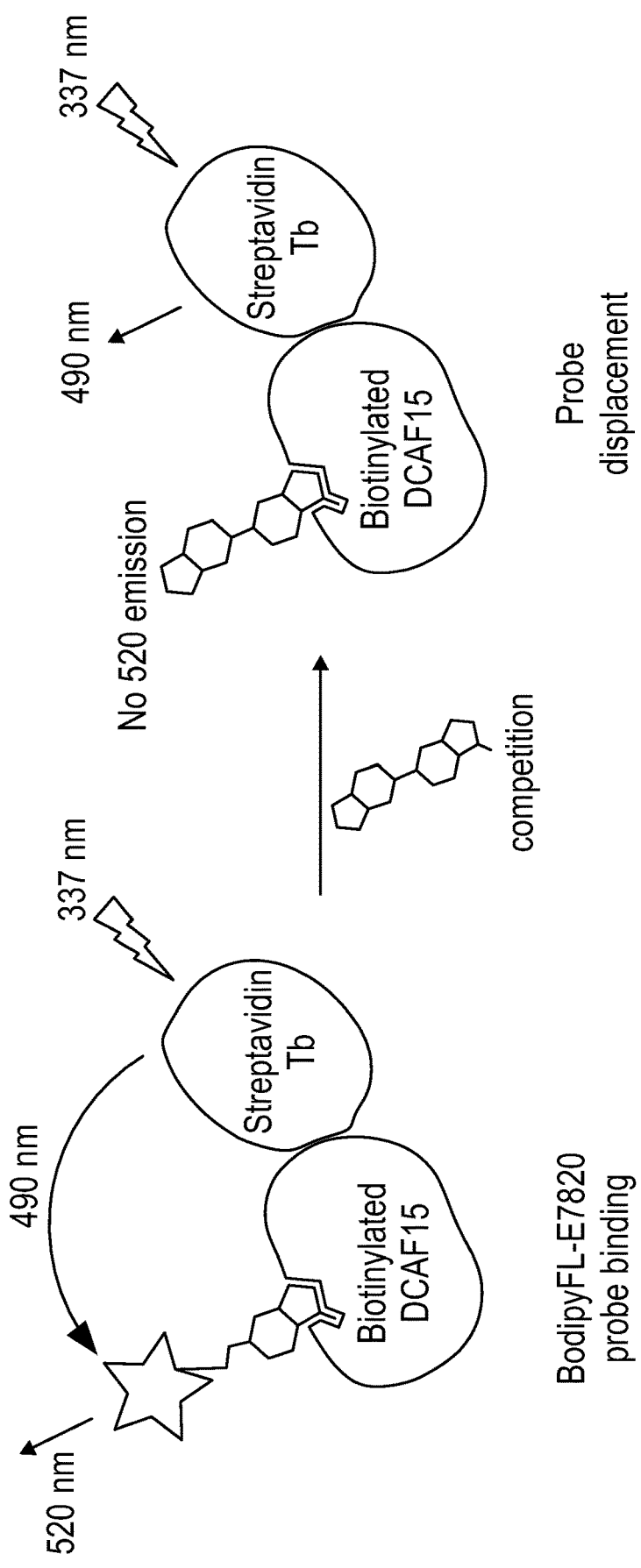
Figure 7E:
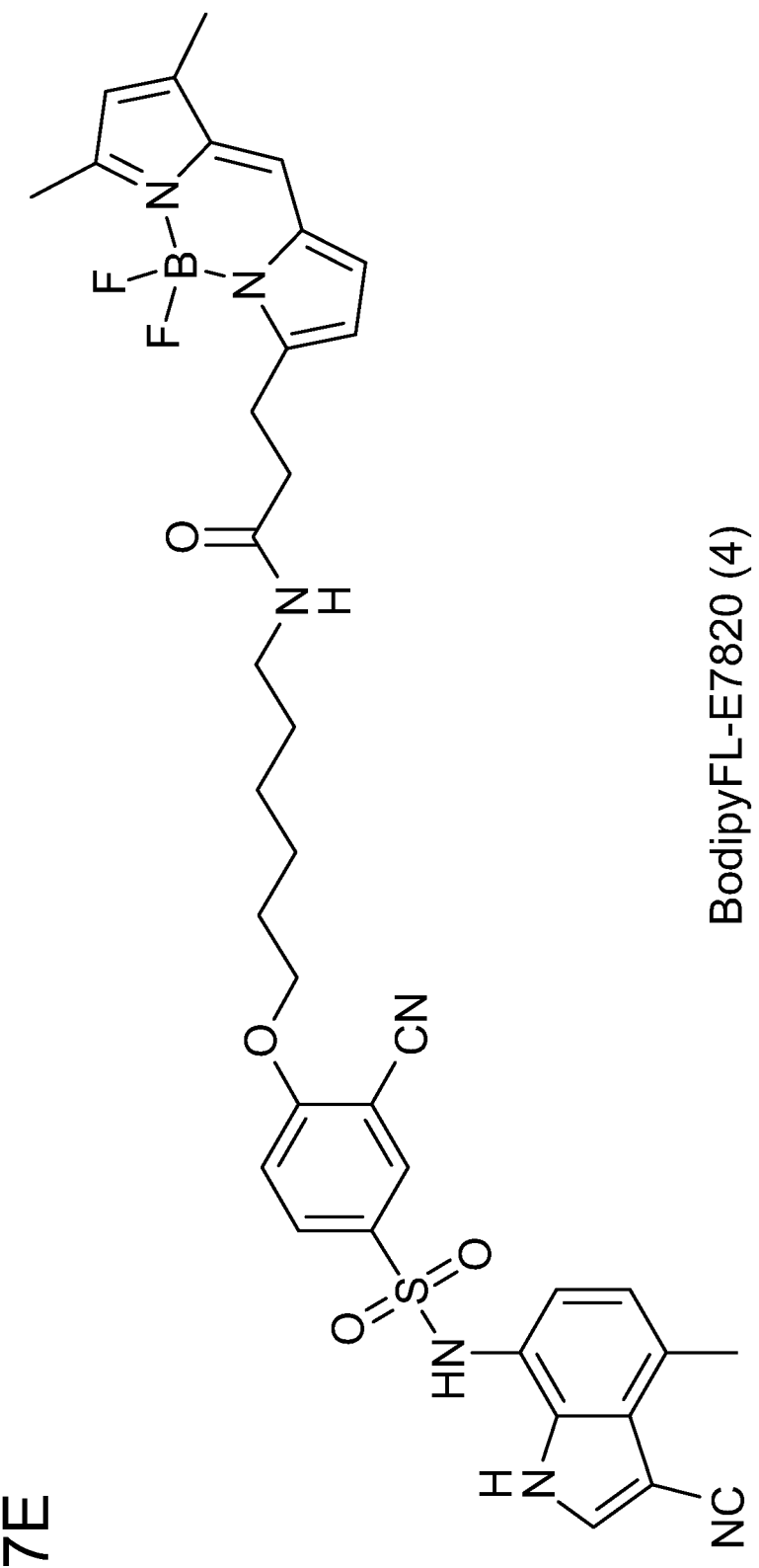
Figure 7F:
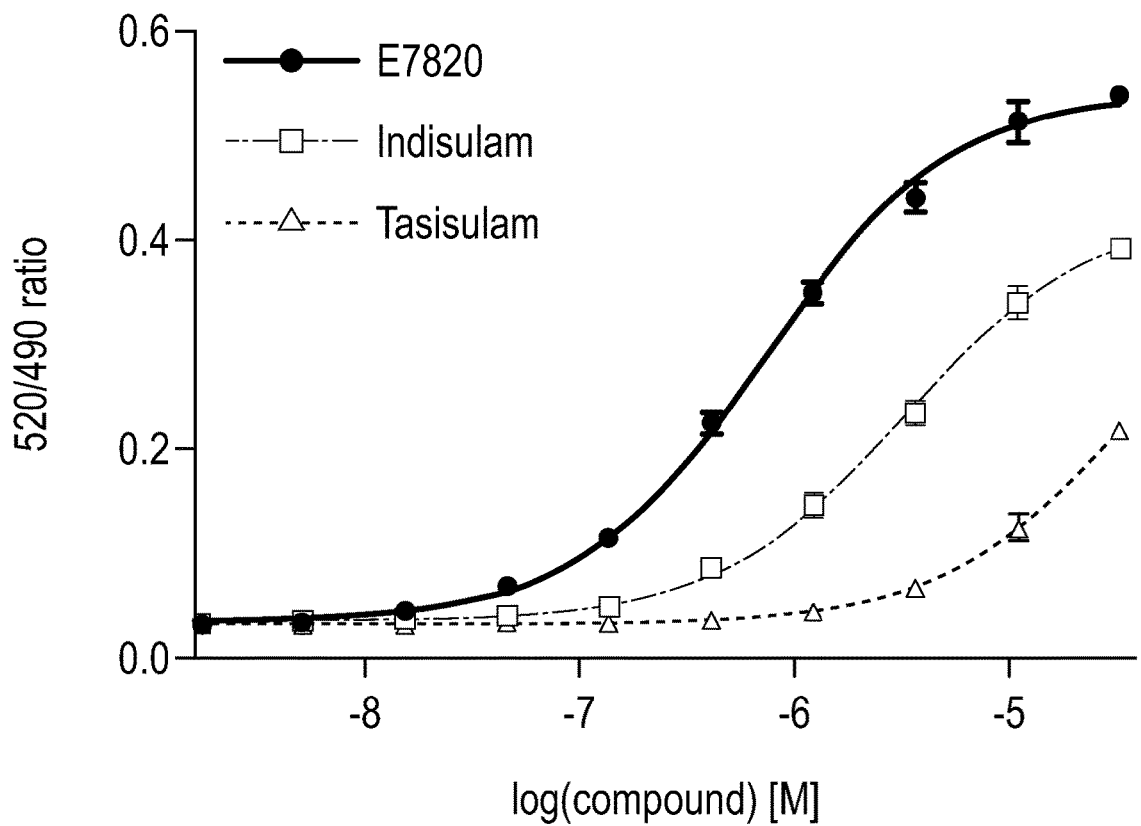
Figure 7G:
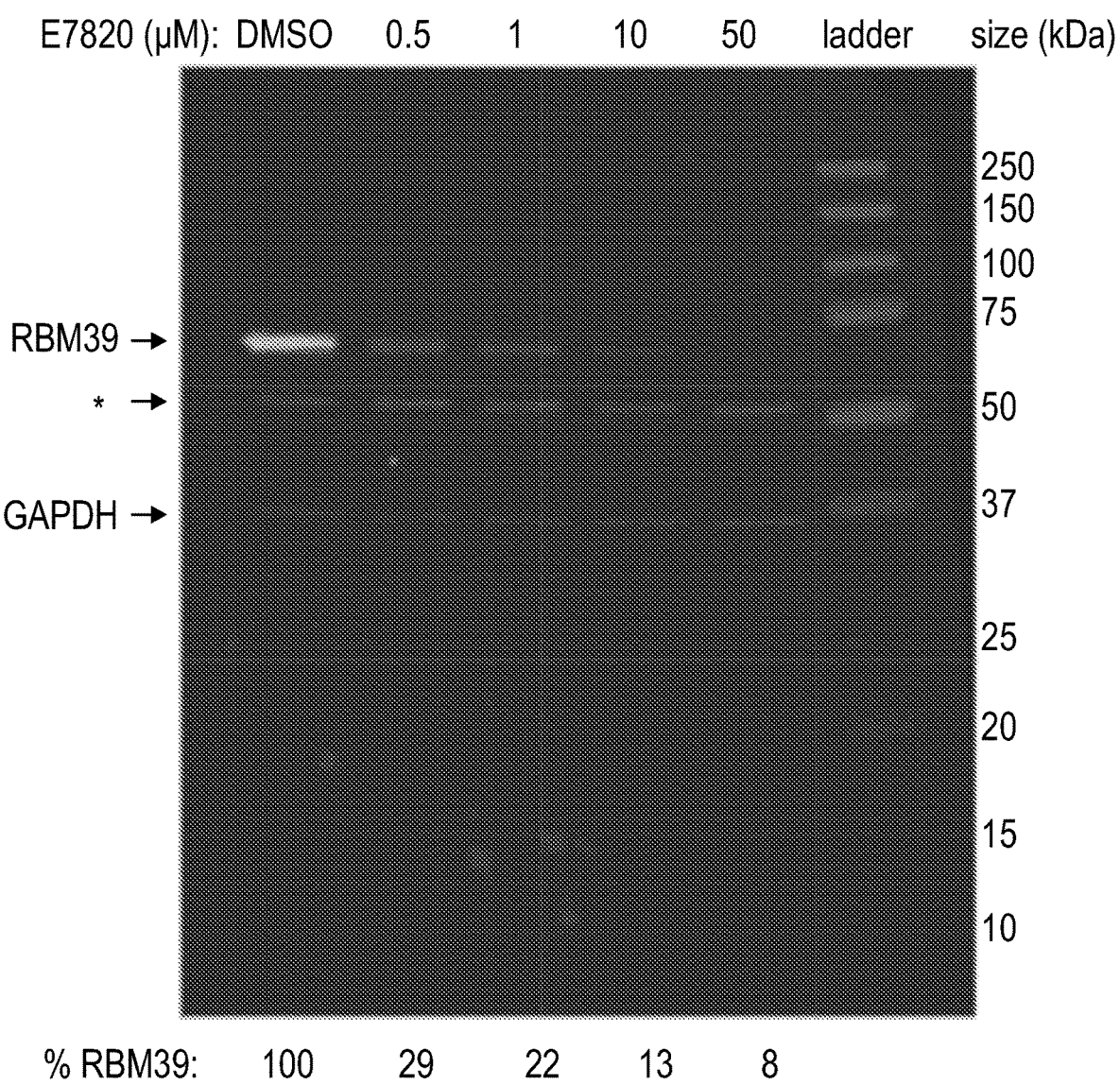
Figure 8A:
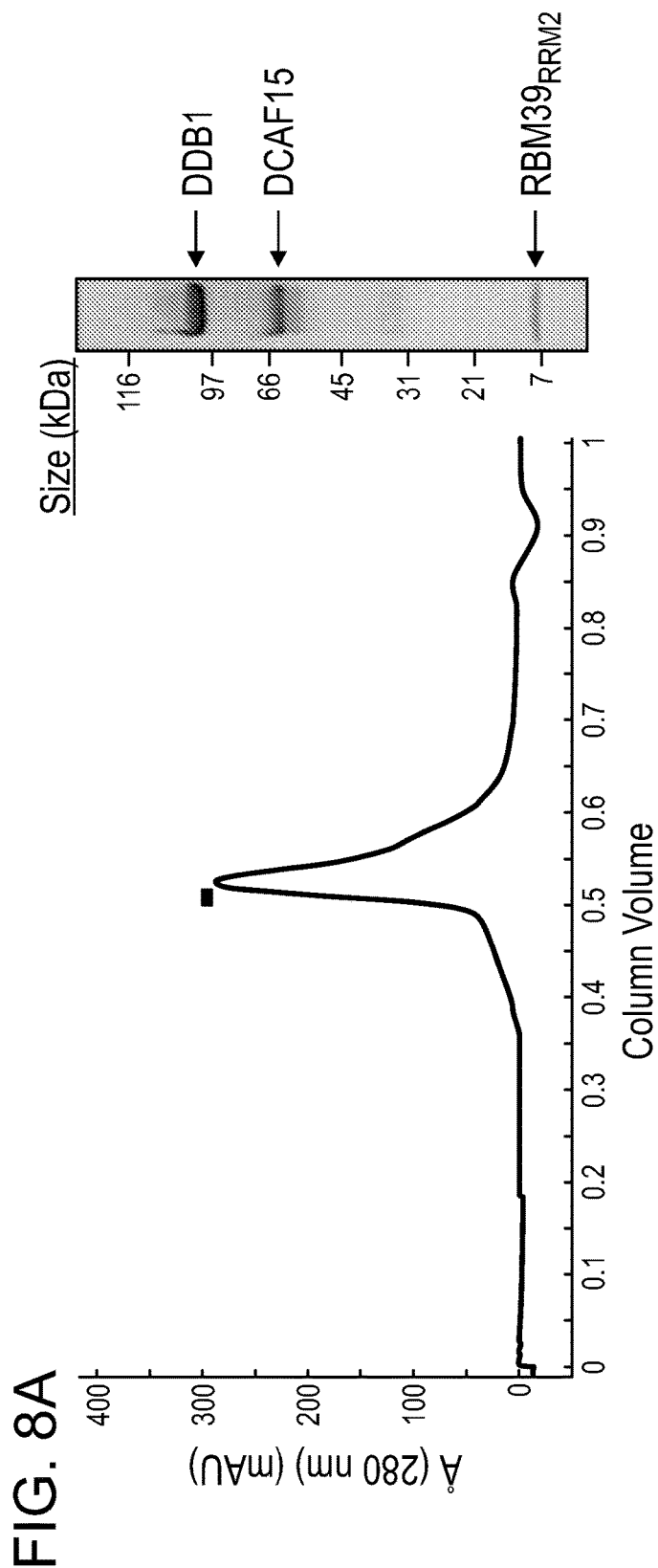
Figure 8B:
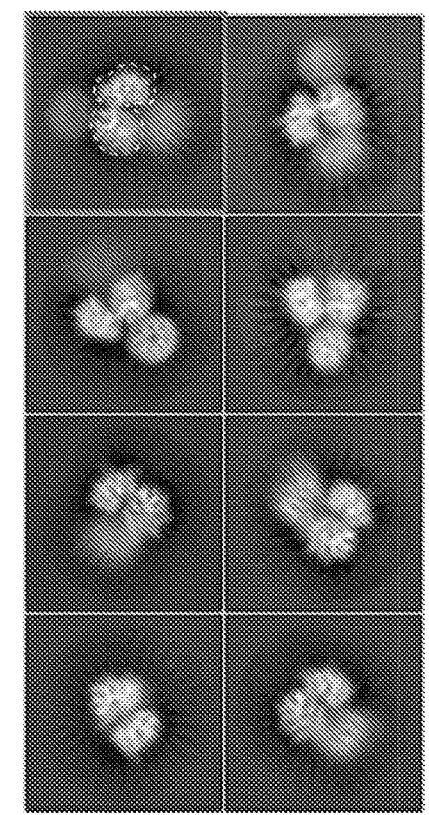
Figure 8C:
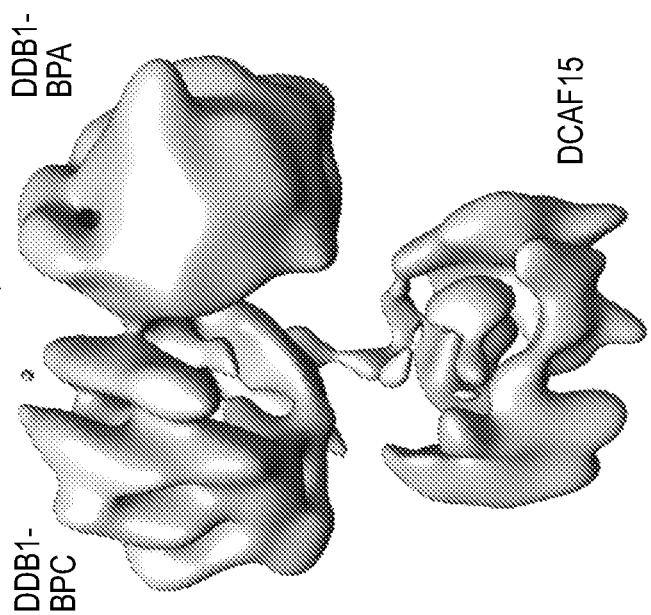
Figure 8D:
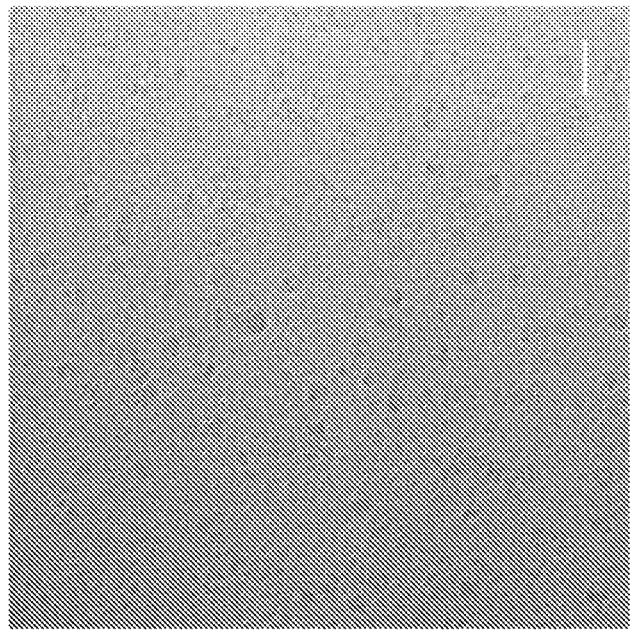
Figure 8G:
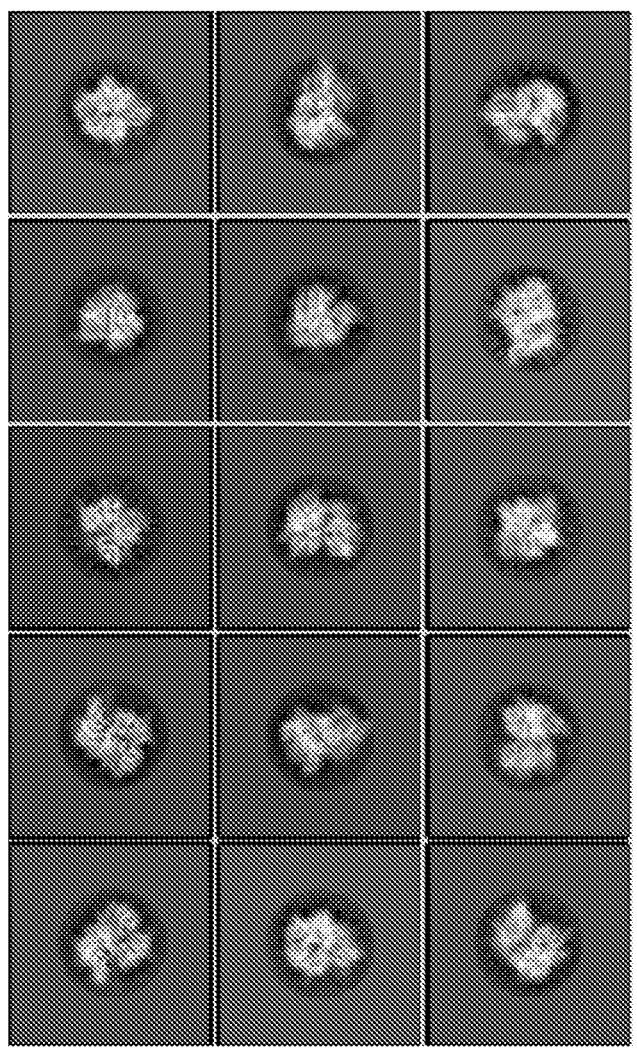
Figure 8F:
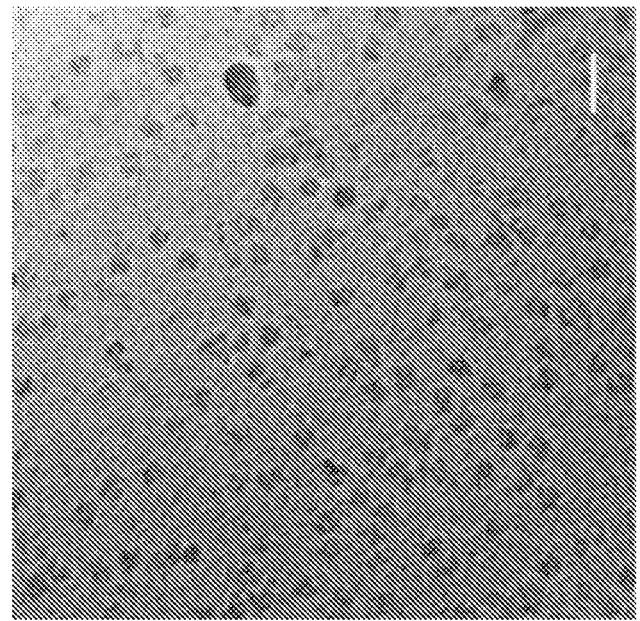
Figure 8H:
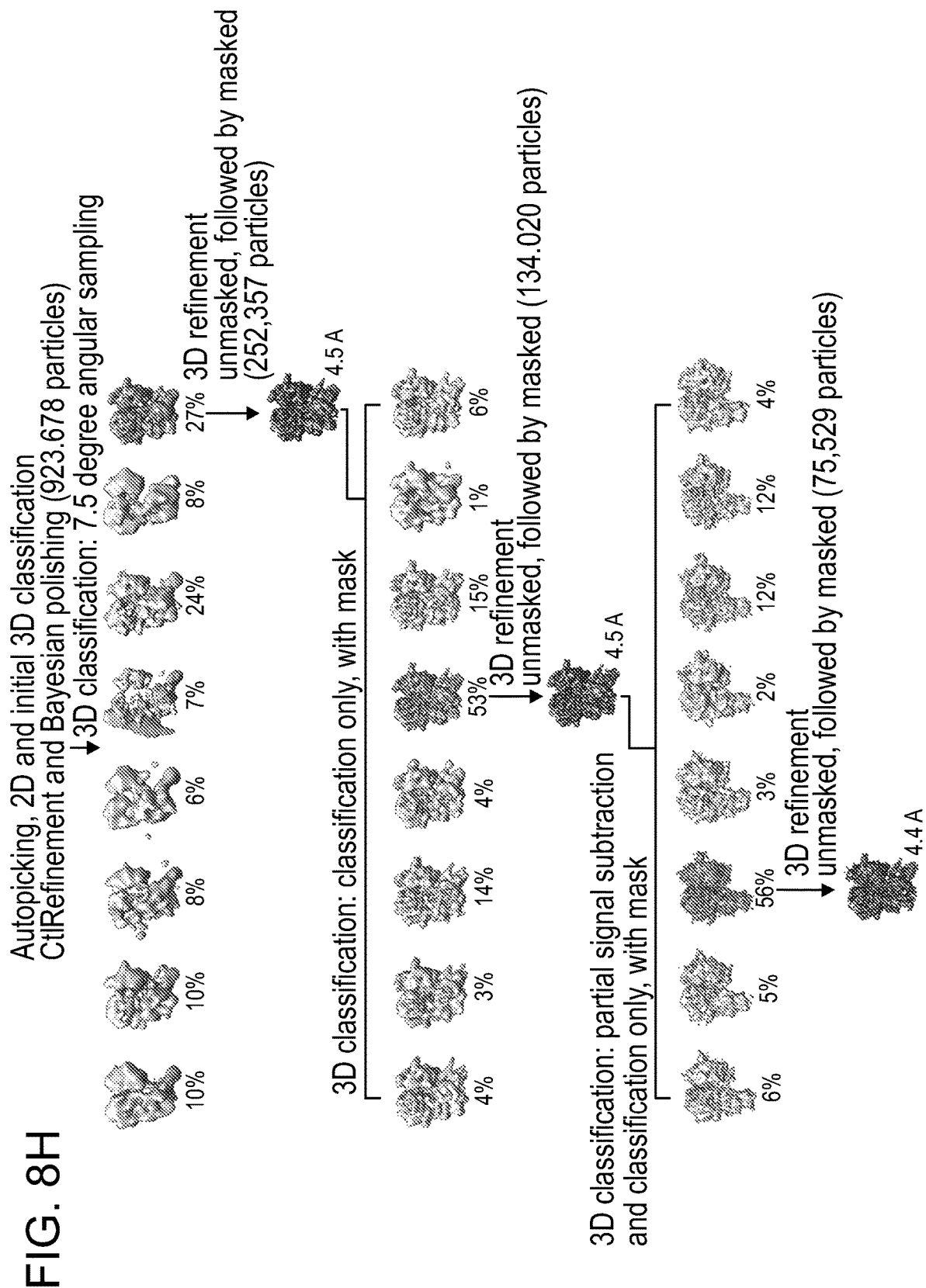

A recent study identified resistance mutations in cells treated with cytotoxic doses of indisulam that arise in the second RRM domain of RBM39 (RBM39$_{RRM2}$) (Uehara et al., Nat. Chem. Biol., 13:675-680 (2017); Han et al., Science 356:aal3755 (2017)). These mutations abrogate the interaction with CRL4$^{DCAF15}$, which suggested that ligase binding is mediated by the RRM2 domain. To better characterize the interaction of RBM39 with DCAF15, the affinity of recombinant DDB1-DCAF15 for RBM39$_{RRM2}$ in the presence of E7820 was measured using time-resolved fluorescence resonance energy transfer (TR-FRET). In the presence of E7820, indisulam or tasisulam at 50 µM, DDB1-DCAF15 and RBM39$_{RRM2}$ associated with $K_D^{app}$ of 2.0 µM, 2.1 µM, and 3.5 µM, respectively (FIG. 1A and FIG. 7A). In contrast, RBM39$_{RRM2}$ did not show measurable affinity with DDB1-DCAF15, even at 10 µM, in the absence of compound (FIG. 7B). E7820 interacted with DCAF15 ($K_D^{app}$ of 3.8 µM), but not with RBM39 (FIG. 1B and FIG. 7C). Based on TR-FRET competition assays (FIG. 7D and FIG. 7E), E7820 binds to DCAF15 with a $K_i$ of 2.9 µM, while the $K_i$ for indisulam and tasisulam is >50 µM (FIG. 1C), which was analogous to the $EC_{50}$ values when each compound was titrated into the RBM39$_{RRM2}$ TR-FRET recruitment assay (FIG. 7F). Notably, RBM39 was potently degraded in cells at 500 nM E7820 (FIG. 7G), which contrasts the relatively weak affinity of E7820 for DCAF15.

Example 2: Cryo-EM Structure of DCAF15 Complex Bound to RBM39$_{RRM2}$

All initial attempts to crystallize full-length human DCAF15 complexes were unsuccessful. As a result, attempts were then made with cryo-electron microscopy (cryo-EM). Initial class averages of DDB1-DCAF15-E7820-RBM39$_{RRM2}$, indicated that DCAF15 and the BPB domain of DDB1 were flexible with respect to the core of DDB1 (FIG. 8A-FIG. 8D). The DDB1 construct lacked the BPB domain, DDB1ΔB (Petzold et al., Nature 532:127-130 (2016)), and chemical crosslinking (FIG. 2E). DDB1ΔB-DCAF15-DDA1-RBM39$_{RRM2}$ were co-expressed in the presence of E7820, and after extensive optimization (see Example 7), a dataset was collected that led to a 3D reconstruction of the 180 kDa complex at an overall resolution of ~4.4 Å (FIG. 1D-FIG. 1F, FIG. 8E-FIG. 8H and FIG. 9A-FIG. 9F).

Figure 1C:
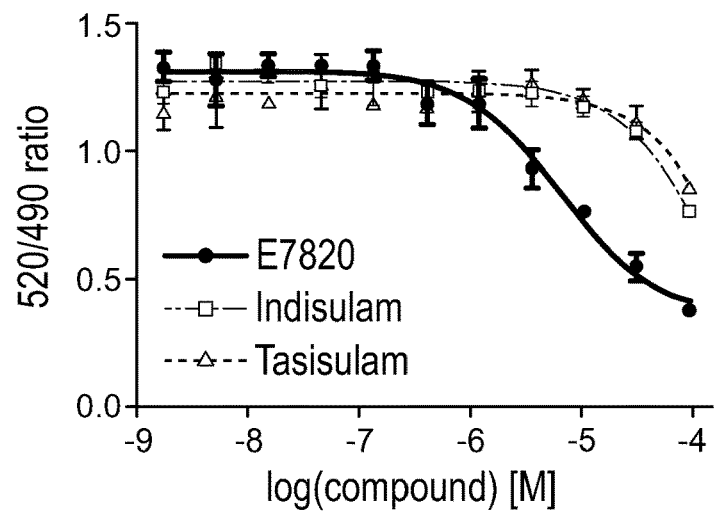
Figure 1D:
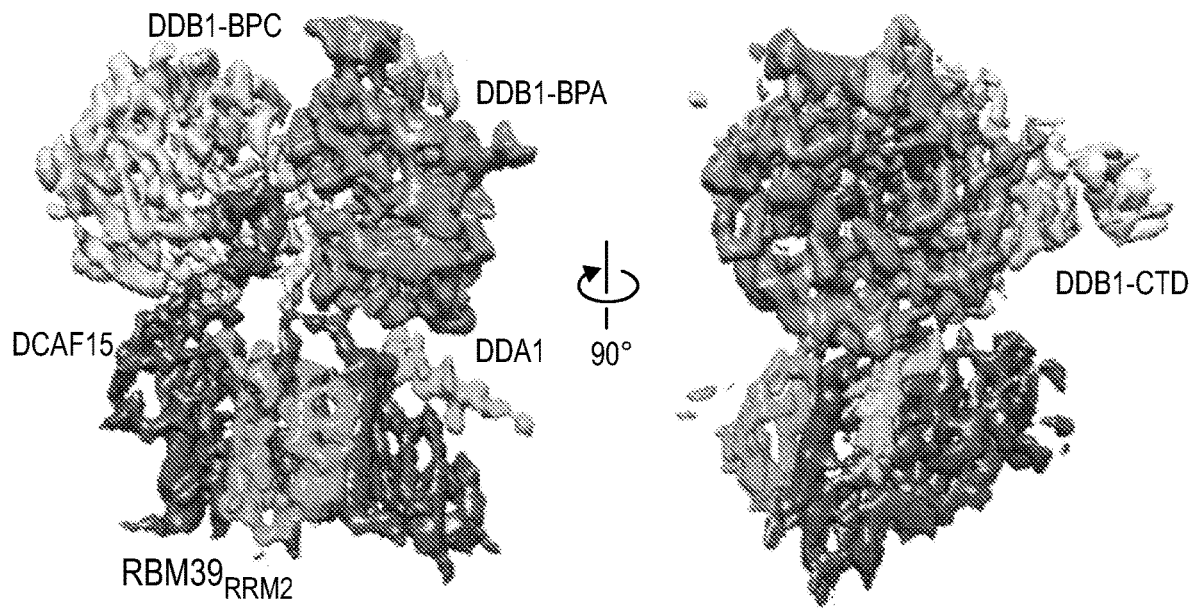
Figure 1E:
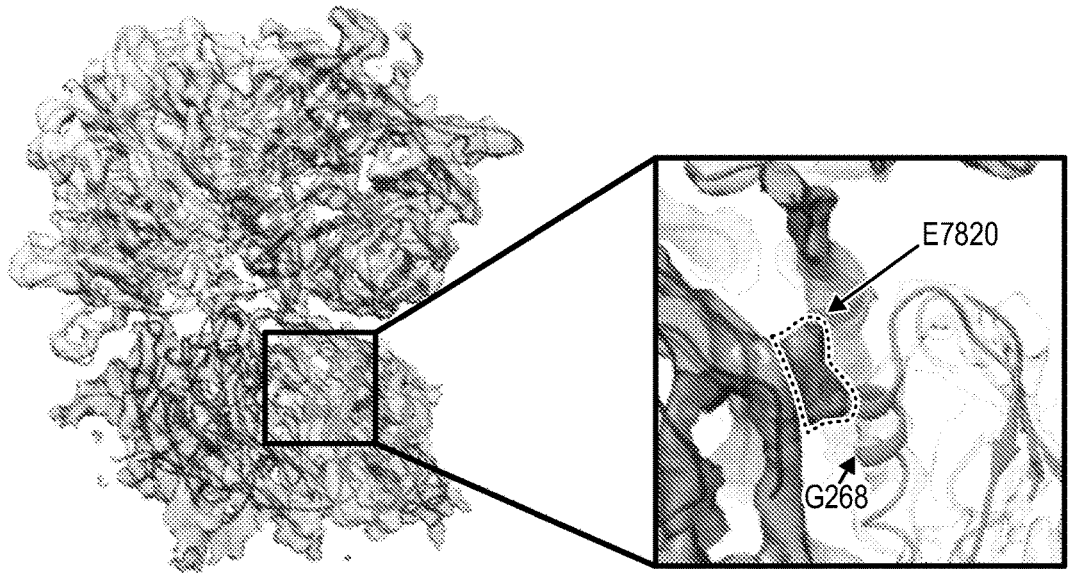
Figure 1F:
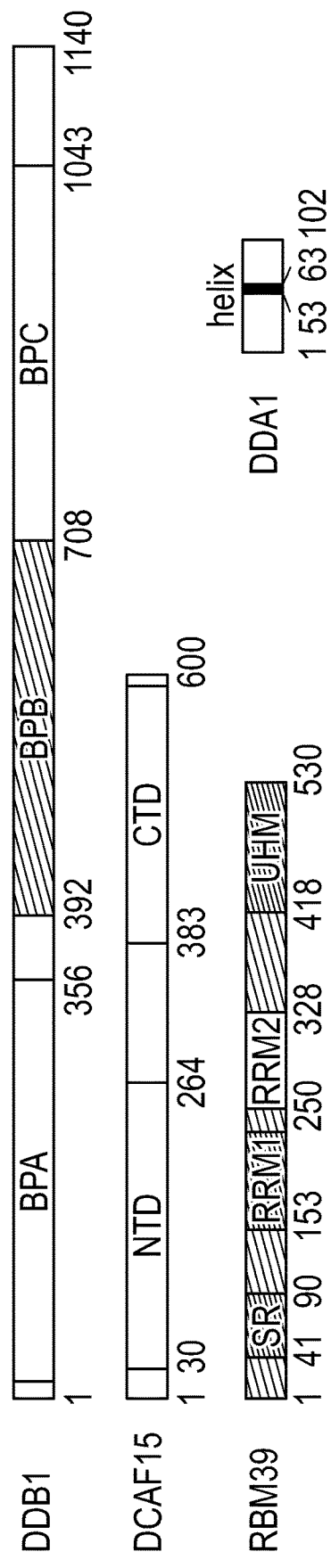

DDB1ΔB was readily placed into the density using the crystal structure (pdb: 5fqd, chain A) as a model, and a search using the balbes-molrep pipeline (Brown et al., Acta Crystallogr. D., 71:136-153 (2015)) located the RRM domain corresponding to RBM39$_{RRM2}$ (FIG. 1E) but did not identify homologous structures in the putative full-length DCAF15 density. The map allowed for segmentation of the density and unambiguous assignment of density to DCAF15 and DDA1 (FIG. 1D and FIG. 1E). While the resolution was not sufficient to build an atomic model (FIG. 9A), an approximate poly-alanine trace of DCAF15 and DDA1 was built using additional information from cross-linking mass spectrometry (Table 1), mutations placed in putative helices (FIG. 10A), and secondary structure prediction. RBM39$_{RRM2}$ packed against an α-helix of DCAF15, and the Gly268 of RBM39, previously found to be a dominant position of indisulam resistance mutations (Uehara et al., Nat. Chem. Biol., 13: 675-680 (2017); Han et al., Science 356: aal3755 (2017)), packed against the DCAF15 helix and did not tolerate a sidechain-bearing residue (FIG. 1E). At the interface between RBM39$_{RRM2}$ and DCAF15 there was density that did not represent amino acid side chains and it was tentatively assigned as E7820 (FIG. 1E). While the proximity of RBM39 residue Met265, which when mutated to leucine abrogated binding (Han et al., Science 356: aal3755 (2017)) supported this assignment, the resolution of the cryo-EM map was insufficient for an unambiguous interpretation of the ligand binding.

Figure 10A:
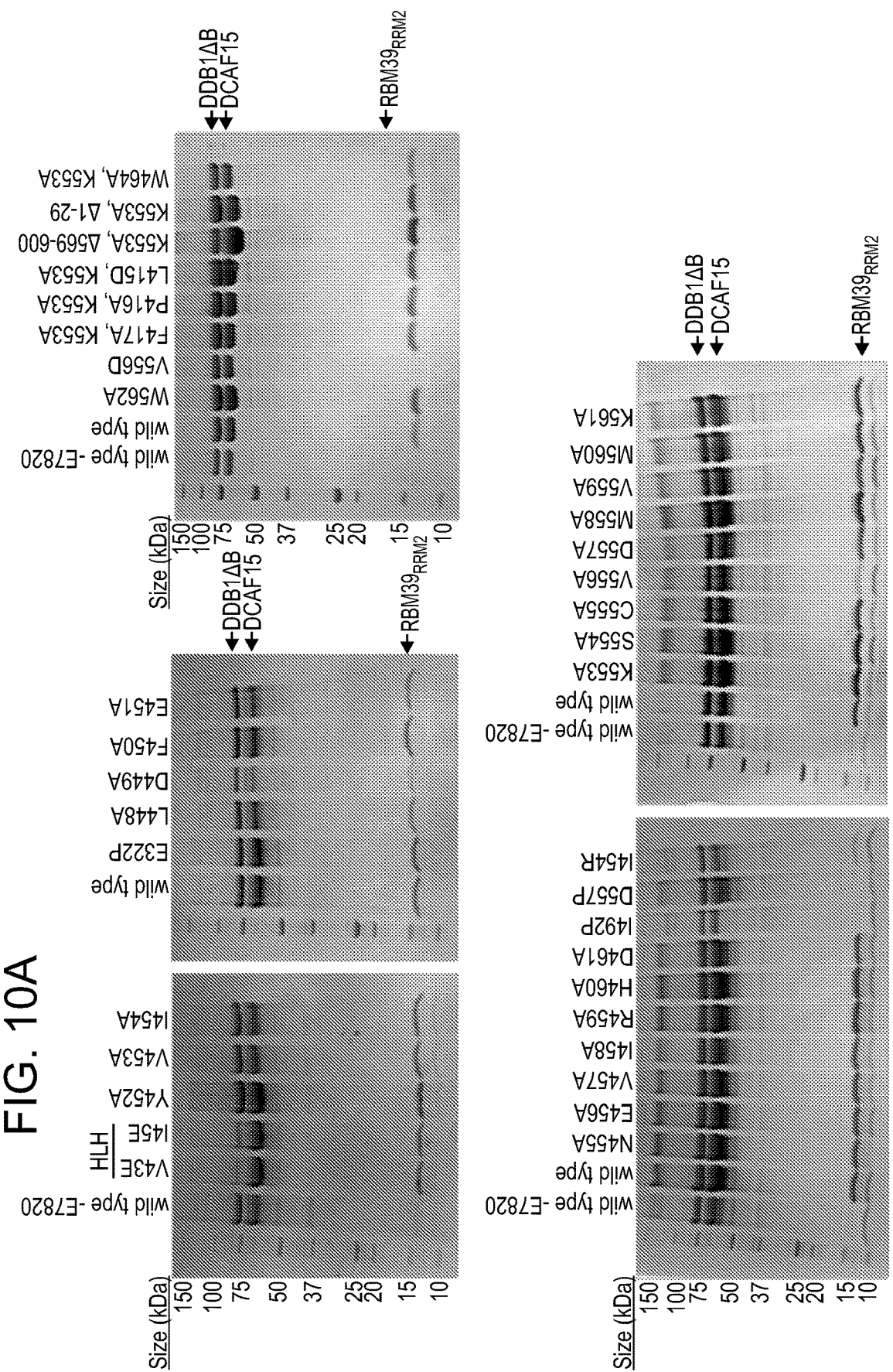
FIG. 10A-FIG. 10E is a series of immunoblots and graphs showing mutant DCAF15 pull down and a DCAF15$_{split}$ construct for crystallographic studies.
Figure 10B:
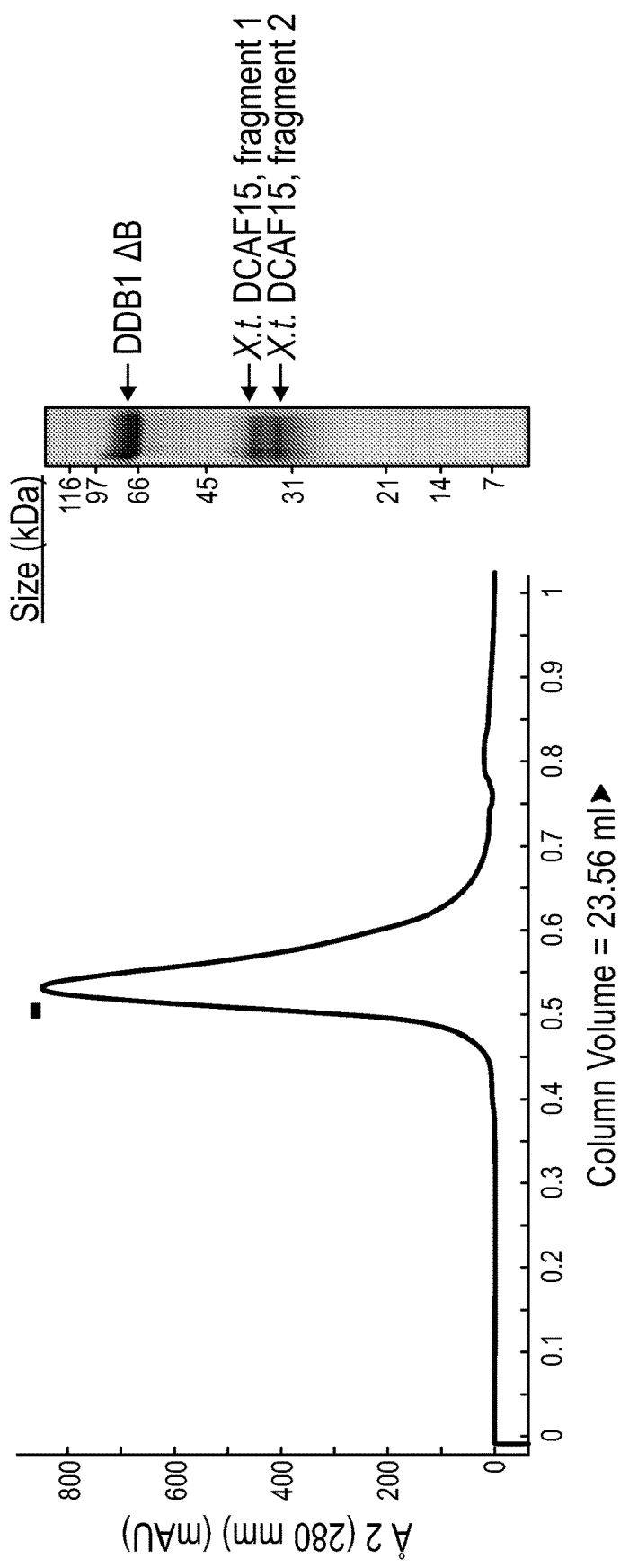
Figure 10C:
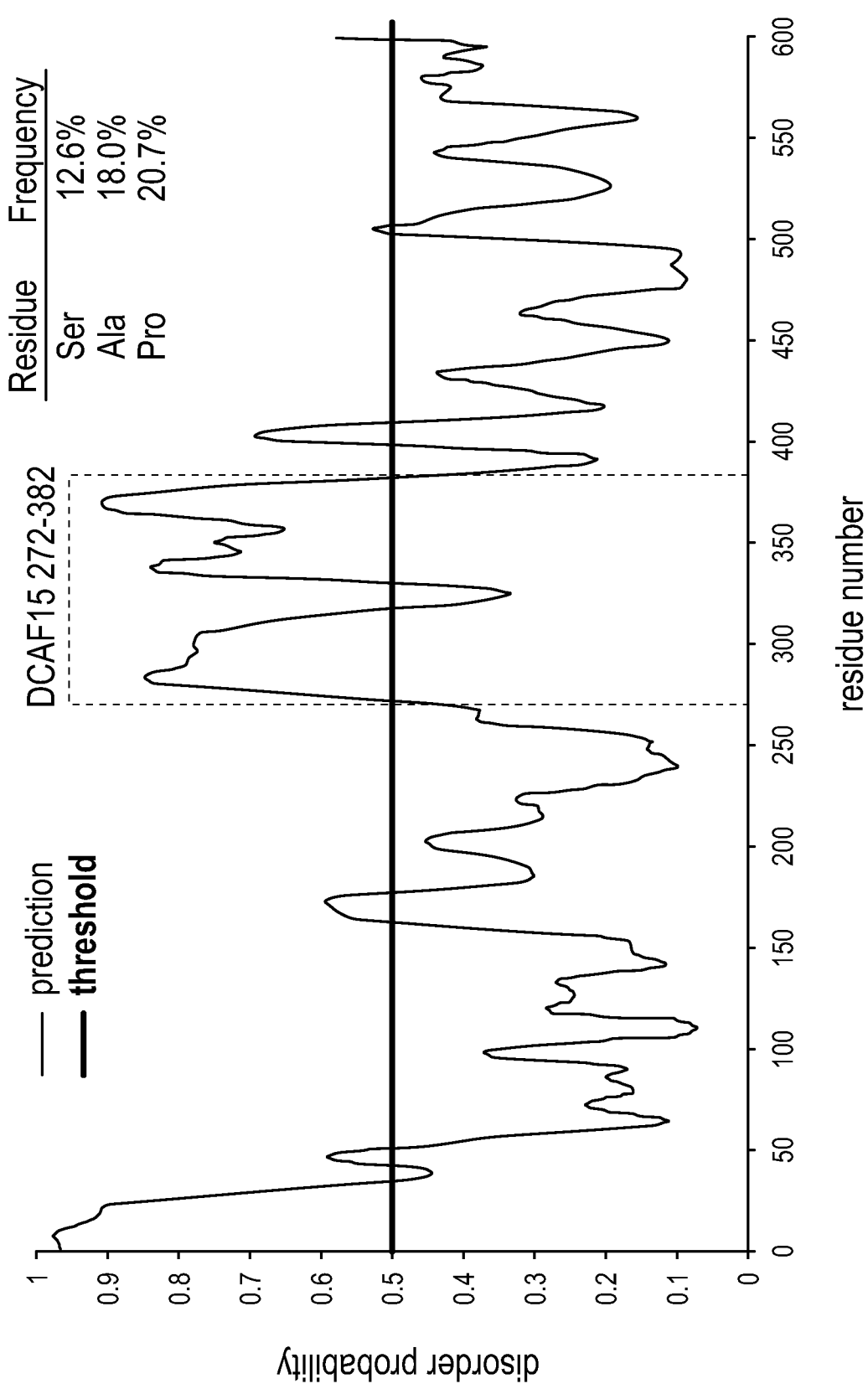
Figure 10D:
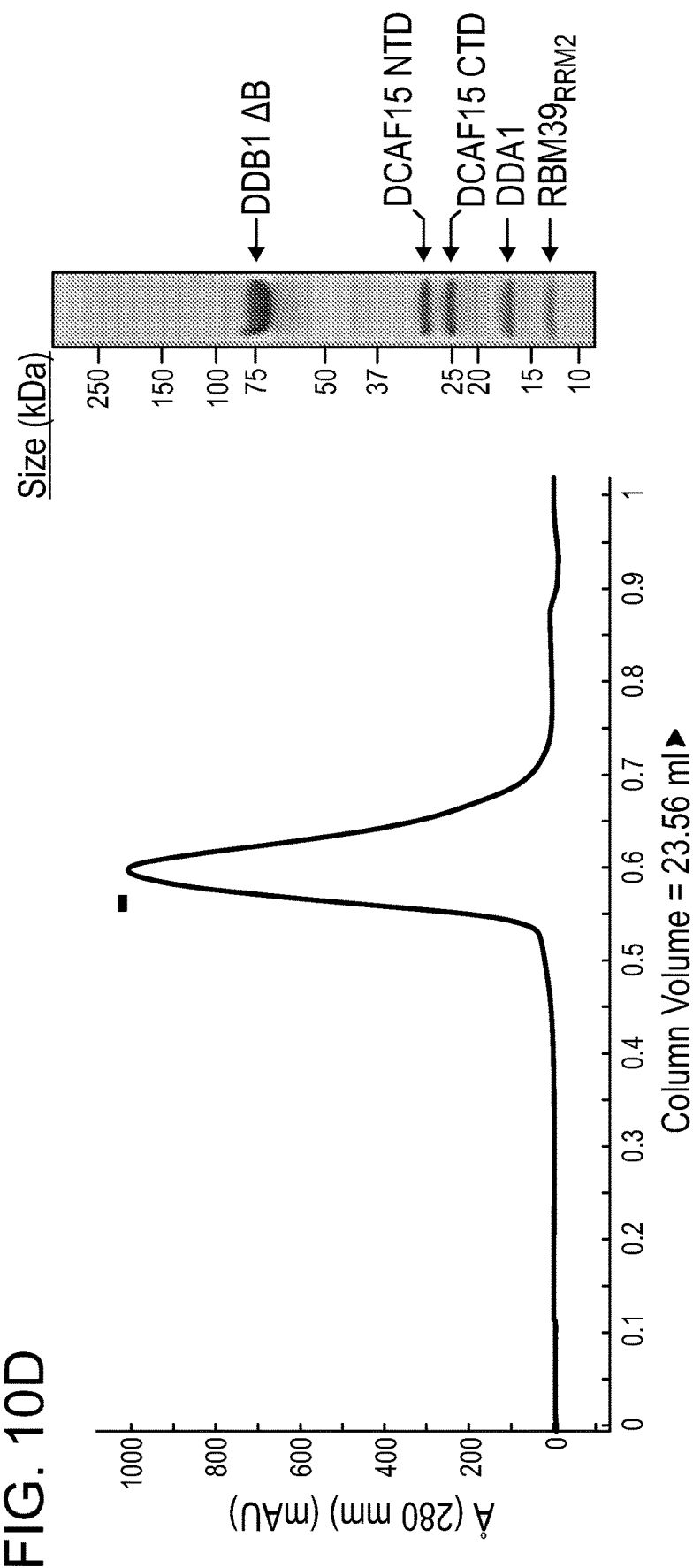
Figure 10E:
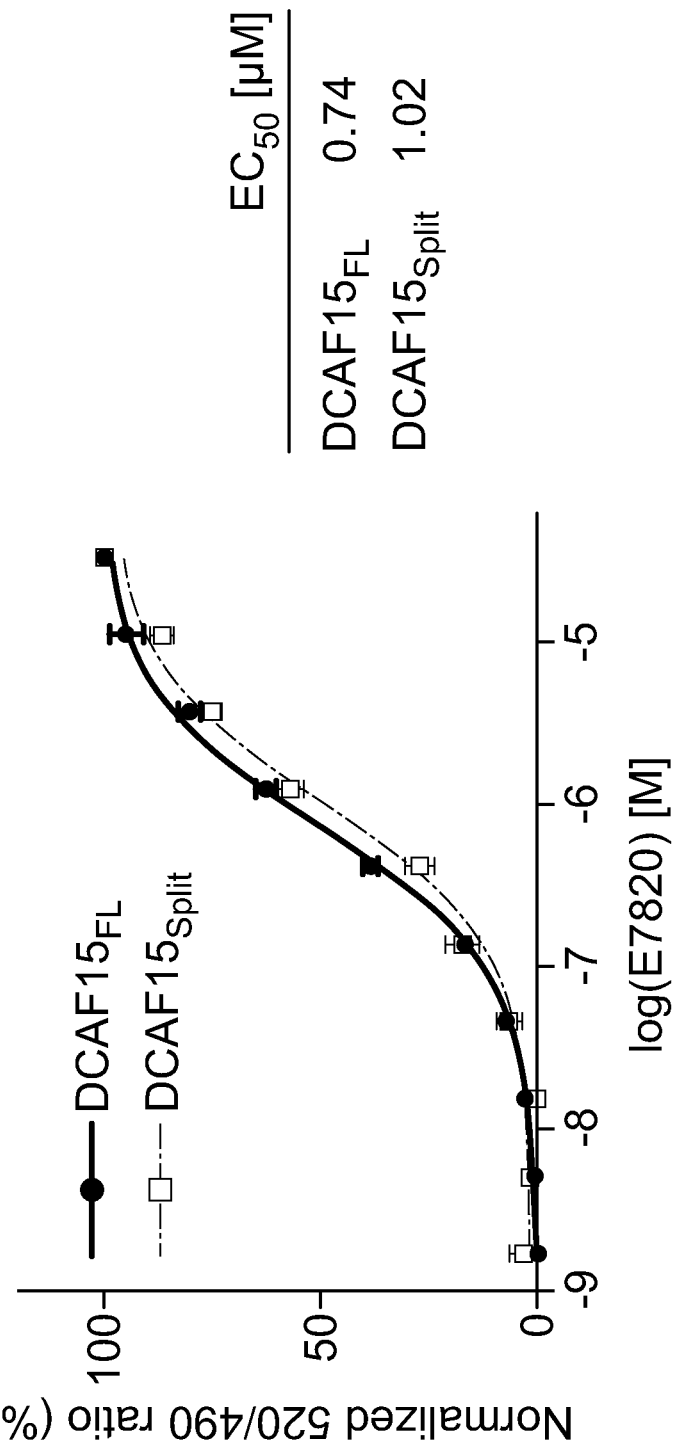

As a result, a minimal complex suitable for crystallographic studies was engineered. Limited proteolysis experiments revealed that similarly sized fragments of DCAF15 were stably associated with DDB1 after gel filtration (FIG. 10B). This result indicated that DCAF15 contained an exposed, likely disordered, region available for proteolytic cleavage and that distinct segments of DCAF15 can independently bind DDB1. Disorder prediction further demonstrated a highly unstructured region of DCAF15 (FIG. 10C), which led to the design of constructs of the N-terminal (residues 30-264) and C-terminal (residues 383-600) fragments of human DCAF15 (DCAF15$_{split}$). Co-expression of these fragments with DDB1ΔB led to the formation of a soluble complex, that exhibited equivalent binding affinity for RBM39 to full-length human DCAF15 (FIG. 10D and FIG. 10E).

TABLE 1

Lysine pairs identified by protein cross-linking

| Protein 1 | Protein 2 | Distance Å | observations | apo | +RBM39 | Crosslinker |
|---|---|---|---|---|---|---|
| DCAF15-K85 | DDB1-K1081 | 14.1 | 3 | | yes | DSBU, DSSO |
| DDA1-K13 | DDB1-K335 | 14.1 | 2 | | yes | DSBU |
| DDA1-K66 | DDB1-K204 | 20 | 1 | | yes | DSBU |
| DCAF15-K56 | DCAF15-K85 | 20.2 | 1 | | yes | DSSO |
| DCAF15-K56 | DCAF15-K587 | 19.8 | 2 | | yes | DSBU |
| DCAF15-K511 | DCAF15-K540 | 6.7 | 3 | | yes | DSSO |
| DCAF15-K582 | DCAF15-K587 | 12.3 | 1 | | yes | DSSO |

TABLE 1-continued

Lysine pairs identified by protein cross-linking

| Protein 1 | Protein 2 | Distance Å | observations | apo | +RBM39 | Crosslinker |
|---|---|---|---|---|---|---|
| DDA1-K65 | DDA1-K70 | 15.3 | 2 | | yes | BS3 |
| DDB1-K11 | DDB1-K35 | 10 | 2 | yes | | DSBU, DSSO |
| DDB1-K35 | DDB1-K857 | 45.8 | 1 | yes | | DSBU |
| DDB1-K53 | DDB1-K1104 | 13.1 | 5 | yes | | DSBU, DSSO |
| DDB1-K70 | DDB1-K150 | 20.7 | 3 | yes | | DSBU, DSSO |
| DDB1-K70 | DDB1-K200 | 19.5 | 2 | yes | | DSBU |
| DDB1-K150 | DDB1-K200 | 13.5 | 2 | yes | | DSBU, DSSO |
| DDB1-K153 | DDB1-K200 | 6.9 | 1 | yes | | DSSO |
| DDB1-K191 | DDB1-K204 | 7.7 | 4 | yes | | DSBU, DSSO |
| DDB1-K244 | DDB1-K298 | 10 | 4 | yes | | DSBU, DSSO |
| DDB1-K769 | DDB1-K857 | 21.2 | 2 | yes | | DSBU, DSSO |
| DDB1-K769 | DDB1-K864 | 10.9 | 3 | yes | | DSBU, DSSO |
| DDB1-K769 | DDB1-K867 | 14.1 | 1 | yes | | DSSO |
| DDB1-K769 | DDB1-K897 | 18.5 | 1 | yes | | DSSO |
| DDB1-K823 | DDB1-K897 | 15.4 | 6 | yes | | DSBU, DSSO |
| DDB1-K857 | DDB1-K897 | 10.1 | 1 | yes | | DSBU |
| DDB1-K867 | DDB1-K897 | 25 | 1 | yes | | DSBU |
| DDBI K917 | DDB1-K979 | 11 | 6 | yes | | DSBU, DSSO |
| DDB1-K936 | DDB1-K979 | 10.1 | 6 | yes | | DSBU, DSSO |
| DCAF15-K26 | RBM39-K291 | n/a | 2 | | yes | BS3 |
| DCAF15-K321 | RBM39-K178 | n/a | 1 | | yes | BS3 |
| DCAF15-K121 | DDB1-K628 | n/a | 1 | | yes | BS3 |
| DCAF15-K321 | DDB1-K864 | n/a | 1 | | yes | DSSO |
| DCAF15-K332 | DDB1-K287 | n/a | 1 | | yes | DSBU |
| DCAF15-K332 | DDA1-K65 | n/a | 7 | | yes | BS3 |
| DDA1-K26 | DDB1-K35 | n/a | 3 | yes | | DSBU |
| DDA1-K26 | DDB1-K53 | n/a | 2 | yes | | DSSO |
| DDA1-K89 | DDB1-K204 | n/a | 1 | yes | | DSSO |
| DCAF15-K6 | DCAF15-K26 | n/a | 9 | yes | yes | BS3, DSBU, DSSO |
| DCAF15-K26 | DCAF15-K38 | n/a | 3 | yes | yes | BS3, DSSO |
| DCAF15-K26 | DCAF15-K56 | n/a | 3 | | yes | BS3 |
| DCAF15-K319 | DCAF15-K332 | n/a | 5 | yes | yes | BS3, DSSO |
| DCAF15-K319 | DCAF15-K335 | n/a | 3 | yes | yes | DSSO |
| DCAF15-K321 | DCAF15-K332 | n/a | 11 | | yes | BS3, DSBU, DSSO |
| DCAF15-K321 | DCAF15-K335 | n/a | 10 | yes | yes | BS3, DSBU, DSSO |
| DCAF15-K332 | DCAF15-K412 | n/a | 1 | | yes | BS3 |
| DCAF15-K335 | DCAF15-K511 | n/a | 1 | yes | | DSBU |
| DDA1-K26 | DDA1-K51 | n/a | 3 | | yes | BS3, DSBU |
| DDA1-K65 | DDA1-K71 | n/a | 1 | | yes | DSBU |
| DDA1-K65 | DDA1-K89 | n/a | 1 | yes | | DSSO |

Distances were measured in PyMOL using the crystal structure, except in cases where one or both lysines were absent from the crystal structure. Observations indicate the number of individual experiments where each cross-link was identified. The DCAF15-DDB1ΔB-DDA1 (apo) and DCAF15-DDB1-DDA1-E7820-RBM39$_{RRM2}$ (+RBM39) complexes were both analyzed by cross-linking mass spec, and the identification of cross-links in either complex is indicated. Also listed are the crosslinkers (BS3, DSSO, or DSBU) that resulted in each crosslink pair.

Example 3: Crystal Structure of DCAF15 Complex Bound to RBM39$_{RRM2}$

Figure 2A:
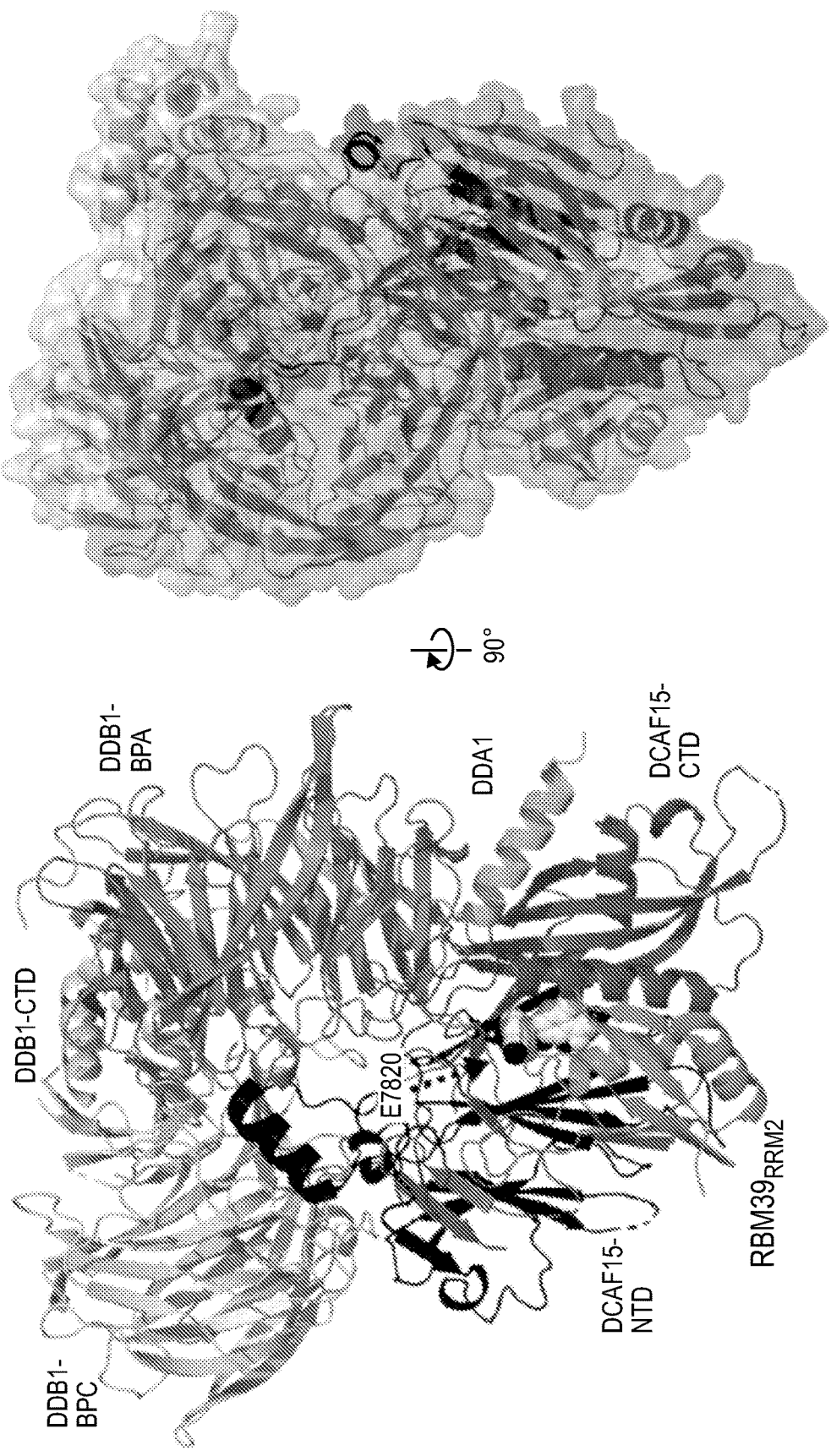
FIG. 2A-FIG. 2C are a series of cartoon representations showing the crystal structure of the DDB1ΔB-DCAF15$_{split}$-DDA1-E7820-RBM39$_{RRM2}$ complex.
Figure 9A:
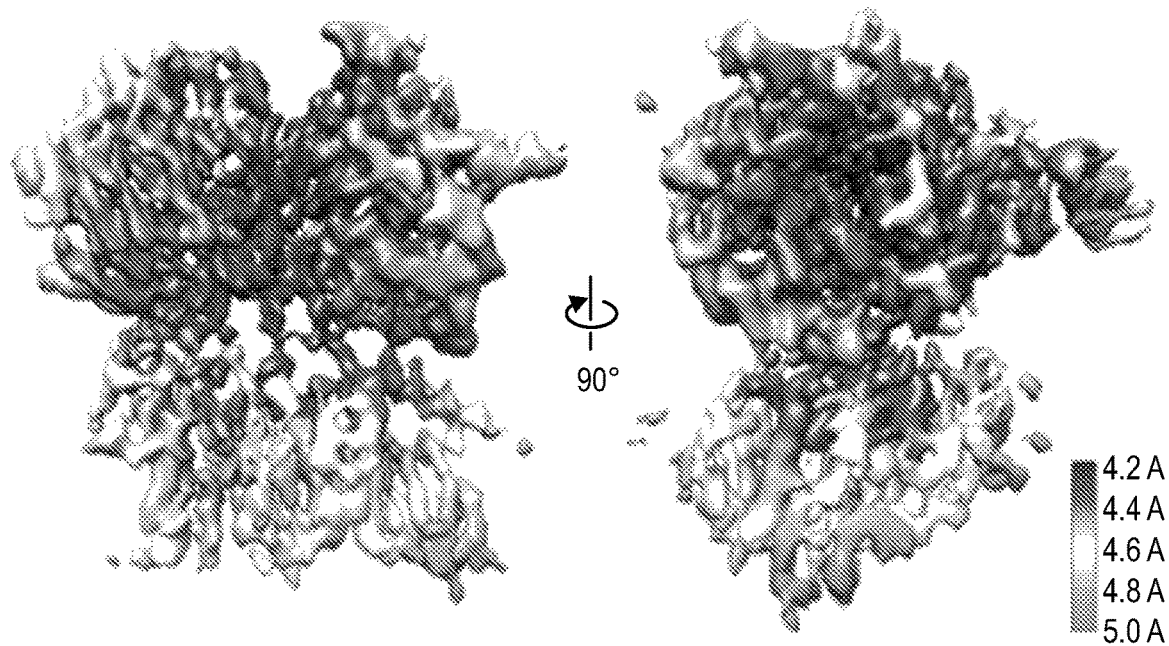
FIG. 9A-FIG. 9F are a series of cartoon representations and graphs depicting the local resolution, angular distribution, and model fitting of final cryo-EM reconstruction for DDB1ΔB-DCAF15-DDA1-E7820-RBM39$_{RRM2}$.
Figure 9B:
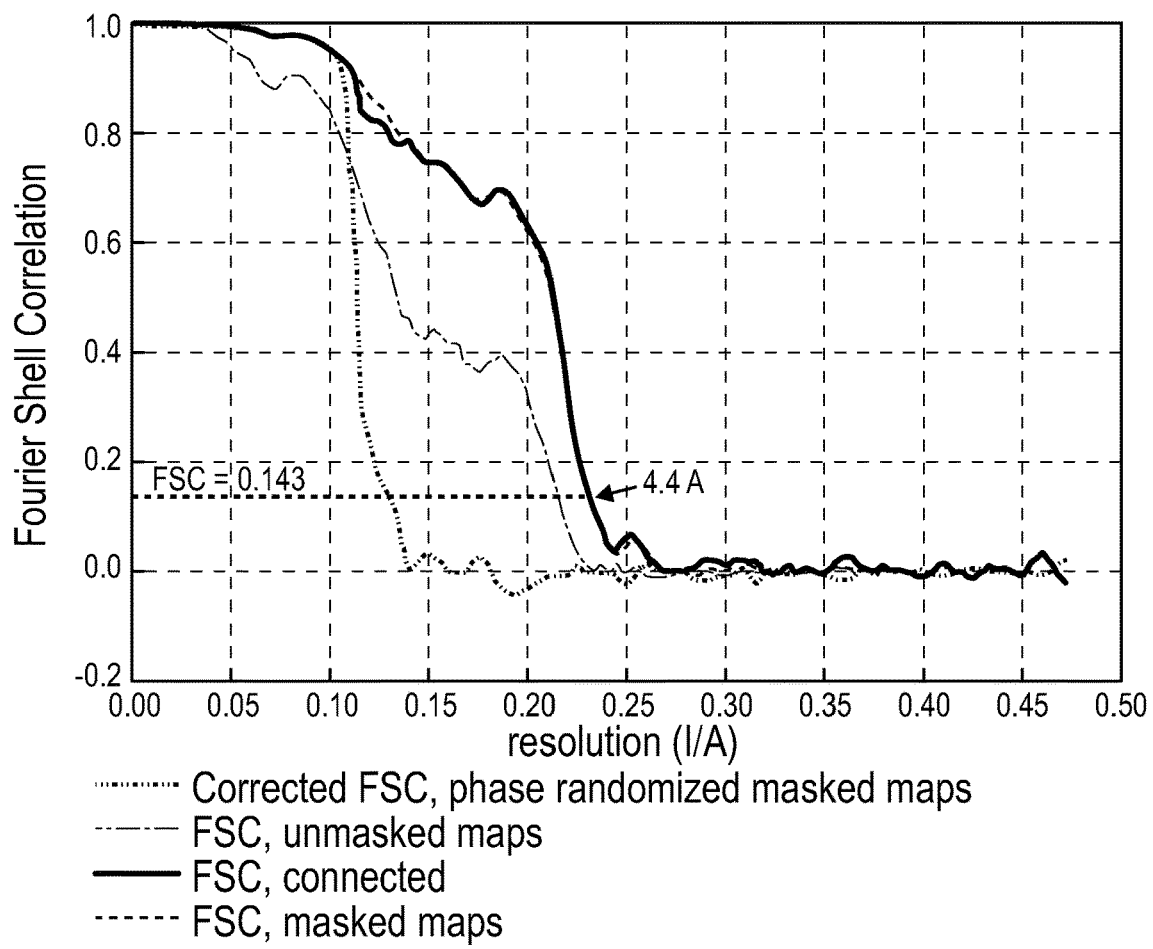
Figure 9C:
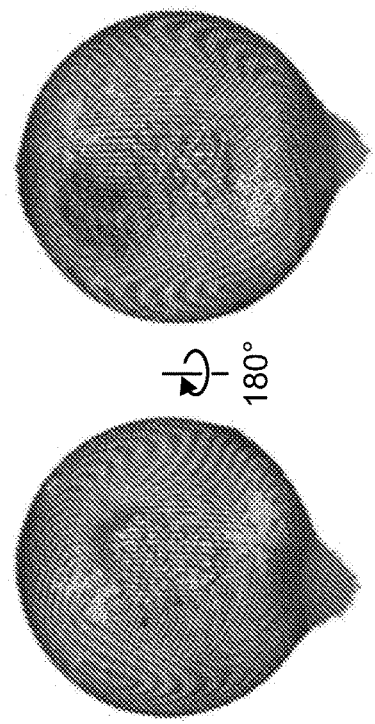
Figure 9D:
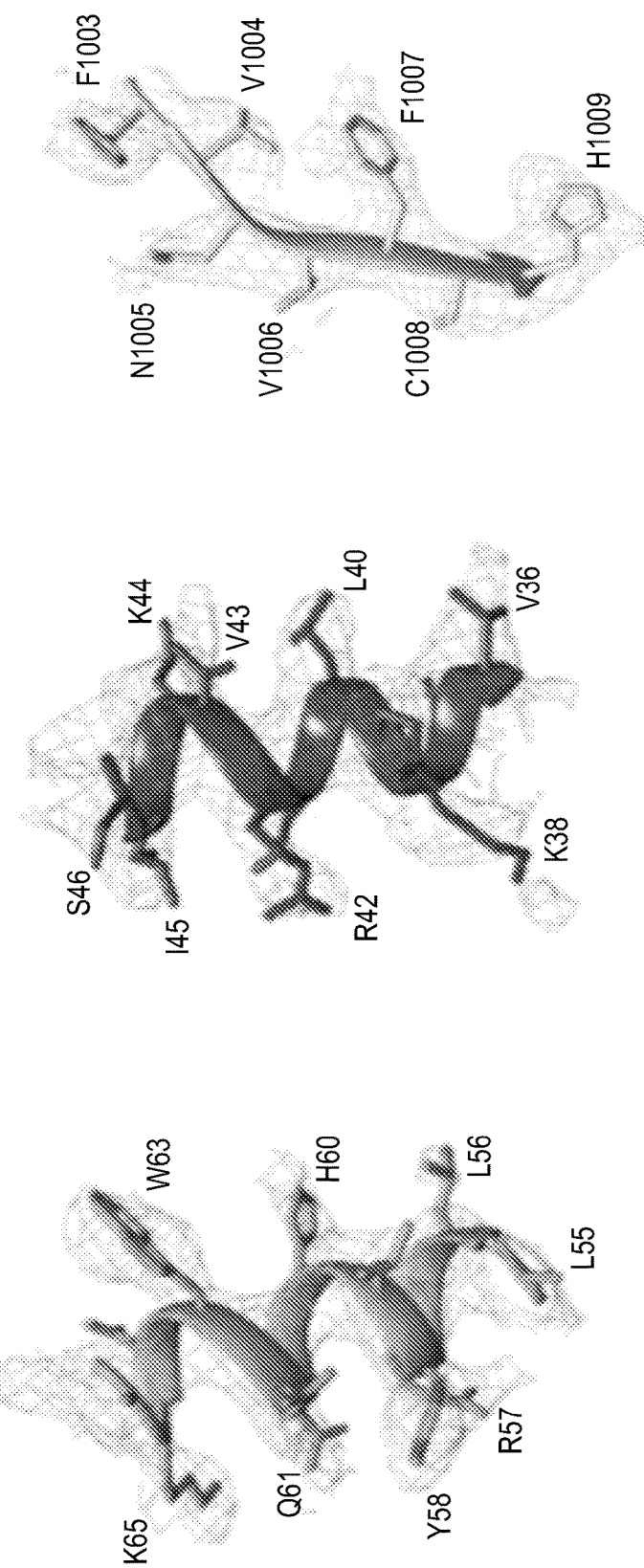
Figure 9E:
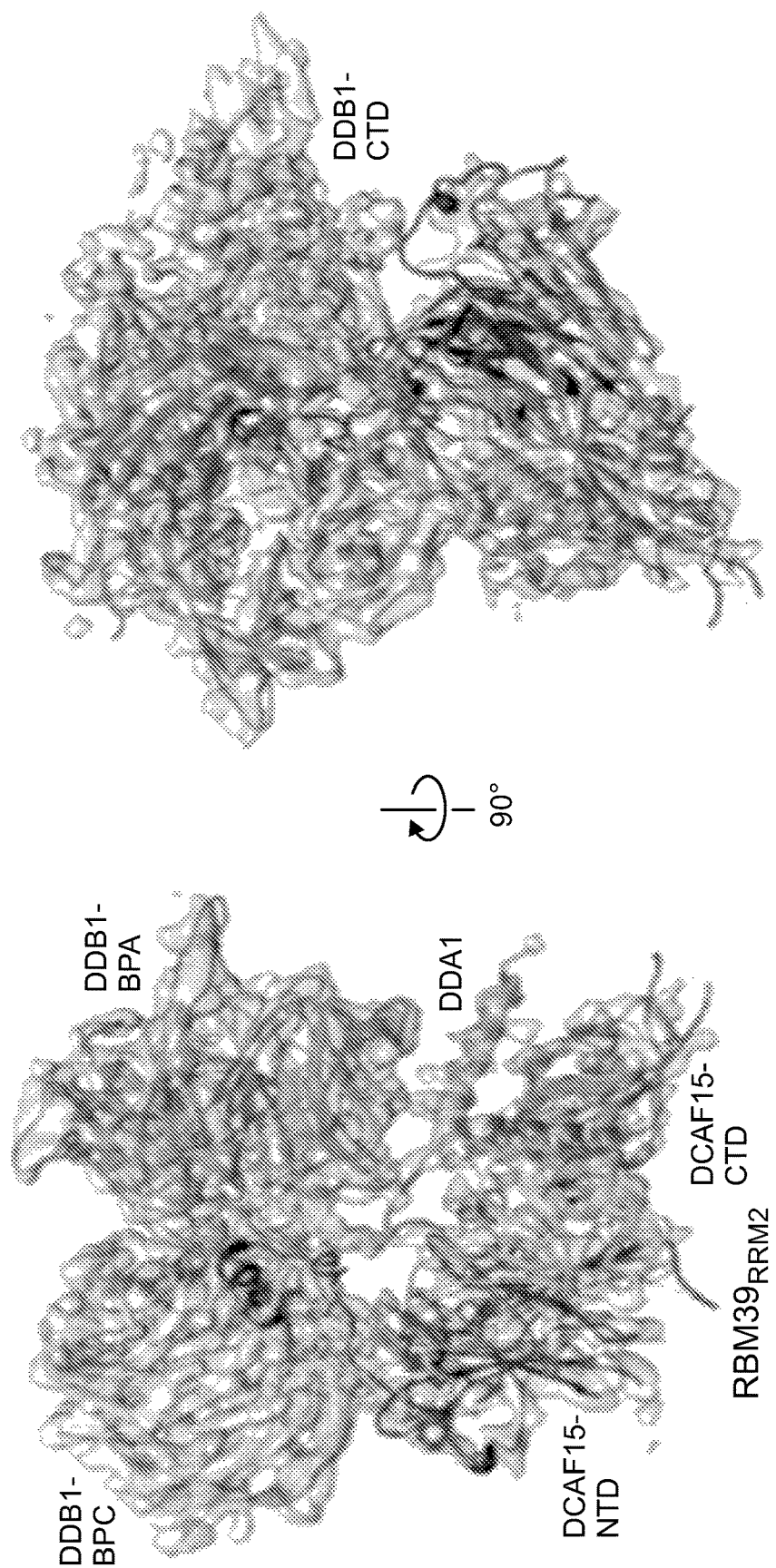
Figure 9F:
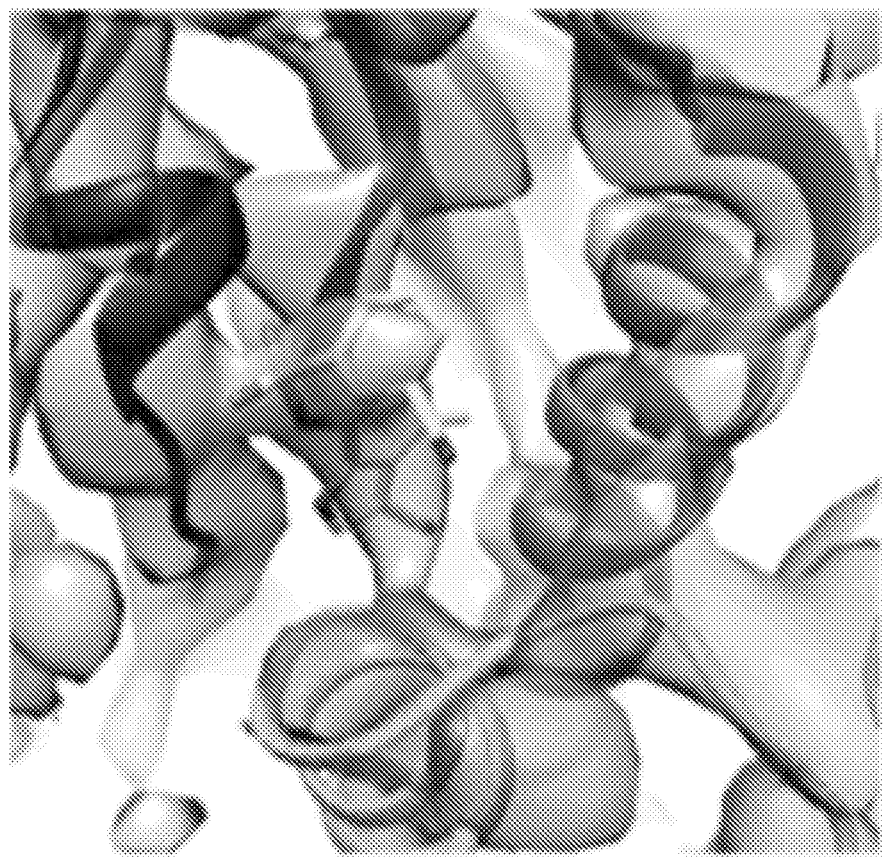

Crystals were obtained for a DDB1ΔB-DCAF15$_{split}$-DDA1-E7820-RBM39$_{RRM2}$ complex, and the structure was determined by molecular replacement with a final model refined to 2.9 Å resolution (FIG. 2A and Table 2). To validate that the engineered DCAF15$_{split}$ resembles the full-length DCAF15 structure, the X-ray model was docked into the cryo-EM map (Adams et al., Acta Crystallogr. D., 66:213-221 (2015)) and found that the crystal structure accounts for all of the full-length DCAF15 density as well as density for E7820 (FIG. 9E and FIG. 9F).

Figure 2B:
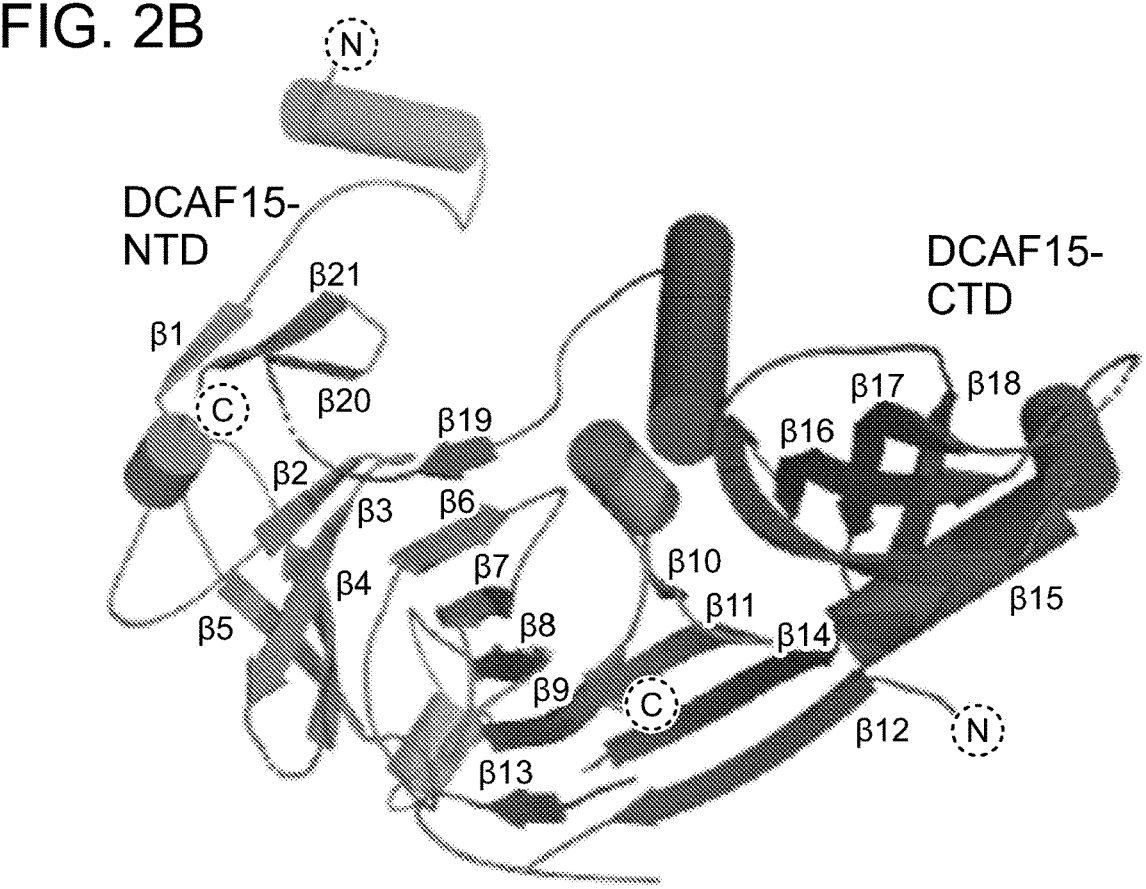
Figure 2C:
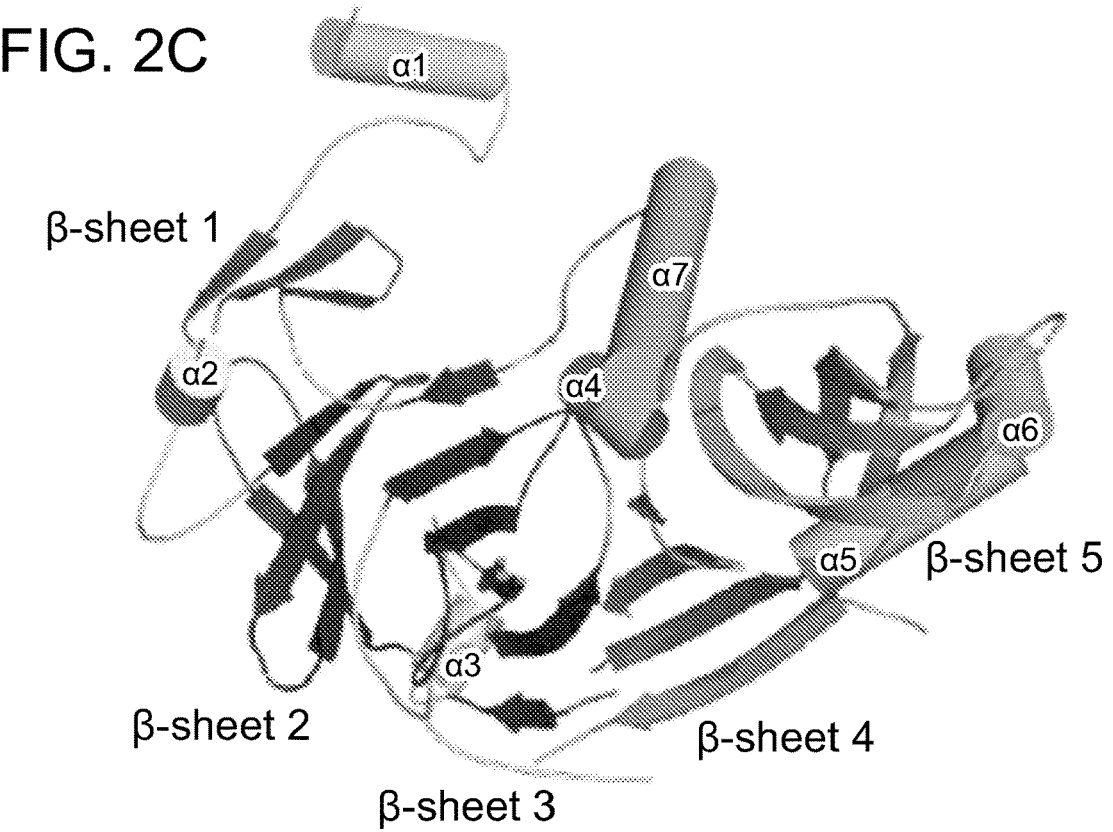
Figure 11B:
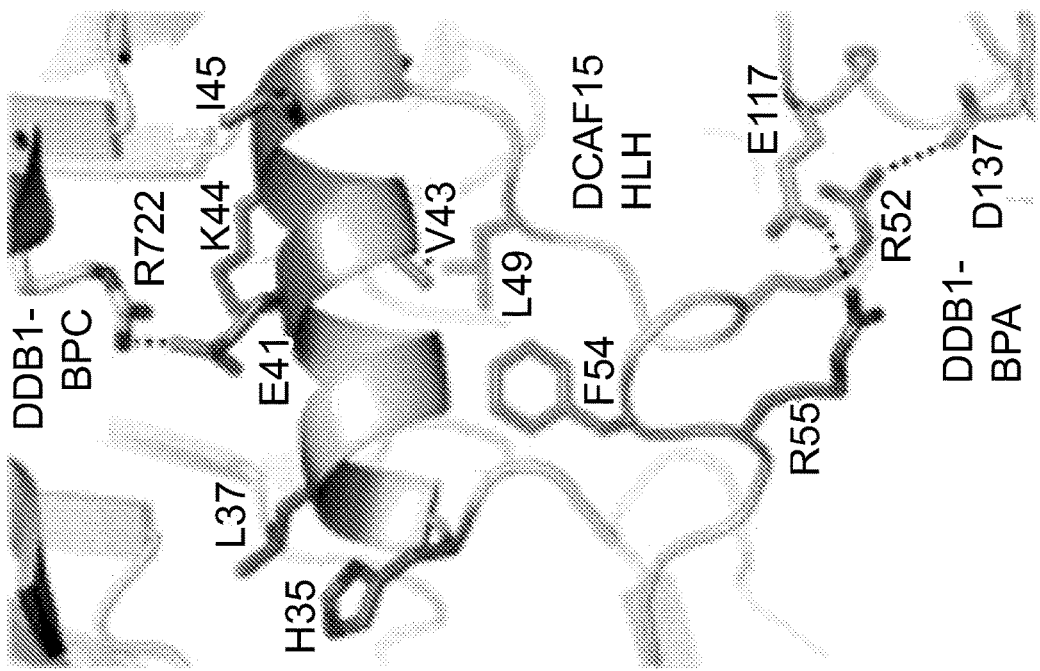
FIG. 11A-FIG. 11E are a series of cartoon representations and graphics depicting DCAF15 helix-loop-helix motif and conservation.
Figure 11A:
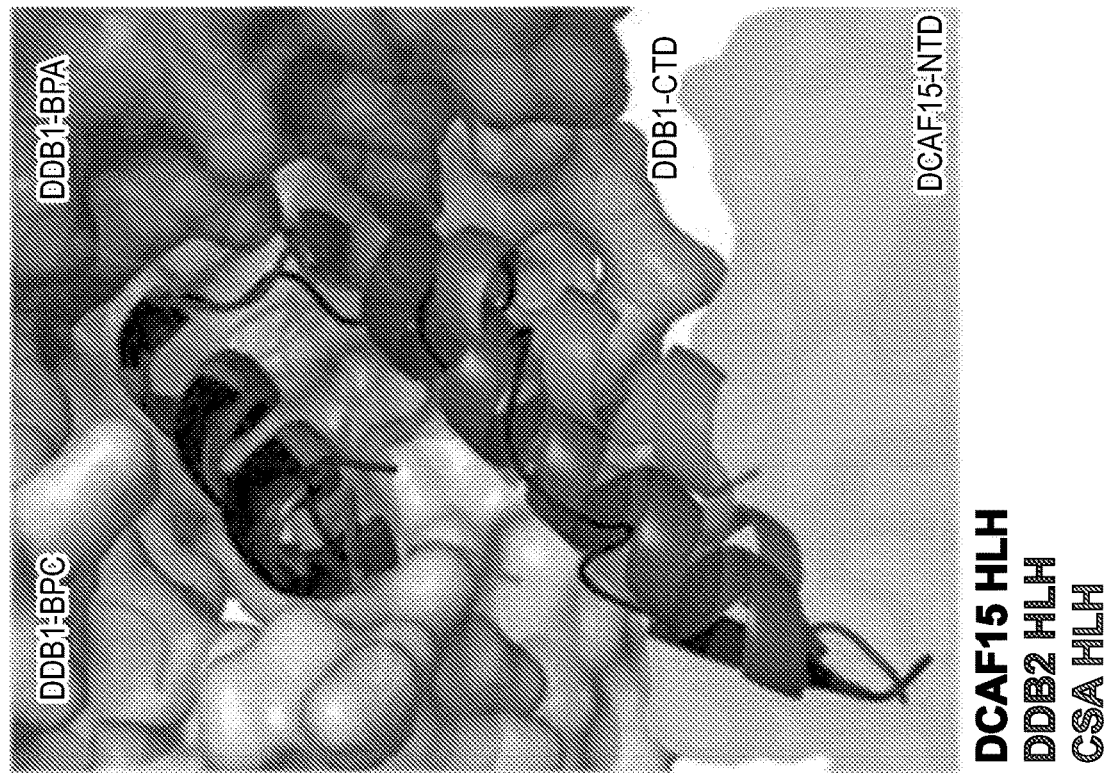
Figure 11C:
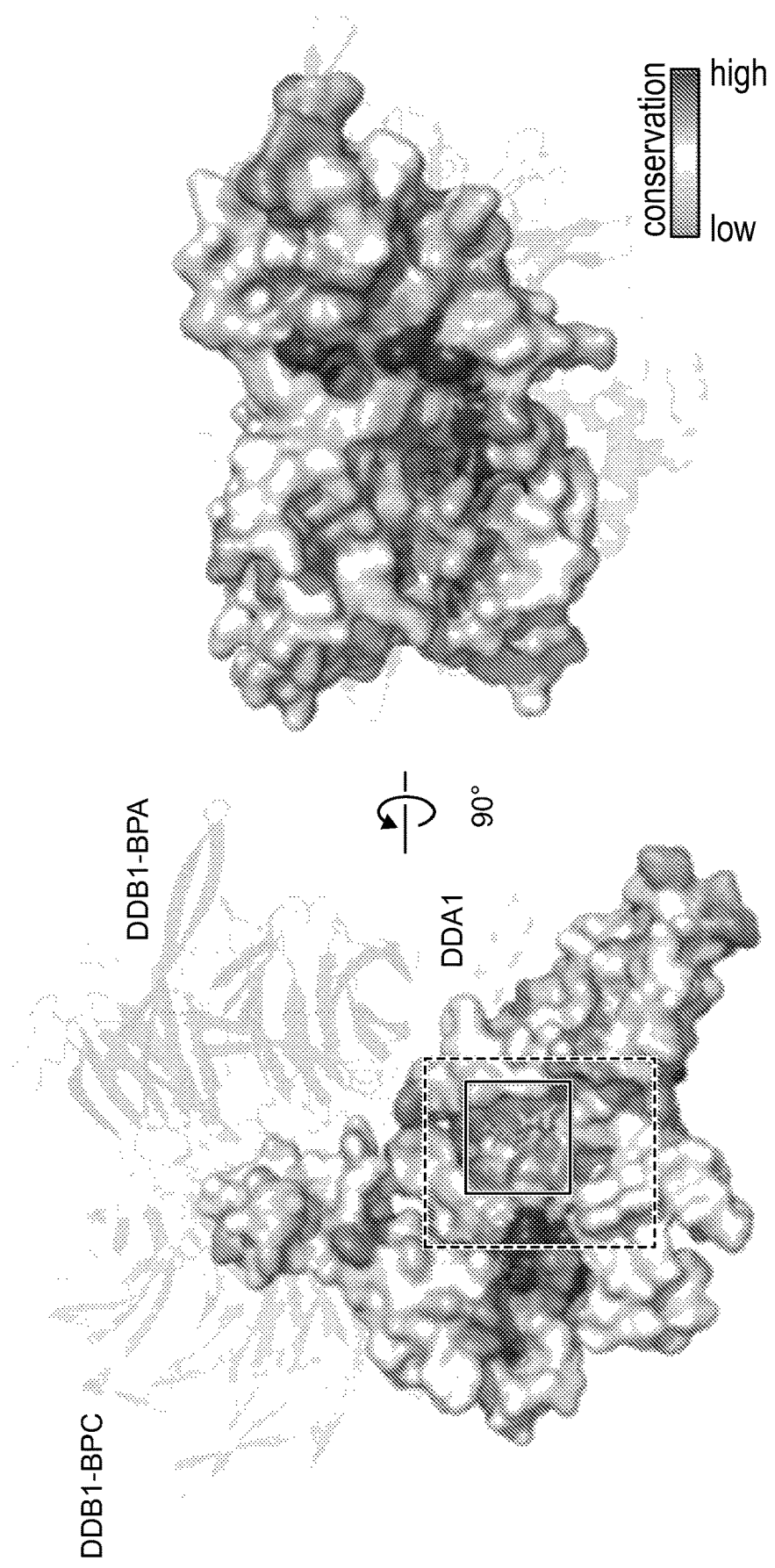
Figure 11E:
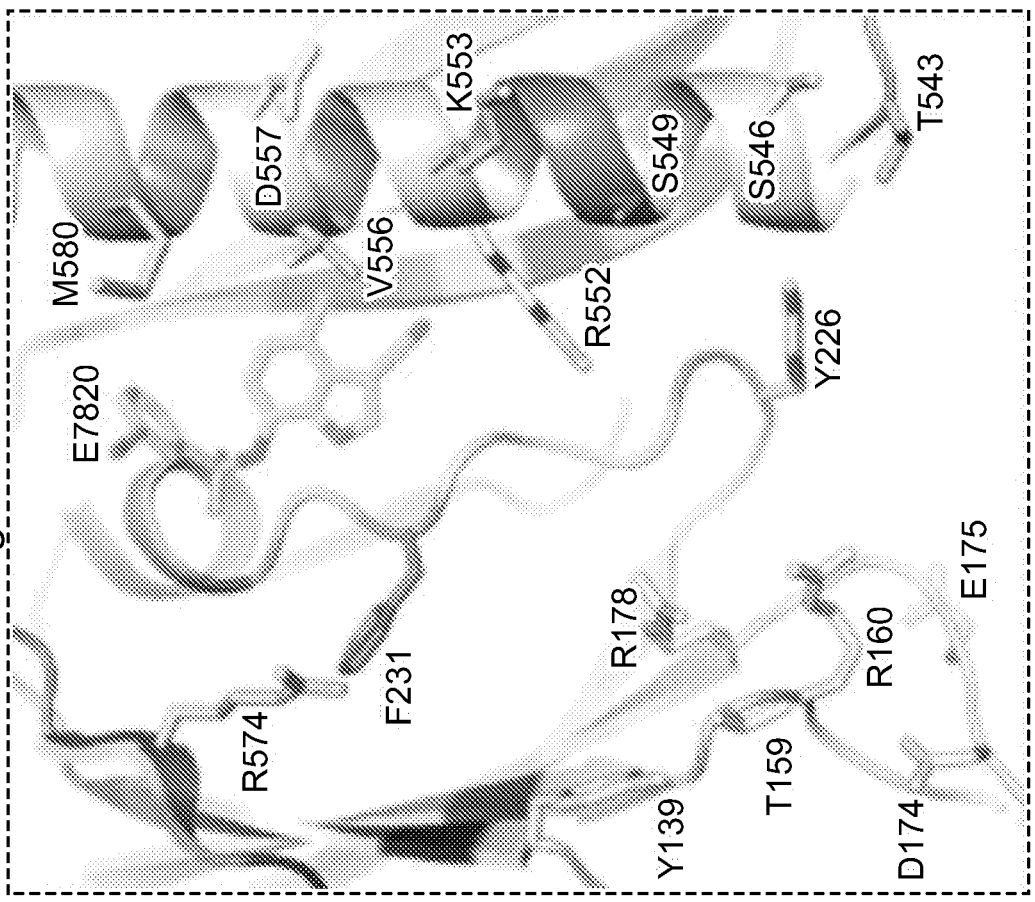
Figure 11D:
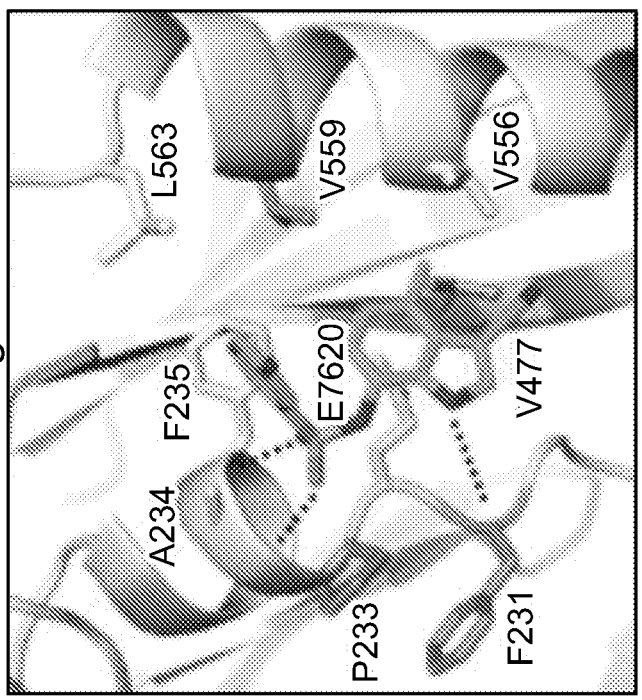

DCAF15$_{split}$ consisted of two predominantly β-sheet containing domains (FIG. 2B and FIG. 2C), the N-terminal domain (NTD, residues 30-264) and the C-terminal domain (CTD, residues 383-600). DCAF15 was bound to DDB1 with a helix-loop-helix motif (Fischer et al., Cell 147:1024-1039 (2011)), which formed contacts with the two DDB1 β-propeller domains BPA and BPC and resembled the helix-loop-helix motif in CSA and DDB2 (FIG. 10A, FIG. 11A and FIG. 11B). DCAF15, unlike most other DDB1 and CUL4-associated factors (DCAFs), does not contain a canonical WD40 β-propeller fold and lacks homology to any other CRL substrate receptor (Zimmerman et al., Curr. Opin. Struct. Biol., 20:714-721 (2010)). Following the helix-loop-helix motif, the DCAF15 NTD and CTD were interwoven into five stacks of antiparallel β-sheets in an open solenoid arrangement, with β-sheets 1, 3, and 4 sharing strands from both the NTD and CTD. While β-sheets 2 and 3 have some resemblance to WD40 repeats, β-sheets 4 and 5 had unique features (FIG. 2B and FIG. 2C). β-sheet 4 was a short helix (α4) angled ~45° away from the sheet, before looping into β-strand 10 and 11. The terminal strands 12 and 14 of β-sheet 4 were contributed by the DCAF15 CTD, which created an extended interface between the two domains. β-sheet 5 was stabilized by two α-helices (DCAF15 α5 and α6), and α7 helix sat on the opposite side which formed the major interactions with RBM39$_{RRM2}$. The overall shape of DCAF15 was clamp-like and embraced RBM39$_{RRM2}$ on the concave surface.

Figure 3B:
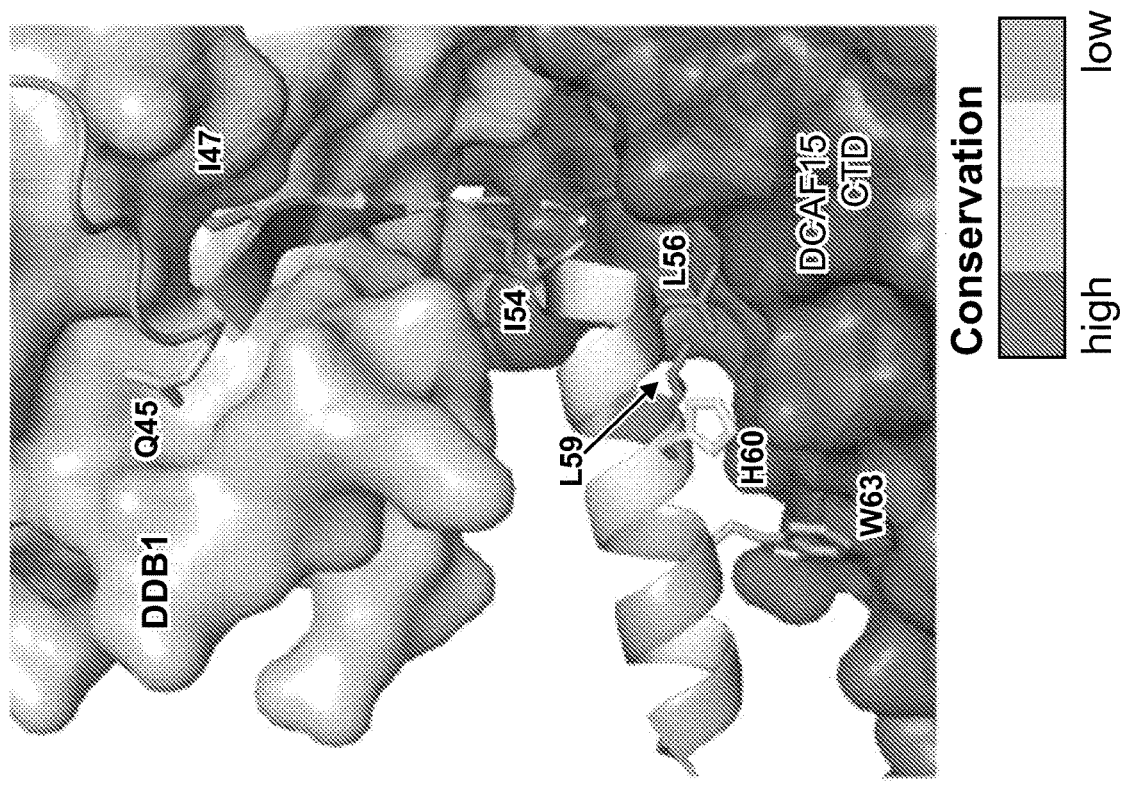
FIG. 3A-FIG. 3E are a series of cartoon representations and graphs that depict DDA1 stabilizing the CRL4$^{DCAF15}$ complex and facilitating RBM39 recruitment.
Figure 3A:
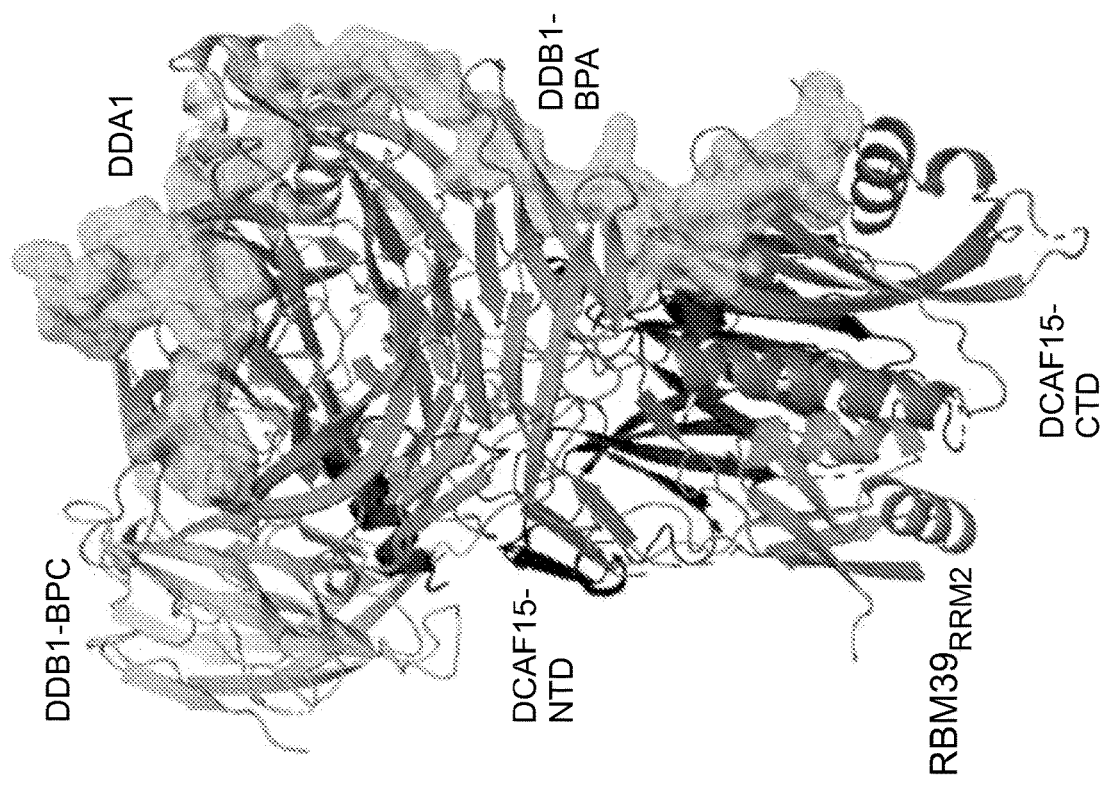
Figure 3C:
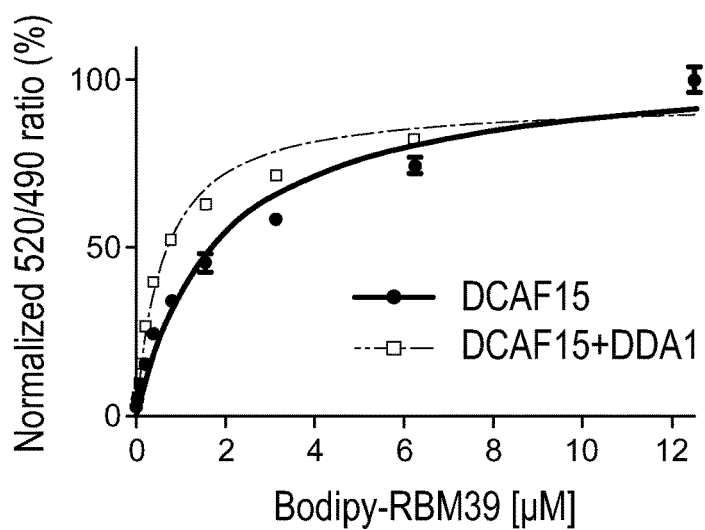
Figure 3D:
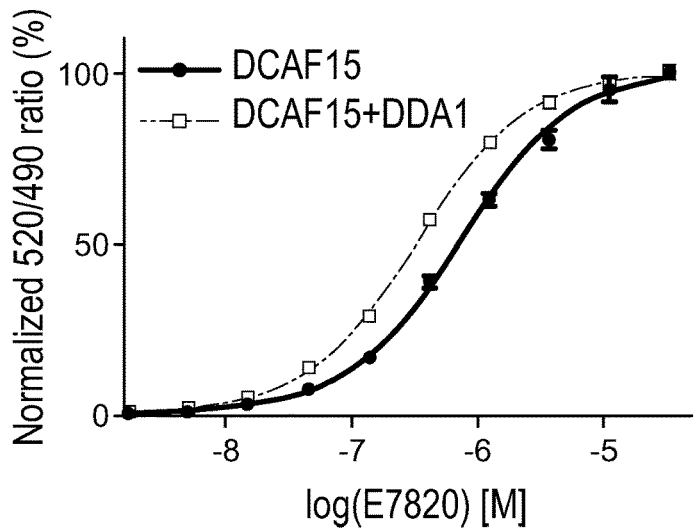
Figure 3E:
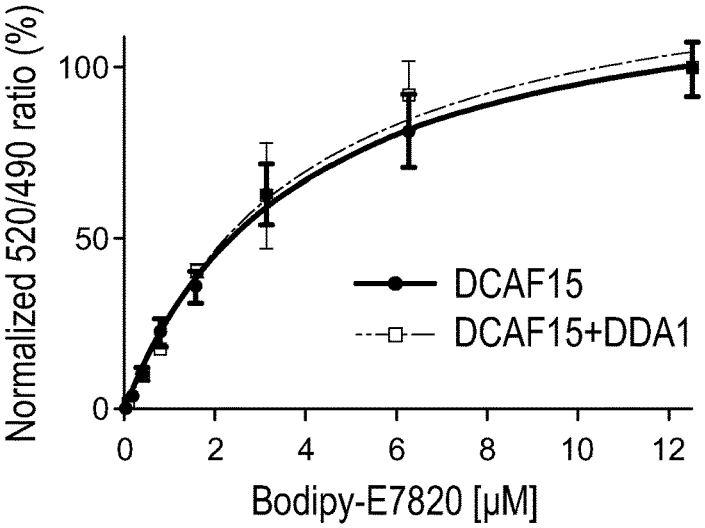

The small protein DDA1 is commonly associated with CRL4 complexes (Jin et al., Mol. Cell 23:709-721 (2006); Shabek et al., Cell Discov. 4:67 (2018)), and knockout of DDA1 was found to reduce the indisulam-mediated degradation of RBM39 (Han et al., Science 356:aal3755 (2017)). In the crystal and cryo-EM structures, DDA1 was bound to the top of the DDB1 BPA before running down the backside of the propeller (FIG. 1D and FIG. 3A). At the bottom of the DDB1 BPA, DDA1 intercalated a β-strand in the DDB1 propeller, using several highly conserved residues (FIG. 3B). Adjacent to this β-strand was an α-helix that buried multiple DDA1 hydrophobic residues (Leu55, Leu56, Leu59, and Trp63) in DCAF15 (FIG. 3B). Given that DDA1 is a core CRL4 component associated with many different substrate receptors (Jin et al., Mol. Cell 23:709-721 (2006); Olma et al., J. Cell Science 122:1035-1044 (2009)), the extent of the DCAF15 interactions were unexpected and suggested that the DDA1 helix represents a plastic binding module for other DCAFs. The affinity of E7820 to recombinant DDB1-DCAF15 and DDB1-DCAF15-DDA1 was measured, as well as the ability of these complexes to bind to RBM39$_{RRM2}$. While the affinity of E7820 to DCAF15 was not altered by the presence of DDA1, the apparent affinity to RBM39$_{RRM2}$ was strengthened ~3-fold with an $K_D^{app}$ of 0.62 µM (FIG. 3C-FIG. 3E), which explains why genetic loss of DDA impairs induced RBM39 degradation (Han et al., Science 356:aal3755 (2017)).

TABLE 2

Crystallization data.

| | X102 E7820 | X180 indisulam | X198 tasisulam |
|---|---|---|---|
| Data collection | | | |
| Space group | P2$_1$2$_1$2$_1$ | P2$_1$2$_1$2$_1$ | P2$_1$2$_1$2$_1$ |
| Cell dimensions | | | |
| a, b, c (Å) | 81.1, 93.6, 258.43 | 93.97, 81.80, 260.98 | 81.77, 94.61, 260.40 |
| α, β, γ (°) | 90.0, 90.0, 90.0 | 90.0, 90.0, 90.0 | 90.0, 90.0, 90.0 |
| Resolution (Å) | 45.3-2.9 (3.0-2.9)* | 45.6-2.9 (3.0-2.9)* | 46.5-2.9 (3.0-2.9)* |
| R$_{sym}$ or R$_{merge}$ | 0.03 (0.80) | 0.17 (2.32) | 0.03 (0.72) |
| I/σI | 13.21 (0.79) | 8.19 (0.71) | 15.97 (0.78) |
| CC 1/2 | 1.00 (0.69) | 0.99 (0.60) | 0.99 (0.82) |
| Completeness (%) | 99.5 (99.6) | 99.6 (98.6) | 99.3 (97.2) |
| Redundancy | 2.0 (2.0) | 6.7 (6.9) | 2.0 (2.0) |
| Refinement | | | |
| Resolution (Å) | 45.3-2.9 | 45.6-2.9 | 46.5-2.9 |
| No. reflections | 44327 | 45335 | 45140 |
| R$_{work}$/R$_{free}$ | 21.5/25.8 | 21.2/23.7 | 20.3/25.1 |
| No. atoms | | | |
| Protein | 10180 | 10314 | 10213 |
| Ligand/ion | 25 | 25 | 21 |
| Water | 11 | 3 | |
| B-factors | | | |
| Protein | 131.5 | 117.1 | 116.9 |
| Ligand/ion | 99.2 | 111.7 | 95.8 |
| Water | 81.6 | 79.1 | |
| R.m.s. deviations | | | |
| Bond lengths (Å) | 0.014 | 0.014 | 0.014 |
| Bond angles (°) | 1.92 | 1.86 | 1.93 |

*Values in parentheses are for highest-resolution shell.
**One crystal was used for each structure.

Example 4: Aryl-Sulfonamides Interact Primarily with DCAF15

Figure 12B:
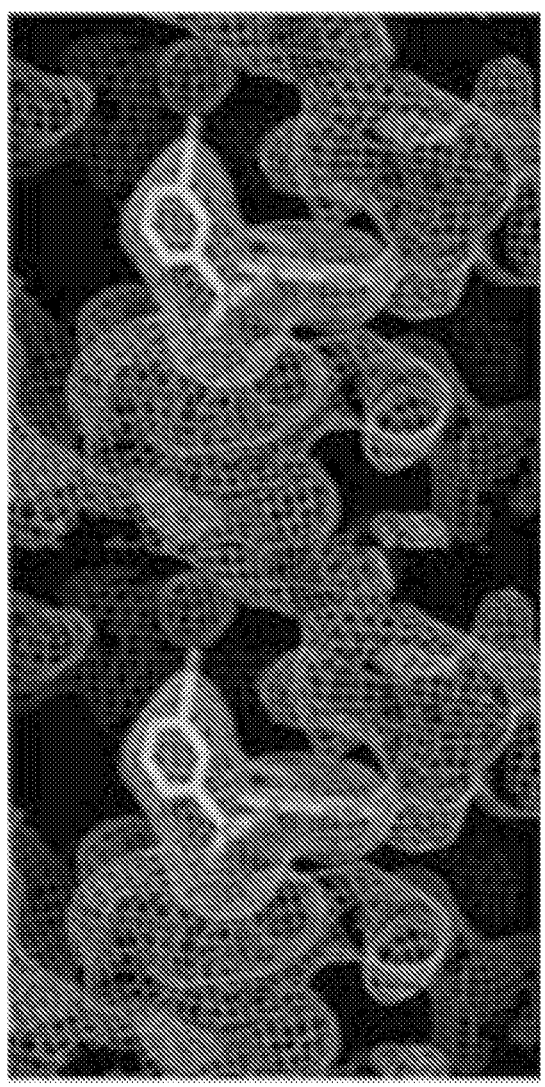
FIG. 12B is a stereo view of a simulated annealing omit map around E7820 and 2Fo-Fc.
Figure 12A:
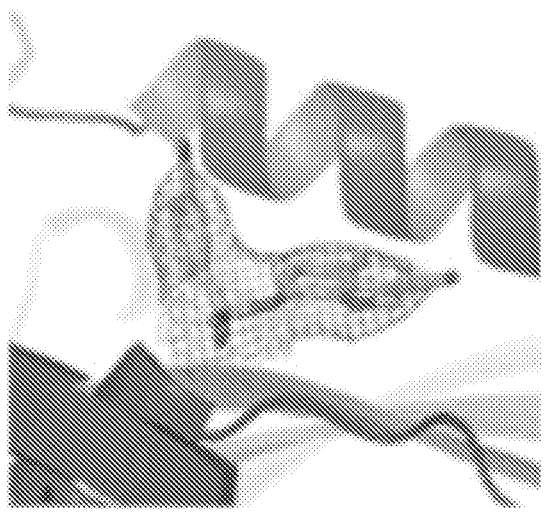
FIG. 12A-FIG. 12N are a series of cartoon representations, graphics, chemical structures, and graphs showing the experimental validation of E7820 binding sites and resistance mutations in RBM39.
Figure 12C:
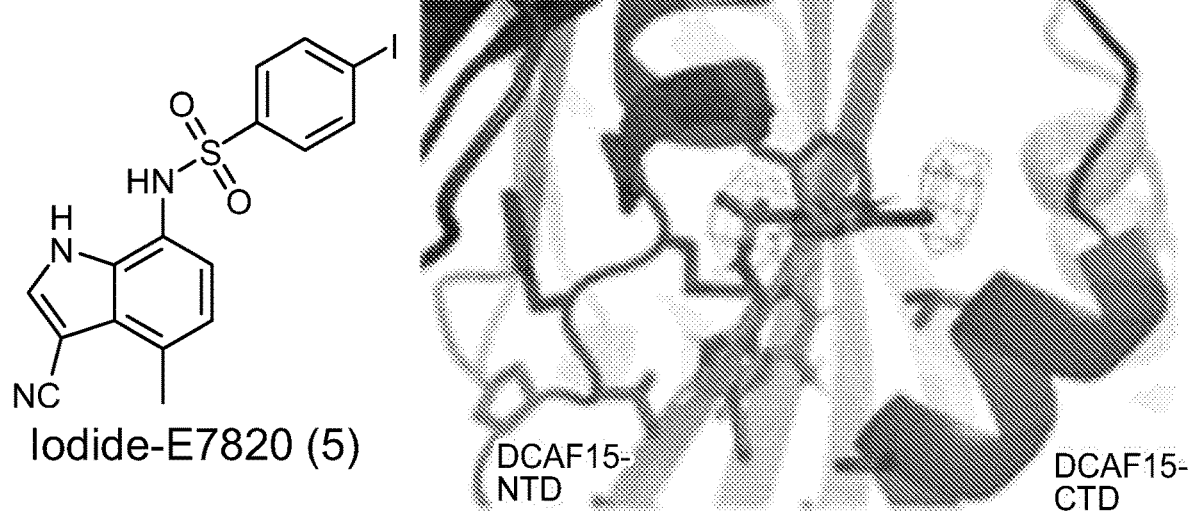
FIG. 12C is a crystal structure of DDB1ΔB-DCAF15$_{split}$-DDA1-RBM39$_{RRM2}$ bound to compound 5 (Iodide-E7820). Shown in mesh is the anomalous difference map contoured at 5 sigma.
Figure 12D:
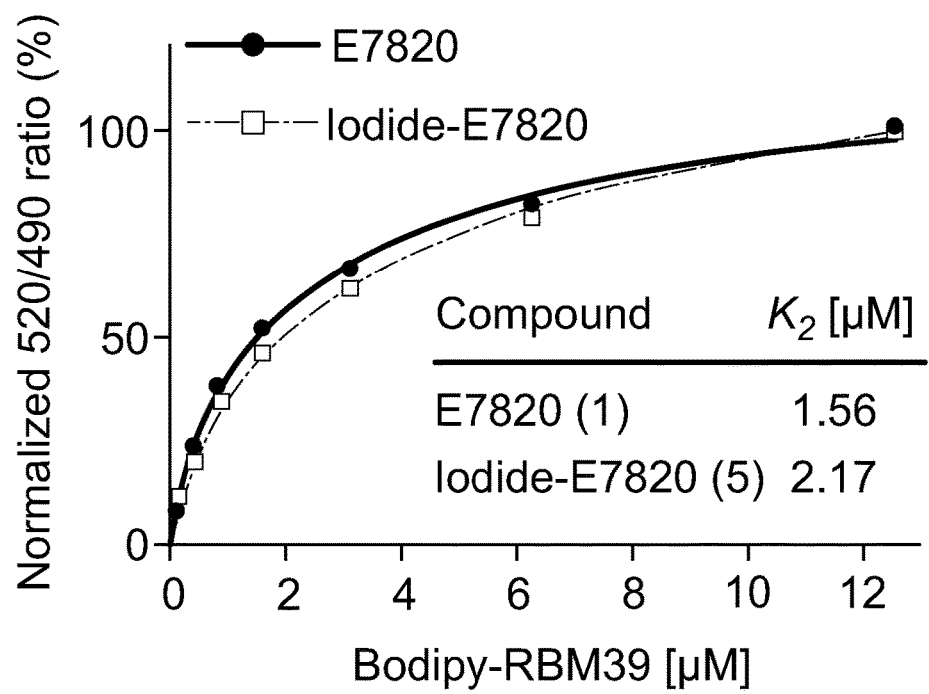
FIG. 12D is a graph of TR-FRET for the titration of BodipyFL-RBM39$_{RRM2}$ to DDB1ΔB-DCAF15$_{biotin}$ at 200 nM pre-treated with E7820 or compound 5 at 50 μM (n=2).
Figure 12E:
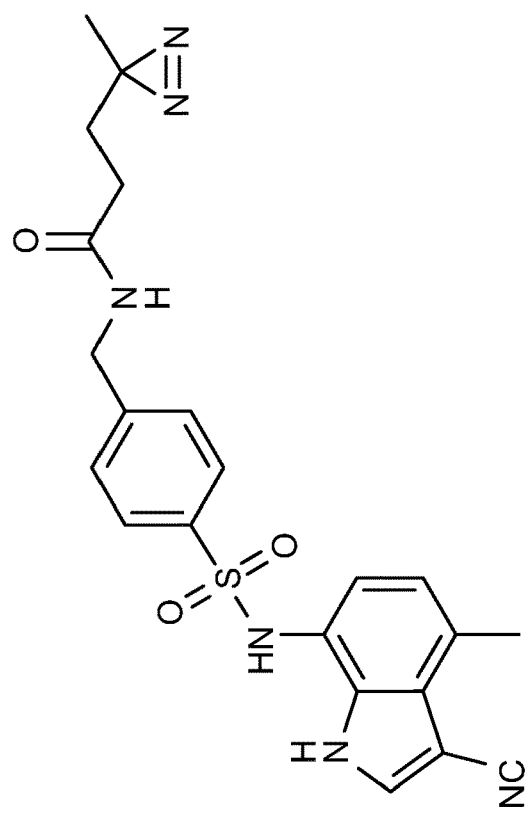
FIG. 12E is the chemical structure of compound 6 (Diazirine-E7820), used for UV-crosslinking.
Figure 12F:
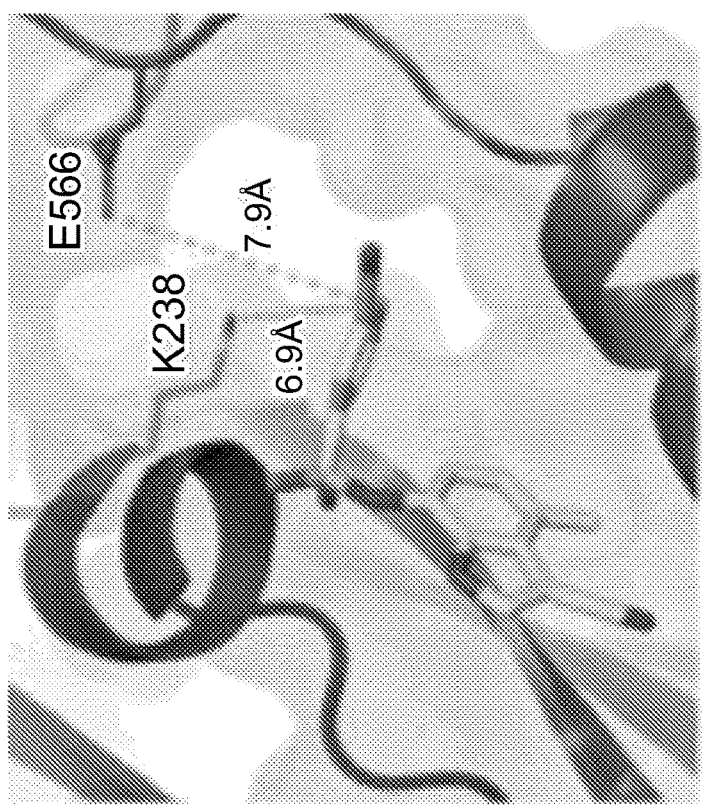
FIG. 12F is a cartoon representation showing the two UV-crosslinked residues (Lys238, Glu566) in DCAF15 are highlighted. The distances from the 4-position of E7820 phenyl ring to the residues are specified (6.9 Å and 7.9 Å, respectively). For FIG. 12G and FIG. 12H UV-crosslinking is coupled with mass spectrometry. Proteins were treated by DMSO, compound 6, or compound 6 with pre-treatment of E7820 then UV-irradiated.
Figure 12H:
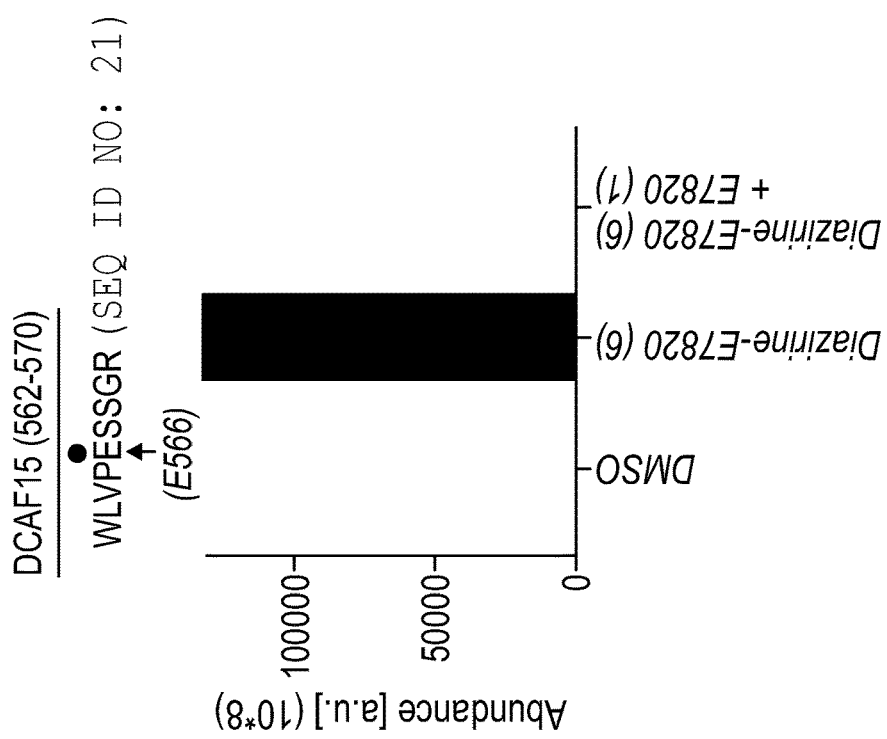
FIG. 12H is a bar graph showing the quantification of modified peptides in DCAF15 562-570. Circle above the sequence indicates the UV-crosslinked residue (Glu566).
Figure 12G:
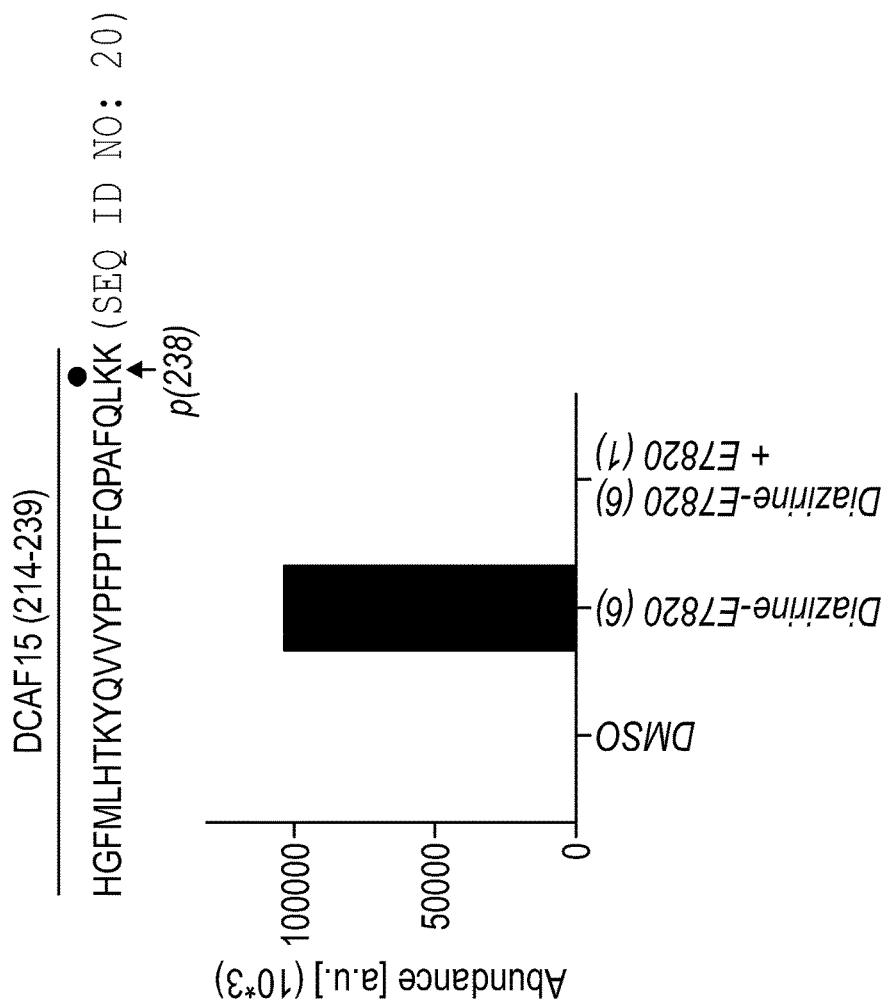
FIG. 12G is a bar graph showing the quantification of modified peptides in DCAF15 214-239. Circle above the sequence indicates the UV-crosslinked residue (Lys238).
Figure 12I:
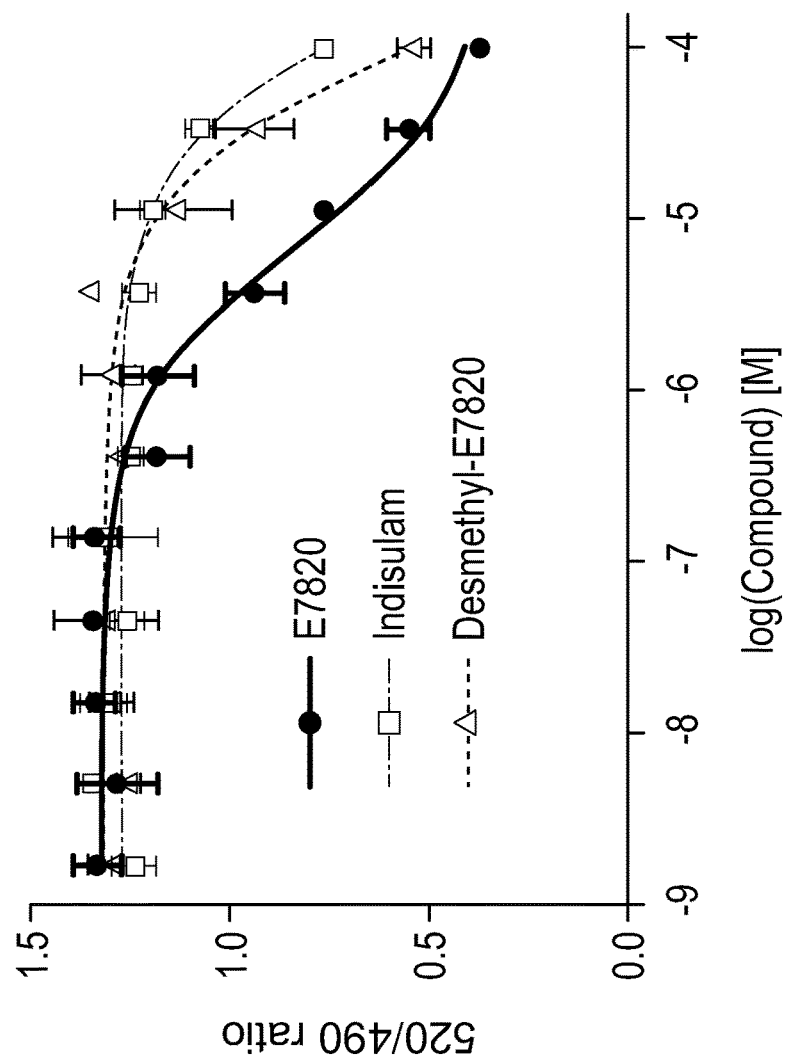
FIG. 12I is a graph of the TR-FRET based competitive binding assay of compound 7 (Desmethyl-E7820). Data is plotted as means±s.d. from three independent replicates (n=3).
Figure 12I:
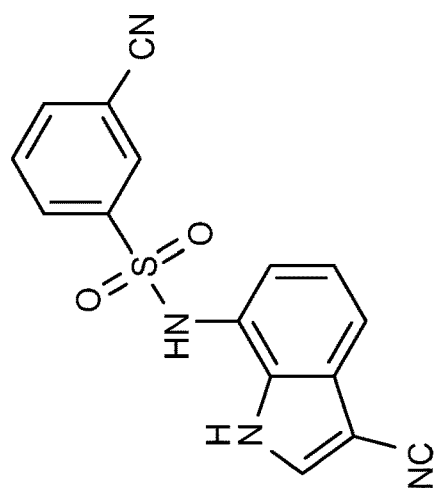

E7820 was bound in a shallow pocket at the interface between DCAF15-NTD and DCAF15-CTD situated in a weakly conserved surface groove proximal to DDB1 (FIG. 4 and FIG. 11C-FIG. 11E). While the placement of E7820 was firmly supported by the electron density (FIG. 12A and FIG. 12B), the arrangement of the ligand was further validated through anomalous diffraction and a UV-crosslinking probe (FIG. 12C-FIG. 12H). E7820 was sandwiched in a hydrophobic pocket between DCAF15 and RBM39$_{RRM2}$, with the indole facing Met265 of RBM39. Notably, the RBM39 Met265Leu mutation was found to confer resistance to E7820-mediated degradation (Han et al., Science 356: aal3755 (2017)), which was in accordance with the sulfur-t interaction observed in the structure. The two sulfonyl oxygens of E7820 formed hydrogen bonds with the backbone amide nitrogens of DCAF15 Ala234 and Phe235, while the indole nitrogen and sulfonamide nitrogen formed extensive water-mediated hydrogen bonds with the side-chain oxygens of RBM39 Thr262 and Asp264. Additional hydrogen bonds between the indole nitrogen and backbone carbonyl oxygen of DCAF15 Phe231, together formed the core pharmacophore. The C4 methyl of E7820 formed hydrophobic interactions with Val477 and Val556 of DCAF15 (FIG. 4A and FIG. 4C), and swapping the methyl for a hydrogen, as in indisulam or desmethyl-E7820, resulted in a significant loss of DCAF15 binding (FIG. 12I). The phenyl ring formed a T-shaped π-π interaction with DCAF15 Phe235 and otherwise was situated in a spacious pocket allowing for structural diversity as observed in indisulam and tasisulam.

Figure 4A:
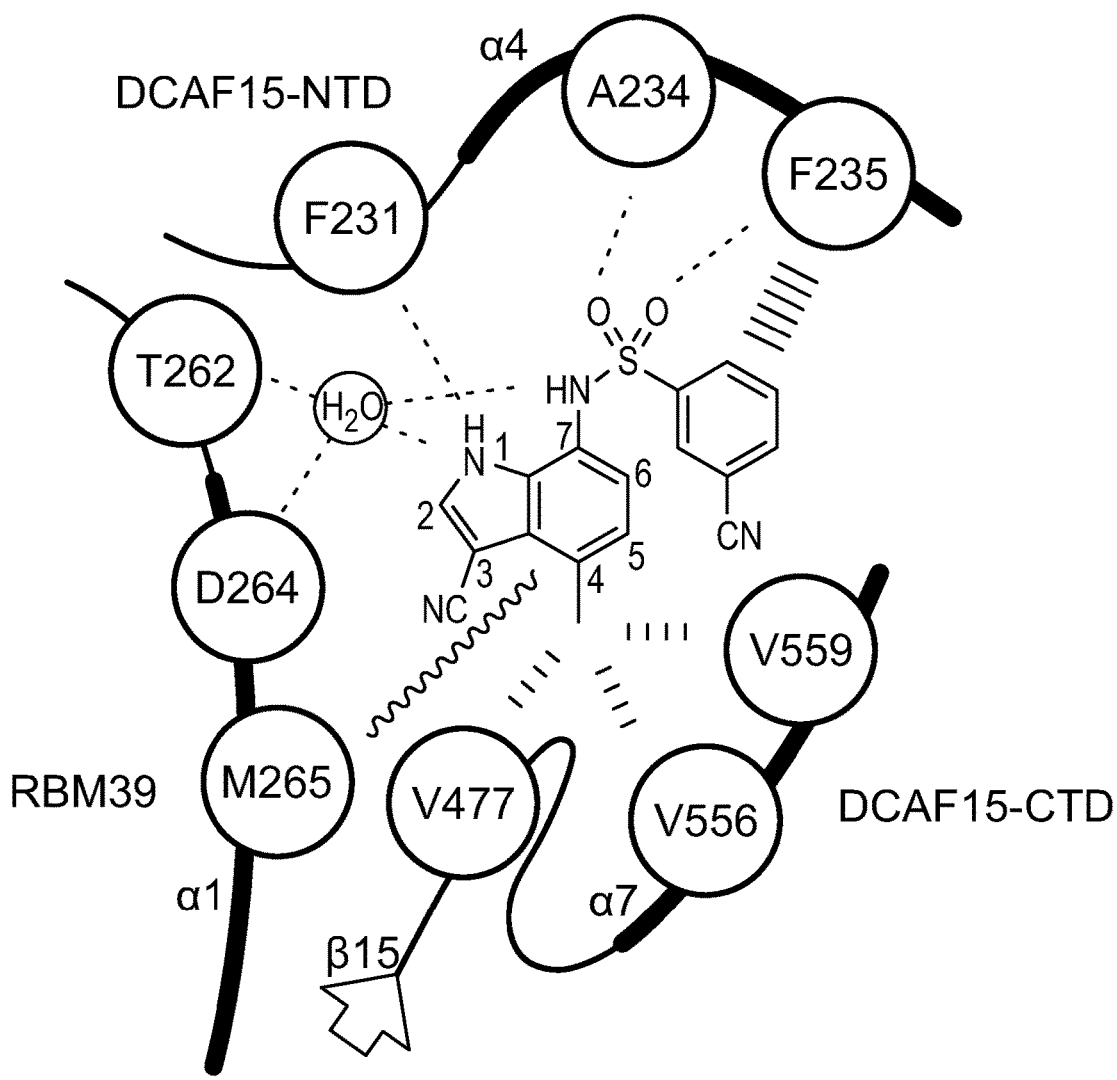
FIG. 4A-FIG. 4D are a series of cartoon representations and structures aryl-sulfonamides binding to DCAF15.
Figure 4B:
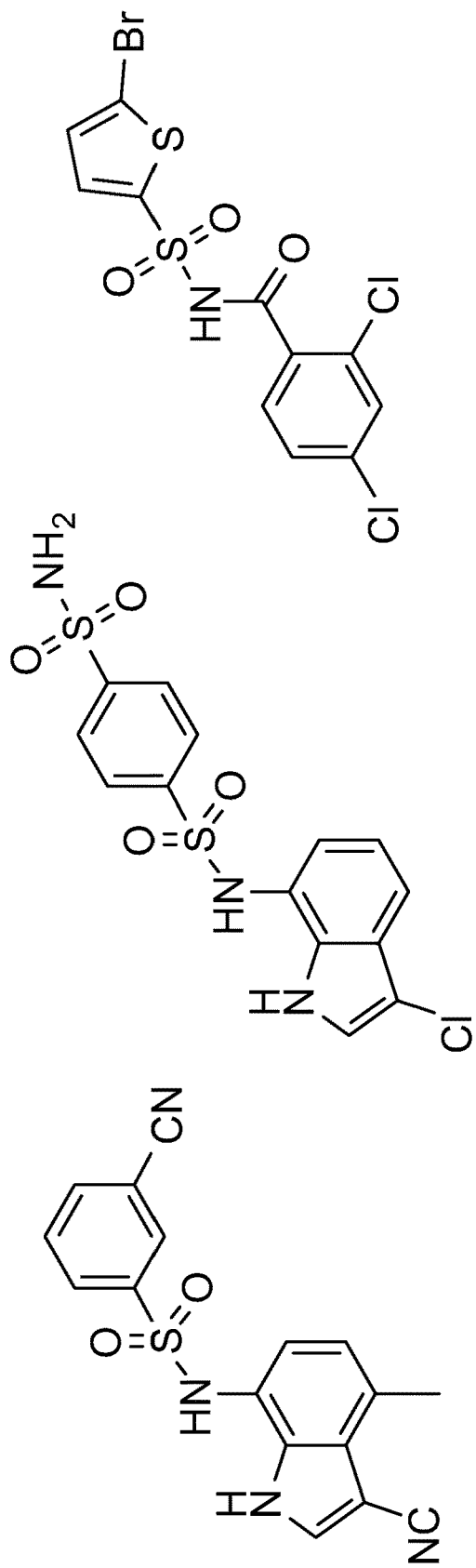
Figure 4C:
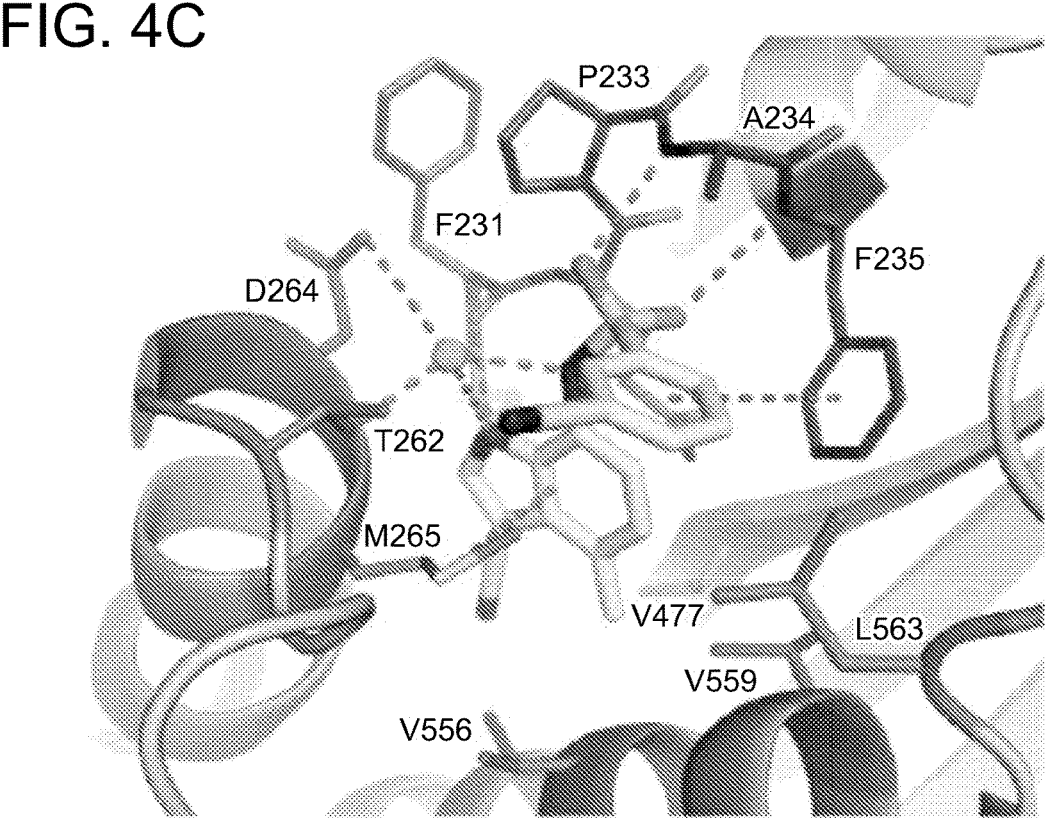
Figure 4D:
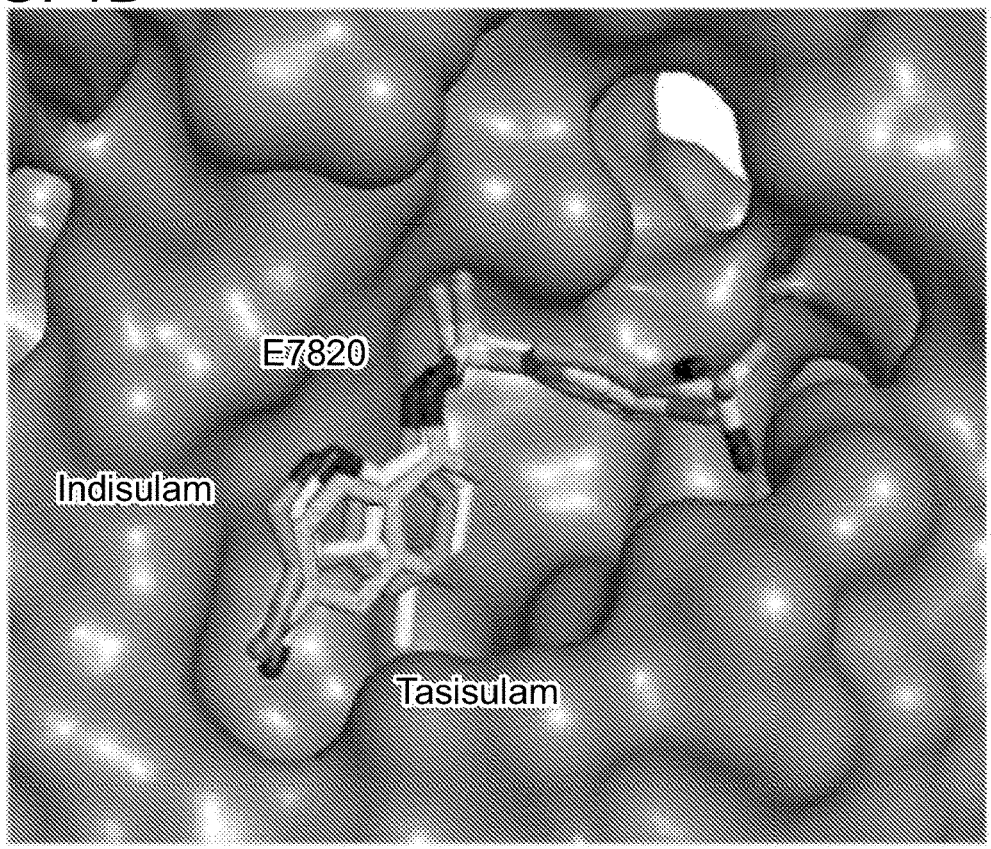
Figure 12J:
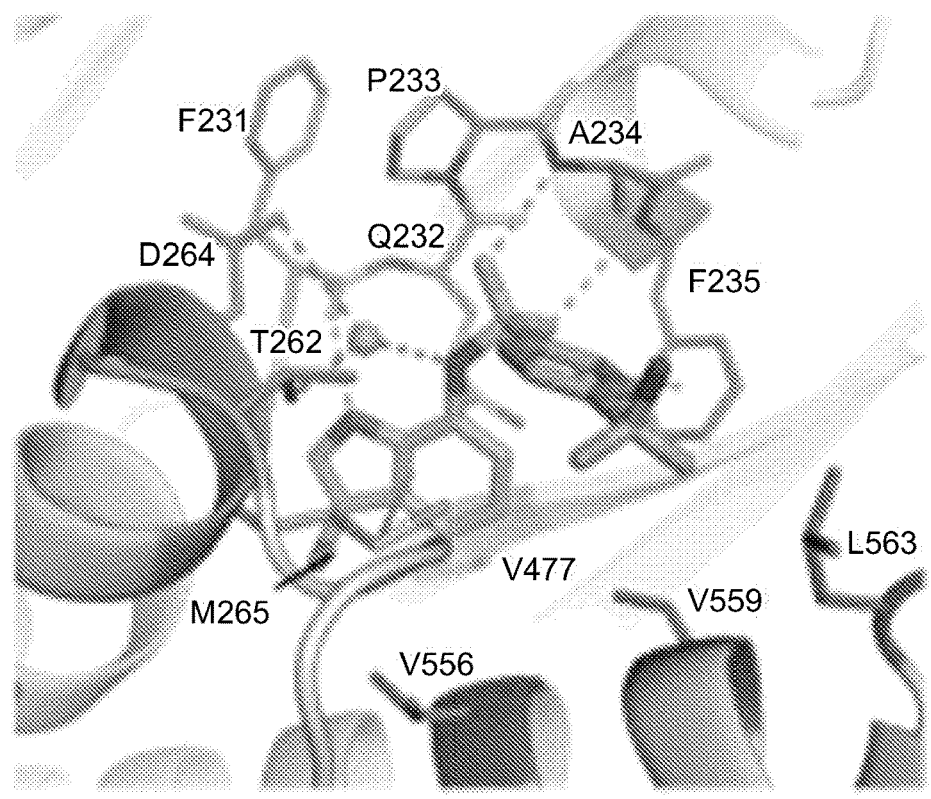
FIG. 12J is a cartoon representation depicting the side chain interactions between DCAF15 NTD, DCAF15 CTD, RBM39$_{RRM2}$, water, and indisulam.
Figure 12K:
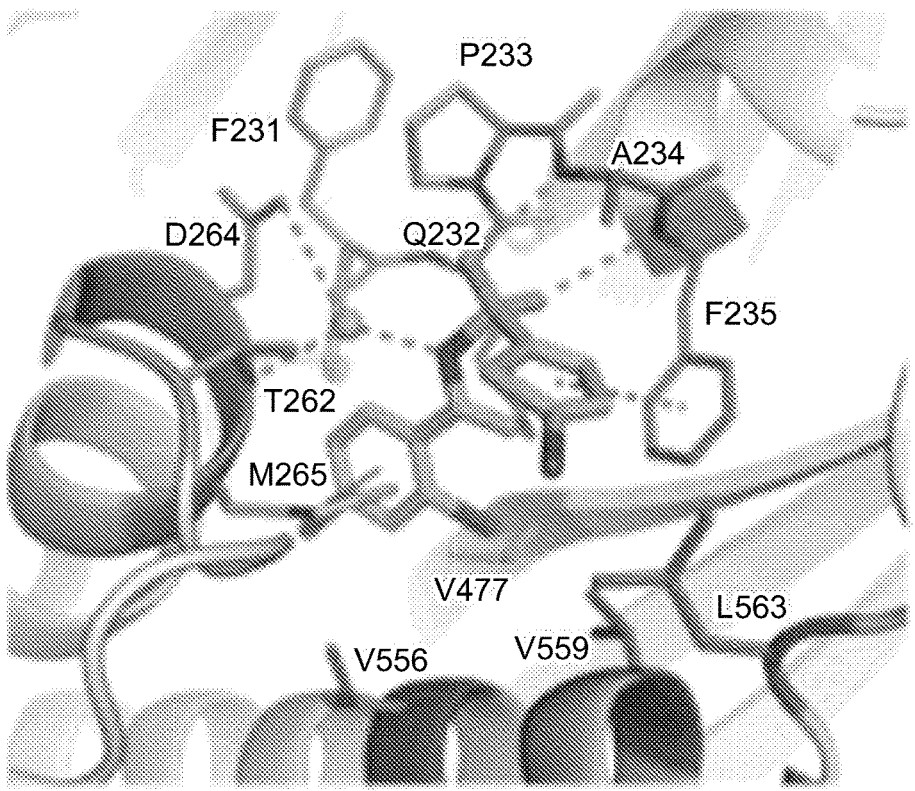
FIG. 12K is a cartoon representation depicting the side chain interactions between DCAF15 NTD, DCAF15 CTD, RBM39$_{RRM2}$, water, and tasisulam.
Figure 12I:
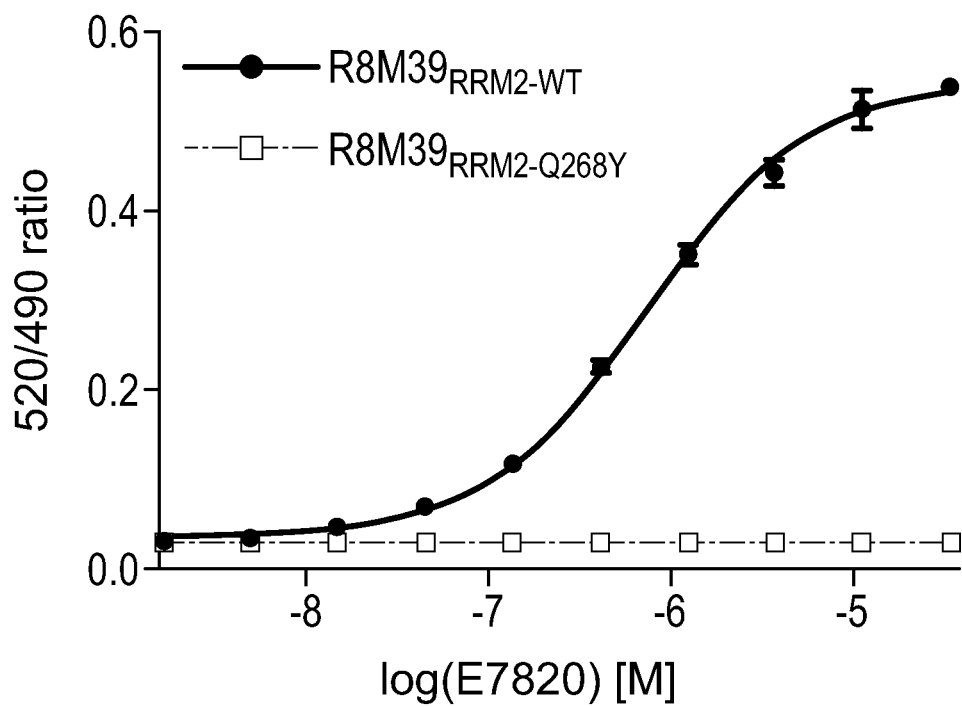

Structures of the related but structurally distinct analogs indisulam and tasisulam to 2.9 Å resolution, respectively we obtained (FIG. 4D, FIG. 12J and FIG. 12K). Indisulam and tasisulam bind DCAF15 in an overall configuration similar to E7820, maintaining the backbone hydrogen bonds from the sulfonyl groups to DCAF15 Ala234 and Phe235 and the water mediated hydrogen bonds. However, the methyl to hydrogen substitution at C4 in indisulam limited the hydrophobic interactions with DCAF15 Val477 and Val556, while tasisulam lacked the indole NH hydrogen bond to the backbone carbonyl of DCAF15 Phe231 (FIG. 12J and FIG. 12K). These differences in indisulam and tasisulam help explain their significant loss in affinity for DCAF15, while maintaining the ability to recruit RBM39 for degradation (FIG. 1A and FIG. 1C).

Example 5: DCAF15-RBM39 Forms Extensive Protein-Protein Contacts

Figure 5A:
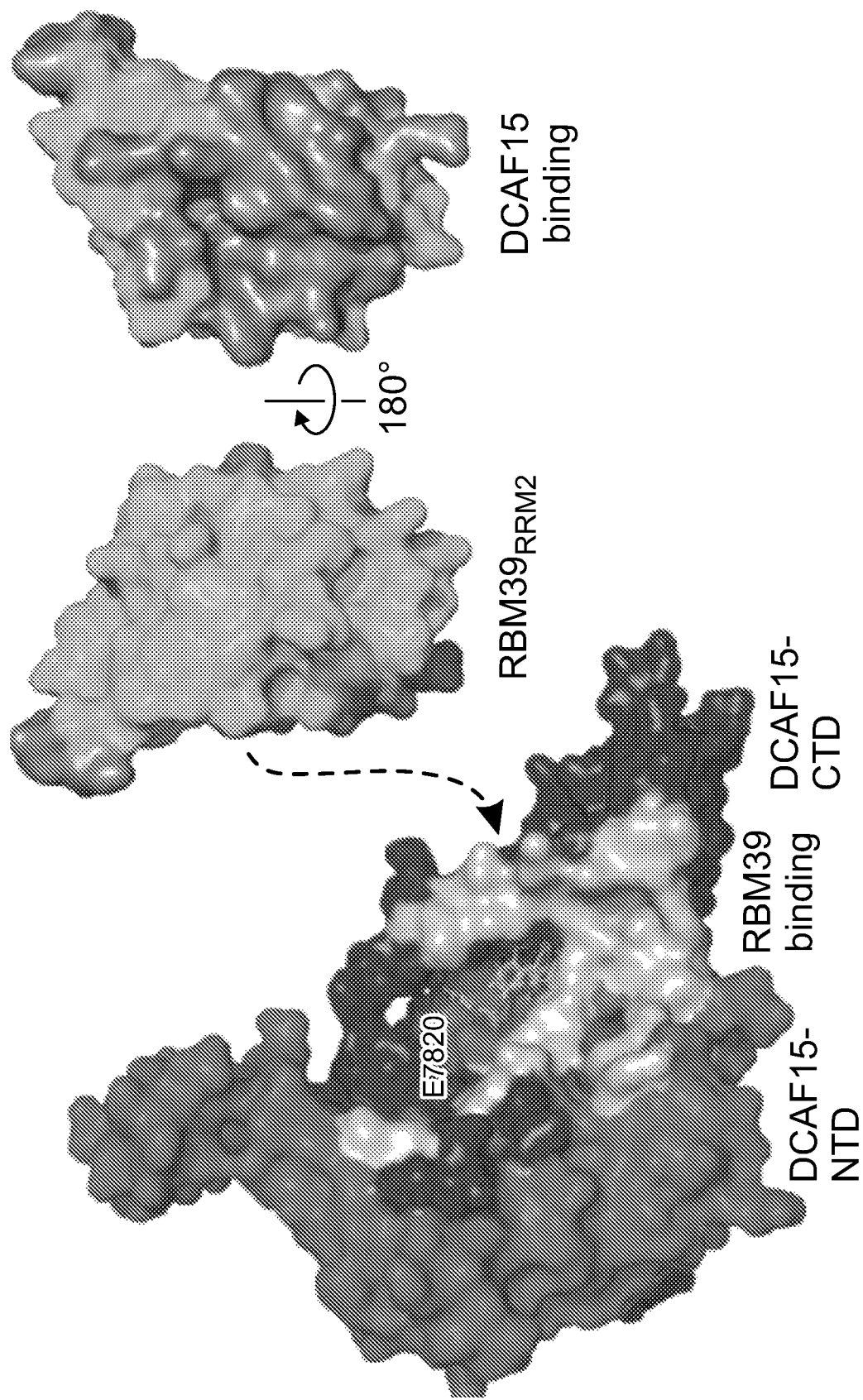
FIG. 5A-FIG. 5E is a series of cartoon representations and graphs depicting the inter-protein contacts between DCAF15 and RBM39.
Figure 5B:
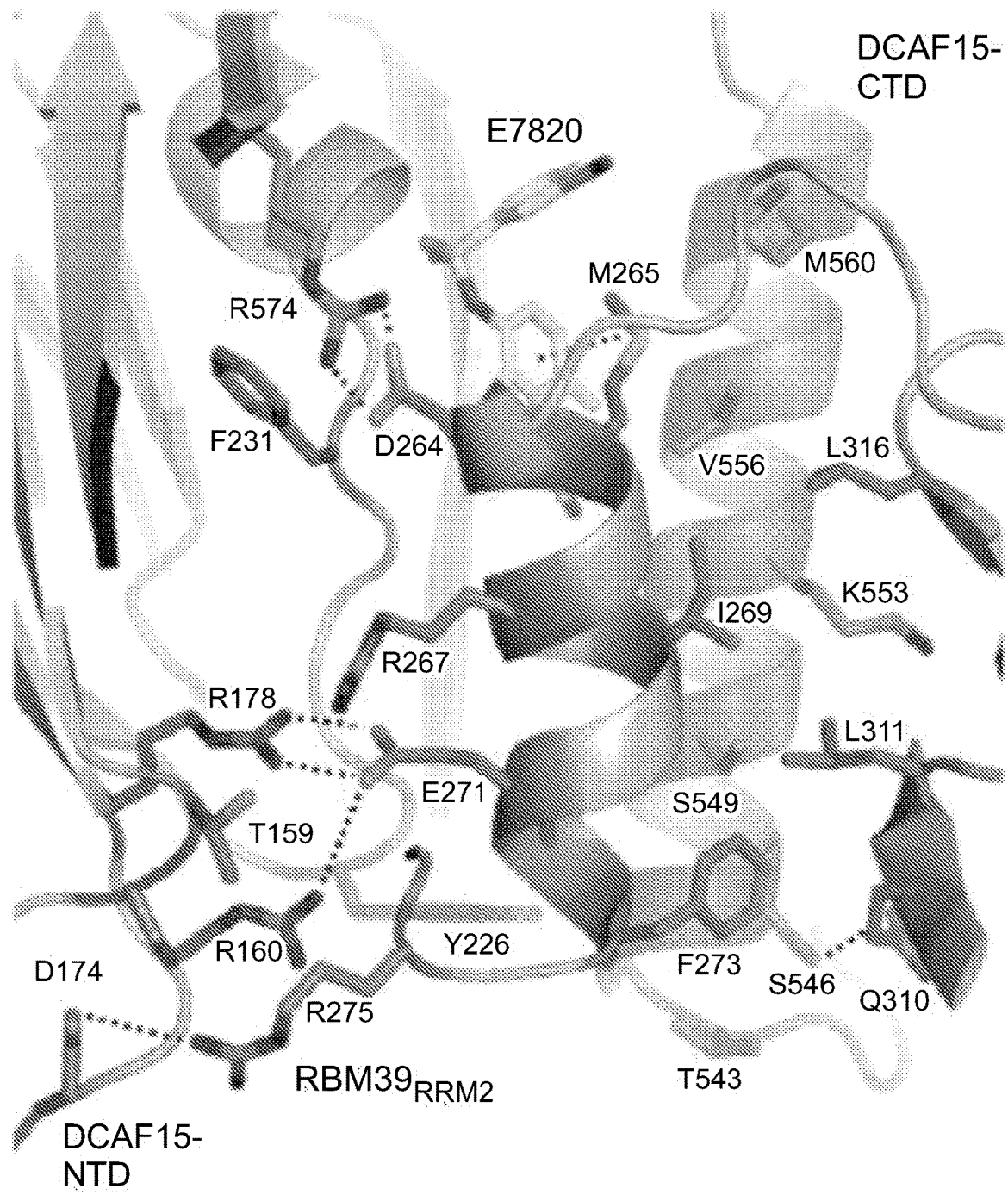
Figure 12M:
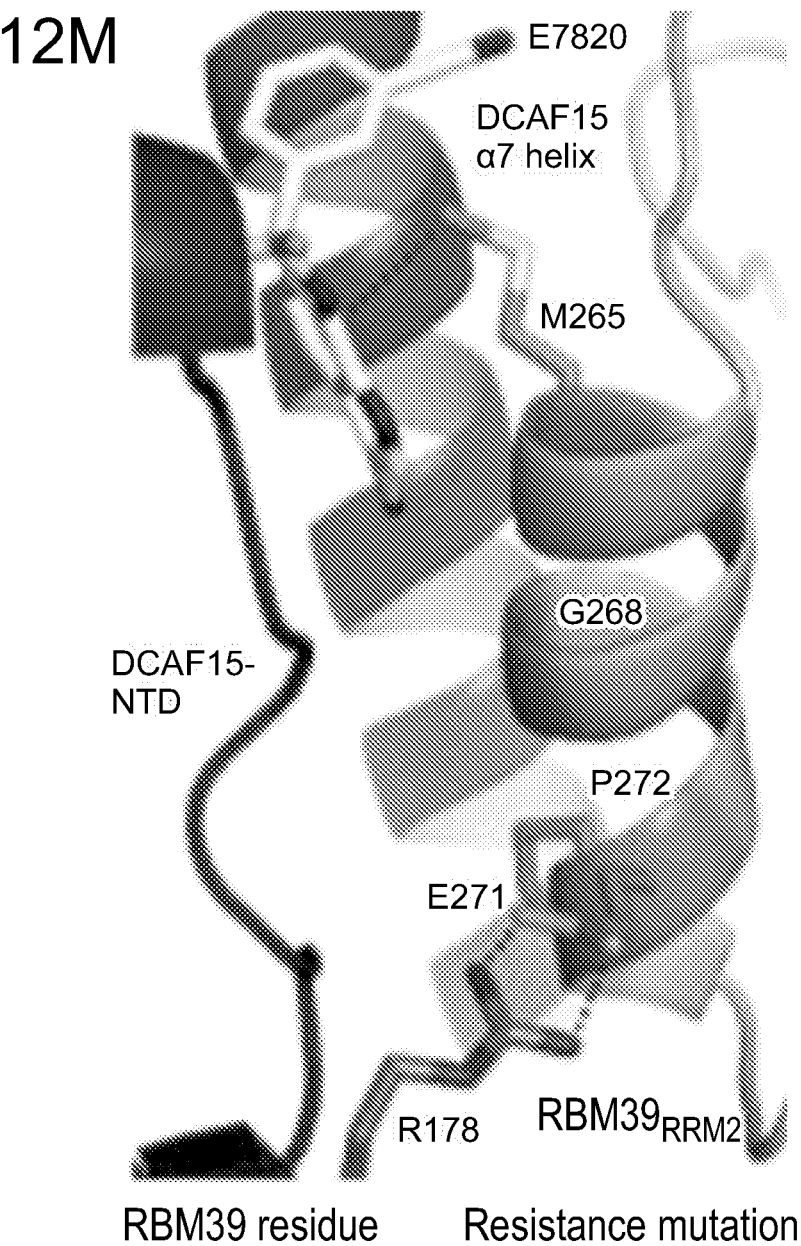
FIG. 12M is a cartoon representation showing RBM39 resistance mutations. Labeled are the four positions in RBM39 that confer resistance to indisulam-dependent toxicity when mutated (Han et al., Science 356: aal3755 (2017)). The table below indicates the resistance mutations at these positions.
Figure 12N:
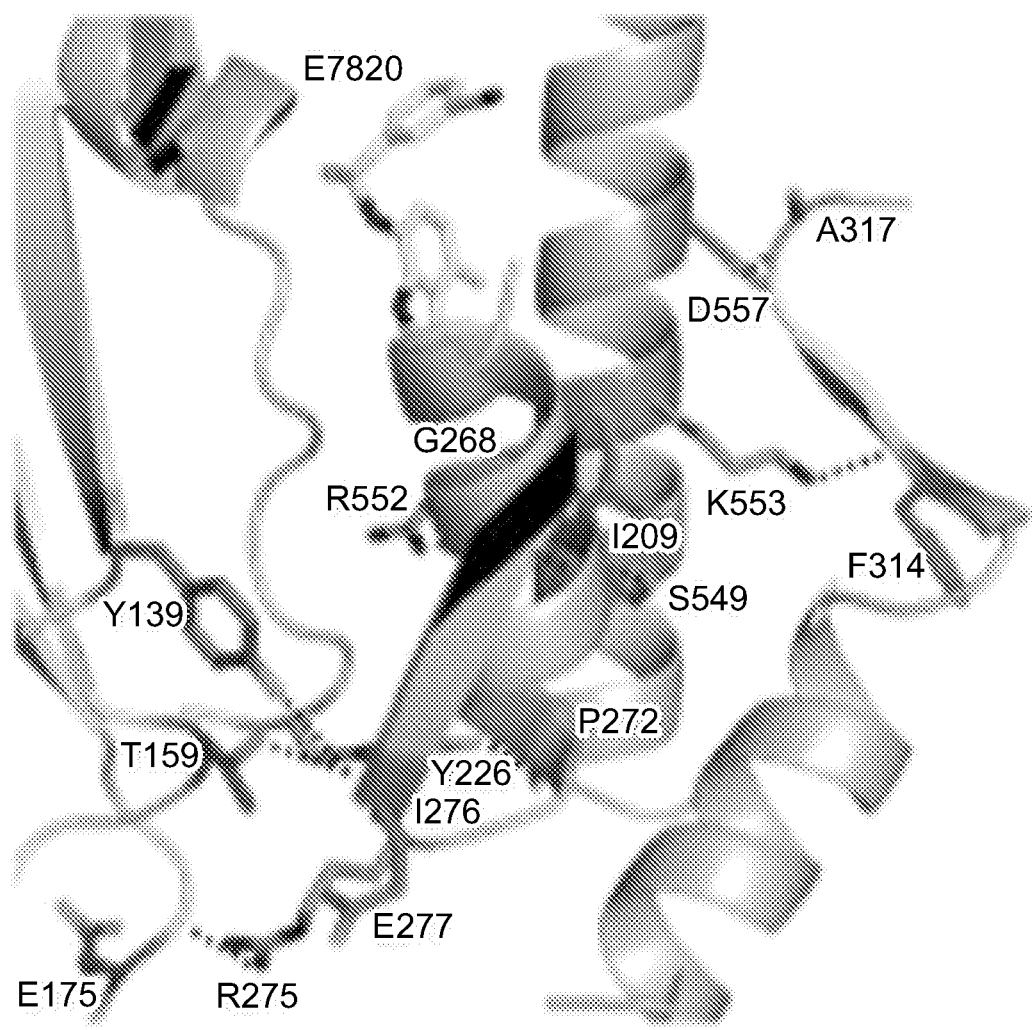
Figure 13A:
FIG. 13A is a sequence logo depicting design of RBM39$_{RRM2}$-derived degron using Rosetta FastDesign algorithm in the presence of DCAF15 and E7820.
Figure 13B:
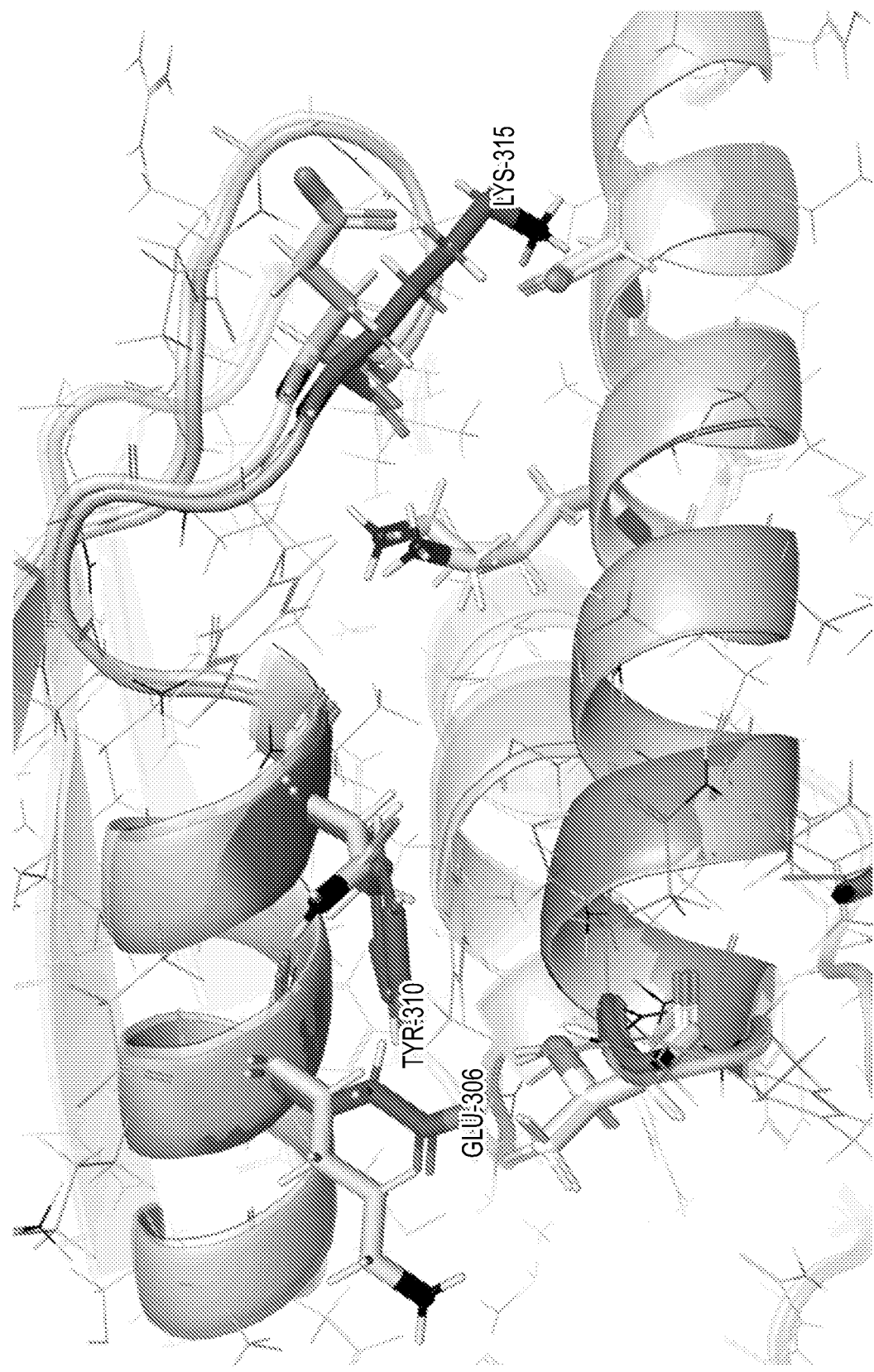
FIG. 13B is a structural representation of the designed interface with a model of DCAF15 and RBM39$_{RRM2}$-derived degron superimposed on the crystal structure depicted in FIG. 2. The designed positions are highlighted as sticks.

The weak affinity of aryl-sulfonamides for DCAF15 (FIG. 7C and FIG. 7F) suggested that protein-protein contacts between DCAF15 and RBM39$_{RRM2}$ stabilized the interaction. RBM39$_{RRM2}$ presents itself as a canonical RRM fold, comprised of a four-stranded anti-parallel β-sheet (β1-β4) stacked on two α-helices (α1 and α2) (FIG. 2A) and interacts with DCAF15 predominantly via the two α-helices. The RBM39$_{RRM2}$ α1 helix docked into the surface groove on DCAF15 that also harbored the E7820 binding site and formed contacts with DCAF15 and E7820. The RBM39$_{RRM2}$-DCAF15 interface comprised ~1,150 Å$^2$ and spanned the DCAF15 NTD and CTD (FIG. 5A). The binding groove is not conserved (FIG. 11E) and is dominated by extensive hydrophobic interactions with the DCAF15 α7 helix in the CTD (FIG. 5B). As was observed in the cryo-EM structure (FIG. 1E), the tight packing of the interface did not allow a side chain-bearing residue at RBM39 Gly268, such that a Gly268Val mutation completely abrogated RMB39$_{RRM2}$ recruitment to DCAF15 (FIG. 12L). The interface included four salt bridges between DCAF15 Arg574, Arg178, Arg160, and Asp174 and RBM39 Asp264, Glu271, and Arg275 respectively, and side chain hydrogen bonds between DCAF15 Ser546 and RBM39 Gln310, respectively (FIG. 5B). An additional indisulam resistance mutation in RBM39, Glu271Gln (Han et al., Science 356:aal3755 (2017)), is likely explained by a loss in the salt bridge interaction with DCAF15 (FIG. 12M). An extended network of backbone hydrogen bonds further stabilized the DCAF15-RBM39 interface (FIG. 12N).

Example 6: Aryl-Sulfonamides Selectively Degrade of RBM39 and RBM23

Figure 5C:
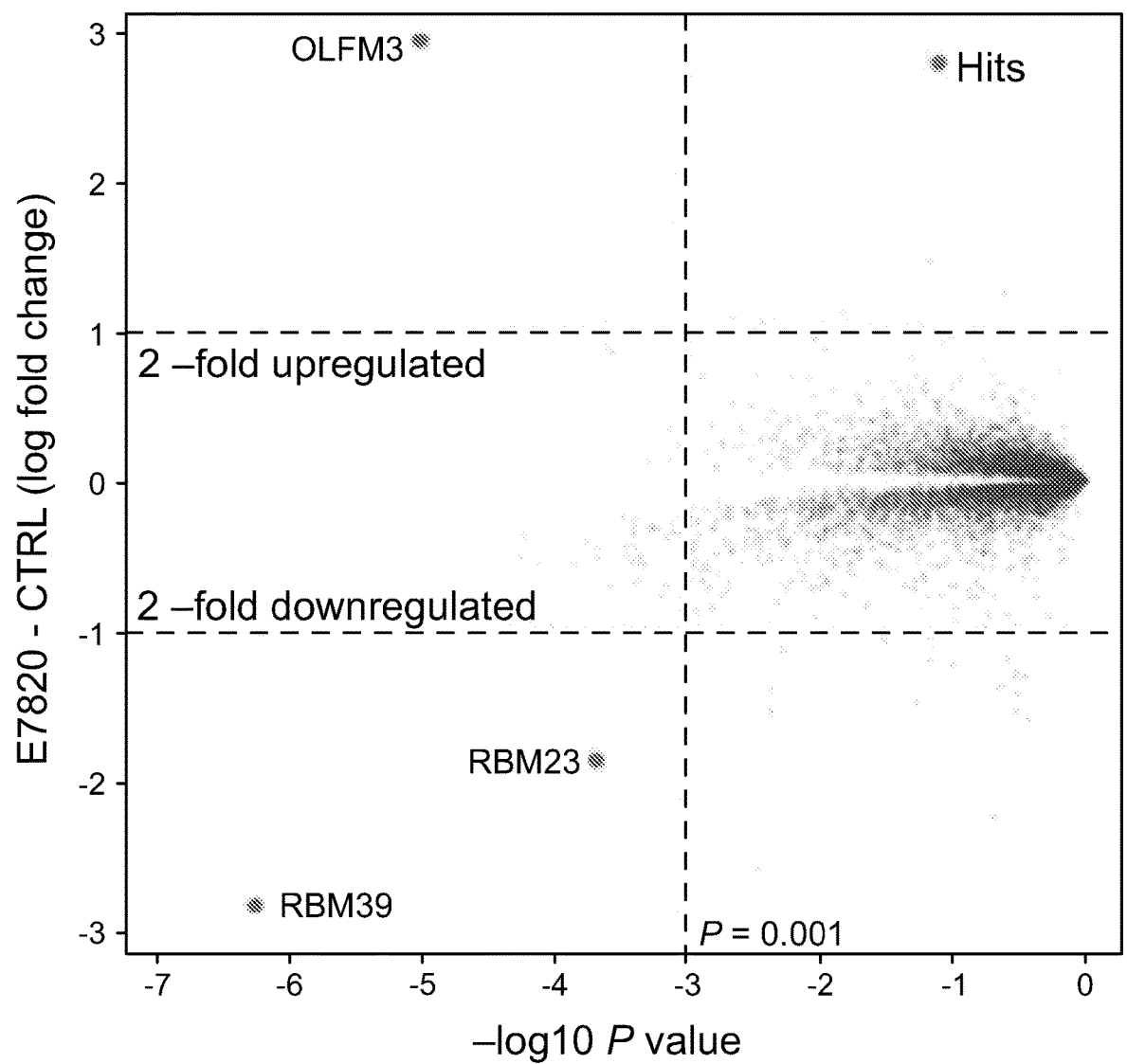
Figures 5D, 5E:
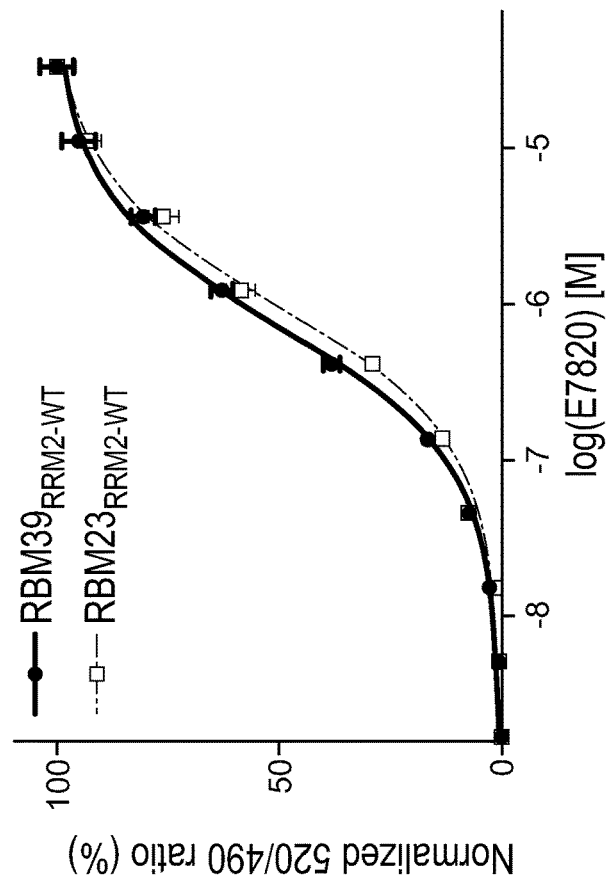
Figure 6A:
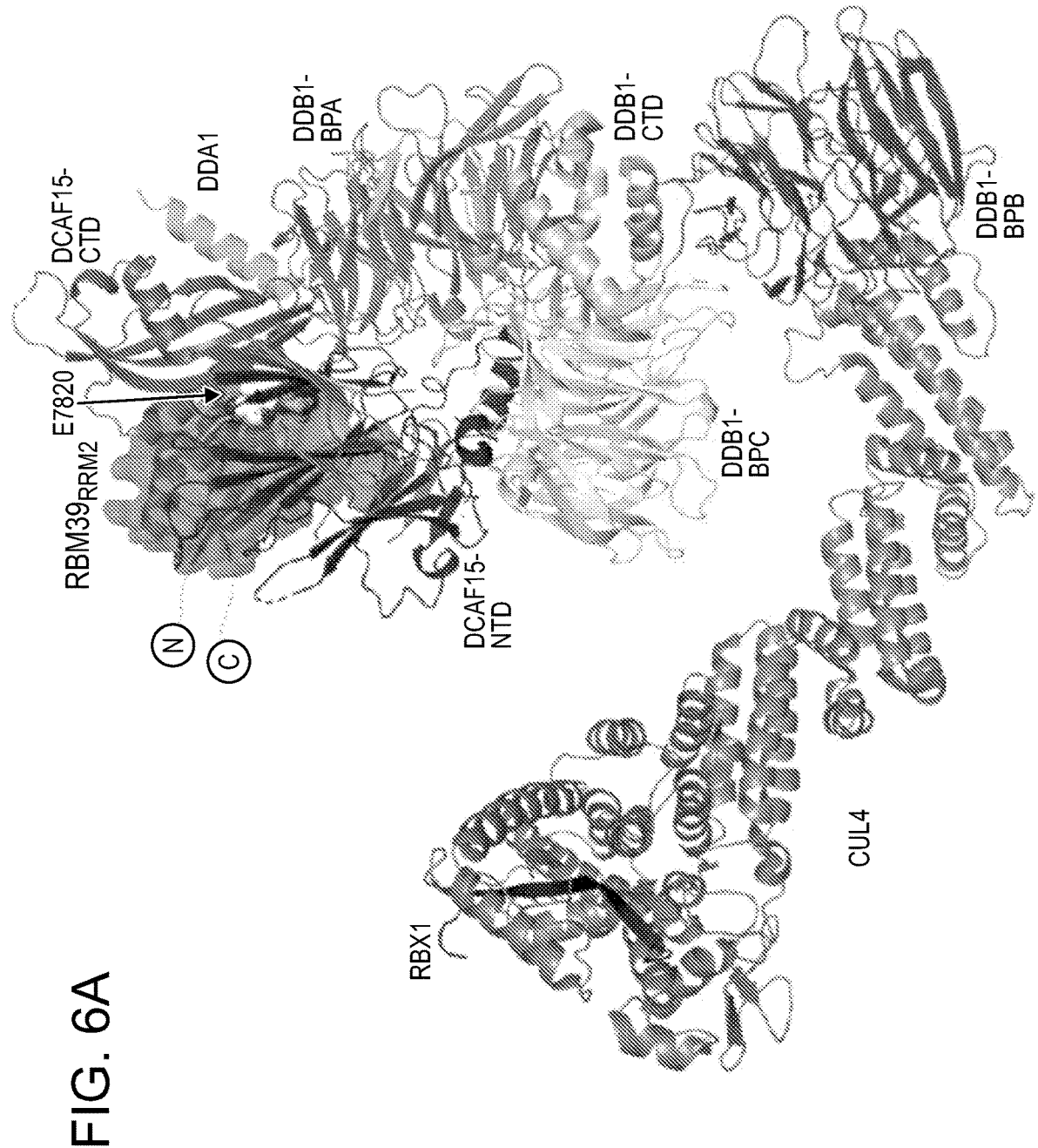
FIG. 6A-FIG. 6B are a series of cartoon representations showing the topological and evolutionary constraints on E7820 activity.
Figure 6B:
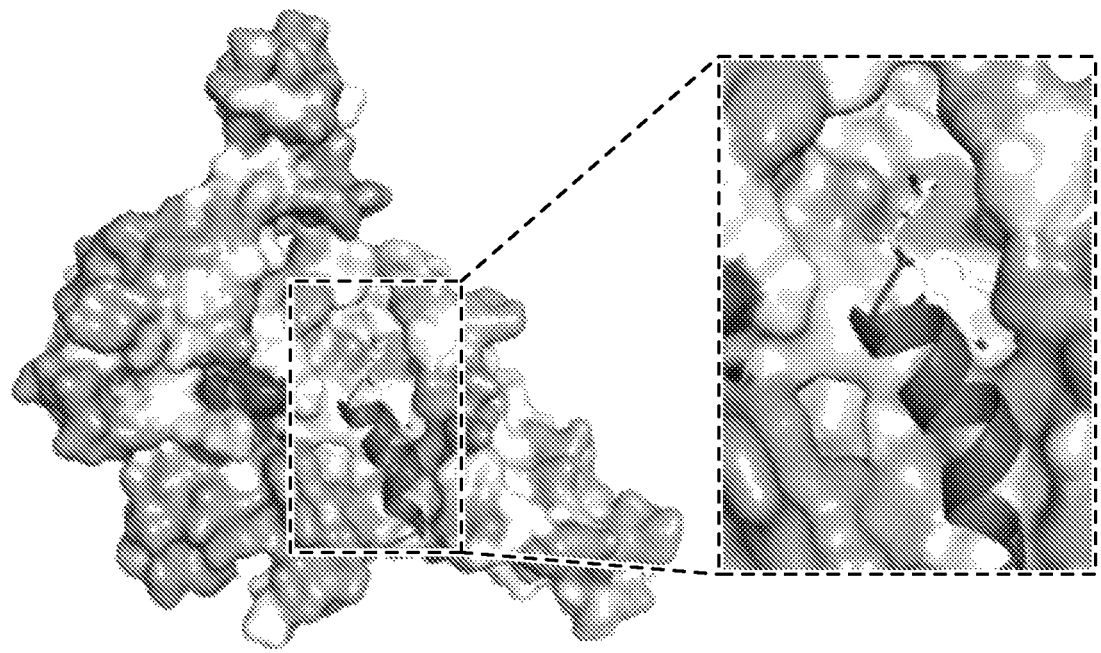
Figure 6B:
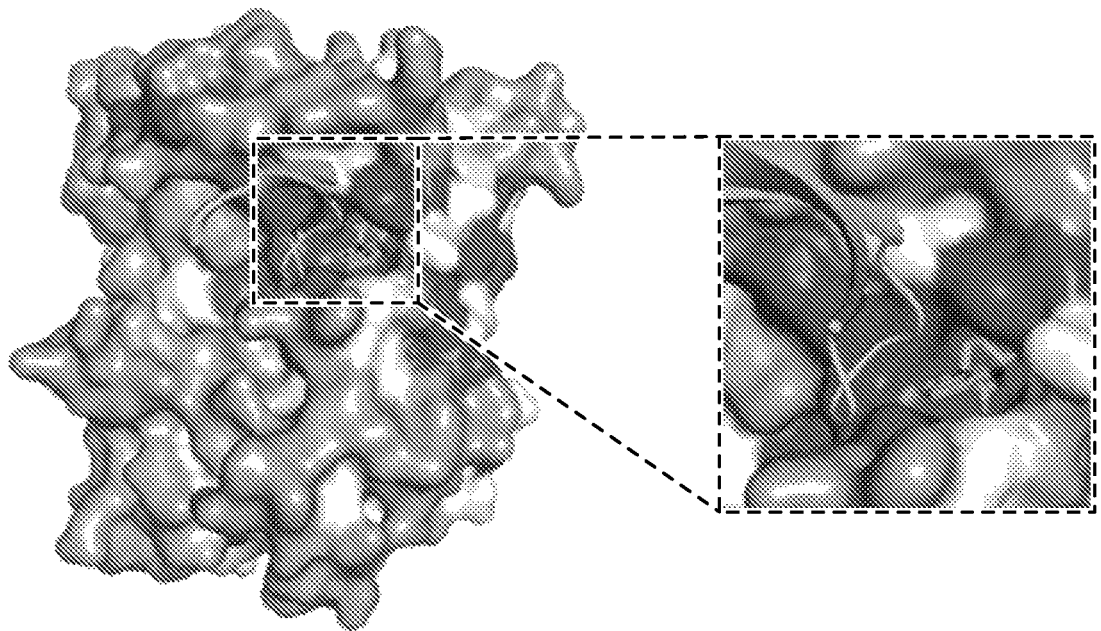
Figure 6B:

As many RRM domains are structurally highly similar and since RBM39 interacts with DCAF15 predominantly through two conserved α-helices in its second RRM, other RRM-containing proteins were considered to be would be targets of DCAF15 and E7820. To assess the degradome of E7820, unbiased mass spectrometry-based proteomics experiments were performed and found only RBM23 to be degraded in addition to RBM39 out of ~11,000 proteins detected (FIG. 5C). Sequence analysis revealed that the second RRM domain of RBM23 (RBM23$_{RRM2}$) was nearly identical to RBM39$_{RRM2}$, with 100% sequence identity across all key residues that formed contacts with DCAF15 and E7820 (FIG. 5D). Consequently, comparable binding affinity was found for RBM23$_{RRM2}$ to that observed for RBM39$_{RRM2}$ (FIG. 5E). Cullin-RING ligases of the CRL4 family tolerate a diverse set of substrate receptors but typically present their substrates in a canonical position (Fischer et al., Cell 147:1024-1039 (2011); Cavadini et al., Nature 531:598-603 (2016)). When superimposed with a Cullin-RING ligase complex (pdb: 4a0k), a model of the full CRL4$^{DCAF15}$ ligase bound to RBM39 can be constructed. RBM39$_{RRM2}$ was bound to a face of DCAF15 that was not directly opposed to RBX1 (FIG. 6A), however the N- and C-termini of RBM39 are positioned towards RBX1, and could tolerate additional domains at both positions. Furthermore, in contrast to CRBN, the ligand and substrate pocket of DCAF15 was not conserved (FIG. 6B), suggesting that the topological and evolutionary constraints on developing molecular glue degraders are rather flexible.

Example 7: Methods

Constructs and Protein Purification

The human genes for full-length DDB1, DDB1ΔB (residues 396-705 replaced with GNGNSG linker), full-length DCAF15, DCAF15 NTD (30-264), DCAF15 CTD (383-600), full-length DDA1, RBM39$_{RRM2}$ (245-332), and RBM23$_{RRM2}$ (263-341) and the *Xenopus tropicalis* gene for full-length DCAF15 were cloned in pAC-derived vectors (Abdulrahman et al., Anal. Biochem., 385:383-385 (2009)). Baculovirus for protein expression (Invitrogen™) was generated by transfection into *Spodoptera frugiperda* (Sf9) cells at a density of 0.9×10$^6$ cells/mL grown in ESF 921™ media (Expression Systems), followed by three rounds of infection in Sf9 cells to increase viral titer. Recombinant proteins were expressed as N-terminal His$_6$, Strep II, Strep II Avi fusions in *Trichoplusia ni* High Five insect cells by infection with high titer baculovirus. Briefly, Hi Five cells grown in Sf-900 II SFM media (Gibco™) at a density of 2.0×10$^6$ cells/mL were infected with baculovirus at 1.5% (v/v). After 40 hours of expression at 27° C., High Five cells were pelleted for 10 minutes at 3,500×g. For purification of StrepII or His$_6$-tagged proteins, pelleted cells were resuspended in buffer containing 50 mM tris(hydroxymethyl) aminomethane hydrochloride (Tris-HCl) pH 8.0, 200 mM NaCl, 2 mM tris(2-carboxyethyl)phosphine (TCEP), 1 mM phenylmethylsulfonyl fluoride (PMSF), and 1× protease inhibitor cocktail (Sigma®) and lysed by sonication. Media and purification buffers contained 10-20 µM E7820, as needed. Following ultracentrifugation, the soluble fraction was passed over the appropriate affinity resin of Strep-Tactin® XT Superflow™ (IBA) or Ni Sepharose® 6 Fast Flow affinity resin (GE Healthcare), eluted with wash buffer (50 mM Tris-HCl pH 8.0, 200 mM NaCl, 1 mM TCEP) supplemented with 50 mM d-Biotin (IBA) or 100 mM imidazole (Fisher Chemical), respectively. The affinity-purified DCAF15 complexes used for structure determination were next applied to an ion exchange column (Poros™ 50HQ) and eluted in 50 mM Tris-HCl pH 8.5, 2 mM TCEP, and 20 µM E7820 by a linear salt gradient (from 50-800 mM NaCl). Peak fractions of DCAF15 complex from ion exchange chromatography were then subjected to size-exclusion chromatography on a Superdex 200 10/300 in 50 mM 4-(2-hydroxyethyl)-1-piperazineethanesulfonic acid (HEPES) pH 7.4 or pH 8.0, 200 mM NaCl and 2 mM TCEP. Peak gel filtration fractions were pooled and concentrated and then either used directly in structural experiments or flash frozen in liquid nitrogen and stored at −80° C. Affinity-purified protein used in biochemical experiments was concentrated and subjected to size-exclusion chromatography as outlined above. The protein-containing fractions were concentrated using ultrafiltration (Millipore) and flash frozen in liquid nitrogen and stored at −80° C.

Limited Proteolysis and Gel Filtration

The DDB1ΔB-X. t. DCAF15 complex was diluted to 20 µM in 25 mM HEPES pH 7.4, 200 mM NaCl, and 1 mM TCEP. *Xenopus tropicalis* DCAF15 is closely related to *Homo sapiens* DCAF15, with 66% sequence identity overall and 76% sequence identity in the structured NTD and CTD regions, and was examined in parallel in initial biochemical experiments. A 200 µM stock of chymotrypsin was diluted to 20 µM with 1 mM HCl and 2 mM CaCl$_2$, which was then added to the DDB1ΔB-X. DCAF15 complex at a 400:1 ratio (50 nM chymotrypsin final concentration). The proteolysis reaction was carried out on ice for 45 minutes, centrifuged at 15,000 rpm at 4° C., and injected onto an EnRich™ 650 column for gel filtration.

Biotinylation of DCAF15 and RBM39

Purified Strep II Avi-tagged human DCAF15 variants or RBM39$_{RRM2}$ were biotinylated in vitro at a concentration of 5-50 µM by incubation with final concentrations of 2.5 µM BirA enzyme and 0.2 mM D-Biotin in 50 mM HEPES pH 7.4, 200 mM NaCl, 10 mM MgCl$_2$, 0.25 mM TCEP and 20 mM ATP. The reaction was incubated for 1 h at room temperature and stored overnight at 4° C. Biotinylated proteins were purified by gel filtration chromatography and flash frozen in liquid nitrogen and stored at −80° C.

BodipyFL-Labeling of RBM39 and RBM23

Purified human RBM39$_{RRM2}$ or RBM23$_{RRM2}$ was incubated with DTT (8 mM) at 4° C. for 1 h. DTT was removed using a 5200 10/300 gel filtration column in a buffer containing 50 mM Tris pH 7.3 and 150 mM NaCl. BodipyFL-maleimide (Invitrogen™) was dissolved in 100% DMSO and mixed with RBM39 or RBM23 to achieve 3-fold molar excess of BodipyFL-maleimide. Labelling was carried out at room temperature for 3 h and stored overnight at 4° C. Labelled RBM39 or RBM23 was purified on a 5200 10/300 gel filtration column in 50 mM Tris pH 7.5, 150 mM NaCl, 0.25 mM TCEP, concentrated by ultrafiltration (Milipore), flash frozen in liquid nitrogen and stored at −80° C.

Time-Resolved Fluorescence Resonance Energy Transfer (TR-FRET)

Titrations of compounds to induce DCAF15-RBM39 or DCAF15-RBM23 complex were carried out by mixing 200 nM biotinylated Strep II Avi-tagged DCAF15, 200 nM BodipyFL-labeled RBM39 or RBM23 variants, and 2 nM terbium-coupled streptavidin (Invitrogen™) in an assay buffer containing 50 mM Tris pH 8.0, 200 mM NaCl, 0.1% Pluronic F-68 solution (Sigma®), and 0.5% BSA (w/v). Full-length human DCAF15 was used in all TR-FRET assays. After dispensing the assay mixture, increasing concentrations of compounds were dispensed in a 384-well microplate (Corning, 4514) using a D300e Digital Dispenser (HP) normalized to 2% DMSO. Before TR-FRET measurements were conducted, the reactions were incubated for 15 min at room temperature. After excitation of terbium fluorescence at 337 nm, emission at 490 nm (terbium) and 520 nm (BodipyFL) were recorded with a 70 μs delay over 600 μs to reduce background fluorescence, and the reaction was followed over 60 cycles of each data point using a PHERAstar® FS microplate reader (BMG Labtech). The TR-FRET signal of each data point was extracted by calculating the 520/490 nm ratio. The half-maximal effective concentration $EC_{50}$ values calculated using [Agonist] vs response (three parameters) equation in GraphPad Prism® 7.

Titrations of BodipyFL-RBM39 were carried out by mixing 400 nM biotinylated Strep II Avi-tagged DCAF15 variants, 100 μM compounds or equivalent volume of DMSO, and 4 nM terbium-coupled streptavidin in the same assay buffer. After dispensing the assay mixture, increasing concentration of BodipyFL-RBM39 was added to the compound-bound DCAF15 in a 1:1 volume ratio and incubated for 15 min at room temperature. The 520/490 nm ratios were plotted to calculate the $K_d$ values estimated using One site-Specific binding equation in GraphPad Prism® 7.

Titrations of BodipyFL-E7820 (4) were carried out by mixing 200 nM biotinylated Strep II Avi-tagged DCAF15 variants or equivalent volume of the assay buffer, 2 nM terbium-coupled streptavidin in the same assay buffer. After dispensing the assay mixture, increasing concentration of BodipyFL-E7820 (4) was dispensed in the 384-well plate using D300e normalized to 2% DMSO, and then incubated for 15 min at room temperature. The 520/490 nm ratios from the sample with DCAF15 was subtracted by the ratios from the sample without DCAF15, and the subtracted values were plotted to calculate the $K_d$ values estimated using One site-Specific binding equation in GraphPad Prism® 7. All TR-FRET results are plotted as means±s.d. from three independent replicates (n=3) unless otherwise indicated.

Crystallization

Frozen aliquots of the Strep II Avi-DCAF15$_{NTD}$ (residues 30-264)-Strep II Avi-DCAF15$_{CTD}$ (residues 383-600)-His$_6$-DDB1ΔB-His$_6$-DDA1-His$_6$-RBM39$_{RRM2}$ complex were thawed, centrifuged for 10 minutes at 15,000 rpm at 4° C., and injected onto a Superdex 200 10/300 column equilibrated with 50 mM HEPES pH 8.0, 150 mM NaCl, 2 mM TCEP, and 20 μM E7820. All proteins used in crystallography are derived from human sequence. Peak fractions were pooled and concentrated at 4° C. to 56.8 μM (10 mg/mL). Concentrated protein was supplemented with 25 μM E7820, and crystallization plates were dispensed as sitting drop with the Formulatrix® NT8® at room temperature. Crystals appeared within one day and continued growing until day 4 when concentrated protein was mixed 2:1 or 1:1 with reservoir containing 200 mM lithium citrate tribasic and 20% (w/v) PEG 3,350 in 96 well, 3 seat vapor diffusion Intelli-Plates® (Art Robbins Instruments). For indisulam and tasisulam crystals, the same aliquots of Strep II Avi-DCAF15$_{NTD}$ (residues 30-264)-Strep II Avi-DCAF15$_{CTD}$ (residues 383-600)-His$_6$-DDB1ΔB-His$_6$-DDA1-His$_6$-RBM39$_{RRM2}$ complex bound to E7820 were thawed and diluted/concentrated two times with buffer containing 20 μM indisulam or 30 μM tasisulam, respectively. The first dilution was with 5-fold excess of gel filtration buffer containing the appropriate compound, and the second dilution was with 15-fold excess gel filtration buffer and compound. During the second dilution step, the protein complex was incubated on ice for 1 hour to allow complete exchange of the compound prior to concentration. After the second concentration step, protein complexes were injected onto a Superdex 200 10/300 column equilibrated with 50 mM HEPES pH 8.0, 150 mM NaCl, 2 mM TCEP and either 20 μM indisulam or 30 μM tasisulam. After gel filtration, purified protein was processed identically to E7820-bound complexes, as described above.

Crystals were cryo-protected in reservoir solution supplemented with 20% glycerol and flash frozen in liquid nitrogen. Diffraction data were collected at the APS Chicago (beamline 24-ID-C) with a Pilatus 6M-F detector at a temperature of 100 K, at wavelength of 0.9792 Å or 1.6531 Å. Data were indexed and integrated using XDS (Kabsch et al., Acta Crystallogr. D., 66:125-132 (2010)) and scaled using AIMLESS supported by other programs of the CCP4 suite (Winn et al., Acta Crystallogr. D., 67:235-242 (2011)). Data processing statistics, refinement statistics and model quality parameters are provided in Table 2.

Structure Determination and Model Building

The DDB1ΔB-DCAF15$_{split}$-DDA1-E7820-RBM39$_{RRM2}$, DDB1ΔB-DCAF15$_{split}$-DDA1-compound 5 (Iodide-E7820)-RBM39$_{RRM2}$, DDB1ΔB-DCAF15$_{split}$-DDA1-indisulam-RBM39$_{RRM2}$, and DDB1ΔB-DCAF15$_{split}$-DDA1-tasisulam-RBM39$_{RRM2}$ complexes all crystallized in space group P2$_1$2$_1$2$_1$ with a single complex in the unit cell. PHASER (McCoy et al., J. Appl. Crystallogr., 40:658-674 (2007)) was used to determine the structures by molecular replacement using a crystallographic model of DDB1ΔB based on a crystal structure pdb: 5fqd. Diffraction data for complexes containing E7820-I or tasisulam were collected at 7500 eV and the MR-SAD pipeline as implemented in phaser (McCoy et al., J. Appl. Crystallogr., 40:658-674 (2007)) used to obtain additional phase information, followed by density modification using parrot (Winn et al., Acta Crystallogr. D., 67:235-242 (2011)). The initial model was iteratively improved with COOT (Emsley et al., Acta Crystallogr. D., 60:2126-2132 (2004)), using information from the density modified maps and sulfur anomalous difference peaks, and refined using PHENIX.REFINE (Afonine et al., Acta Crystallogr. D., 68:352-367 (2012)) and autoBUSTER (BUSTER version 2.10.2 v. 2.10.2 (Global Phasing Ltd., Cambridge, United Kingdom, 2011)) with ligand restraints generated by Grade server (Global Phasing) or phenix.elbow (Afonine et al., Acta Crystallogr. D., 68:352-367 (2012)). Figures were generated with PyMOL (The PyMOL Molecular Graphics System, Version 2.3.0 Schrödinger, LLC) and model quality was assessed with MOLPROBITY. Interaction surfaces were determined with PISA, and conservation mapped using consurf (Landau et al., Nucleic Acids Res., 33:299-302 (2005)).

Sample Preparation and Cryo-EM Data Collection

The DDB1-DCAF15-E7820-RBM39$_{RRM2}$ complex was purified by gel filtration on a Superdex 5200 10/300 column. A single peak fraction was collected and diluted to 0.075 mg/mL. This diluted fraction was applied (4 μL) to a glow-discharged 1.2/1.3 Quantifoil® copper 300 mesh grid, blotted for 3 seconds, and vitrified in liquid ethane with the Leica EM-GP blotting system. Micrographs were collected on a FEI Titan Krios™ at 300 kV, equipped with a K2 Summit camera and GIF energy filter. 1,457 micrographs were collected at the National Cryo-Electron Microscopy Facility (NCI) in super resolution mode at a pixel size of 0.532 Å. Each micrograph was recorded at a total dose of 40 e⁻/Å² over 40 frames at a defocus range of 1.5-3.0 μm.

The DDB1ΔB-DCAF15-DDA1-E7820-RBM39$_{RRM2}$ complex was purified by gel filtration, and peak fractions were pooled and concentrated for BS3 crosslinking. Briefly, 5 μM of complex was incubated with 60-fold molar excess of BS3 for 30 minutes at room temperature, quenched with 50 mM Tris-HCl pH 8.0, and re-injected on a Superdex 200 10/300. A peak fraction of crosslinked protein at 0.048 mg/mL was applied (4 μL) to a glow-discharged 1.2/1.3 Quantifoil® copper 300 mesh grid, blotted for 3 seconds, and vitrified in liquid ethane with the Lecia EM-GP blotting system. Data was collected from 2 grids over 4 imaging sessions on the same FEI Titan Krios™ at the UMass Cryo-EM facility, operating at 300 kV and equipped with a K2 Summit camera and GIF energy filter. The Volta phase plate (VPP) was used during all imaging sessions for this complex, and the position on the VPP was changed approximately every 400 micrographs. A total of 9,393 micrographs were collected in super resolution mode at a pixel size of 0.5294 Å. Each micrograph was recorded with a total dose of ~54 e⁻/Å² over 35 or 40 frames, depending on the session. The defocus range was 0.2-2 μm across all micrographs.

Image Processing

For the DDB1-DCAF15-E7820-RBM39$_{RRM2}$ complex, all processing steps were performed in RELION 2. Movie frames were aligned and binned by a factor of 2 yielding a final pixel size of 1.064 Å and averaged with MotionCor2 (Zheng et al., Nat. Methods 14:331-332 (2017)), and CTF parameters were estimated with CTFFIND4 (Rohou et al., J. Struct. Biol., 192:216-221 (2015)). A set of 1,000 particles were manually picked to generate 2D class averages for autopicking. Initial 2D classification was used to generate a starting set of 318,187 particles. From this set, two subsequent rounds of 3D classification with 7.5 degree angular sampling resulted in 68,324 particles for the final refinement, resulting in a reconstruction at 10 Å.

For the DDB1ΔB-DCAF15-DDA1-E7820-RBM39$_{RRM2}$ complex, movie frames were aligned and binned by a factor of 2 yielding a final pixel size of 1.059 Å and averaged with MotionCor2 (Zheng et al., Nat. Methods 14:331-332 (2017)) and CTF parameters as well as the estimated phase shift were determined with CTFFIND4 CTFFIND4 (Rohou et al., J. Struct. Biol., 192:216-221 (2015)). For the first three imaging sessions, 5,000 particles were picked from each session to generate reference-free 2D class averages for automated picking in Relion. For the fourth session, crYOLO (Moriya et al., J. Vis. Exp., 123:55448 (2017)) was used to pick particles with a model that was trained on the data. All subsequent processing steps for all sessions were performed with Relion 3.0 (Zivanov et al., Elife 7:42166 (2018)). Initial 2D classification was used to clean the data from each session independently, after which particles were pooled for further 3D classification. A round of 3D classification at 7.5 degree sampling was used to remove additional bad particles from the dataset, after which a set of 923,678 particles were used for CTF refinement and Bayesian polishing (Zivanov et al., Elife 7:42166 (2018)). An initial round of CTF refinement on a consensus 3D refinement from all particles was performed to fit per-particle defocus. Thereafter, Bayesian polishing was performed independently on particles from each session. Particle images were then combined again, and it was found that an additional round of CTF refinement to estimate per-particle defocus led to an improved consensus 3D refinement. With the polished particles, one round of 3D classification with coarse (7.5 degree) angular sampling resulted in two main classes, one of which resulted in a reconstruction at 4.5 Å. The particles from this consensus refinement were further classified without image alignment, leading to a major class with 53% of the particles. 3D refinement of these particles improved the map quality, with a resolution of 4.5 Å. Finally, signal subtraction was performed on this consensus refinement with a soft subtraction mask around the DCAF15 CTD. An additional round of masked 3D classification without image alignment and a T value of 12, to account for the reduced signal in the particle box, again led to a dominant class with 56% of the particles. A final refinement with unsubtracted particles (75,529 particles in total) resulted in the final reconstruction at 4.4 Å. Local resolution was estimated using Relion.

Cryo-EM Model Building

The refined and sharpened map from Relion (Zivanov et al., Elife 7:42166 (2018)) was converted to structure factors using phenix map to structure factors (Afonine et al., Acta Crystallogr. D., 68:352-367 (2012)). DDB1ΔB was placed using phenix dock in map, and the balbes-molrep pipeline (Brown et al., Acta Crystallogr. D., 71:136-153 (2015)) used to place RBM39$_{RRM2}$. The structure of the N-terminal region of DDA1 in complex with DDB1 (Shabek et al., Cell Discov., 4:67 (2018)) was used to trace DDA1. An approximate, partial poly-Ala model of DCAF15 was built in Coot (Emsley et al., Acta Crystallogr. D., 60:2126-2132 (2004)). First, well defined α-helices in the DCAF15 density were assigned based on secondary structure prediction, and mutations introduced to break helical fold or interactions (e.g. V43E and I45E in the putative helix-loop-helix motif anchoring DCAF15 to DDB1) and therefore further validate assignment. The remaining density was traced assisted by secondary structure predictions and distant constraints obtained through crosslinking mass spectrometry. Models were refined using phenix realspace refine (Afonine et al., Acta Crystallogr. D., 68:352-367 (2012)). To cross validate cryo-EM and X-ray structures, the final model obtained from the crystal structure was fitted into the cryo-EM volume using phenix dock in map, and subsequently realspace refined using phenix realspace refinement.

Mutant DCAF15 Pulldown

High five insect cells were infected with 1.5% (v/v) baculovirus expressing His$_6$-DDB1ΔB, His$_6$-RBM39$_{RRM2}$, and wild type or mutant STREP II-DCAF15 full-length. After 40 hours, 1.5 mL of 50 mM Tris pH 8.0, 200 mM NaCl, 0.1% Triton X-100, 1 mM PMSF, 10 μM E7820, 2 mM TCEP and 1× protease cocktail (Sigma®) was added to cell pellets and further lysed by sonication. Clarified lysates were then incubated with 50-100 μL of STREP-tactin XT superflow slurry (IBA), rocking at 4° C. for one hour. Protein bound to STREP resin was washed 3× with 1 mL of lysis buffer and eluted with 2× packed bead volume of lysis buffer+50 mM biotin. Eluted proteins were analyzed by SDS-PAGE.

BS3, DSBU, DSSO Cross-Linking and MS

Recombinant DDB1-DCAF15-DDA1-E7820-RBM39R1 and DDB1ΔB-DCAF15-DDA1 were analyzed by the amine-reactive crosslinker DSSO and DSBU, while the DDB1-DCAF15-DDA1-E7820-RBM39$_{RRM2}$ complex was also analyzed by BS3 crosslinking. For BS3 crosslinking, the protein complex was first injected onto a Superdex 200

10/300 and peak fractions were collected and concentrated to 1 mg/mL (4.6 µM) and 10 mM BS3 was added at 20, 40, 60, or 80× molar excess. Crosslinking reactions were incubated for 30 minutes at room temperature, followed by 5 minutes quench with 50 mM Tris-HCl pH 8.0. Similarly for DSSO and DSBU crosslinking, protein complexes were first injected onto a Superdex 200 10/300, peak fractions collected and concentrated to 10 µM. 50 mM of DSSO or DSBU was added at a 50, 100, or 200 molar excess. Crosslinking reactions were incubated for 30 minutes at room temperature, followed by 5 minutes quench with 20 mM Tris-HCl pH 8.0. All crosslinked samples were precipitated with tricholoracetic acid (TCA) following standard protocols (Link et al., Cold Spring Harb. Protoc., 2011:993-994 (2011)). Precipitated protein was then dissolved in 10 µL, of 0.5 M Tris-HCl pH 8.6, 6 M guanidinium-hydrochloride and reduced, alkylated, and digested with either 200 ng trypsin or 600 ng chymotrypsin following standard protocols (Gundry et al., Curr. Protoc. Mol. Biol., 10:1025 (2009)). The digests were acidified with formic acid (ThermoFisher Scientific™) and desalted using SOLAµ™ SPE Plates (ThermoFisher Scientific™)

Data were collected using an Orbitrap Fusion™ Lumos™ mass spectrometer (ThermoFisher Scientific™) coupled with a Proxeon EASY-nLC™ 1200 LC pump (ThermoFisher Scientific™). Peptides were separated on an Easy Spray™ ES803 75 µm inner diameter microcapillary column (ThermoFisher Scientific™). DSSO crosslinked peptides were separated using a 100 min gradient of 6-41% acetonitrile in 1.0% formic acid with a flow rate of 350 nL/min. The data were acquired using a mass range of m/z 375-1500, resolution 60,000, AGC target $4 \times 10^5$, maximum injection time 50 ms, dynamic exclusion of 30 seconds for the peptide measurements in the Orbitrap. Data dependent MS2 spectra were acquired in the Orbitrap with a normalized collision energy (NCE) set at 25%, AGC target set to $5 \times 10^4$ and a maximum injection time of 100 ms. For HCD-MS, MS2 fragment ions with a mass difference of 31.9721 Da (DSSO) or 26.0000 Da (DSBU) with 10-100% precursor intensity range were selected for fragmentation with HCD collision energy set to 30% and scans acquired in the Ion Trap with AGC target set to $2 \times 10^4$, maximum injection time of 150 ms.

Chemical Crosslinking LC-MS Data Analysis

Proteome Discoverer 2.2 (ThermoFisher Scientific™) with XLinkX version 2.2 was used for .RAW file processing and controlling peptide and protein level false discovery rates, assembling proteins from peptides, and protein quantification from peptides. MS/MS spectra were searched against a truncated (~200 proteins including the sequences for DCAF15, DDB1 and DDA1) Uniprot human database (September 2016) with both the forward and reverse sequences. Database search criteria are as follows: tryptic or chymotryptic with two missed cleavages, a precursor mass tolerance of 10 ppm, fragment ion mass tolerance of 0.6 Da, static alkylation of cysteine (57.0211 Da), variable oxidation of methionine (15.9951 Da), variable phosphorylation of serine, threonine and tyrosine (79.966 Da). DSSO crosslinked samples included the following variable modifications of lysines: DSSO (158.004 Da), amidated DSSO (142.050 Da) and hydrolysed DSSO (176.014 Da), and DSBU crosslinked samples included the following variable modifications of lysines: DSBU (196.085 Da), amidated DSBU (213.111 Da) and hydrolysed DSBU (214.095 Da).

UV-Crosslinking-Coupled Mass Spectrometry

Purified DDB1ΔB-DCAF15 full-length (3 µM) and His$_6$-RBM39$_{RRM2}$ (6 µM), and DMSO or E7820 (100 µM) were mixed and incubated for 15 min on ice. Compound 6 (Diazirine-E7820, 20 µM) or DMSO was added and incubated for 15 min on ice. The pre-mixed samples were irradiated with long-wave UV light for 15 min using a Spectrolinker UV Crosslinker (model XL1000, Spectronics Corp., Westbury, NY). The irradiated samples were processed as described above.

Data were collected using an Orbitrap Fusion™ Lumos™ mass spectrometer coupled with a Proxeon EASY-nLC™ 1200 LC pump. Peptides were separated on an EasySpray™ ES803 75 µm inner diameter microcapillary column. Peptides were separated using a 100 min gradient of 6-38% acetonitrile in 1.0% formic acid with a flow rate of 350 nL/min. The data were acquired using a mass range of m/z 200-2000, resolution 120,000, AGC target $4 \times 10^5$, maximum injection time 500 ms, dynamic exclusion of 60 seconds for the peptide measurements in the Orbitrap. Data dependent MS2 spectra were acquired in the ion trap with a normalized collision energy (NCE) set at 27%, AGC target set to $5 \times 10^4$ and a maximum injection time of 100 ms.

Proteome Discoverer 2.2 was used to analyse the LC-MS data. MS/MS spectra were searched against a truncated (~200 proteins) Uniprot human database (September 2016) with both the forward and reverse sequences. Database search criteria are as follows: tryptic or chymotryptic with two missed cleavages, a precursor mass tolerance of 10 ppm, fragment ion mass tolerance of 0.02 Da, static alkylation of cysteine (57.0211 Da), variable oxidation of methionine (15.9951 Da), variable phosphorylation of serine, threonine and tyrosine (79.966 Da) and variable acetylation (42.011 Da) of the protein N-terminus and variable crosslinked compound 6 (possible adduct sizes: 422.141 Da or 83.049 Da) on all amino acids. Unique peptides were quantified in PD2.2 and the abundances of compound 6 modified peptides on DCAF15 for each of the treatments (DMSO, compound 6 (20 µM), and compound 6 (20 µM)+E7820 competition (100 µM)) were analysed for potential modification sites.

TMT LC-MS3 Mass Spectrometry

Kelly cells were treated with DMSO vehicle (triplicate) or 10 µM of E7820 in singlicate for 5 h. Treated Kelly cells were washed in PBS (Corning VWR, Radnor PA, USA) and collected at 3000 g centrifugation. Sample preparation and LC-MS analysis for whole proteome identification of novel E7820-dependent substrates was performed as described previously (Donovan et al., Elife 7:38430 (2018)).

Data and Materials Availability

Structural coordinates for DDB1ΔB-DDA1-DCAF15-E7820-RBM39, DDB1ΔB-DDA1-DCAF15-tasisulam-RBM39, and DDB1ΔB-DDA1-DCAF15-indisulam-RBM39 have been deposited in the Protein Data Bank under accession numbers 6Q0R, 6Q0V, and 6Q0W. The cryo-EM volume data are available at the EMDB, accession numbers: EMD-20554 and EMD-20553. Mass spectrometry raw data files have been deposited in PRIDE Archive under the accession numbers: PXD014536.

Example 8: Docking Simulations and Binding Funnel Estimation

Figure 14A:
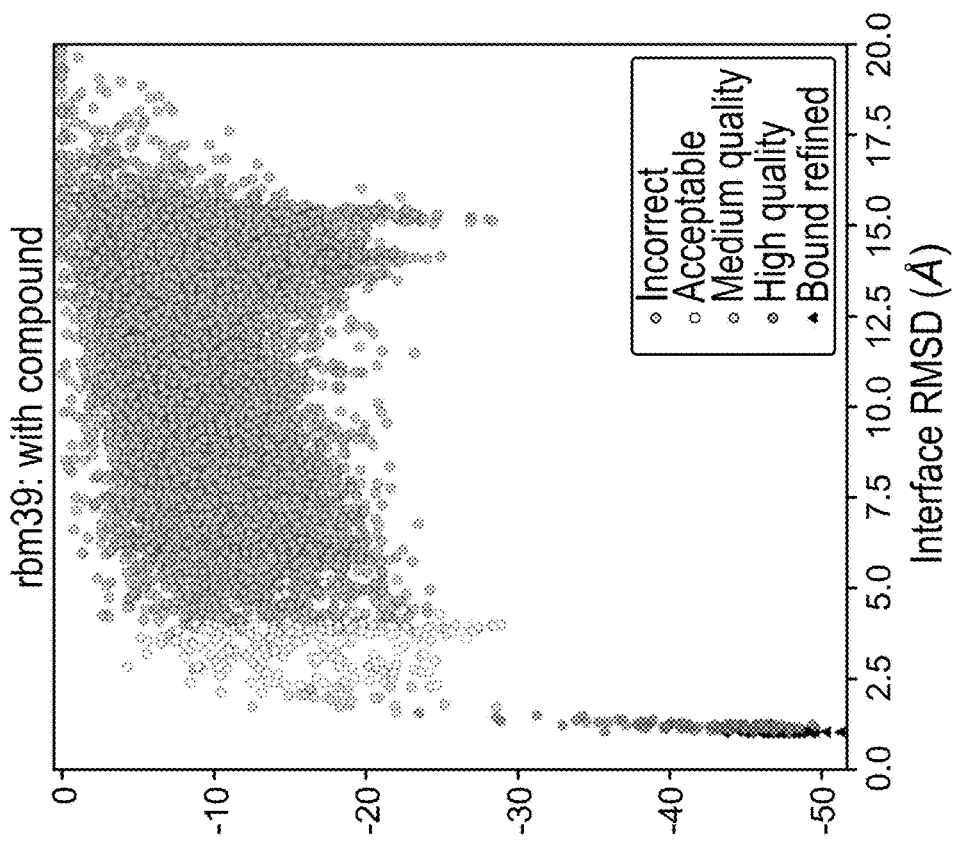
FIG. 14A and FIG. 14B are graphs of docking models of RBM39 and DCAF15 without (FIG. 14A) and with (FIG. 14B) E7820. Each circle represents a model and shows the interface score and the interface root-mean-square-deviation of the model. Models are colored by their similarity to the crystal structure. The triangles represents a perturbation of the crystal structure. The results indicate a deep binding energy funnel between RBM39 and DCAF15, which deepens further in the presence of the compound.
Figure 14B:
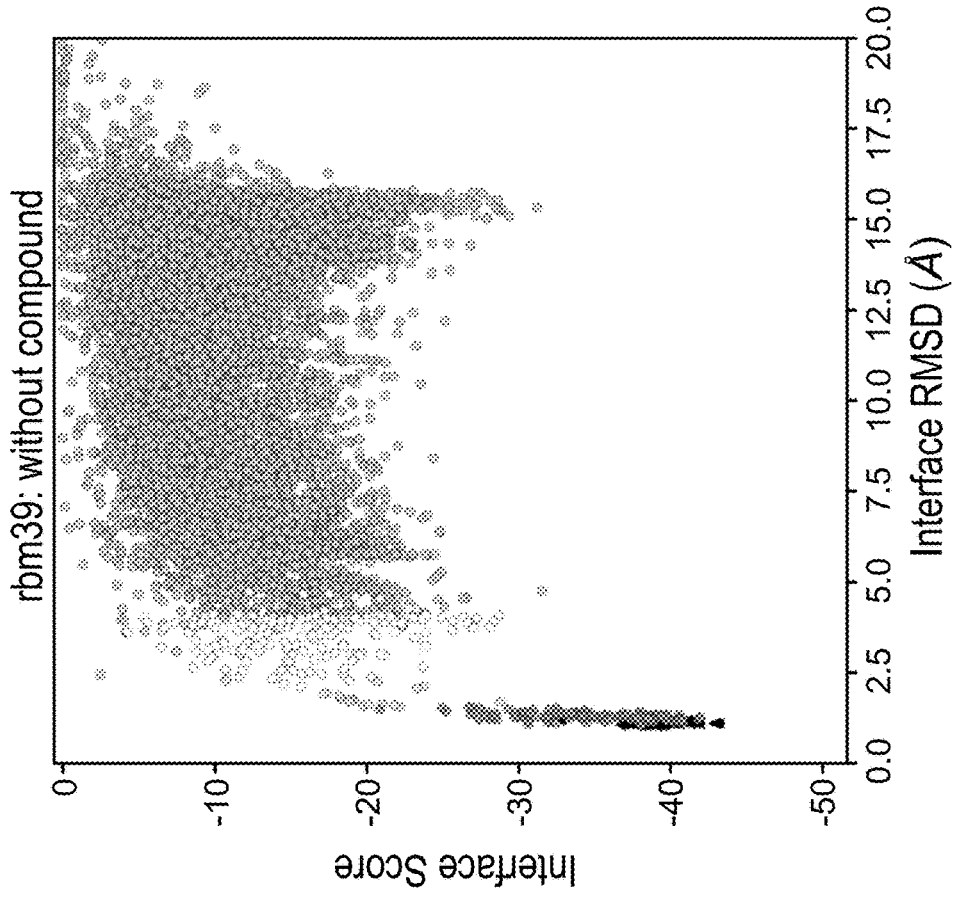
Figure 15A:
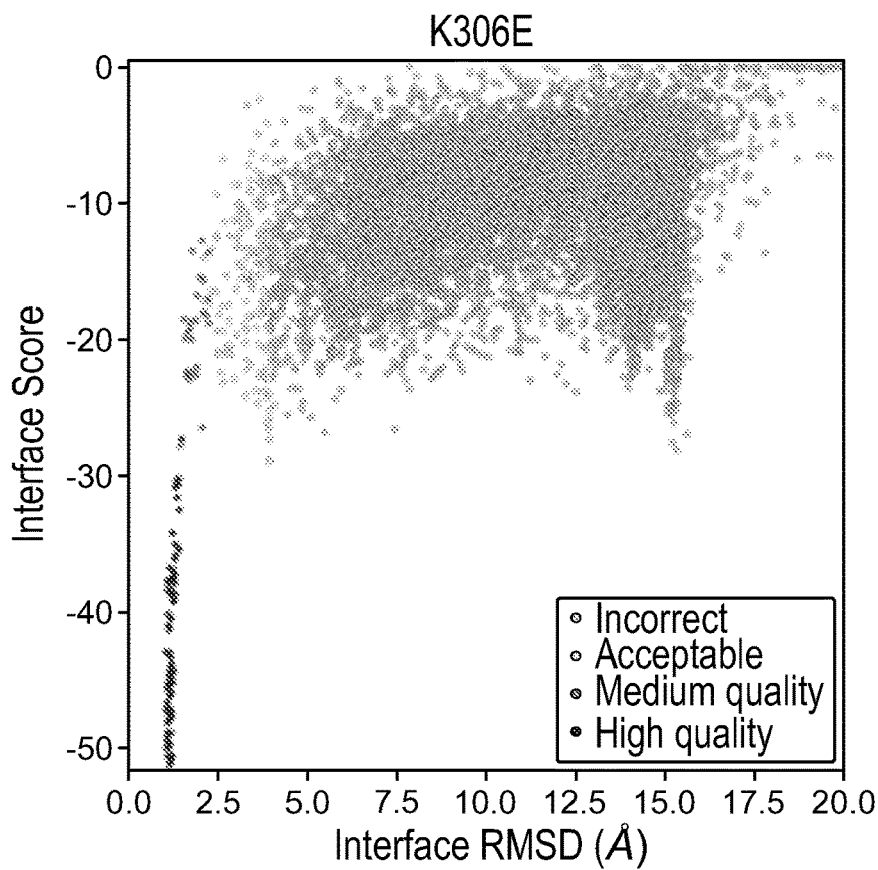
FIG. 15A-FIG. 15G are a series of graphs of docking models of RBM39$_{RRM2}$-derived degrons and DCAF15 in the presence of E7820. The simulations suggested that there are deep binding funnels comparable to the wild-type sequence for the indicated amino acid substitutions.
Figure 15B:
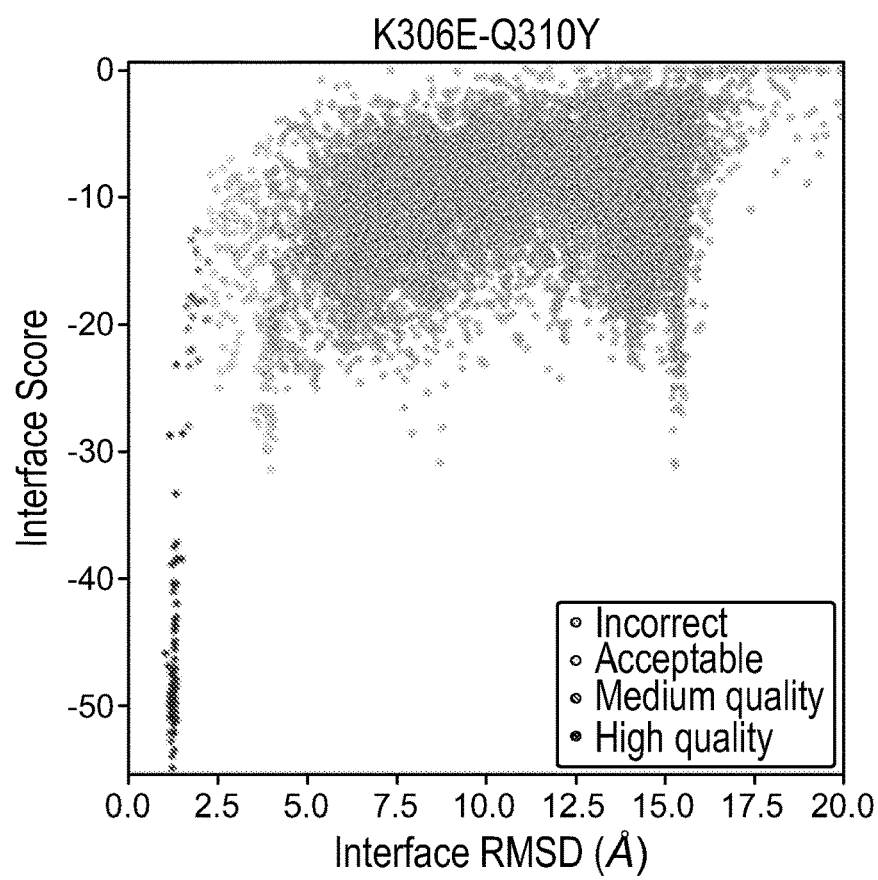
Figure 15C:
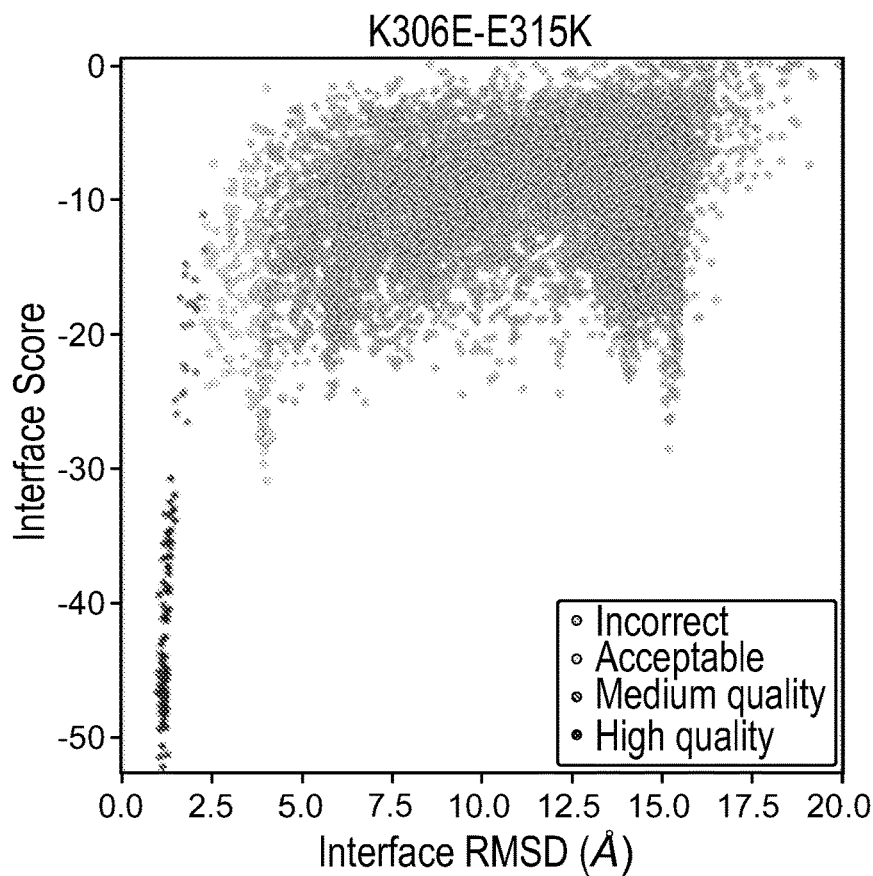
Figure 15D:
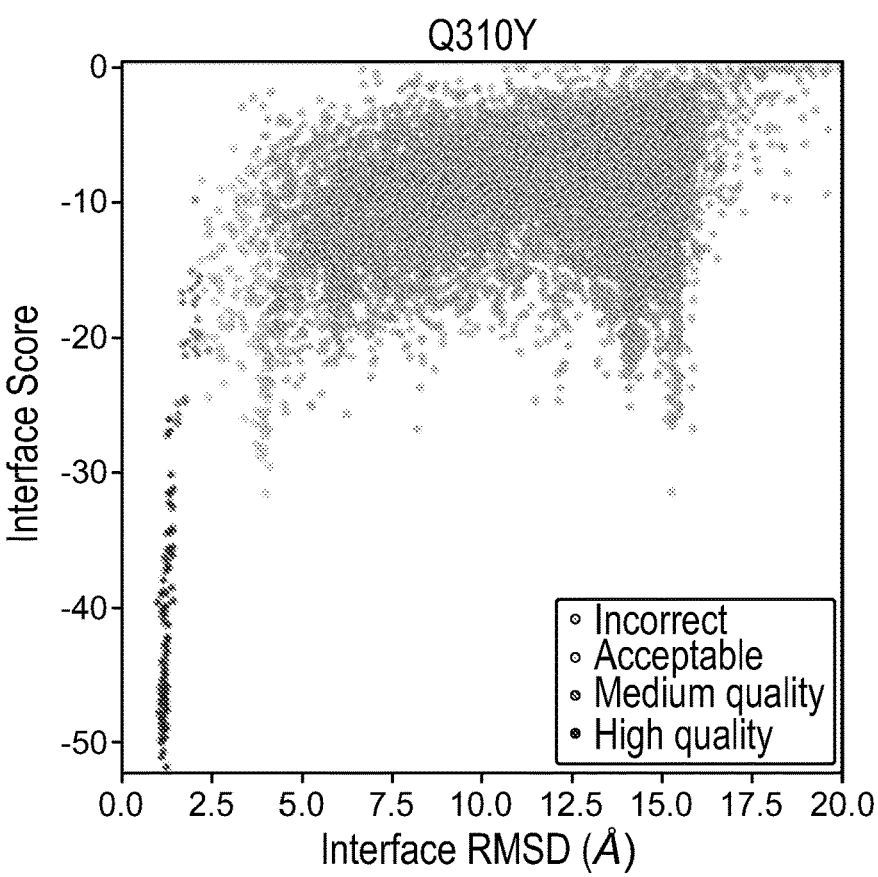
Figure 15E:
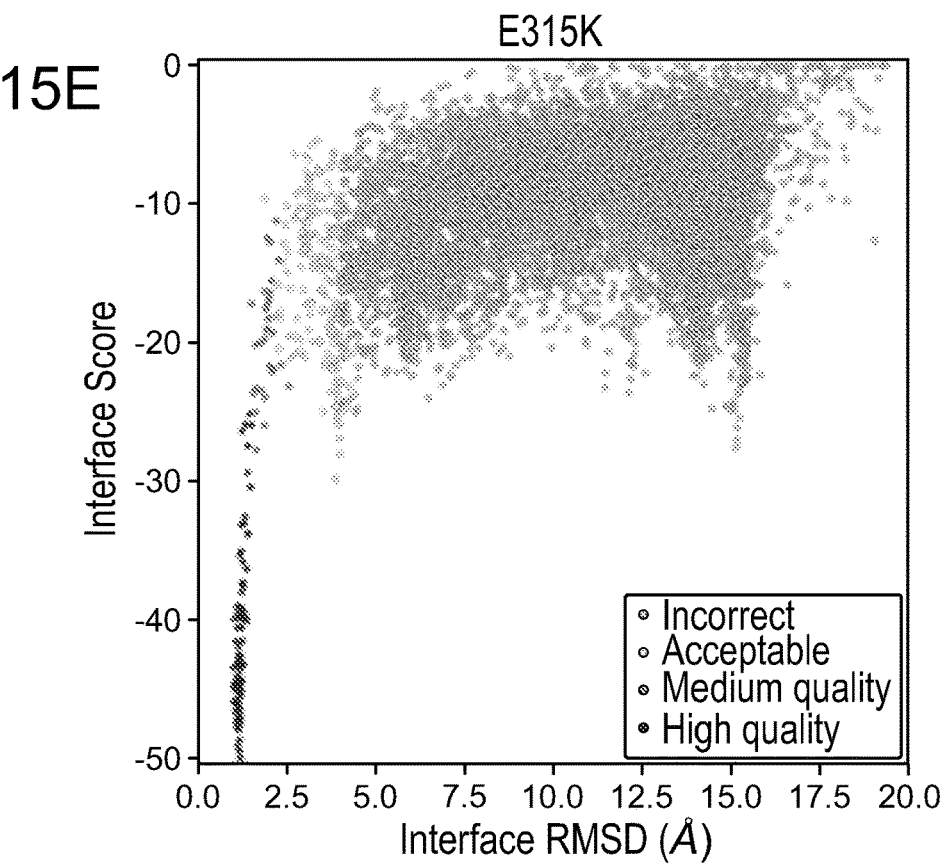
Figure 15F:
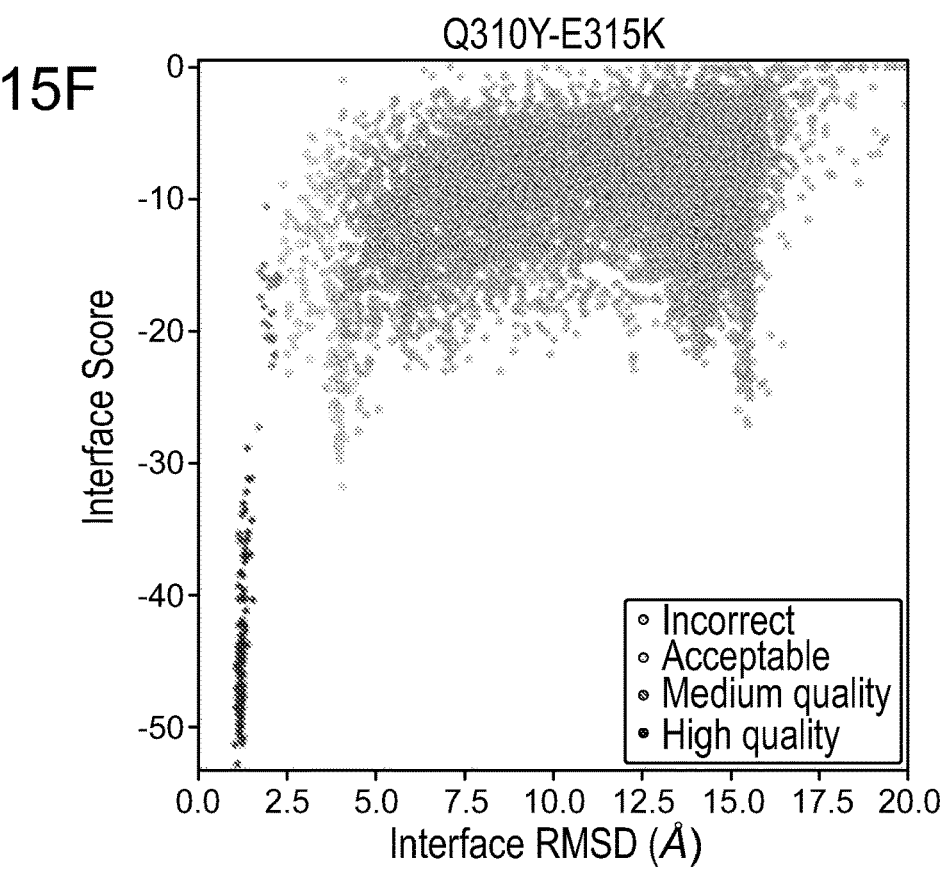
Figure 15G:
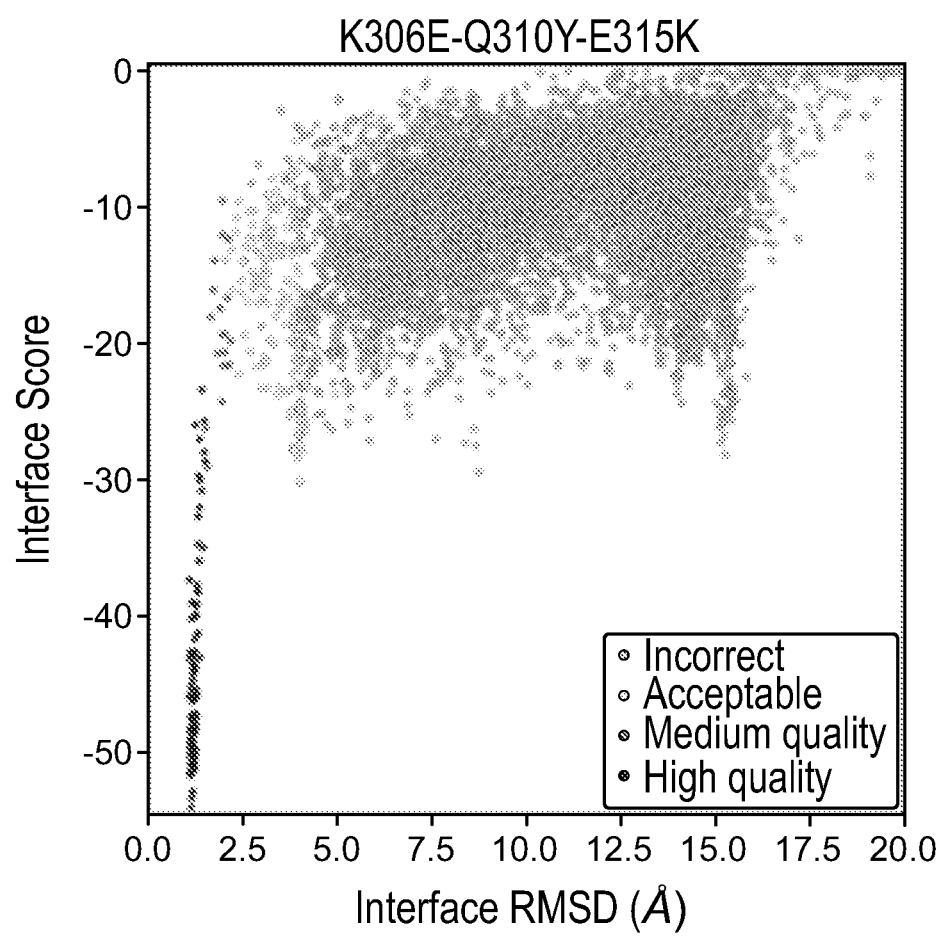

For docking the wild-type RBM39$_{RRM2}$ to DCAF15 in the presence of E7820, RosettaDock4.0 was used with the standard options. Briefly, RBM39$_{RRM2}$ was placed in the vicinity of DCAF15-E7820 as found in the crystal structure (FIG. 2), but away from the binding pocket. A Monte Carlo-plus-minimization simulation comprising random rigid-body perturbations (3 Å and 8°) and interface side-chain repacking was used to find the binding mode with the lowest score. This simulation was repeated 5000 times, each time starting at a different relative orientation of RBM39$_{RRM2}$ and DCAF15-E7820. Each circular point in FIG. 14 represents the score and the root-mean-square-deviation of one of the 5000 models. Docking simulations were performed for each of the designed degron tags to estimate binding energy (FIG. 15). To estimate the depth of the binding energy funnel, a similar docking algorithm was used, but the starting model was the crystal structure and the perturbations were smaller (0.5 Å and 5°). Each triangular point in FIG. 14 represents the score and the root-mean-square-deviation of one of the 100 models generated in this manner.

Example 9: Degron Tag Design

For designing degron tags, Rosetta FastDesign was used on the crystal structure (FIG. 2) of RBM39$_{RRM2}$ bound to DCAF15 in the presence of E7820. Briefly, a Monte Carlo-plus-minimization simulation was used to mutate the residues at the interface of RBM39$_{RRM2}$ to all amino acids (except cysteine), while the residues at the interface of DCAF15 were repacked accordingly. Simultaneously, the side chain and backbone torsion angles were optimized for the interface. The best scoring mutants in the 2000 models generated were selected and visually analyzed. The relative orientation of RBM39$_{RRM2}$ and DCAF15-E7820 was also optimized for each design.

Example 10: In Vitro TR-FRET Binding Assay

Figure 16:
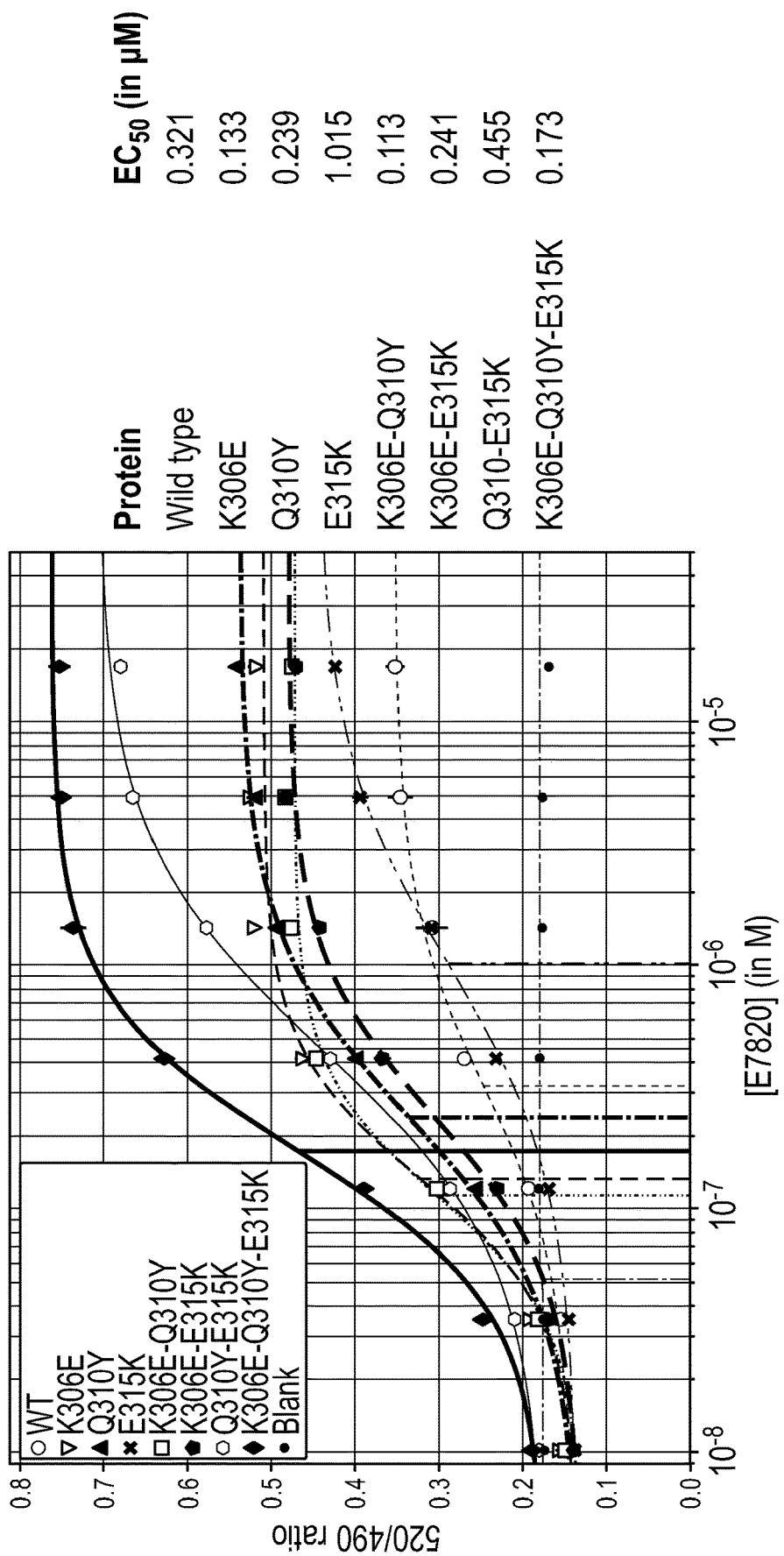
FIG. 16 is a graph showing the result of the TR-FRET assay of designed degrons that bind more strongly (higher saturated 520/490 emission ratio) at lower doses of E7820 (lower EC$_{50}$ value) than the wild-type.

To investigate formation of complexes between the designed degrons and DCAF15 in the presence of E7820, in vitro TR-FRET assay was performed. 200 nM of BodipyFL-maleimide-labelled DCAF15-Spycatcher, 200 nM of biotinylated Strep II Avi-tagged RBM39$_{RRM2}$ or designed degrons, and 2 nM terbium-coupled streptavidin were incubated with increasing concentration of E7820. After excitation of terbium at 337 nm, emission of terbium (at 490 nm) and that of BodipyFL (520 nm) were recorded over 60 cycles of 90 s each. The TR-FRET signal of 520/490 was recorded as shown in FIG. 16 and the corresponding half-maximal effective concentrations (EC$_{50}$) were calculated. Up to 2.84-fold higher affinity was observed between the designed degrons and DCAF15 as compared to the wild-type RBM39$_{RRM2}$.

Example 11: Compound-Dependent Degradation of the Designed Degron Tags

Figure 17A:
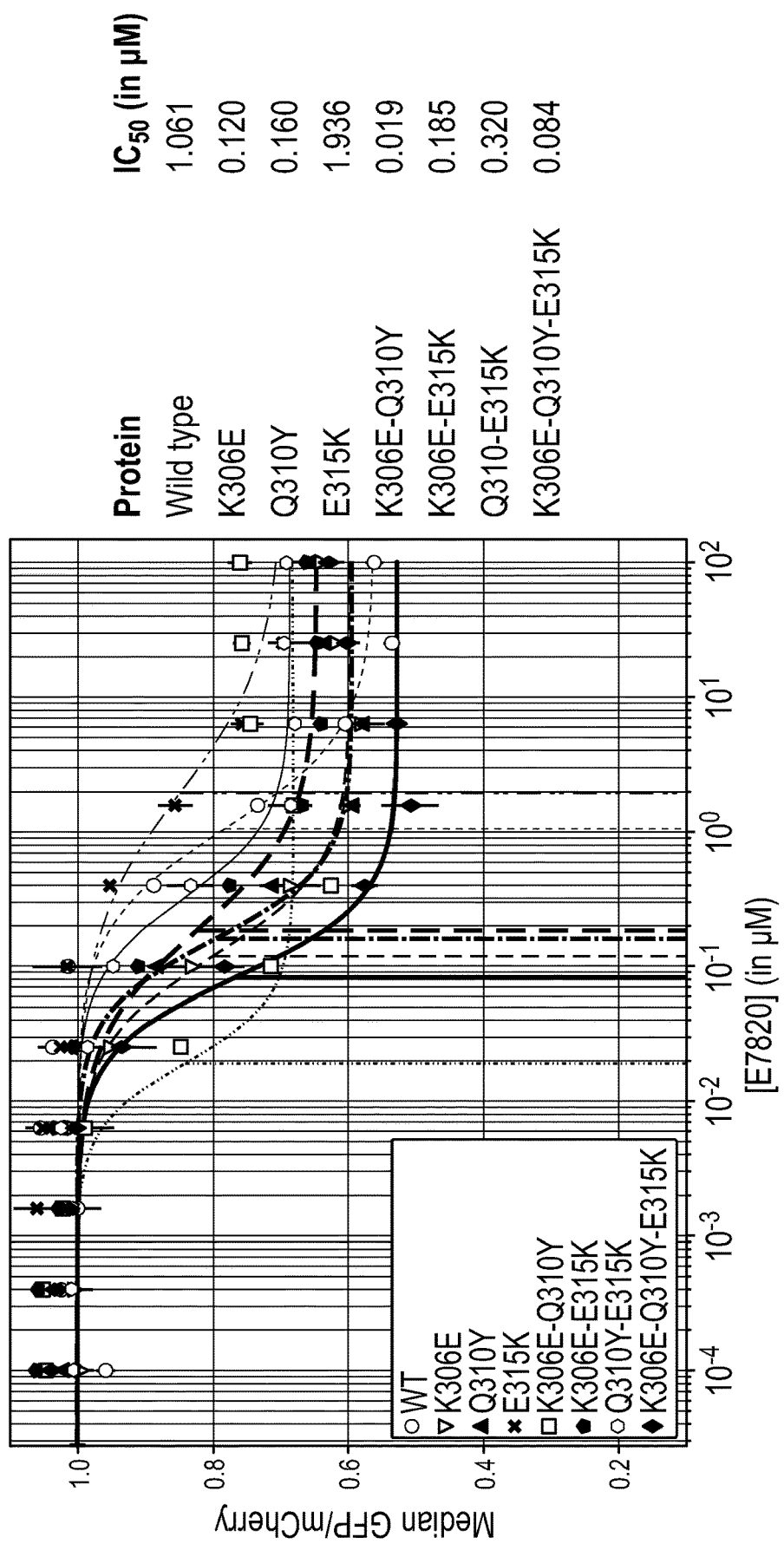
Figure 17B:
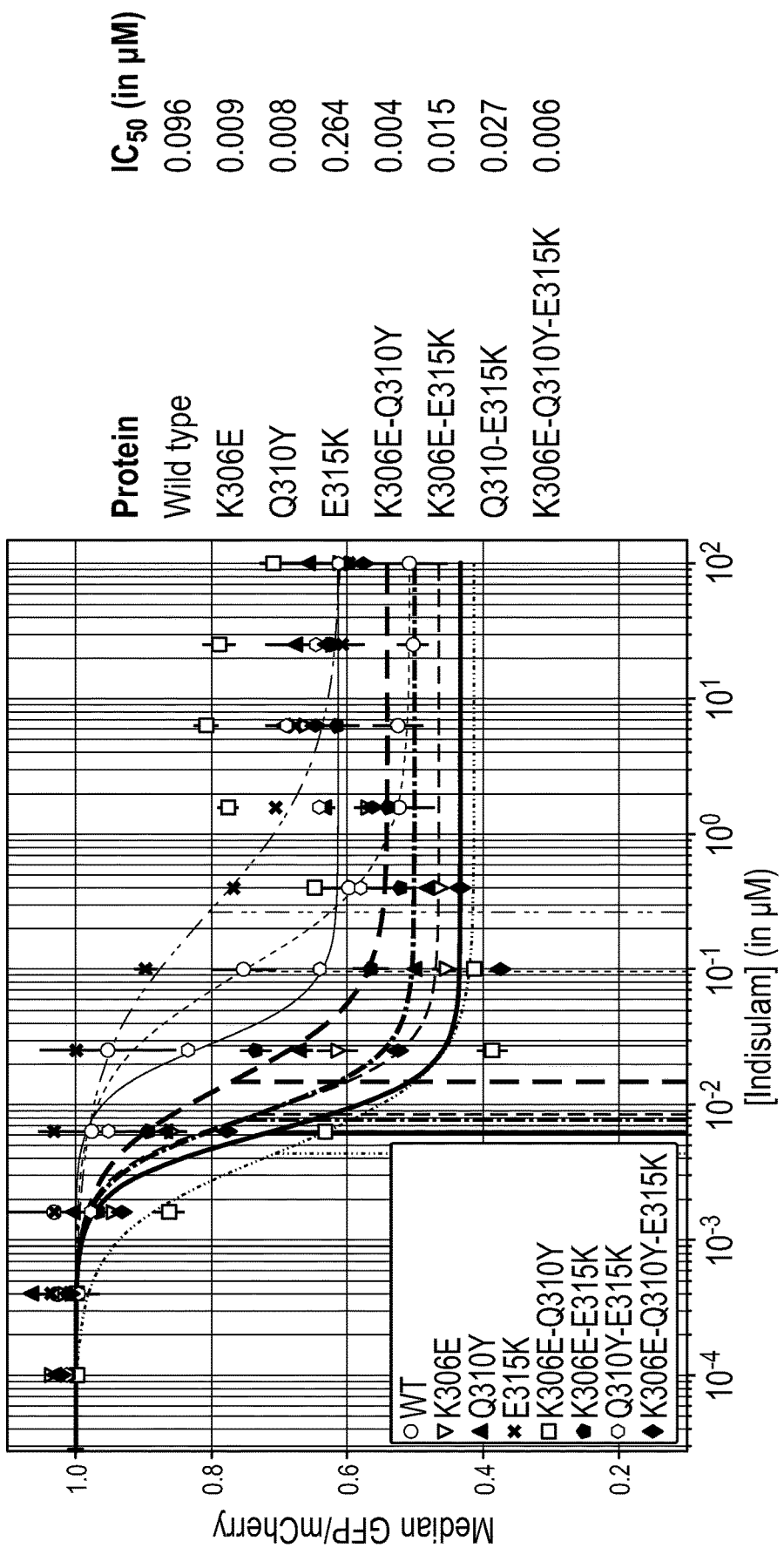

To test compound-dependent degradation of the designed degron tags, a fusion protein of the tags and enhanced green fluorescence protein (eGFP) was stably expressed in HEK293T cells using a lentiviral vector. As an internal control, the cells also expressed an untagged mCherry protein downstream of the same promoter as degron-eGFP separated by an internal ribosomal entry site. Using the eGFP/mCherry ratio as the metric to measure tag protein levels in the cell, dose-dependent degradation was observed for the designs with E7820 (FIG. 17A), Indisulam (FIG. 17B), and Tasisulam (FIG. 17C) upon 20-hour treatment. A lower value of eGFP/mCherry at the same compound concentration indicates a higher rate of degradation. Designed degrons have higher degradation at low doses of aryl-sulfonamides and also lower IC50 values. Specifically, as much as 50-fold reduction in the half maximal inhibitory concentration (IC50) values was observed for the designs DCAF15 as compared to the wild-type RBM39$_{RRM2}$.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A degron tag comprising a polypeptide which is a variant of ribonucleic acid (RNA) recognition motif (RRM), wherein in the presence of an aryl sulfonamide, the variant of RRM, is selectively bound and targeted for degradation by E3 ubiquitin ligase Cullin Really Interesting New Gene (RING) ligase 4 (CRL4) deoxyribonucleic acid (DNA) damage binding protein 1 (DDB 1) and Cullin-4 (CUL4) associated factor 15 (DCAF15) (CRL4DCAF15) wherein the presence of an aryl sulfonamide leads to degradation of the variant of RRM mediated by CRL4DCAF15 that is 2-100 fold greater than degradation of the wild-type RRM or RRM-containing protein mediated by CRL4DCAF15 wherein the variant of RRM differs from wild-type RRM or an RRM present in an RRM-containing protein by comprising an amino acid substitution at H258, S285, T287, K306, Q310, or E315, or a combination of two or more thereof, said amino acid substitution numbered in accordance with SEQ ID NO: 1, and wherein the amino acid substitution at K306 comprises K306E, K306L, K306T, or K306A.

2. The degron tag of claim 1, wherein the variant of RRM comprises a variant of RRM2, a variant of RBM39uM2 or a variant of RBM 23 1um2.

3. The degron tag of claim 1, which comprises a substitution of K306, said amino acid substitution numbered in accordance with SEQ ID NO: 1.

4. The degron tag of claim 1, which comprises a substitution of Q310, or which comprises a substitution of E315, said amino acid substitution when numbered in accordance with SEQ ID NO: 1.

5. The degron tag of claim 4, which comprises a Q310Y substitution, or which comprises a E315K substitution, said amino acid substitution when numbered in accordance with SEQ ID NO: 1.

6. The degron tag of claim 1, which comprises a combination of two or more substitutions at K306, Q310 and E315, said amino acid substitutions numbered in accordance with SEQ ID NO: 1.

7. The degron tag of claim 6, which comprises substitutions at K306 and Q310, or which comprises substitutions at K306 and E315, or which comprises substitutions at Q310 and E315, said amino acid substitutions numbered in accordance with SEQ ID NO: 1.

8. The degron tag of claim 7, which comprises K306E and Q310Y substitutions, or which comprises K306E and E315K substitutions, or which comprises Q310Y and E315K substitutions, said amino acid substitutions numbered in accordance with SEQ ID NO: 1.

9. The degron tag of claim 6, which comprises substitutions at K306, Q310 and E315, said amino acid substitutions numbered in accordance with SEQ ID NO: 1.

10. The degron tag of claim 9, which comprises K306E, Q310Y and E315K substitutions, said amino acid substitutions numbered in accordance with SEQ ID NO: 1.

11. The degron tag of claim 1, which is selected from the group consisting of:

```
                                           (SEQ ID NO: 11)
MRLYVGSLHFNITEDMLRGIFEPFGRIESIQLMMDSETGRSKGYGFITF
SDSECAKEALEQLNGFELAGRPMKVGHVTERTDA, (SEQ ID NO: 12)
MRLYVGSLHFNITEDMLRGIFEPFGRIESIQLMMDSETGRSKGYGFITF
SDSECAKKALEYLNGFELAGRPMKVGHVTERTDA, (SEQ ID NO: 13)
MRLYVGSLHFNITEDMLRGIFEPFGRIESIQLMMDSETGRSKGYGFITF
SDSECAKKALEQLNGFKLAGRPMKVGHVTERTDA, (SEQ ID NO: 14)
MRLYVGSLHFNITEDMLRGIFEPFGRIESIQLMMDSETGRSKGYGFITF
SDSECAKEALEYLNGFELAGRPMKVGHVTERTDA, (SEQ ID NO: 15)
MRLYVGSLHFNITEDMLRGIFEPFGRIESIQLMMDSETGRSKGYGFITF
SDSECAKEALEQLNGFKLAGRPMKVGHVTERTDA, (SEQ ID NO: 16)
MRLYVGSLHFNITEDMLRGIFEPFGRIESIQLMMDSETGRSKGYGFITF
SDSECAKKALEYLNGFKLAGRPMKVGHVTERTDA, (SEQ ID NO: 17)
MRLYVGSLHFNITEDMLRGIFEPFGRIESIQLMMDSETGRSKGYGFITF
SDSECAKEALEYLNGFKLAGRPMKVGHVTERTDA, (SEQ ID NO: 18)
MRLYVGSLHFNITEDMLRGIFEPFGRIESIQLMMDSETGRSKGYGFITF
SDSECAKKALEQLNGFELAGRPMKVGHVTE,
and (SEQ ID NO: 19)
MRLYVGSLHFNITEDMLRGIFEPFGKIDNIVLMKDSDTGRSKGYGFITF
SDSECARRALEQLNGFELAGRPMRVGHVTE.
```

12. A fusion protein comprising a protein of interest and the degron tag of claim 1.

13. The fusion protein of claim 12, wherein the degron tag is located N-terminal to the protein of interest or wherein the degron tag is located C-terminal to the protein of interest; or wherein the protein of interest comprises a chimeric antigen receptor (CAR) protein comprising, from N-terminus to C-terminus: a) an extracellular ligand binding domain that binds a tumor associated antigen; b) a transmembrane domain; and c) a cytoplasmic domain comprising at least one intracellular signaling domain.

14. The fusion protein of claim 13, wherein said extracellular ligand binding domain binds the tumor associated antigen CD 19.

15. The fusion protein of claim 14, wherein said a)-c) comprise tisagenlecleucel chimeric antigen receptor (CAR) or axicabtagene ciloleucel CAR.

16. A nucleic acid molecule having a nucleotide sequence encoding the degron tag of claim 1.

17. A nucleic acid molecule having a nucleotide sequence encoding the fusion protein of claim 12.

18. A vector comprising the nucleic acid sequence of claim 16.

19. A cell stably transformed with the nucleic acid of claim 16.

20. The cell of claim 19, which is an immune effector cell.

21. The cell of claim 20, which is a T-cell, or which is a mammalian cell, or which is a human cell.

22. A method of degrading an endogenous protein of interest, comprising: contacting a cell in vitro or in vivo with an effective amount of an aryl-sulfonamide compound, wherein the cell expresses the nucleic acid of claim 16 which is situated in-frame with an endogenous nucleic acid encoding an endogenous protein of interest.

23. A method of degrading an exogenous protein of interest, comprising: contacting a cell in vitro or in vivo with an effective amount of an aryl-sulfonamide compound, wherein the cell expresses the nucleic acid of claim 17, wherein said protein of interest is exogenous to the cell.

24. A method of degrading a protein of interest, comprising: administering an effective amount of an aryl-sulfonamide compound to a subject, wherein the subject has previously been treated via gene therapy causing at least some endogenous cells to express the nucleic acid of claim 17.

25. The method of claim 24, wherein said gene therapy comprises gene knock-in, administration of viral vectors or clustered regularly interspaced short palindromic repeats (CRISPR)-mediated knock in; or wherein said aryl-sulfonamide compound is E7820, indisulam, or tasisulam.

26. A method of degrading a chimeric antigen receptor protein comprising: administering an effective amount of an aryl-sulfonamide compound to a subject, wherein the subject has previously been treated with allogeneic or autologous immune effector cells that express a nucleic acid encoding the fusion protein of claim 12.

27. The method of claim 22, wherein said aryl-sulfonamide compound is E7820, indisulam, or tasisulam.

* * * * *